(12) United States Patent
Deprez et al.

(10) Patent No.: US 8,324,396 B2
(45) Date of Patent: Dec. 4, 2012

(54) DERIVATIVES OF UREA AND RELATED DIAMINES, METHODS FOR THEIR MANUFACTURE, AND USES THEREFOR

(75) Inventors: Pierre Deprez, Thiais (FR); Christopher Fotsch, Thousand Oaks, CA (US); Paul Harrington, Camarillo, CA (US); Sarah Lively, San Carlos, CA (US); Kanaka Pattabiraman, Palo Alto, CA (US); David St. Jean, Camarillo, CA (US); Taoues Temal-Laib, Saint Gratien (FR)

(73) Assignee: Amgen Inc., Thousand Oaks, CA (US)

( * ) Notice: Subject to any disclaimer, the term of this patent is extended or adjusted under 35 U.S.C. 154(b) by 424 days.

(21) Appl. No.: 12/218,228

(22) Filed: Jul. 10, 2008

(65) Prior Publication Data
US 2009/0054463 A1    Feb. 26, 2009

Related U.S. Application Data

(60) Provisional application No. 60/959,058, filed on Jul. 10, 2007.

(51) Int. Cl.
*C07D 277/32* (2006.01)
*A61K 31/425* (2006.01)

(52) U.S. Cl. .................................. 548/198; 514/371
(58) Field of Classification Search .................. 548/198; 514/371
See application file for complete search history.

(56) References Cited

U.S. PATENT DOCUMENTS

| | | | |
|---|---|---|---|
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,313,146 B1 | 11/2001 | Van Wagenen et al. | |
| 7,875,609 B2 * | 1/2011 | Jary et al. | 514/234.5 |
| 2007/0179134 A1 * | 8/2007 | Jary et al. | 514/232.5 |
| 2010/0240889 A1 * | 9/2010 | Deprez et al. | 544/58.7 |

FOREIGN PATENT DOCUMENTS

| | | | |
|---|---|---|---|
| EP | 0415413 A | | 3/1991 |
| FR | 2820136 A | | 8/2002 |
| FR | 2885129 | * | 11/2006 |
| FR | 2885129 A | | 11/2006 |
| JP | 58-109464 | | 6/1983 |
| JP | 08-041006 | | 2/1996 |
| JP | 10-195037 | | 7/1998 |
| JP | 11-139969 | | 5/1999 |
| WO | WO 96/12697 | | 5/1996 |
| WO | WO 01/00576 | | 1/2001 |
| WO | WO 02/059102 | | 8/2002 |
| WO | WO 2006/117211 | | 11/2006 |
| WO | WO 2007/060026 | | 5/2007 |
| WO | WO 2007060026 A1 | * | 5/2007 |
| WO | WO 2008/006625 | | 1/2008 |

OTHER PUBLICATIONS

Eiden et al. (CAPLUS Abstract of: Deutsche Apotheker Zeitung (1983), 123(20), 958-62).*
Kubinyi (3D QSAR in Drug Design: Ligand-Protein Interactions and Molecular Similarity, vol. 2-3, Springer, 1998, 800 pages), TOC and p. 243-44 provided.*
Devries et al. (CAPLUS Abstract of: DE 3247581).*
Deprez et al. (CAPLUS Abstract of WO 2002059102 (published Aug. 1, 2002)).*
Devries et al. (CAPLUS Abstract of: DE 3247581 (published Aug. 4, 1983)).*
Devries et al.; "Potential antitherosclerotic agents. 6. hypocholesterolemic trisubstituted urea analogues", Journal of Medicinal Chemistry, vol. 32, pp. 2318-2325, 1989.

* cited by examiner

*Primary Examiner* — Robert Havlin
(74) *Attorney, Agent, or Firm* — Olga Mekhovich

(57) ABSTRACT

The present invention relates generally to compounds represented in Formula I, pharmaceutical compositions comprising them and methods of treating of diseases or disorders related to the function of the calcium sensing receptor. The invention also relates to processes for making such compounds and to intermediates useful in these processes.

I $$\begin{array}{c} R^1 \\ \diagdown \\ Z-(CH_2)_p-N-Q-N-R^6 \\ \diagup \quad\quad\quad\quad | \quad\quad | \\ R^2 \quad\quad\quad\quad R^3 \quad H \end{array}$$

6 Claims, No Drawings

DERIVATIVES OF UREA AND RELATED DIAMINES, METHODS FOR THEIR MANUFACTURE, AND USES THEREFOR

CROSS-REFERENCE TO RELATED PATENT APPLICATIONS

This application claims the benefit of priority of U.S. Provisional Patent Application No. 60/959,058 filed on Jul. 10, 2007.

FIELD OF THE INVENTION

The present invention relates generally to the field of medicine and, more specifically, to derivatives of urea and related diamines, processes for the preparation thereof, the application thereof as medicaments, pharmaceutical compositions containing them and uses thereof, particularly as calcium receptor modulating compounds, and pharmaceutical compositions comprising them.

BACKGROUND OF THE INVENTION

Extracellular calcium ion concentration is involved in a variety of biological processes, such as blood clotting, nerve and muscle excitability and bone formation (Cell Calcium 11:319, 1990). One of the key elements of this regulation is the calcium receptor known as the Ca sensing receptor or CaSR. Calcium ion receptors, which are present on the membranes of various cells in the body, such as parathyroid and kidney cells (Nature 366:574, 1993; J. Bone Miner. Res. 9, Supple. 1, s282, 1994; J. Bone Miner. Res. 9, Supple. 1, s409, 1994; Endocrinology 136:5202, 1995), are important to the regulation of the extracellular calcium ion concentration. For example, concentration of extracellular calcium ion regulates the bone resorption by osteoclasts (Bioscience Reports 10:493, 1990), secretion of parathyroid hormone (PTH) from parathyroid cells and secretion of calcitonin from C-cells (Cell Calcium 11:323, 1990). Parathyroid cells thus have at their surface the calcium receptor (CaSR), which detects changes in extracellular calcium concentration and initiates the functional response of this cell, which is a modulation of the secretion of the parathyroid hormone (PTH). Secretion of PTH increases extracellular calcium ion concentration by acting on various cells, such as bone and kidney cells, and the extracellular calcium ion concentration reciprocally inhibits the secretion of PTH by acting on parathyroid cells. The reciprocal relationship between calcium concentration and PTH level is an essential mechanism for calcium homeostasis maintenance.

The cloning of the calcium receptor by Brown in 1993 consequently demonstrated two possible signaling pathways for this G protein coupled receptor: one pathway by activation of the Gi protein (sensitive to the pertussis toxin) which stimulates phospholipase C and inhibits adenylate cyclase; the other pathway by activating the Gq protein responsible for mobilising intracellular calcium. These two signaling pathways, either independently of one another or together, can be activated so as to trigger the associated biological effect. On its extracellular portion, the calcium receptor is a low affinity receptor which is stimulated by millimolar concentrations of agonists, in particular the calcium ion $Ca^{2+}$. In addition, this receptor can also be activated by some divalent metals (magnesium) or trivalent metals (gadolinium, lanthanum, etc.) or else by polycationic compounds such as neomycin or spermine.

Several classes of calcimimetic compounds have been disclosed for regulating extracellular calcium ion concentration, particularly for reducing or inhibiting secretion of PTH. For example, U.S. Pat. Nos. 6,011,068 and 5,981,599 disclose arylalkylamines that are calcium receptor active molecules. EP 933354; WO 0021910, WO 96/12697; WO 95/11221; WO 94/18959; WO 93/04373; Endocrinology 128:3047, 1991; Biochem. Biophys. Res. Commun. 167:807, 1990; J. Bone Miner. Res. 5:581, 1990; and Nemeth et al., "Calcium-binding Proteins in Health and Disease," Academic Press, Inc., pp. 33-35 (1987) disclose various agents that interact with calcium receptors.

Dauban et al., Bioorg. Med. Chem. Let. 10:2001-4, 2000, disclose various N1-arylsulfonyl-N2-(1-aryl)ethyl-3-phenyl-propane-1,2-diamine compounds as calcimimetics acting on the calcium sensing receptor.

Oikawa et al., in U.S. Pat. No. 6,403,832, and publication No. US2002/143212, describes aryl amine compounds useful as chiral intermediates in the synthesis of optically active propionic acid derivatives. Chassot et al., U.S. Pat. No. 6,436,152, describes arylalkylamine compounds useful as hair dye precursor compounds.

Bös et al., U.S. Pat. No. 6,407,111, describes phenyl substituted pyridine and benzene derivates that are antagonistic to the NK-1 receptor.

SUMMARY OF THE INVENTION

The present invention relates to selected calcimimetic compounds and pharmaceutically acceptable salts thereof. In one aspect, the invention compounds advantageously reduce or inhibit PTH secretion. Therefore, this invention also encompasses pharmaceutical compositions, methods for reducing or inhibiting PTH secretion and methods for treatment or prophylaxis of diseases associated with bone disorders, such as osteoporosis, or associated with excessive secretion of PTH, such as hyperparathyroidism. The subject invention also relates to processes for making such compounds as well as to intermediates useful in such processes.

The invention encompasses compounds that are represented by the following general structure:

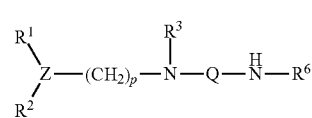

I or a stereoisomer, a tautomer, a solvate, a pharmaceutically acceptable salt, or a prodrug thereof, wherein the variables are defined in Detailed Description below.

In one aspect, $R^1$ and $R^2$ can be the same or different, and each represents a monocyclic aryl group, a monocyclic heteroaryl group, or Z, $R^1$ and $R^2$ together form the fused ring structure, wherein each of $R^1$ and $R^2$, or the fused ring structure formed thereby, is optionally substituted by at least one substituent selected from the group 'c'. In another aspect, $R^1$ and $R^2$ each represent a phenyl, pyridinyl, or thienyl radical, or $R^1$ and $R^2$ represent a fused ring structure formed thereby, wherein each of $R^1$ and $R^2$, or the fused ring structure, is optionally substituted. In a further aspect, $R^1$ and $R^2$ each represent an optionally substituted phenyl radical. In one aspect, each of $R^1$ and $R^2$, or the fused ring structure formed thereby, is optionally substituted by at least one substituent selected from the group c', consisting of: fluorine and chlorine atoms, hydroxyl, linear and branched alkyl, alkylthio, hydroxyalkyl, and fluoroalkyl groups; linear and branched alkoxyl groups; trifluoromethyl; trifluoromethoxyl; —CN; alkylcarbonyl groups; alkylsulphonyl groups, and any alkyl component has from 1 to 4 carbon atoms, and wherein, when there is more than one substituent, then each said substituent is the same or different. In another aspect, each of $R^1$ and $R^2$, or the fused ring structure formed thereby, is optionally substituted by at least one substituent selected from the group consisting of fluorine and chlorine atoms, hydroxy groups, linear or branched alkoxy groups containing from 1 to 5 carbon atoms, linear or branched alkyl groups containing from 1 to 5 carbon atoms, trifluoromethyl and trifluoromethoxy groups, and —CN groups, and wherein, when there is more than one substituent, then each substituent is the same or different. For example, each of $R^1$ and $R^2$ can be an optionally substituted phenyl, pyridinyl, or thienyl group.

The invention provides compounds of Formula I, wherein $R^6$ is an aryl or heteroaryl group selected from the group consisting of: fluorenyl, phenyl, naphthyl, monocyclic heteroaryls, and bicyclic heteroaryls, optionally substituted as defined. In one aspect, $R^6$ can be selected from the group consisting of: phenyl, naphthyl, benzothiazolyl, fluorenyl, benzazolyl, benzoxazolyl, thienyl, thiazolyl, isothiazolyl, furyl, oxazolyl, isoxazolyl, imidazolyl, triazolyl, indolyl, pyrrolyl, quinolyl, pyridinyl, pyrazolyl, pyrazinyl, pyrimidinyl, pyridazinyl, pyrrolyl, furanyl, 1,2,3-triazolyl, 1,2,4-triazolyl, tetrazolyl, 1,2,4-triazinyl, 1,3,5-triazinyl, 1,3,4-thiadiazolyl, 1,3,5-thiadiazolyl, benzofuranyl, benzothiazyl, benzimidazolyl, indazolyl, tetraquinolinyl, tetrahydroisoquinolinyl, isoquinolinyl, indolyl, carbazolyl, indolinyl, alpha- or beta-carbolinyl, and benzothienyl groups. In a further aspect, $R^6$ can be benzothiazolyl or thiazolyl. In one aspect, $R^6$ can be substituted by at least one substituent selected from substituents a': fluorine atoms; chlorine atoms; hydroxyl groups; carboxyl groups; aldehyde groups; linear and branched alkyl, hydroxyalkyl, and fluoroalkyl groups; linear and branched alkoxyl groups; linear and branched thioalkyl groups; alkoxycarbonyl groups; benzylcarbonyl groups; hydroxycarbonylalkyl groups; alkoxycarbonylalkyl groups; trifluoromethyl groups; trifluoromethoxy groups; —CN groups; amino, alkylamino, dialkylamino, acylamino, and diacylamino groups; alkoxycarbonylamino, alkylcarbonylamino groups; alkylaminocarbonyloxy groups; alkyl groups substituted with an amino, alkylamino, dialkylamino, acylamino, or diacylamino group; $CONH_2$; alkylamido groups; alkylthio; alkylsulphoxide; sulphonyl, and alkylsulphonyl groups; sulphonamide, alkylsulphonamide, and di(alkylsulphonyl) amino groups; trifluoromethylsulphoxide; trifluoromethylsulphonyl groups; trifluoromethylsulphonamide, and di(trifluoromethyl-sulphonyl)amino groups; alkylcarbonylalkyl; phenyl, phenoxy, phenylthio, and benzyl groups; and saturated monocyclic heterocyclyl groups, said aryl and heterocyclyl groups being optionally substituted by one or more substituents, which may be the same or different, selected from the group b. In a further aspect, $R^6$ can be substituted by at least one substituent selected from fluorine atoms, chlorine atoms, hydroxyl group and phenyl group. For example, substituents b can be selected from substituents b' consisting of: chlorine atoms; hydroxyl groups; linear and branched alkyl, hydroxyalkyl, and alkoxyl groups; trifluoromethyl groups; trifluoromethoxy groups; —CN groups; amino, alkylamino, and dialkylamino groups; sulphonyl, alkylsulphonyl groups; and sulphonamide, alkylsulphonamide, and di(alkylsulphonyl)amino groups. For example, substituents b' can be selected from the group consisting of: sulphonyl, alkylsulphonyl, sulphonamide, alkylsulphonamide, and di(alkylsulphonyl)amino groups.

The invention provides compounds of Formula I and pharmaceutically acceptable salts thereof, wherein $R^7$ and $R^8$ each represent hydrogen, methyl, isopropyl or ethyl. In one aspect, $R^7$ and $R^8$, together with the carbon to which they are attached, form an optionally substituted phenyl group. In one aspect, $R^7$ and $R^8$, together with the carbon to which they are attached, form an optionally substituted carbocycle, for example, cyclopropyl, cyclobutyl, cyclopentyl or cyclohexyl group. In one aspect, the cycle can be substituted by a COOH group. In another aspect, $R^7$ and $R^8$, together with the carbon to which they are attached, form an optionally substituted heterocyclic group, for example, pyridinyl, piperidinyl, pyrazinyl, pyrimidinyl, or tetrahydropyranyl.

The invention provides compounds of Formula I and pharmaceutically acceptable salts thereof, wherein Z is >CH—. In another aspect, Z can be >C=CH— or >N—.

The invention provides compounds of Formula I and pharmaceutically acceptable salts thereof, wherein p is 2. In another aspect, p can be 1 or 3.

The invention provides compounds of Formula I and pharmaceutically acceptable salts thereof, wherein Q is >C=O or Q is >C=S.

The invention further provides pharmaceutical compositions comprising a compound of Formula I and a pharmaceutically acceptable carrier.

The invention further provides methods of using compounds of Formula I, or pharmaceutical compositions comprising them, for the treatment of hyperparathyroidism. In a further aspect, the invention provides methods of using compounds of Formula I, or pharmaceutical compositions comprising them, for the treatment of vascular calcification. In one aspect, the invention provides methods of using compounds of Formula I, or pharmaceutical compositions comprising them, for the treatment of an abnormal intestinal motility. In one aspect, the abnormal intestinal motility is diarrhea. The invention further provides methods of using compounds of Formula I, or pharmaceutical compositions comprising them, for the treatment of malassimilation or malnutrition. In one aspect, the invention provides methods of using compounds of Formula I, or pharmaceutical compositions comprising them for the treatment of polycystic kidney disease or a podocyte related disorder. The podocyte related disorder can be, for example, podocytopenia, increase in the foot process width, effacement or a decrease in slit diaphragm length, a diminution of podocyte density or podocyte injury.

DETAILED DESCRIPTION OF THE INVENTION

I. Definitions "Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., *Adv Pharmacol* 47: 209-253, 2000).

Unless otherwise specified, the following definitions apply to terms found in the specification and claims:

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, ($C_1$-$C_8$) alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, iso-heptene, 1-octene, 2-octene, 3-octene, 4-octene, and isooctene.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a ($C_2$-$C_8$) alkenylene group include —CH=CH—, —$CH_2$CH=CH—, —$CH_2$CH=CH$CH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Also included in the term "heteroalkyl" are those radicals described in more detail below as "heteroalkylene" and "heterocycloalkyl."

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The terms "heterocycloalkyl" and "heterocycloalkylene" as used herein, refer to cyclic versions of heteroalkyl and heteroalkylene as described above. Examples of heterocycloalkyl include pyrrolidinyl, tetrahydrofuranyl, dioxolanyl, imidazolinyl, pyrazolidinyl, piperidinyl, morpholinyl, dithanyl, thiomorpholinyl, piperainyl, and trithanyl. Examples of heterocycloalkenyl include pyrrolinyl. imidazolinyl, and 2H-pyranyl.

The term "aryl" as used herein refers to a 6- to 14-membered monocyclic, bicyclic or tricyclic aromatic hydrocarbon ring system. Examples of an aryl group include phenyl and naphthyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The terms "arylalkyl" and "heteroarylalkyl" are meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like). "Heteroarylalkyl" is meant to include those radicals in which a heteroaryl group is attached to an alkyl group.

The term "heterocycle", "heterocyclic residue" or "heterocyclyl" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "alkoxy" as used herein refers to an —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to an —O-aryl group. The term "alkoxyaryl" refers to an alkoxy group attached to an aryl radical.

The term "amino" refers to a chemical functionality —NR'R", wherein R' and R' are independently hydrogen, alkyl or aryl.

The term "aminoalkyl," as used herein, refers to an alkyl group (typically one to eight carbon atoms) wherein one or more of the $C_1$-$C_8$ alkyl group's hydrogen atoms is replaced with an amine of formula —$N(R^d)_2$, wherein each occurrence of $R^d$ is independently —H or ($C_1$-$C_8$)alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like. The term "alkylamino" refers to an amino group wherein one or more hydrogen atoms is replaced with an alkyl group. Similarly, the term "dialkylamino" refers to an amino group having two attached alkyl groups that can be the same or different.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., ($3^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses calcium-sensing receptor modulators and their uses as described herein in the form of their optical isomers, and mixtures thereof, including a racemic mixture. Optical isomers of the calcium-sensing receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Calcium Sensing Receptor and Pharmaceutical Compositions Comprising them, Administration and Dosage As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less than 30 seconds (for example, by mobilizing internal calcium); it evokes a rapid increase in $[Ca^{2+}]_i$ occurring within thirty seconds; it evokes a sustained increase (greater than thirty seconds) in $[Ca^{2+}]_i$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}]_i$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V.

While the compounds of the invention are believed to exert their effects by interacting with the calcium sensing receptor (CaSR), the mechanism of action by which the compounds act is not a limiting embodiment of the invention. For example, compounds of the invention may interact with calcium sensing receptors other than CaSR.

Compounds contemplated by the invention include, but are not limited to, the exemplary compounds provided herein.

In certain aspects, the calcimimetic compound is chosen from compounds of Formula I or a pharmaceutically acceptable salt thereof:

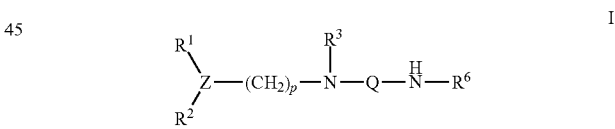

I wherein:

Z is >CH—, >C=CH— or >N—, $R^1$ and $R^2$ are the same or different, and each represents an aryl group or a heteroaryl group, or Z, $R^1$ and $R^2$ form a fused ring structure of formula:

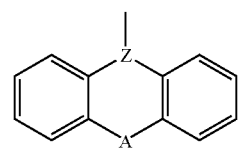

in which A represents a single bond, a methylene group, a dimethylene group, oxygen, nitrogen or sulphur, said sulphur optionally being in the sulphoxide or sulphone forms, wherein each of $R^1$ and $R^2$, or the fused ring structure formed thereby, is optionally substituted by at least one substituent selected from the group c wherein the group c consists of halogen atoms, hydroxyl, carboxyl, linear and branched alkyl, hydroxyalkyl, haloalkyl, alkylthio, alkenyl, and alkynyl groups; linear and branched alkoxyl groups; linear and branched thioalkyl groups; hydroxycarbonylalkyl; alkylcarbonyl; alkoxycarbonylalkyl; alkoxycarbonyl; trifluoromethyl; trifluoromethoxyl; —CN; —NO$_2$; sulphonamido groups; alkylsulphonyl groups optionally in the sulphoxide or sulphone forms; amino, alkylamino; dialkylamino; alkylaminocarbonyl; dialkylaminocarbonyl, alkylaminocarbonylalkyl; dialkylaminocarbonylalkyl; alkylaminocarbonylamino; dialkylaminocarbonylamino, alkylaminocarbonylaminoalkyl; dialkylaminocarbonylaminoalkyl, wherein any alkyl component has from 1 to 6 carbon atoms, and any alkenyl or alkynyl components have from 2 to 6 carbon atoms, and wherein, when there is more than one substituent, then each substituent is the same or different, $R^3$ is -AlkR$^7$R$^8$, wherein Alk is a straight or branched chain $C_{1-4}$ alkylene group, and $R^7$ and $R^8$, which may be the same or different, each represents: a hydrogen atom; a linear or branched alkyl group containing from 1 to 6 carbon atoms and optionally substituted by at least one of a phenyl group or a halogen atom; a saturated or unsaturated cycle containing 0, 1, 2, or 3 heteroatoms and having 5, 6, or 7 ring atoms, said cycle being optionally substituted by at least one substituent selected from the group 'c' defined above, or $R^7$ and $R^8$, together with the carbon in Alk to which they are linked, form a saturated or unsaturated cycle containing 0, 1 or 2 heteroatoms and having 3 to 7 ring atoms, said cycle being optionally substituted by at least one substituent selected from the group 'c' defined above, and wherein, when there is more than one substituent, said substituent is the same or different, Q is >C=O or >C=S, p is 1, 2 or 3, $R^6$ is an aryl or heteroaryl ring, two linked rings each being selected from aryl or heteroaryl rings, or a fused double or triple ring system comprising at least two rings each being selected from aryl or heteroaryl rings, and wherein said ring or rings forming $R^6$ are optionally substituted by at least one substituent selected from the group a, wherein the group a consists of: halogen atoms; hydroxyl; carboxyl; aldehyde groups; aryl groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aryl groups; saturated or unsaturated heterocycyl groups; aralkoxy groups; aryloxy groups; alkoxycarbonyl; aralkoxycarbonyl; aryloxycarbonyl; hydroxycarbonylalkyl; alkoxycarbonylalkyl; aralkoxycarbonylalkyl; aryloxycarbonylalkyl; perfluoroalkyl; perfluoroalkoxy; —CN; —NO$_2$; acyl; amino, alkylamino, aralkylamino, arylamino, dialkylamino, diaralkylamino, diarylamino, alkylsulphonylamino, haloalkylsulphonylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aminoalkylamino, alkylaminoalkylamino, aralkylamino, arylamino, aryloxy, arylthio, heterocycyloxy, heterocycylthio, dialkylamino, diaralkylamino, diarylamino, acylamino, trifluoromethylcarbonyl-amino, fluoroalkylcarbonylamino, diacylamino group; a carbamoyl group optionally substituted by an alkyl, alkylsulphonamide, sulphonamide, alkylsulphonyl, sulphonyl, aminoalkyl, or alkylaminoalkyl group; a sulphonamide group optionally substituted by an alkyl, acyl, alkoxycarbonyl, carbamoyl, alkylcarbamoyl, or carbamoyl further substituted by a carboxylic acid, aminoalkyl, or alkylaminoalkyl group; alkyl-, aralkyl-, and aryl-amido groups; alkylthio, arylthio and aralkylthio and the oxidised sulphoxide and sulphone forms thereof; sulphonyl, alkylsulphonyl, haloalkylsulphonyl, arylsulphonyl and aralkylsulphonyl groups; alkylsulphonamide, haloalkylsulphonamide, di(alkylsulphonyl)amino, aralkylsulphonamide, di(aralkylsulphonyl)amino, arylsulphonamide, and di(arylsulphonyl)amino; and saturated and unsaturated heterocyclyl groups, said aryl and heterocyclyl groups being mono- or bi-cyclic and being optionally substituted by one or more substituents, which may be the same or different, selected from the group b, wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group; CONH$_2$; alkylamido groups; alkylthio and the oxidised sulphoxide and sulphone forms thereof; sulphonyl, alkylsulphonyl groups; and sulphonamide, alkylsulphonamide, and di(alkylsulphonyl)amino groups wherein two groups a, where present, optionally form a fused carbocycle or heterocycle with the ring on which they are located, and are optionally substituted with a keto or a substituent selected from group b, as defined, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group.

In one aspect, the invention provides compounds or pharmaceutically acceptable salts thereof, wherein the compounds are selected from the group consisting of:

3-(benzo[d]thiazol-2-yl)-1-(3,3-diphenylpropyl)-1-isopropylurea, 1-(3,3-diphenylpropyl)-1-isopropyl-3-(4-(4-(methylsulfonamido)phenyl)thiazol-2-yl)urea, 1-(3,3-diphenylpropyl)-3-(4-(4-(methylsulfonamido)phenyl)thiazol-2-yl)-1-propylurea, 1-cyclopropyl-1-(3,3-diphenylpropyl)-3-(4-(4-(methylsulfonamido)phenyl)thiazol-2-yl)urea, 3-(5-chloro-4-(4-(methylsulfonamido)-phenyl)thiazol-2-yl)-1-(3,3-diphenylpropyl)-1-methylurea, 1-(3,3-diphenylpropyl)-1-methyl-3-(4-(4-(methylsulfonamido)phenyl)thiazol-2-yl)urea, 3-(5-chloro-4-(4-(methylsulfonamido)phenyl)thiazol-2-yl)-1-(3,3-diphenylpropyl)-1-phenylurea, 1-benzyl-3-(5-chloro-4-(4-(methylsulfonamido)phenyl)thiazol-2-yl)-1-(3,3-diphenylpropyl)urea, 3-(5-chloro-4-(4-(methylsulfonamido)phenyl)thiazol-2-yl)-1-(3,3-diphenylpropyl)-1-phenethylurea, 3-(5-chloro-4-(4-(methylsulfonamido)phenyl)thiazol-2-yl)-1-(3,3-diphenylpropyl)-1-(3-phenylpropyl)urea, 3-(5-chloro-4-(4-(methylsulfonamido)phenyl)thiazol-2-yl)-1-(3,3-diphenylpropyl)-1-(2-(pyridin-3-yl)ethyl)urea,
3-(5-chloro-4-(4-(methylsulfonamido)phenyl)thiazol-2-yl)-1-(3,3-diphenylpropyl)-1-(2-(pyridin-2-yl)ethyl)urea,
3-(5-chloro-4-(4-(methylsulfonamido)phenyl)thiazol-2-yl)-1-(3,3-diphenylpropyl)-1-(2-(pyridin-4-yl)ethyl)urea,
1-(4-methoxyphenethyl)-3-(5-chloro-4-(4-(methylsulfonamido)phenyl)thiazol-2-yl)-1-(3,3-diphenylpropyl)urea,
1-(4-fluorophenethyl)-3-(5-chloro-4-(4-(methylsulfonamido)phenyl)thiazol-2-yl)-1-(3,3-diphenylpropyl)urea,
3-(benzo[d]thiazol-2-yl)-1-(3,3-diphenylpropyl)-1-methylurea,
1-(3,3-diphenylpropyl)-1-methyl-3-(4-phenylthiazol-2-yl)urea,
3-(benzo[d]thiazol-2-yl)-1-(3,3-diphenylpropyl)-1-propylurea,
3-(3-(benzo[d]thiazol-2-yl)-1-(3,3-diphenylpropyl)ureido)cyclopentanecarboxylic acid,
2-((3-(benzo[d]thiazol-2-yl)-1-(3,3-diphenylpropyl)ureido)methyl)cyclopropanecarboxylic acid,
3-(5-chloro-4-(4-(methylsulfonamido)phenyl)thiazol-2-yl)-1-(3,3-diphenylpropyl)-1-(2-(piperidin-4-yl)ethyl)urea,
1-(3,3-diphenylpropyl)-3-(4-(4-(methylsulfonyl)phenyl)thiazol-2-yl)-1-(2-(piperidin-4-yl)ethyl)urea,
methyl 4-(2-(3-(3,3-diphenylpropyl)-3-(2-(piperidin-4-yl)ethyl)ureido)thiazol-4-yl)benzoate,
3-(5-chloro-4-(4-(methylsulfonyl)phenyl)thiazol-2-yl)-1-(3,3-diphenylpropyl)-1-(2-(piperidin-4-yl)ethyl)urea,
1-(3,3-diphenylpropyl)-3-(4-(4-(methylsulfonamido)phenyl)thiazol-2-yl)-1-(2-(piperidin-3-yl)ethyl)urea,
1-(3,3-diphenylpropyl)-3-(4-(4-(methylsulfonamido)phenyl)thiazol-2-yl)-1-(2-(piperidin-4-yl)ethyl)urea,
3-(5-chloro-4-(4-(methylsulfonamido)phenyl)thiazol-2-yl)-1-(3,3-diphenylpropyl)-1-(2-(piperidin-3-yl)ethyl)urea,
3-[3-(2-Cyclohexyl-ethyl)-3-(3,3-diphenyl-propyl)-ureido]-benzoic acid methyl ester,
3-[3-Benzyl-3-(3,3-diphenyl-propyl)-ureido]-benzoic acid methyl ester,
1-(3,3-Diphenyl-propyl)-1-isobutyl-3-(3-methoxy-phenyl)-urea,
N-(4-(5-chloro-2-(((3,3-diphenylpropyl)(4-(2-hydroxyethyl)phenyl)carbamoyl)amino)-1,3-thiazol-4-yl)phenyl)methanesulfonamide,
N-(4-(5-chloro-2-(((3,3-diphenylpropyl)(1-methylethyl)carbamoyl)amino)-1,3-thiazol-4-yl)phenyl)methanesulfonamide,
1-(3,3-bis(4-fluorophenyl)propyl)-3-(5-chloro-4-(4-(1H-1,2,3-triazol-1-yl)phenyl)-1,3-thiazol-2-yl)-1-(2-(2-pyridinyl)ethyl)urea,
3-(5-chloro-4-(4-(1H-1,2,3-triazol-1-yl)phenyl)-1,3-thiazol-2-yl)-1-(3,3-diphenylpropyl)-1-(2-(2-pyridinyl)ethyl)urea,
3-(((5-chloro-4-(4-((methylsulfonyl)amino)phenyl)-1,3-thiazol-2-yl)carbamoyl)(3,3-diphenylpropyl)amino)benzoic acid,
(4-(((5-chloro-4-(4-((methylsulfonyl)amino)phenyl)-1,3-thiazol-2-yl)carbamoyl)(3,3-diphenylpropyl)amino)phenyl)acetic acid,
4-(2-(((5-chloro-4-(4-((methylsulfonyl)amino)phenyl)-1,3-thiazol-2-yl)carbamoyl)(3,3-diphenylpropyl)amino)ethyl)benzoic acid,
4-(((5-chloro-4-(4-((methylsulfonyl)amino)phenyl)-1,3-thiazol-2-yl)carbamoyl)(3,3-diphenylpropyl)amino)benzoic acid,
3-(3-(5-chloro-4-(4-(methylsulfonamido)phenyl)thiazol-2-yl)-1-(3,3-diphenylpropyl)ureido)benzoic acid,
3-(((5-chloro-4-(4-((methylsulfonyl)amino)phenyl)-1,3-thiazol-2-yl)carbamoyl)(3,3-diphenylpropyl)amino)-N-methylbenzamide,
2-(4-(((5-chloro-4-(4-((methylsulfonyl)amino)phenyl)-1,3-thiazol-2-yl)carbamoyl)(3,3-diphenylpropyl)amino)phenyl)-N-methylacetamide,
2-(4-(((5-chloro-4-(4-((methylsulfonyl)amino)phenyl)-1,3-thiazol-2-yl)carbamoyl)(3,3-diphenylpropyl)amino)phenyl)acetamide,
4-(2-(((5-chloro-4-(4-((methylsulfonyl)amino)phenyl)-1,3-thiazol-2-yl)carbamoyl)(3,3-diphenylpropyl)amino)ethyl)-N-methylbenzamide,
4-(((5-chloro-4-(4-((methylsulfonyl)amino)phenyl)-1,3-thiazol-2-yl)carbamoyl)(3,3-diphenylpropyl)amino)-N-methylbenzamide,
4-(5-chloro-2-(((3,3-diphenylpropyl)(2-(2-pyridinyl)ethyl)carbamoyl)amino)-1,3-thiazol-4-yl)benzenesulfonamide,
4-(2-(((3,3-bis(4-fluorophenyl)propyl)(2-(2-pyridinyl)ethyl)carbamoyl)amino)-5-chloro-1,3-thiazol-4-yl)benzenesulfonamide,
4-(5-(((3,3-diphenylpropyl)(2-(2-pyridinyl)ethyl)carbamoyl)amino)-1,2,4-thiadiazol-3-yl)benzenesulfonamide,
4-(5-(((3,3-bis(4-fluorophenyl)propyl)(2-(2-pyridinyl)ethyl)carbamoyl)amino)-1,2,4-thiadiazol-3-yl)benzenesulfonamide,
4-(5-chloro-2-(((3,3-diphenylpropyl)(2-(2-pyrazinyl)ethyl)carbamoyl)amino)-1,3-thiazol-4-yl)benzenesulfonamide,
4-(5-(((3,3-diphenylpropyl)(2-(2-pyrazinyl)ethyl)carbamoyl)amino)-1,2,4-thiadiazol-3-yl)benzenesulfonamide,
4-(5-chloro-2-(((3,3-diphenylpropyl)(2-(2-pyrimidinyl)ethyl)carbamoyl)amino)-1,3-thiazol-4-yl)benzenesulfonamide,
4-(5-chloro-2-(((2-(4-chloro-2-pyridinyl)ethyl)(3,3-diphenylpropyl)carbamoyl)amino)-1,3-thiazol-4-yl)benzenesulfonamide,
4-(2-(((3,3-bis(4-fluorophenyl)propyl)(2-(2-pyrazinyl)ethyl)carbamoyl)amino)-5-chloro-1,3-thiazol-4-yl)benzenesulfonamide,
4-(5-(((3,3-bis(4-fluorophenyl)propyl)(2-(2-pyrazinyl)ethyl)carbamoyl)amino)-1,2,4-thiadiazol-3-yl)benzenesulfonamide,
4-(5-(((3,3-diphenylpropyl)(2-(2-pyrimidinyl)ethyl)carbamoyl)amino)-1,2,4-thiadiazol-3-yl)benzenesulfonamide,
4-(2-(((3,3-bis(4-fluorophenyl)propyl)(2-(2-pyrimidinyl)ethyl)carbamoyl)amino)-5-chloro-1,3-thiazol-4-yl)benzenesulfonamide,
4-(5-(((3,3-bis(4-fluorophenyl)propyl)(2-(2-pyrimidinyl)ethyl)carbamoyl)amino)-1,2,4-thiadiazol-3-yl)benzenesulfonamide,
N-(4-(5-chloro-2-(((3,3-diphenylpropyl)(3-pyridinyl)carbamoyl)amino)-1,3-thiazol-4-yl)phenyl)methanesulfonamide,
N-(4-(5-chloro-2-(((3,3-diphenylpropyl)(2-pyridinyl)carbamoyl)amino)-1,3-thiazol-4-yl)phenyl)methanesulfonamide,
N-(4-(5-chloro-2-(((3,3-diphenylpropyl)(2-(3-fluorophenyl)ethyl)carbamoyl)amino)-1,3-thiazol-4-yl)phenyl)methanesulfonamide,
N-(4-(5-chloro-2-(((3,3-diphenylpropyl)(2-(2-fluorophenyl)ethyl)carbamoyl)amino)-1,3-thiazol-4-yl)phenyl)methanesulfonamide,
N-(4-(5-chloro-2-(((3,3-diphenylpropyl)(2-(2-methoxyphenyl)ethyl)carbamoyl)amino)-1,3-thiazol-4-yl)phenyl)methanesulfonamide,
N-(4-(5-chloro-2-(((3,3-diphenylpropyl)(2-fluorophenyl)carbamoyl)amino)-1,3-thiazol-4-yl)phenyl)methanesulfonamide, N-(4-(5-chloro-2-(((3,3-diphenylpropyl)(3-fluorophenyl)
carbamoyl)amino)-1,3-thiazol-4-yl)phenyl)methane-
sulfonamide,
N-(4-(5-chloro-2-(((3,3-diphenylpropyl)(4-fluorophenyl)
carbamoyl)amino)-1,3-thiazol-4-yl)phenyl)methane-
sulfonamide,
ethyl4-(((5-chloro-4-(4-((methylsulfonyl)amino)phenyl)-1,
3-thiazol-2-yl)carbamoyl)(3,3-diphenylpropyl)amino)
phenyl)acetate,
methyl4-(2-(((5-chloro-4-(4-((methylsulfonyl)amino)phe-
nyl)-1,3-thiazol-2-yl)carbamoyl)(3,3-diphenylpropyl)
amino)ethyl)benzoate,
methyl4-(((5-chloro-4-(4-((methylsulfonyl)amino)phenyl)-
1,3-thiazol-2-yl)carbamoyl)(3,3-diphenylpropyl)amino)
benzoate,
N-(4-(5-chloro-2-((cyclopropyl(3,3-diphenylpropyl)car-
bamoyl)amino)-1,3-thiazol-4-yl)phenyl)methanesulfona-
mide,
3-(5-chloro-4-(4-(methylsulfonyl)phenyl)-1,3-thiazol-2-yl)-
1-(3,3-diphenylpropyl)-1-(2-(2-pyridinyl)ethyl)urea,
N-(4-(5-chloro-2-(((3,3-diphenylpropyl)(2-(2-pyrazinyl)
ethyl)carbamoyl)amino)-1,3-thiazol-4-yl)phenyl)meth-
anesulfonamide,
3-(5-chloro-4-(4-(methylsulfonyl)phenyl)-1,3-thiazol-2-yl)-
1-(3,3-diphenylpropyl)-1-(2-(2-pyrazinyl)ethyl)urea,
1-(3,3-diphenylpropyl)-1-(2-(2-pyridinyl)ethyl)-3-[1,3]thia-
zolo[5,4-b]pyridin-2-ylurea,
1-(3,3-diphenylpropyl)-1-(2-(2-pyridinyl)ethyl)-3-[1,3]thia-
zolo[4,5-c]pyridin-2-ylurea,
N-(4-(2-(((3,3-bis(4-fluorophenyl)propyl)(2-(2-pyridinyl)
ethyl)carbamoyl)amino)-5-chloro-1,3-thiazol-4-yl)phe-
nyl)methanesulfonamide,
N-tert-butyl-4-(5-chloro-2-(((3,3-diphenylpropyl)(2-(2-py-
ridinyl)ethyl)carbamoyl)amino)-1,3-thiazol-4-yl)benze-
nesulfonamide,
4-(2-(((3,3-bis(4-fluorophenyl)propyl)(2-(2-pyridinyl)ethyl)
carbamoyl)amino)-5-chloro-1,3-thiazol-4-yl)-N-tert-bu-
tylbenzenesulfonamide,
N-(4-(5-(((3,3-bis(4-fluorophenyl)propyl)(2-(2-pyridinyl)
ethyl)carbamoyl)amino)-1,2,4-thiadiazol-3-yl)phenyl)
methanesulfonamide,
1-(3,3-diphenylpropyl)-3-(3-(4-(methylsulfonyl)phenyl)-1,
2,4-thiadiazol-5-yl)-1-(2-(2-pyridinyl)ethyl)urea,
1-(3,3-bis(4-fluorophenyl)propyl)-3-(3-(4-(methylsulfonyl)
phenyl)-1,2,4-thiadiazol-5-yl)-1-(2-(2-pyridinyl)ethyl)
urea,
N-(4-(5-(((3,3-diphenylpropyl)(2-(2-pyridinyl)ethyl)car-
bamoyl)amino)-1,2,4-thiadiazol-3-yl)phenyl)methane-
sulfonamide,
1-(3,3-diphenylpropyl)-1-(2-(2-pyridinyl)ethyl)-3-(3-(4-
(1H-1,2,3-triazol-1-yl)phenyl)-1,2,4-thiadiazol-5-yl)urea,
1-(3,3-bis(4-fluorophenyl)propyl)-1-(2-(2-pyridinyl)ethyl)-
3-(3-(4-(1H-1,2,3-triazol-1-yl)phenyl)-1,2,4-thiadiazol-
5-yl)urea,
N-(4-(5-chloro-2-(((3,3-diphenylpropyl)(2-(2-pyrazinyl)
ethyl)carbamoyl)amino)-1,3-thiazol-4-yl)phenyl)aceta-
mide,
3-(5-chloro-4-(4-(1H-1,2,3-triazol-1-yl)phenyl)-1,3-thiazol-
2-yl)-1-(3,3-diphenylpropyl)-1-(2-(2-pyrazinyl)ethyl)
urea,
N-(4-(5-(((3,3-diphenylpropyl)(2-(2-pyrazinyl)ethyl)car-
bamoyl)amino)-1,2,4-thiadiazol-3-yl)phenyl)methane-
sulfonamide,
1-(3,3-diphenylpropyl)-1-(2-(2-pyrazinyl)ethyl)-3-(3-(4-
(1H-1,2,3-triazol-1-yl)phenyl)-1,2,4-thiadiazol-5-yl)urea,
1-(2-(5-chloro-2-pyridinyl)ethyl)-3-(5-chloro-4-(4-(1H-1,2,
3-triazol-1-yl)phenyl)-1,3-thiazol-2-yl)-1-(3,3-diphenyl-
propyl)urea,
3-(5-chloro-4-(4-(1H-1,2,3-triazol-1-yl)phenyl)-1,3-thiazol-
2-yl)-1-(3,3-diphenylpropyl)-1-(2-(2-pyrimidinyl)ethyl)
urea,
1-(2-(4-chloro-2-pyridinyl)ethyl)-1-(3,3-diphenylpropyl)-3-
(3-(4-(1H-1,2,3-triazol-1-yl)phenyl)-1,2,4-thiadiazol-5-
yl)urea,
N-(4-(5-chloro-2-(((3,3-diphenylpropyl)(2-(2-pyridinyl)
ethyl)carbamoyl)amino)-1,3-thiazol-4-yl)phenyl)aceta-
mide,
N-(4-(2-(((3,3-bis(4-fluorophenyl)propyl)(2-(2-pyridinyl)
ethyl)carbamoyl)amino)-5-chloro-1,3-thiazol-4-yl)phe-
nyl)acetamide,
N-(4-(5-(((3,3-diphenylpropyl)(2-(2-pyridinyl)ethyl)car-
bamoyl)amino)-1,2,4-thiadiazol-3-yl)phenyl)acetamide,
N-(4-(5-(((3,3-bis(4-fluorophenyl)propyl)(2-(2-pyridinyl)
ethyl)carbamoyl)amino)-1,2,4-thiadiazol-3-yl)phenyl)ac-
etamide.
N-(4-(5-(((3,3-diphenylpropyl)(2-(2-pyrazinyl)ethyl)car-
bamoyl)amino)-1,2,4-thiadiazol-3-yl)phenyl)acetamide,
1-(3,3-diphenylpropyl)-3-(3-(4-(methylsulfonyl)phenyl)-1,
2,4-thiadiazol-5-yl)-1-(2-(2-pyrazinyl)ethyl)urea,
1-(3,3-bis(4-fluorophenyl)propyl)-3-(5-chloro-4-(4-(meth-
ylsulfonyl)phenyl)-1,3-thiazol-2-yl)-1-(2-(2-pyrazinyl)
ethyl)urea,
N-(4-(2-(((3,3-bis(4-fluorophenyl)propyl)(2-(2-pyrazinyl)
ethyl)carbamoyl)amino)-5-chloro-1,3-thiazol-4-yl)phe-
nyl)methanesulfonamide,
N-(4-(2-(((3,3-bis(4-fluorophenyl)propyl)(2-(2-pyrazinyl)
ethyl)carbamoyl)amino)-5-chloro-1,3-thiazol-4-yl)phe-
nyl)acetamide,
1-(3,3-bis(4-fluorophenyl)propyl)-3-(5-chloro-4-(4-(1H-1,
2,3-triazol-1-yl)phenyl)-1,3-thiazol-2-yl)-1-(2-(2-pyrazi-
nyl)ethyl)urea,
1-(3,3-bis(4-fluorophenyl)propyl)-3-(3-(4-(methylsulfonyl)
phenyl)-1,2,4-thiadiazol-5-yl)-1-(2-(2-pyrazinyl)ethyl)
urea,
N-(4-(5-(((3,3-bis(4-fluorophenyl)propyl)(2-(2-pyrazinyl)
ethyl)carbamoyl)amino)-1,2,4-thiadiazol-3-yl)phenyl)
methanesulfonamide,
N-(4-(5-(((3,3-bis(4-fluorophenyl)propyl)(2-(2-pyrazinyl)
ethyl)carbamoyl)amino)-1,2,4-thiadiazol-3-yl)phenyl)ac-
etamide,
N-(4-(5-chloro-2-(((3,3-diphenylpropyl)(2-(2-pyrimidinyl)
ethyl)carbamoyl)amino)-1,3-thiazol-4-yl)phenyl)meth-
anesulfonamide,
1-(3,3-diphenylpropyl)-1-(2-(2-pyrimidinyl)ethyl)-3-(3-(4-
(1H-1,2,3-triazol-1-yl)phenyl)-1,2,4-thiadiazol-5-yl)urea,
N-(4-(5-(((3,3-diphenylpropyl)(2-(2-pyrimidinyl)ethyl)car-
bamoyl)amino)-1,2,4-thiadiazol-3-yl)phenyl)methane-
sulfonamide,
N-(4-(5-chloro-2-(((3,3-diphenylpropyl)(2-(2-pyrimidinyl)
ethyl)carbamoyl)amino)-1,3-thiazol-4-yl)phenyl)aceta-
mide,
N-(4-(5-(((3,3-diphenylpropyl)(2-(2-pyrimidinyl)ethyl)car-
bamoyl)amino)-1,2,4-thiadiazol-3-yl)phenyl)acetamide,
3-(5-chloro-4-(4-(1H-1,2,3-triazol-1-yl)phenyl)-1,3-thiazol-
2-yl)-1-(3,3-diphenyl-2-propen-1-yl)-1-(2-(2-pyrimidi-
nyl)ethyl)urea,
N-(4-(2-(((3,3-bis(4-fluorophenyl)propyl)(2-(2-pyrimidi-
nyl)ethyl)carbamoyl)amino)-5-chloro-1,3-thiazol-4-yl)
phenyl)methanesulfonamide,
1-(3,3-bis(4-fluorophenyl)propyl)-3-(5-chloro-4-(4-(1H-1,
2,3-triazol-1-yl)phenyl)-1,3-thiazol-2-yl)-1-(2-(2-pyrim-
idinyl)ethyl)urea, N-(4-(2-(((3,3-bis(4-fluorophenyl)propyl)(2-(2-pyrimidinyl)ethyl)carbamoyl)amino)-5-chloro-1,3-thiazol-4-yl)phenyl)acetamide,
N-(4-(5-(((3,3-bis(4-fluorophenyl)propyl)(2-(2-pyrimidinyl)ethyl)carbamoyl)amino)-1,2,4-thiadiazol-3-yl)phenyl)methanesulfonamide,
1-(3,3-bis(4-fluorophenyl)propyl)-1-(2-(2-pyrimidinyl)ethyl)-3-(3-(4-(1H-1,2,3-triazol-1-yl)phenyl)-1,2,4-thiadiazol-5-yl)urea,
N-(4-(5-(((3,3-bis(4-fluorophenyl)propyl)(2-(2-pyrimidinyl)ethyl)carbamoyl)amino)-1,2,4-thiadiazol-3-yl)phenyl)acetamide,
N-(4-(3-(((3,3-diphenylpropyl)(2-(2-pyridinyl)ethyl)carbamoyl)amino)-1,2,4-thiadiazol-5-yl)phenyl)acetamide,
N-(4-(3-(((3,3-bis(4-fluorophenyl)propyl)(2-(2-pyridinyl)ethyl)carbamoyl)amino)-1,2,4-thiadiazol-5-yl)phenyl)methanesulfonamide,
N-(4-(3-(((3,3-diphenylpropyl)(2-(2-pyridinyl)ethyl)carbamoyl)amino)-1,2,4-thiadiazol-5-yl)phenyl)methanesulfonamide,
4-(3-(benzo[d]thiazol-2-yl)-1-(3,3-diphenylpropyl)ureido)cyclohexanecarboxylic acid,
4-(3-(benzo[d]thiazol-2-yl)-1-(3,3-diphenylpropyl)ureido)cyclohexanecarboxylic acid,
methyl 4-(3-(5-chloro-4-(4-(methylsulfonamido)phenyl)thiazol-2-yl)-1-(3,3-diphenylpropyl)ureido)cyclohexanecarboxylate,
4-(3-(5-chloro-4-(4-(methylsulfonamido)phenyl)thiazol-2-yl)-1-(3,3-diphenylpropyl)ureido)cyclohexanecarboxylic acid,
methyl 4-(1-(3,3-diphenylpropyl)-3-(5-methyl-4-phenylthiazol-2-yl)ureido) cyclohexanecarboxylate,
methyl 4-(3-(5-chloro-4-(4-(methylsulfonamido)phenyl)thiazol-2-yl)-1-(3,3-diphenylpropyl)ureido)cyclohexanecarboxylate,
4-(3-(5-chloro-4-(4-(methylsulfonamido)phenyl)thiazol-2-yl)-1-(3,3-diphenylpropyl)ureido)cyclohexanecarboxylic acid,
4-(3-(5-chloro-4-(4-(methylsulfonyl)phenyl)thiazol-2-yl)-1-(3,3-diphenylpropyl)ureido) cyclohexanecarboxylic acid,
4-(3-(5-chloro-4-(4-(methylsulfonyl)phenyl)thiazol-2-yl)-1-(3,3-diphenylpropyl)ureido) cyclohexanecarboxylic acid,
3-(5-chloro-4-(4-(methylsulfonamido)phenyl)thiazol-2-yl)-1-(2-cyanoethyl)-1-(3,3-diphenylpropyl)urea,
methyl 2-(4-(5-chloro-2-(3-(3,3-diphenylpropyl)-3-isopropylureido)thiazol-4-yl)phenyl)acetate,
methyl 4-(5-chloro-2-(3-(3,3-diphenylpropyl)-3-(tetrahydro-2H-pyran-4-yl)ureido)thiazol-4-yl)benzoate,
3-(5-chloro-4-(4-(hydroxymethyl)phenyl)thiazol-2-yl)-1-(3,3-diphenylpropyl)-1-isopropylurea,
3-(5-chloro-4-(4-(morpholinomethyl)phenyl)thiazol-2-yl)-1-(3,3-diphenylpropyl)-1-isopropylurea,
3-(5-chloro-4-(4-(piperazin-1-ylmethyl)phenyl)thiazol-2-yl)-1-(3,3-diphenylpropyl)-1-isopropylurea,
3-(5-chloro-4-(4-(morpholinomethyl)phenyl)thiazol-2-yl)-1-(3,3-diphenylpropyl)-1-(tetrahydro-2H-pyran-4-yl)urea,
4-(2-(((3,3-bis(4-fluorophenyl)propyl)(cyclopropyl)carbamoyl)amino)-5-chloro-1,3-thiazol-4-yl)benzenesulfonamide,
4-(5-chloro-2-((cyclopropyl(3,3-diphenylpropyl)carbamoyl)amino)-1,3-thiazol-4-yl)benzenesulfonamide,
4-(5-chloro-2-(((3,3-diphenylpropyl)(tetrahydro-2H-pyran-4-yl)carbamoyl)amino)-1,3-thiazol-4-yl)benzenesulfonamide,
4-(5-chloro-2-(((3,3-diphenylpropyl)(1-methylethyl)carbamoyl)amino)-1,3-thiazol-4-yl)benzenesulfonamide,
N-(4-(5-chloro-2-(((3,3-diphenylpropyl)(tetrahydro-2H-thiopyran-4-yl)carbamoyl)amino)-1,3-thiazol-4-yl)phenyl)methanesulfonamide,
1-cyclopropyl-1-(3,3-diphenylpropyl)-3-(3-(2-pyridinyl)-1,2,4-thiadiazol-5-yl)urea,
N-(4-(5-(((3,3-bis(4-fluorophenyl)propyl)(cyclopropyl)carbamoyl)amino)-1,2,4-thiadiazol-3-yl)phenyl)methanesulfonamide,
N-(4-(5-(((3,3-diphenylpropyl)(tetrahydro-2H-pyran-4-yl)carbamoyl)amino)-1,2,4-thiadiazol-3-yl)phenyl)methanesulfonamide,
N-(4-(5-(((3,3-diphenylpropyl)(1-methylethyl)carbamoyl)amino)-1,2,4-thiadiazol-3-yl)phenyl)methanesulfonamide,
3-(5-chloro-4-(2-oxo-2,3-dihydro-1H-indol-5-yl)-1,3-thiazol-2-yl)-1-(3,3-diphenylpropyl)-1-(1-methylethyl)urea,
3-(5-chloro-4-(2-oxo-2,3-dihydro-1H-indol-5-yl)-1,3-thiazol-2-yl)-1-(3,3-diphenylpropyl)-1-(tetrahydro-2H-pyran-4-yl)urea,
N-(4-(5-chloro-2-(((1,1-dioxidotetrahydro-2H-thiopyran-4-yl)(3,3-diphenylpropyl)carbamoyl)amino)-1,3-thiazol-4-yl)phenyl)methanesulfonamide,
4-(5-((cyclopropyl(3,3-diphenylpropyl)carbamoyl)amino)-1,2,4-thiadiazol-3-yl)benzenesulfonamide,
4-(5-(((3,3-bis(4-fluorophenyl)propyl)(cyclopropyl)carbamoyl)amino)-1,2,4-thiadiazol-3-yl)benzenesulfonamide,
4-(5-(((3,3-diphenylpropyl)(tetrahydro-2H-pyran-4-yl)carbamoyl)amino)-1,2,4-thiadiazol-3-yl)benzenesulfonamide,
4-(5-(((3,3-diphenylpropyl)(1-methylethyl)carbamoyl)amino)-1,2,4-thiadiazol-3-yl)benzenesulfonamide,
3-(5-chloro-4-(6-methylpyridin-3-yl)thiazol-2-yl)-1-(3,3-diphenylpropyl)-1-(piperidin-4-yl)urea,
N-(4-(5-chloro-2-(((3,3-diphenylpropyl)(4-piperidinyl)carbamoyl)amino)-1,3-thiazol-4-yl)phenyl)methanesulfonamide,
3-(5-chloro-4-(6-chloro-3-pyridinyl)-1,3-thiazol-2-yl)-1-(3,3-diphenylpropyl)-1-(4-piperidinyl)urea,
N-(4-(5-chloro-2-(((3,3-diphenylpropyl)(tetrahydro-2H-pyran-4-yl)carbamoyl)amino)-1,3-thiazol-4-yl)phenyl)methanesulfonamide,
3-(5-chloro-4-(4-(methylsulfonyl)phenyl)-1,3-thiazol-2-yl)-1-(3,3-diphenylpropyl)-1-(tetrahydro-2H-pyran-4-yl)urea,
3-(5-chloro-4-(4-(methylsulfonamido)phenyl)thiazol-2-yl)-1-(3,3-diphenylpropyl)-1-(4-hydroxycyclohexyl)urea,
3-(5-chloro-4-(4-(methylsulfonamido)phenyl)thiazol-2-yl)-1-cyclohexyl-1-(3,3-diphenylpropyl)urea,
3-(5-chloro-4-(4-(methylsulfonyl)phenyl)thiazol-2-yl)-1-(3,3-diphenylpropyl)-1-(2-(tetrahydro-2H-pyran-4-yl)ethyl)urea,
4-(5-chloro-2-(((3,3-diphenylpropyl)(2-(4-tetrahydropyranyl)ethyl)carbamoyl)amino)-1,3-thiazol-4-yl)benzenesulfonamide,
4-(2-(((3,3-bis(4-fluorophenyl)propyl)(2-(4-tetrahydropyranyl)ethyl)carbamoyl)amino)-5-chloro-1,3-thiazol-4-yl)benzenesulfonamide,
3-(5-chloro-4-(4-(methylsulfonamido)phenyl)thiazol-2-yl)-1-(3,3-diphenylpropyl)-1-(2-(tetrahydro-2H-pyran-4-yl)ethyl)urea,
1-(3,3-diphenylpropyl)-3-(3-(4-(methylsulfonamido)phenyl)-1,2,4-thiadiazol-5-yl)-1-(2-(tetrahydro-2H-pyran-4-yl)ethyl)urea,
4-(5-(((3,3-diphenylpropyl)(2-(4-tetrahydropyranyl)ethyl)carbamoyl)amino)-1,2,4-thiadiazol-3-yl)benzenesulfonamide, 1-(3,3-bis(4-fluorophenyl)propyl)-3-(3-(4-(methylsulfonamido)phenyl)-1,2,4-thiadiazol-5-yl)-1-(2-(tetrahydro-2H-pyran-4-yl)ethyl)urea, 4-(5-(((3,3-bis(4-fluorophenyl)propyl)(2-(4-tetrahydropyranyl)ethyl)carbamoyl)amino)-1,2,4-thiadiazol-3-yl)benzenesulfonamide, 2-(4-(5-chloro-2-(3-(3,3-diphenylpropyl)-3-(2-(tetrahydro-2H-pyran-4-yl)ethyl)ureido)thiazol-4-yl)phenyl)acetate, 3-(5-chloro-4-(4-(hydroxymethyl)phenyl)thiazol-2-yl)-1-(3,3-diphenylpropyl)-1-(2-(tetrahydro-2H-pyran-4-yl)ethyl)urea, 3-(5-chloro-4-(4-(morpholinomethyl)phenyl)thiazol-2-yl)-1-(3,3-diphenylpropyl)-1-(2-(tetrahydro-2H-pyran-4-yl)ethyl)urea, and 3-(5-chloro-4-(4-(piperazin-1-ylmethyl)phenyl)thiazol-2-yl)-1-(3,3-diphenylpropyl)-1-(2-(tetrahydro-2H-pyran-4-yl)ethyl)urea, or a stereoisomer or a pharmaceutically acceptable salt thereof.

A. Preparation of Compounds

Methods A-T below provide exemplary synthetic methods for the preparation of the compounds of the present invention. One of skill in the art will understand that additional methods are also useful. A person skilled in the art will appreciate that alternative reagents, temperatures and solvents may be used to effect the same transformations. In other words, the compounds of the invention can be made using organic synthesis using starting materials, reagents and reactions well known in the art.

Certain compounds of the invention may be conveniently prepared by a general process below.

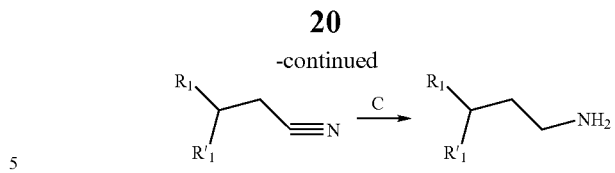

The synthesis of 2-(9H-fluoren-9-yl)-ethylamine in which $R^1$, $R'_1$=fluorenyl is described by way of example.

Step A: Synthesis of fluoren-9-ylidene-acetonitrile 528 mg of NaH (in a 55-65% suspension in oil; 13.2 mmol, 2.2 eq) in suspension in 20 mL of DME were introduced into a 100 mL Woulff bottle equipped with a straight condenser. 1.94 mL of diethyl cyanomethylphosphonate (12 mmol, 2 eq) in solution in 5 mL of DME were then added dropwise. After the release of gas, the reaction medium was heated under reflux for 15 min, then 1.08 g of fluoren-9-one (6 mmol, 1 eq) in solution in 5 mL of DME were added dropwise. After refluxing for 2 hours, the reaction was stopped by addition of 40 mL of an aqueous ammonium chloride solution. The medium was taken up with ethyl acetate, and the aqueous phase was extracted with ethyl acetate. The organic phases were collected, dried over $MgSO_4$, filtered and concentrated. The fluoren-9-ylidene-acetonitrile was purified by chromatography over silica gel ($CH_2Cl_2$/heptane elution gradient: 80/20).

Step B: Synthesis of (9H-fluoren-9-yl)-acetonitrile 610 mg (3 mmol, 1 eq) of fluoren-9-ylidene-acetonitrile in solution in 40 mL of methanol and 10 mL of ethyl acetate, then 225 mg of palladium hydroxide over coal were introduced into a 250 mL flask under a nitrogen atmosphere. The reaction medium was purged then placed under a hydrogen atmosphere (skin flask) and stirred for 6 hours while stirring. The catalyst was removed by filtration over Clarcel. The solvent was evaporated and the expected product was obtained.

Step C: Synthesis of 2-(9H-fluoren-9-yl)-ethylamine 6.3 mL (6.3 mmol, 2.7 eq) of a 1 M solution of $LiAlH_4$ in THF were dissolved in 20 mL of THF in a 250 mL flask under argon. The reaction medium was cooled to −78° C. and 478 mg (2.3 mmol, 1 eq) of (9H-fluoren-9-yl)-acetonitrile in solution in 20 mL of THF were added dropwise. The temperature

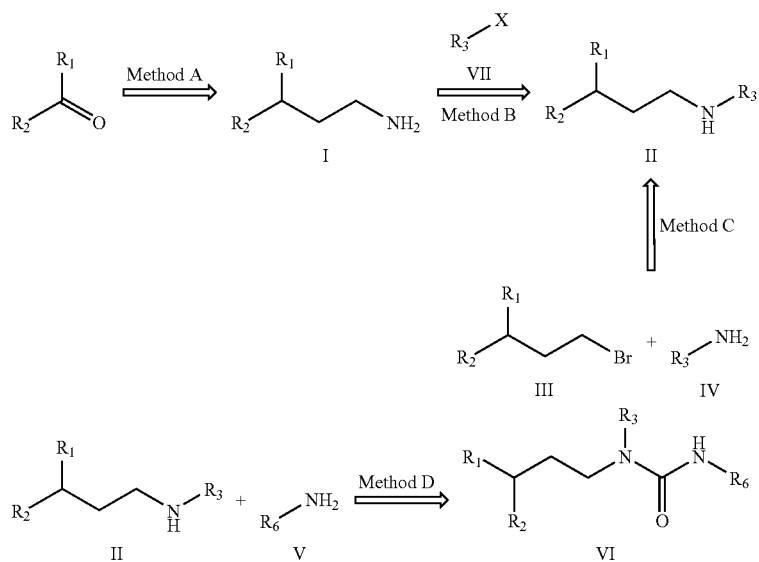

Preparation of Primary Amines of Formula I

Method A

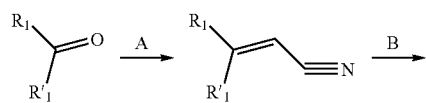

was allowed to rise progressively to ambient temperature. Stirring was continued for 5 hours, then the medium was hydrolysed at 0° C. by addition of 30 mL of a sodium and potassium tartrate solution. The THF was evaporated and the aqueous phase was extracted with ethyl acetate. After drying over MgSO₄ and evaporation of the solvent, the crude product was subjected to chromatography over silica gel (elution gradient: CH₂Cl₂—CH₂Cl₂/MeOH: 9/1 to CH₂Cl₂/MeOH/NH₄OH: 9/1/0.5). The 2-(9H-fluoren-9-yl)-ethylamine was obtained.

Other compounds used in the synthesis of amines of formula (I) are exemplified in the tables below.

| Step A | |
|---|---|
| Structure | MS |
| 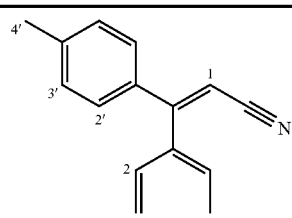 | MS/EI 233: [M]⁺ 218: [M :]⁺ —CH₃ 203: [M :]⁺ —2(CH₃) |
| 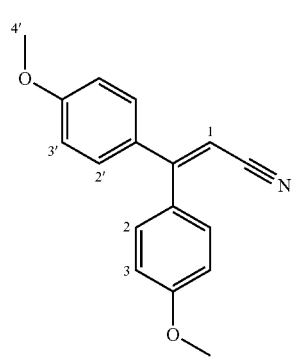 | Electrospray 266:[MH]⁺ |
| 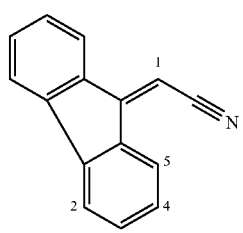 | MS/EI 203: [M]⁺ 176: [M :]⁺ —HCN |
| 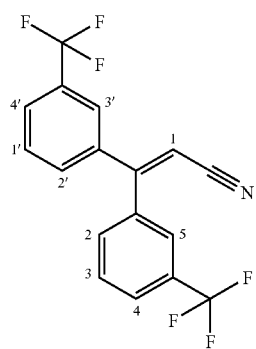 | MS/EI 341: [M]⁺ 322: [M :]⁺ —F 272: [M :]⁺ —CF₃ 252: [M :]⁺ —CF₃—HF |

| Step B | |
|---|---|
| Structure | MS |
| (structure) | MS/EI 235: [M]⁺ 207: [M:]⁺ —HCN 195: [M]⁺ —(CH₂CH₂NH₂) |
| (structure) | MS/EI 267: [M]⁺ |
| (structure) | MS/EI 205: [M]⁺ 165: [M]⁺ —(CH₂CH₂NH₂) |
| (structure) | MS/EI 343: [M]⁺ |

| Step C | |
|---|---|
| Structure | MS |
| (structure 1) | MS/EI 239: [M]⁺ 222: [M]⁺ – NH₃ 195: [M]⁺ – (CH₂CH₂NH₂) |
| (structure 2) | Electrospray 271: [MH]⁺ 255: [MH]⁺ – NH₃ 195: [MH]⁺ – (CH₂CH₂NH₂) |
| (structure 3) | MS/EI 209: [M]⁺ 191: [M]⁺ – NH₃ 178: [M]⁺ – (CH₂NH₂) 165: [M]⁺ – (CH₂CH₂NH₂) |
| (structure 4) | MS/EI 347: [M]⁺ 330: [M]⁺ – NH₃ 318: [M]⁺ – CH₃NH₂ 303: [M]⁺ – CH₃CH₂NH₂ |

Preparation of Secondary Amines of Formula II

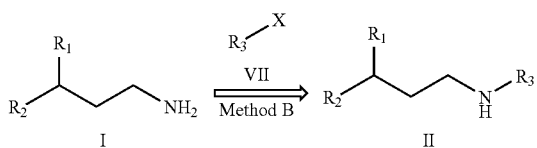

Method B

The alkyl halide (1 mmol, 1 eq) of formula (I) was dissolved in 40 mL of acetonitrile in a 100 mL flask equipped with a straight condenser, then 1 eq of $K_2CO_3$ was added to the medium. The primary amine of formula (VII) in excess (5 mmol, 5 eq) was subsequently added and the medium is heated under reflux for 12 hours. After evaporation of acetonitrile, the residue was taken up with ethyl acetate. The organic phase was washed with an ammonium chloride solution, then with brine, dried over $MgSO_4$ and concentrated. The oil obtained was subjected to chromatography over silica gel (elution gradient: $CH_2Cl_2$ to $CH_2Cl_2$/MeOH: 9/1 then $CH_2Cl_2$/MeOH/$NH_3$: 9/1/0.1) and the amine of formula (II) was obtained.

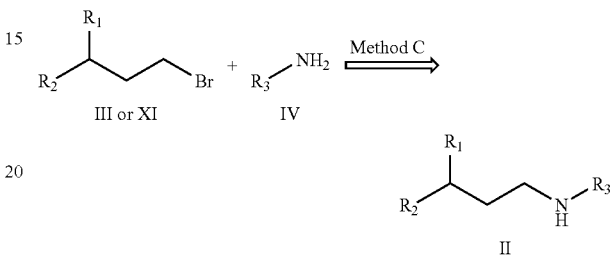

Method C

The synthesis of tert-butyl 4-(2-(3,3-diphenylpropylamino)ethyl)piperidine-1-carboxylate is shown as an example of general method C.

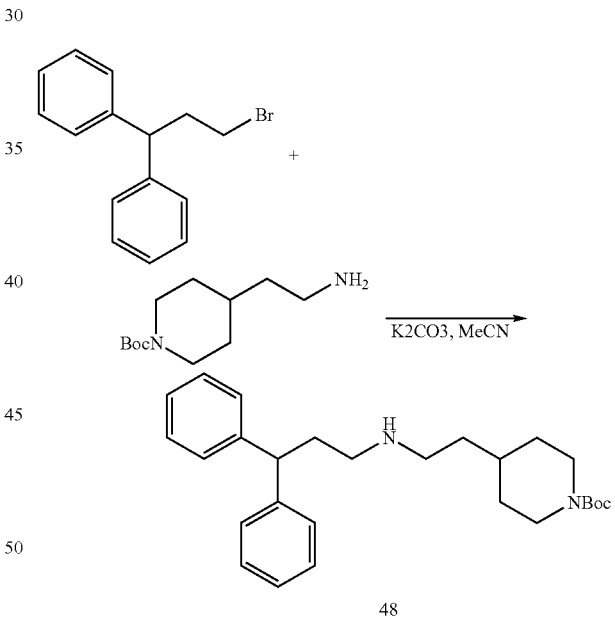

48

3-bromo-1,1-diphenylpropane (2.6 g, 9 mmol) and tert-butyl 4-(2-aminoethyl)piperidine-1-carboxylate (4.7 g, 21 mmol) were mixed together in acetonitrile (100 ml) and potassium carbonate (1.3 g, 9 mmol) was added. The resulting mixture was heated to 65° C. with stirring under $N_2$ overnight. After that time the mixture was cooled and concentrated under reduced pressure. The residue was partitioned between DCM and water. The DCM layer was washed with water, dried over MgSO4 and concentrated under reduced pressure to give the crude product as a clear oil. The crude product was purified by combiflash (0-10% MeOH/DCM) to give tert-butyl 4-(2-(3,3-diphenylpropylamino) ethyl)piperidine-1-carboxylate 48

Preparation of Ureas of Formula VI

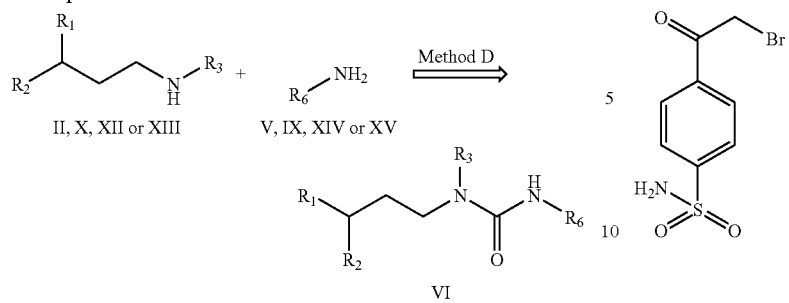

Method D

The synthesis of 3-(5-chloro-4-(4-(methylsulfonamido)-phenyl)thiazol-2-yl)-1-(3,3-diphenylpropyl)-1-methylurea is shown as an example of general Method D.

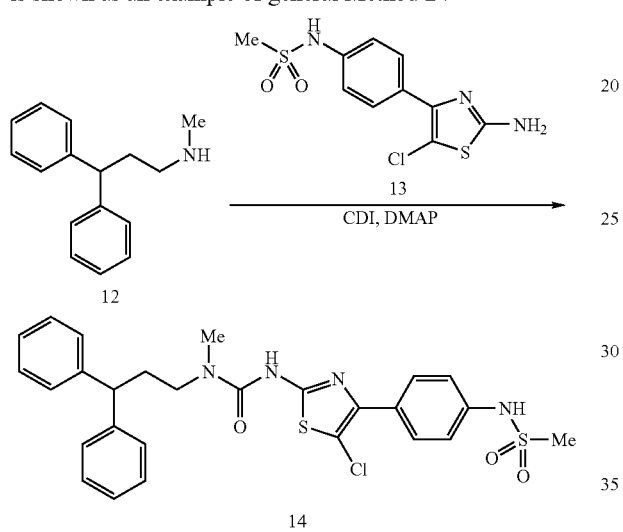

To a mixture of N-(4-(2-amino-5-chlorothiazol-4-yl)phenyl)methanesulfonamide 13 (0.100 g, 0.33 mmol), DMAP (0.056 g, 0.46 mmol), and CDI (0.085 g, 0.52 mmol) was added DMF (0.5 mL). The reaction mixture was heated to 40° C. for 13 h and N-methyl-3,3-diphenylpropan-1-amine 12 (0.111 g, 0.49 mmol) was added. The reaction mixture was heated to 40° C. for 2 d. Direct purification by flash column chromatography on silica gel (eluted with 10% to 50% EtOAc in DCM), followed by purification by flash column chromatography on silica gel (eluted with 1% to 5% MeOH in DCM) gave 3-(5-chloro-4-(4-(methylsulfonamido)-phenyl)thiazol-2-yl)-1-(3,3-diphenylpropyl)-1-methylurea 14 as a white foam. Mass spectrum: calculated for $C_{27}H_{27}ClN_4O_3S_2$ 554.2; found 555.2 (M++1).

Certain compounds of the invention have $R^6$=optionally substituted thiazole and the following describes synthesis of appropriate starting materials.

Synthesis of Aminothiazoles of Formula V

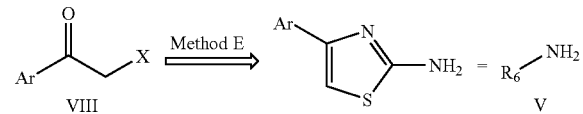

Method E

Thiazoles not commercially available were prepared according to the procedures described in WO 07/060,026.

The synthesis of 4-(2-aminothiazol-4-yl)benzenesulfonamide is shown below and illustrates general method E.

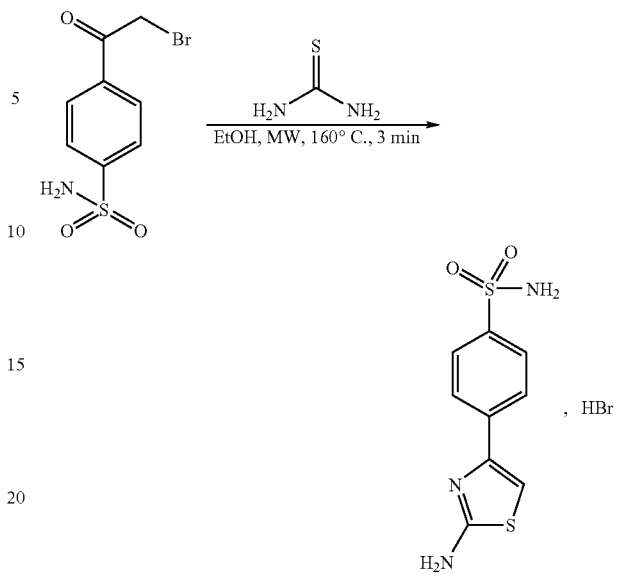

900 mg (3.24 mmol, 1 eq) of the bromoketone were dissolved in 5 mL in MW specific flask, 246 mg (3.24 mmol, 1 eq) of thiourea are added to solution. The mixture was irradiated with MW at 160° C. during 3 minutes. A precipitate of the aminothiazole is formed then filtered and washed with $Et_2O$.

Synthesis of Haloketones of Formula VIII

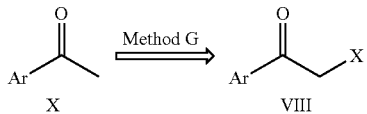

Method G

The synthesis of 4-(2-bromoacetyl)benzenesulfonamide is shown as an example of general method G.

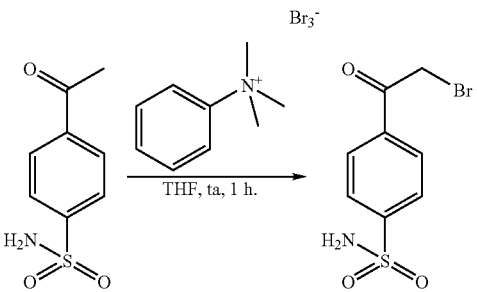

4 g (20.08 mmol, 1 eq) of 4-acetylbenzene sulfonamide were dissolved into 150 mL of dry THF 7.93 (21.08 mmo, 1.05 eq) of phenyl trimethylammonium tribromide were added slowly at RT. The stirring was kept during 20 minutes (a white precipitate is formed). 0.07 eq of trimethylammonium tribromide were added to the mixture to go to completion. Water was added and the aqueous phase was extracted with AcOEt. The organic phase was washed with brine, dried over $MgSO_4$, filtered and concentrated. The crude product was recrystallised with AcOEt, then the solid was washed with AcOEt, and with $Et_2O$. 2.69 g of the desired bromoketone were obtained.

In some cases the 5-chloro thiazole derivative was prepared. Chlorination was achieved by I of 2 procedures: either the 5-chloro group was introduced onto the thiazole before urea formation, or else following urea formation. Chlorination of urea products is described individually.

Preparation of Chloro-thiazoles of Formula IX
Method F

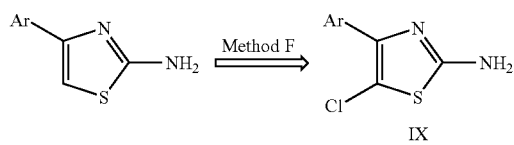

The synthesis of 4-(2-amino-5-chlorothiazol-4-yl)-N,N-dimethylbenzenesulfonamide is shown as an example of general method F.

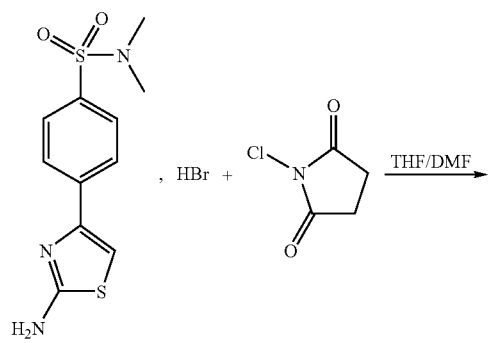

300 mg (1.06 mmol, 1 eq) of 4-dimethylsulfonamide aminothiazole were dissolved into 4 mL of dry THF (low solubility in THF), and 3 mL of dry DMF then 170 mg (1.27 mmol, 1.2 eq) of NCS were added to the solution mixture. The mixture became red within 5 minutes, and was stirred overnight at RT. After evaporation of the solvents, the crude was purified by flash chromatography (DCM/AcOEt, gradient from 100/0 to 3/1) to give the desired chloride compound.

Synthesis of Amines of Formula X

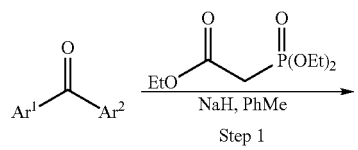

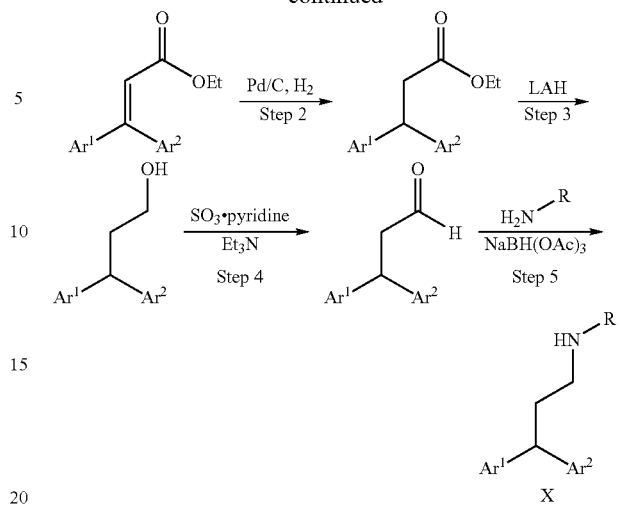

Method H

The synthesis of 3,3-bis(4-fluorophenyl)-N-(2-(pyridin-2-yl)ethyl)propan-1-amine in which $Ar^1$, $Ar^2$=4-fluorophenyl and R=2-(pyridin-2-yl)ethyl is described by way of example of general method H.

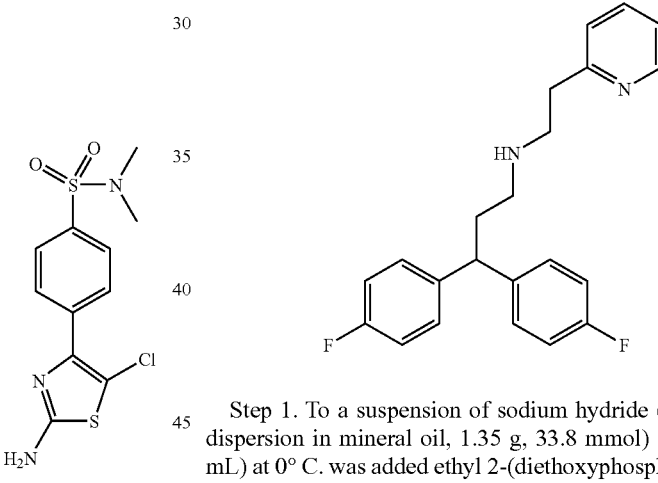

Step 1. To a suspension of sodium hydride (60% weight dispersion in mineral oil, 1.35 g, 33.8 mmol) in PhMe (35 mL) at 0° C. was added ethyl 2-(diethoxyphosphoryl)acetate (7.57 g, 33.8 mmol, 6.7 mL). The reaction mixture was stirred at 0° C. for 20 min and a solution of bis(4-fluorophenyl) methanone (5.65 g, 25.9 mmol) in PhMe (35 mL) was added. The reaction mixture was warmed to room temperature, stirred for 1 h, and heated to 50° C. for 3 d. The reaction mixture was diluted with $Et_2O$, washed with water (2×), brine (1×), dried over $MgSO_4$, filtered, and concentrated to give ethyl 3,3-bis(4-fluorophenyl)acrylate which was used in the next step without further purification.

Step 2. To a mixture of ethyl 3,3-bis(4-fluorophenyl)acrylate, prepared in the previous step, and palladium (10% weight on carbon, 2.68 g, 25.2 mmol) under a nitrogen atmosphere was added EtOH (100 mL). The nitrogen atmosphere was replaced by hydrogen from a double balloon and the reaction mixture was stirred at room temperature. After 16 h, the reaction mixture was filtered through a pad of Celite and concentrated to give ethyl 3,3-bis(4-fluorophenyl)propanoate which was used in the next step without further purification.

Step 3. To a solution of ethyl 3,3-bis(4-fluorophenyl)propanoate, prepared in the previous step, in THF (75 mL) at −78° C. was added LAH (1 M in PhMe, 35 mL, 35.0 mmol). The reaction mixture was warmed to 0° C. over 15 min, quenched with 6 mL of water, 12 mL of 2.5 M NaOH, followed by 18 mL of water. The mixture was stirred at room temperature for 30 min. The solids were removed by filtration and the solution was concentrated to provide 3,3-bis(4-fluorophenyl)propan-1-ol which was used in the next step without further purification.

Step 4. To a solution of 3,3-bis(4-fluorophenyl)propan-1-ol, prepared in the previous step, in DMSO (100 mL) at room temperature was added triethylamine (13.1 g, 129 mmol, 18 mL) and $SO_3$·pyridine (4.52 g, 28.4 mmol). The reaction mixture was stirred at room temperature for 30 min, diluted with $Et_2O$, washed with water (1×), saturated $NH_4Cl$ (1×), brine (1×), dried over $MgSO_4$, filtered, and concentrated. Purification by flash column chromatography on silica gel (eluted with 5% to 40% EtOAc in hexanes) gave 3,3-bis(4-fluorophenyl)propanal.

Step 5. To a solution of 3,3-bis(4-fluorophenyl)propanal (0.967 g, 3.93 mmol) in DCE (15 mL) at room temperature was added 2-(pyridin-2-yl)ethanamine (1.73 g, 14.2 mmol) and $NaBH(OAc)_3$ (1.08 g, 5.10 mmol). The reaction mixture was stirred at room temperature for 17 h, diluted with EtOAc, washed with 5 M NaOH (1×), brine (1×), dried over $MgSO_4$, filtered, and concentrated. Purification by flash column chromatography on silica gel (eluted with 2% to 8% MeOH (2M $NH_3$) in DCM) followed by purification by flash column chromatography on silica gel (eluted with 50% to 100% EtOAc (10% 2M $NH_3$ in MeOH) in hexanes) gave 3,3-bis(4-fluorophenyl)-N-(2-(pyridin-2-yl)ethyl)propan-1-amine.

Synthesis of Bromides of Formula XI

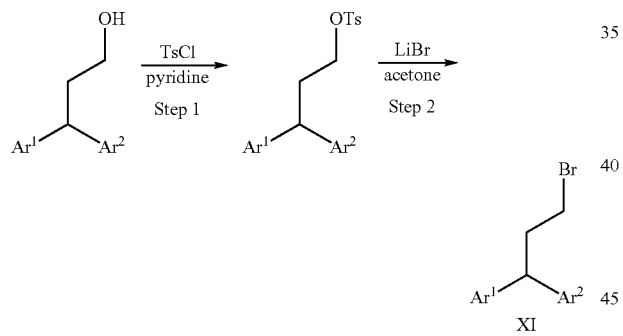

Method I

The synthesis of 3-bromo-1,1-bis(4-fluorophenyl)propane in which $Ar^1$, $Ar^2$=4-fluorophenyl is described by way of example of general method I.

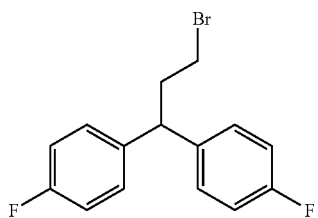

Step 1. To a solution of 3,3-bis(4-fluorophenyl)propan-1-ol (4.99 g, 20.1 mmol) in pyridine (60 mL) at 0° C. was added 4-methylbenzene-1-sulfonyl chloride (4.20 g, 22.0 mmol). The reaction mixture was stirred at 0° C. for 4 h, warmed to room temperature and stirred for 4 h. The reaction mixture was partially concentrated, diluted with EtOAc, washed with 1 M HCl (2×), saturated $NaHCO_3$ (1×), brine (1×), dried over $MgSO_4$, filtered, and concentrated to give 3,3-bis(4-fluorophenyl)propyl 4-methylbenzenesulfonate which was used in the next step without further purification.

Step 2. To a solution of 3,3-bis(4-fluorophenyl)propyl 4-methylbenzenesulfonate, prepared in the previous step, in acetone (100 mL) was added lithium bromide (17.83 g, 205 mmol). The reaction mixture was stirred at room temperature for 17 h, and concentrated. The crude reaction mixture was diluted with $Et_2O$, washed with water (2×), brine (1×), dried over $MgSO_4$, filtered, and concentrated. Purification by flash column chromatography on silica gel (eluted with 0% to 20% EtOAc in hexanes) gave 3-bromo-1,1-bis(4-fluorophenyl)propane.

Synthesis of Amines of Formula XII

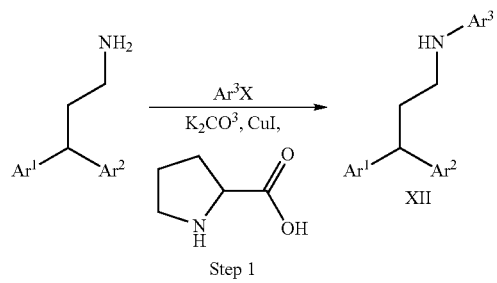

Method J

The synthesis of N-(3,3-diphenylpropyl)pyridin-3-amine in which $Ar^1$, $Ar^2$=phenyl and $Ar^3$=3-pyridyl is described by way of example of general method J.

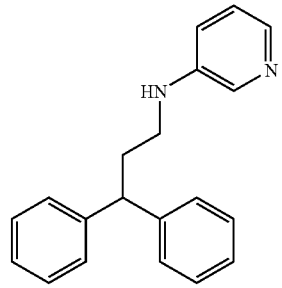

Step 1. To a mixture of 3-iodopyridine (1.12 g, 5.46 mmol) and 3,3-diphenylpropan-1-amine (1.72 g, 8.14 mmol) was added potassium carbonate (1.49 g, 10.8 mmol), copper(I) iodide (0.126 g, 0.662 mmol), (S)-pyrrolidine-2-carboxylic acid (0.154 g, 1.34 mmol), and DMSO (3.5 mL). The reaction mixture was heated to 75° C. for 18 h and diluted with EtOAc. The organic phase was washed with water (1×), brine (1×), dried over $MgSO_4$, filtered, and concentrated. Purification by flash column chromatography on silica gel (eluted with 30% to 80% EtOAc in hexanes) gave N-(3,3-diphenylpropyl)pyridin-3-amine.

Synthesis of Amines of Formula XIII

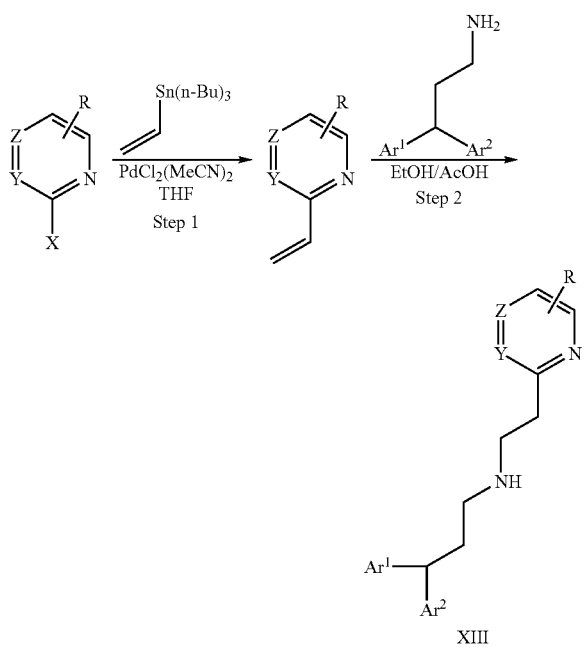

Method K

The synthesis of 3,3-diphenyl-N-(2-(pyrimidin-2-yl)ethyl)propan-1-amine in which $Ar^1$, $Ar^2$=phenyl, R=H, X=Br, Y=N, and Z=CH is described by way of example of general method K.

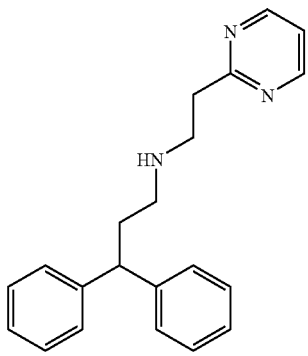

Step 1. To a solution of $PdCl_2(MeCN)_2$ (1.39 g, 5.36 mmol) and 2-bromopyrimidine (8.48 g, 53.3 mmol) in THF (200 mL) at room temperature was added tributyl(vinyl)stannane (21 mL, 22.8 g, 71.9 mmol). The reaction mixture was degassed by bubbling nitrogen through the solution for 5 minutes and the reaction mixture was heated to 50° C. After 16 h, the reaction mixture was filtered and concentrated. Purification by flash column chromatography on silica gel (eluted with 0% to 20% EtOAc in DCM) gave 2-vinylpyrimidine.

Step 2. To a solution of 2-vinylpyrimidine (0.373 g, 3.51 mmol) in EtOH (6 mL) at room temperature was added AcOH (1 mL) and 3,3-diphenylpropan-1-amine (2.21 g, 10.5 mmol). The reaction mixture was heated to reflux for 1 d, cooled to 0° C., and the solids were removed by filtration. The filtrate was concentrated and diluted with 5 M NaOH, brine, and EtOAc. The aqueous phase was extracted with EtOAc (2×) and the combined organic extracts were washed with brine (1×), dried over $MgSO_4$, filtered, and concentrated. Purification by flash column chromatography on silica gel (eluted with 10% MeOH in DCM) gave 3,3-diphenyl-N-(2-(pyrimidin-2-yl)ethyl)propan-1-amine.

Synthesis of Thiadiazoles of Formula XIV

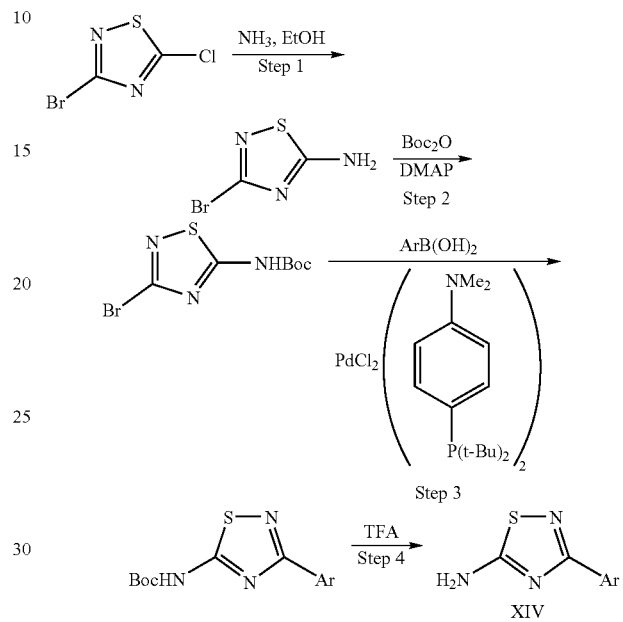

Method L

The synthesis of 3-(4-(methylsulfonyl)phenyl)-1,2,4-thiadiazol-5-amine in which Ar=4-(methylsulfonyl)phenyl is described by way of example of general method L.

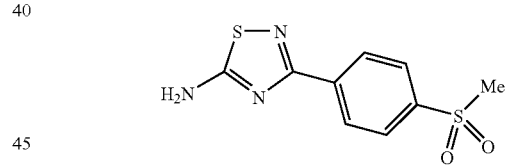

Step 1. A solution of 3-bromo-5-chloro-1,2,4-thiadiazole (10.0 g, 50.1 mmol) in 2M ammonia in EtOH (47.8 mL, 95.5 mmol) was heated at 70° C. for 4 h. The reaction mixture was cooled to room temperature and the solid was collected by filtration. The solid was washed with $Et_2O$ followed by water and dried under high vacuum to give 3-bromo-1,2,4-thiadiazol-5-amine.

Step 2. To a solution of 3-bromo-1,2,4-thiadiazol-5-amine (2.50 g, 13.9 mmol) and N,N-dimethylpyridin-4-amine (0.0848 g, 0.694 mmol) in THF (50 mL) was added Boc anhydride (3.64 g, 16.7 mmol). The reaction mixture was stirred overnight at 25° C. and heated to 50° C. for 3 h. The solvent was removed by concentration under reduced pressure. Purification by chromatography on silica (eluted with 0% to 25% EtOAc in hexanes) gave tert-butyl 3-bromo-1,2,4-thiadiazol-5-ylcarbamate.

Step 3. To a mixture of tert-butyl 3-bromo-1,2,4-thiadiazol-5-ylcarbamate (1.90 g, 6.78 mmol), 4-(methylsulfonyl)phenylboronic acid (2.07 g, 10.3 mmol), cesium fluoride (2.09 g, 13.8 mmol), and the palladium catalyst (0.271 g, 0.383 mmol) was added dioxane (20 mL) and water (2 mL). The reaction mixture was degassed by bubbling nitrogen through the solution for 5 min and the reaction mixture was heated to 80° C. for 3 h. The reaction mixture was diluted with EtOAc, and the organic phase was washed with saturated NH$_4$Cl (1×), brine (1×), dried over MgSO$_4$, filtered, and concentrated. Purification by flash column chromatography on silica gel (eluted with 10% to 50% EtOAc in hexanes) gave tert-butyl 3-(4-(methylsulfonyl)phenyl)-1,2,4-thiadiazol-5-ylcarbamate.

Step 4. To a solution of tert-butyl 3-(4-(methylsulfonyl)phenyl)-1,2,4-thiadiazol-5-ylcarbamate (1.57 g, 4.42 mmol) in DCM (20 mL) was added anisol (0.50 mL) and TFA (10 mL). The reaction mixture was stirred at room temperature for 6 h and concentrated. The solid was suspended in saturated NaHCO$_3$ (~200 mL) and stirred for 30 min. The solid was collected by filtration, washed with water (~500 mL) followed by hexanes (~50 mL), and dried under high vacuum to give 3-(4-(methylsulfonyl)phenyl)-1,2,4-thiadiazol-5-amine.

Synthesis of Thiadiazoles of Formula XV

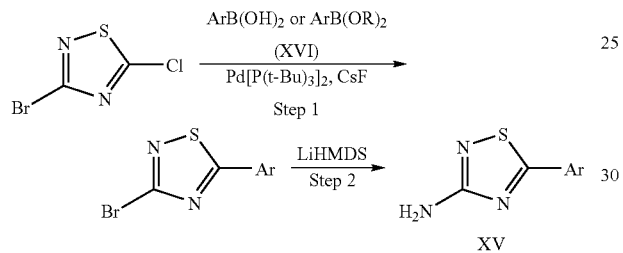

Method M

The synthesis of tert-butyl 4-(3-amino-1,2,4-thiadiazol-5-yl)phenylcarbamate in which Ar=4-(tert-butoxycarbonyl)phenyl is described by way of example of general method M.

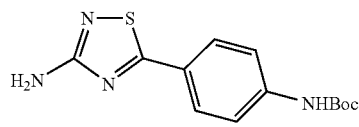

Step 1. To a mixture of 4-(tert-butoxycarbonyl)phenylboronic acid (4.05 g, 17.1 mmol), cesium fluoride (5.57 g, 36.7 mmol), and Pd[P(t-Bu)$_3$]$_2$ (0.708 g, 1.39 mmol) was added dioxane (65 mL) and 3-bromo-5-chloro-1,2,4-thiadiazole (5.02 g, 25.2 mmol). The reaction mixture was degassed by bubbling nitrogen through the solution for 10 minutes and the solution was heated to 100° C. After 16 h, the reaction mixture was partially concentrated and diluted with EtOAc. The organic phase was washed with water (1×), brine (1×), dried over MgSO$_4$, filtered, and concentrated. Purification by flash column chromatography on silica gel (eluted with 5% to 10% EtOAc in hexanes) gave tert-butyl 4-(3-bromo-1,2,4-thiadiazol-5-yl)phenylcarbamate.

Step 2. To a solution of tert-butyl 4-(3-bromo-1,2,4-thiadiazol-5-yl)phenylcarbamate (3.22 g, 9.04 mmol) in THF (35 mL) at 0° C. was added LiHMDS (1 M in PhMe, 23 mL, 23.0 mmol). The reaction mixture was warmed to room temperature and stirred for 1.5 h. Water (20 mL) was added and the mixture was stirred at room temperature for 2 h. The reaction mixture was diluted with water, saturated NH$_4$Cl, and EtOAc. The aqueous phase was extracted with EtOAc (2×), and the combined organic extracts were washed with brine (1×), dried over MgSO$_4$, filtered, and concentrated. The concentrate was dissolved in 10% MeOH in DCM (200 mL), filtered through a pad of silica (2 cm), and diluted with hexanes (150 mL). The precipitate that formed was collected by filtration, washed with hexanes, and dried under high vacuum to give tert-butyl 4-(3-amino-1,2,4-thiadiazol-5-yl)phenylcarbamate.

Synthesis of Thiadiazoles of Formula XIV from Amidines

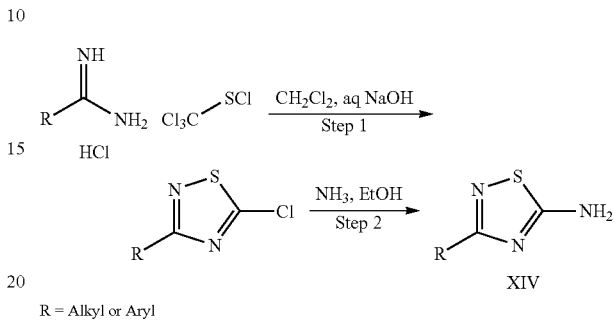

R = Alkyl or Aryl

Method N

The synthesis of 3-(pyridin-2-yl)-1,2,4-thiadiazol-5-amine in which R=2-pyridyl is described by way of example of general method N.

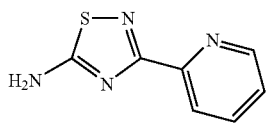

Step 1. To solution of picolinamidine hydrochloride (1.97 g, 12.5 mmol) in CH$_2$Cl$_2$ (10 ml) was added trichloromethyl hypochlorothioite (1.45 ml, 13.3 mmol). The reaction mixture was cooled to 5° C. and a solution of sodium hydroxide (2.50 g, 62.5 mmol) in water (4 mL) was added by slow dropwise addition. The reaction mixture was stirred for 1.5 h at 5° C. The reaction mixture was poured into 50 mL of water and extracted with ethyl acetate (6×30 mL). The combined organic extracts were dried with magnesium sulfate, filtered, and concentrated. Purification by chromatography on silica (eluted with 0% to 25% EtOAc in hexanes) gave tert-butyl 3-bromo-1,2,4-thiadiazol-5-ylcarbamate. Purification chromatography on silica (eluted with 0->10% MeOH/CH$_2$Cl$_2$+ 0->1% NH$_4$OH) gave 2-(5-chloro-1,2,4-thiadiazol-3-yl)pyridine.

Step 2. A solution of 2-(5-chloro-1,2,4-thiadiazol-3-yl)pyridine in 2 M ammonia in EtOH (10 ml) was heated overnight at 70° C. Volatiles were removed by concentration under reduced pressure. Purification by chromatography on silica (eluted with 0->10% MeOH/CH$_2$Cl$_2$+0->1% NH$_4$OH) gave 3-(pyridin-2-yl)-1,2,4-thiadiazol-5-amine.

Synthesis of Aryl Bronate Esters of formula XVI

Method O

The synthesis of 1-(4-(4,4,5,5-tetramethyl-1,3,2-dioxaborolan-2-yl)phenyl)-1H-1,2,3-triazole is described by way of illustration of general method O.

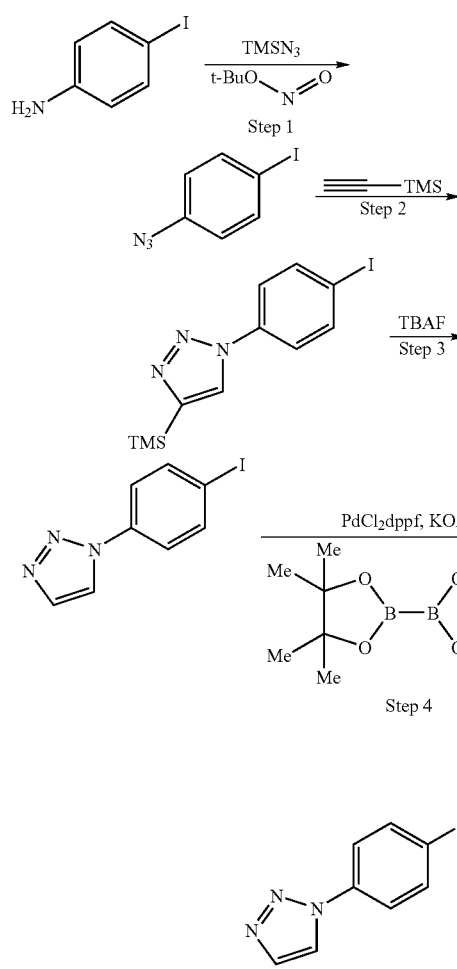

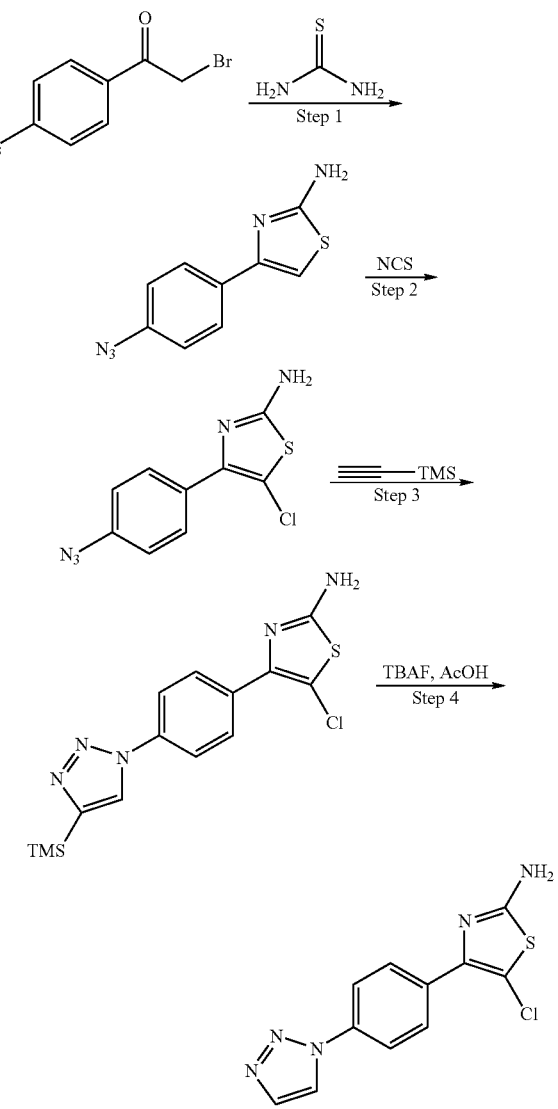

2-yl)-1,3,2-dioxaborolane (2.45 g, 9.65 mmol), and potassium acetate (2.56 g, 26.1 mmol) was added DMSO (25 mL). The reaction mixture was degassed by bubbling nitrogen through the solution for 10 minutes and heated to 80° C. for 2 h. The reaction mixture was cooled to room temperature and diluted with EtOAc and water. The aqueous phase was extracted with EtOAc (4×) and the combined organic extracts were washed with water (1×), brine (1×), dried over MgSO$_4$, filtered through a pad of silica gel (2 cm), and concentrated. Purification by flash column chromatography on silica gel (eluted with 20% to 60% EtOAc in hexanes) gave 1-(4-(4,4,5,5-tetramethyl-1,3,2-dioxaborolan-2-yl)phenyl)-1H-1,2,3-triazole.

Methods for the Synthesis of Aminothiazoles of formula V or IX

Method P. Synthesis of 4-(4-(1H-1,2,3-triazol-1-yl)phenyl)-5-chlorothiazol-2-amine Step 1. To a solution of 4-iodobenzenamine (2.38 g, 10.9 mmol) in MeCN (20 mL) at 0° C. was added tert-butyl nitrite (1.95 mL, 1.69 g, 16.4 mmol) and azidotrimethylsilane (1.70 mL, 1.49 g, 12.9 mmol). The reaction mixture was warmed to room temperature and stirred for 6 h, heated to 40° C. for 18 h, and diluted with EtOAc. The aqueous phase was washed with water (2×), brine (1×), dried over MgSO$_4$, filtered, and concentrated to give 1-azido-4-iodobenzene which was used in the next step without further purification.

Step 2. To a solution of 1-azido-4-iodobenzene, prepared in the previous step, in DMF (26 mL) in a sealed tube was added ethynyltrimethylsilane (6.90 mL, 4.89 g, 49.8 mmol). The reaction mixture was heated to 10° C. for 21 h and concentrated. The product, 1-(4-iodophenyl)-4-(trimethylsilyl)-1H-1,2,3-triazole, was used in the next step without further purification.

Step 3. To 1-(4-iodophenyl)-4-(trimethylsilyl)-1H-1,2,3-triazole, prepared in the previous step, at room temperature was added tetrabutylammonium fluoride (1 M in THF, 50 mL, 50 mmol). The reaction mixture was heated to 50° C. for 1.5 h and diluted with EtOAc. The organic phase was washed with water (2×), brine (1×), dried over MgSO$_4$, filtered, and concentrated. Purification by flash column chromatography on silica gel (eluted with 10% to 50% EtOAc in hexanes) gave 1-(4-iodophenyl)-1H-1,2,3-triazole.

Step 4. To a mixture of 1-(4-iodophenyl)-1H-1,2,3-triazole (2.28 g, 8.41 mmol), PdCl$_2$dppf (0.335 g, 0.458 mmol), 4,4,5,5-tetramethyl-2-(4,4,5,5-tetramethyl-1,3,2-dioxaborolan- Step 1. To a solution of 1-(4-azidophenyl)-2-bromoethanone (1.37 g, 5.71 mmol) in EtOH (15 mL) at room temperature was added thiourea (0.476 g, 6.25 mmol). The reaction mixture was heated to 70° C. for 3 d, poured into a solution of NaHCO$_3$ (602 mg) in water (50 mL) and stirred for 30 min.

The precipitate that formed was collected by filtration, washed with water, and dried under high vacuum to give 4-(4-azidophenyl)thiazol-2-amine.

Step 2. To a solution of 4-(4-azidophenyl)thiazol-2-amine (1.18 g, 5.43 mmol) in DMF (18 mL) at 0° C. was added 1-chloropyrrolidine-2,5-dione (0.746 g, 5.59 mmol). The reaction mixture was warmed to room temperature and stirred for 2 h. The reaction mixture was poured into water (100 mL). The precipitate that formed was collected by filtration, washed with water, and dried under high vacuum to give 4-(4-azidophenyl)-5-chlorothiazol-2-amine.

Step 3. To a solution of 4-(4-azidophenyl)-5-chlorothiazol-2-amine (0.501 g, 2.0 mmol) in DMF (5 mL) was added ethynyltrimethylsilane (1.4 mL, 10 mmol). The reaction mixture was heated to 100° C. in a sealed tube for 20 h and concentrated. The product, 5-chloro-4-(4-(4-(trimethylsilyl)-1H-1,2,3-triazol-1-yl)phenyl)thiazol-2-amine, was used in the next step without further purification.

Step 4. To a solution of 5-chloro-4-(4-(4-(trimethylsilyl)-1H-1,2,3-triazol-1-yl)phenyl)thiazol-2-amine (0.70 g, 2.0 mmol), prepared in the previous step, in THF (10 mL) at 0° C. was added acetic acid (0.125 mL, 2.2 mmol) and tetrabutylammonium fluoride (2.2 mL, 1 M in THF, 2.2 mmol). The reaction mixture was warmed to room temperature and stirred for 1 h, heated to 40° C. for 2 h, and additional AcOH (0.035 mL, 0.61 mmol) and TBAF (0.60 mL, 1 M in THF, 0.60 mmol) were added. Stirring was continued at 40° C. After 3 h, the reaction mixture was poured into water (300 mL). The precipitate that formed was collected by filtration, washed with water, and dried under high vacuum. Purification by flash column chromatography on silica gel (eluted with 50% to 100% EtOAc in hexanes gave 4-(4-(1H-1,2,3-triazol-1-yl)phenyl)-5-chlorothiazol-2-amine.

Method Q. Synthesis of 4-(2-amino-4-chlorothiazol-5-yl)-N-tert-butylbenzenesulfonamide

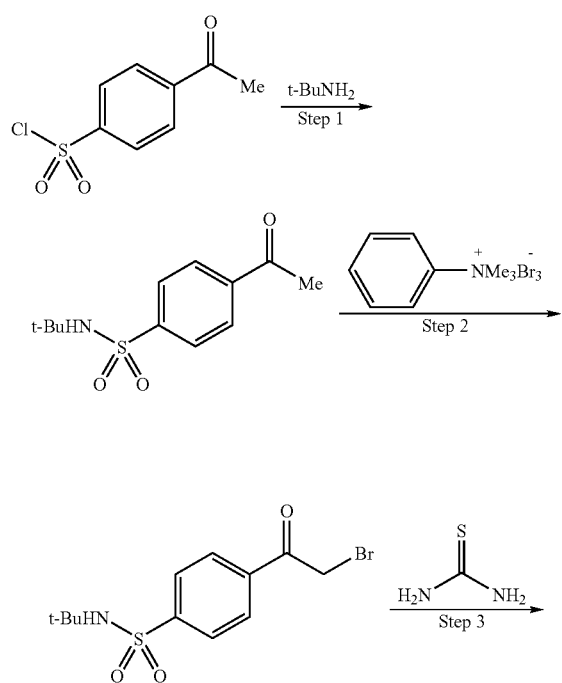

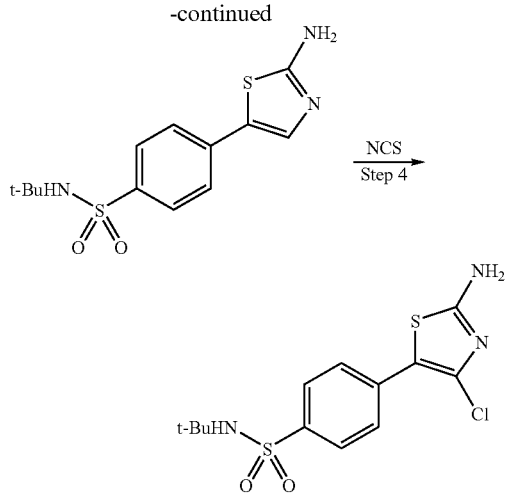

Step 1. To a solution of 2-methylpropan-2-amine (13 mL, 9.01 g, 123 mmol) in DCM (200 mL) at 0° C. was added 4-acetylbenzene-1-sulfonyl chloride (10.05 g, 46.0 mmol). The reaction mixture was warmed to room temperature and stirred for 3 d. The reaction mixture was partially concentrated, diluted with EtOAc, washed with water (1×), brine (1×), dried over MgSO₄, filtered, and concentrated. The product, 4-acetyl-N-tert-butylbenzenesulfonamide, was used in the next step without further purification.

Step 2. To a solution of 4-acetyl-N-tert-butylbenzenesulfonamide, prepared in the previous step, in THF (150 mL) at room temperature was added PhNMe₃Br₃ (18.17 g, 48.3 mmol). The reaction mixture was stirred at room temperature for 30 min and heated to 40° C. for 30 min until a precipitate formed. The reaction mixture was partially concentrated, diluted with EtOAc, washed with water (2×), brine (1×), dried over MgSO₄, filtered, and concentrated. A slurry was formed with DCM (150 mL). The solid was collected by filtration, washed with DCM, and dried under high vacuum to give 4-(2-bromoacetyl)-N-tert-butylbenzenesulfonamide.

Step 3. To a solution of 4-(2-bromoacetyl)-N-tert-butylbenzenesulfonamide (8.71 g, 26.1 mmol) in EtOH (45 mL) was added thiourea (2.38 g, 31.3 mmol). The reaction mixture was heated to 70° C. for 15 h and poured into an aqueous solution of NaHCO₃. The mixture was stirred for 30 min. The precipitate that formed was collected by filtration, washed with water, and dried under high vacuum to give 4-(2-aminothiazol-4-yl)-N-tert-butylbenzenesulfonamide.

Step 4. To a solution of 4-(2-aminothiazol-4-yl)-N-tert-butylbenzenesulfonamide (7.56 g, 24.3 mmol) in DMF (100 mL) at 0° C. was added 1-chloropyrrolidine-2,5-dione (3.30 g, 24.7 mmol). The reaction mixture was warmed to room temperature, stirred for 6 h, and poured into water (500 mL). The solid was collected by filtration, washed with water, and dried under high vacuum to give 4-(2-amino-5-chlorothiazol-4-yl)-N-tert-butylbenzenesulfonamide.

Method R. Synthesis of thiazolo[4,5-c]pyridin-2-amine

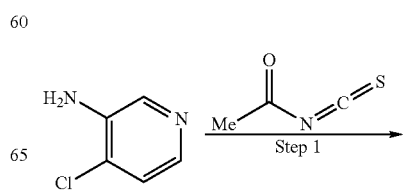

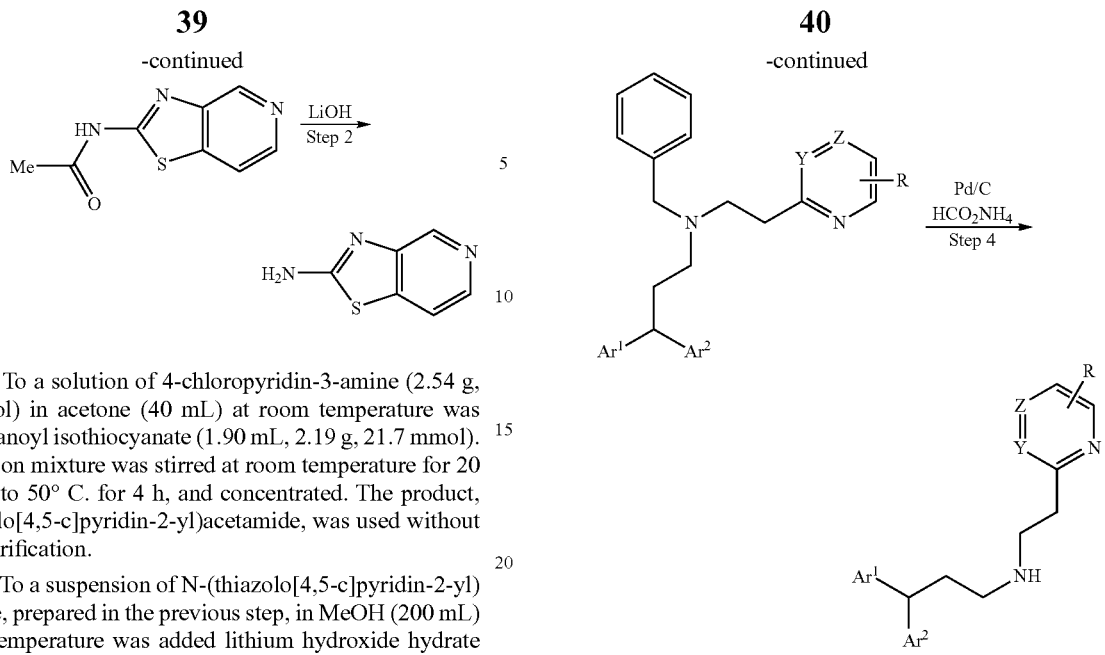

Step 1. To a solution of 4-chloropyridin-3-amine (2.54 g, 19.8 mmol) in acetone (40 mL) at room temperature was added ethanoyl isothiocyanate (1.90 mL, 2.19 g, 21.7 mmol). The reaction mixture was stirred at room temperature for 20 h, heated to 50° C. for 4 h, and concentrated. The product, N-(thiazolo[4,5-c]pyridin-2-yl)acetamide, was used without further purification.

Step 2. To a suspension of N-(thiazolo[4,5-c]pyridin-2-yl) acetamide, prepared in the previous step, in MeOH (200 mL) at room temperature was added lithium hydroxide hydrate (7.08 g, 169 mmol). The reaction mixture was stirred at room temperature for 30 min and then warmed to 40° C. After 3 h, additional lithium hydroxide hydrate (7.48 g) was added. The reaction mixture was heated to 50° C. for 20 h and concentrated. The reaction mixture was diluted with DCM/MeOH (~10:1, 500 mL). The undissolved material was removed by filtration and the filtrate was concentrated. Purification by flash column chromatography on silica gel (eluted with 2% to 10% MeOH in DCM) gave thiazolo[4,5-c]pyridin-2-amine.

Method S. Synthesis of Amines of Formula XVI

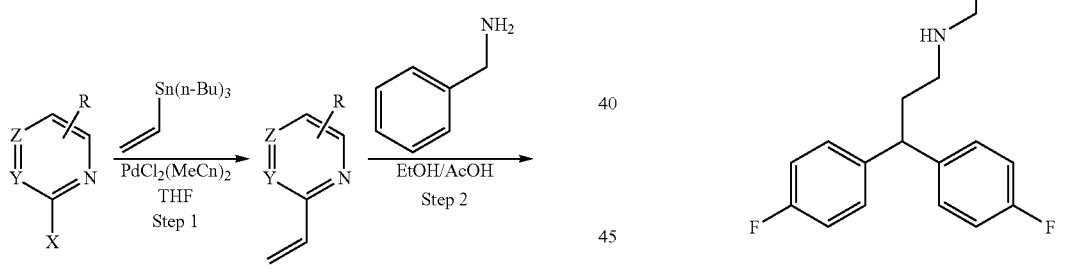

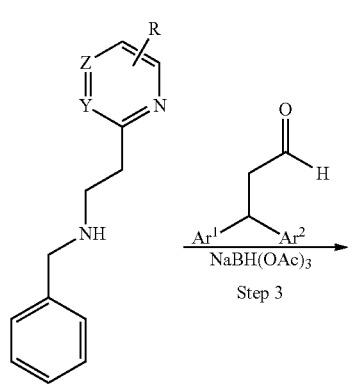

The synthesis of 3,3-bis(4-fluorophenyl)-N-(2-(2-pyrimidinyl)ethyl)-1-propanamine in which $Ar^1$, $Ar^2$=phenyl, R=H, X=Br, Y=N, and Z=CH is described by way of example of general method S.

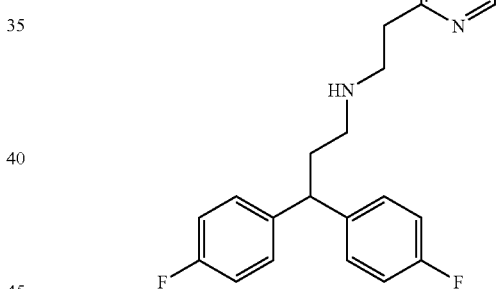

Step 1. To a solution of $PdCl_2(MeCN)_2$ (1.39 g, 5.36 mmol) and 2-bromopyrimidine (8.48 g, 53.3 mmol) in THF (200 mL) at room temperature was added tributyl(vinyl)stannane (21 mL, 22.8 g, 71.9 mmol). The reaction mixture was degassed by bubbling nitrogen through the solution for 5 minutes and the reaction mixture was heated to 50° C. After 16 h, the reaction mixture was filtered and concentrated. Purification by flash column chromatography on silica gel (eluted with 0% to 20% EtOAc in DCM) gave 2-vinylpyrimidine.

Step 2. To a solution of 2-vinylpyrimidine (1.55 g, 14.6 mmol) in EtOH (15 mL) at room temperature was added AcOH (2.0 mL) and benzylamine (3.14 g, 29.3 mmol) (3.2 mL). The reaction mixture was heated to reflux for 18 h, and concentrated. Diluted with EtOAc, washed with 5 M NaOH (1×), brine (1×), dried over $MgSO_4$, filtered, and concentrated. Purification by flash column chromatography on silica gel (eluted with 2% to 10% MeOH in DCM) gave N-benzyl-2-(pyrimidin-2-yl)ethanamine.

Step 3. To a solution of 3,3-bis(4-fluorophenyl)propanal (0.908 g, 3.69 mmol) in DCE (12 mL) at room temperature was added N-benzyl-2-(pyrimidin-2-yl)ethanamine (0.704 g, 3.30 mmol), acetic acid (0.208 g, 3.46 mmol) (0.20 mL). and NaBH(OAc)$_3$ (0.834 g, 3.94 mmol) The reaction mixture was stirred at room temperature for 3 h, quenched with 5 M NaOH (1×), diluted with EtOAc, washed with brine (1×), dried over MgSO$_4$, filtered, and concentrated. Purification by flash column chromatography on silica gel (eluted with 40% to 70% EtOAc in hexanes) gave N-benzyl-3,3-bis(4-fluorophenyl)-N-(2-(pyrimidin-2-yl)ethyl)propan-1-amine.

Step 4. To a mixture of N-benzyl-3,3-bis(4-fluorophenyl)-N-(2-(pyrimidin-2-yl)ethyl)propan-1-amine (1.23 g, 2.77 mmol), ammonium formate (0.985 g, 15.6 mmol), and palladium (10% wt on carbon) (0.382 g, 3.59 mmol) was added MeOH (10 mL). The reaction mixture was heated to 50° C. for 1 h, diluted with DCM, filtered and partially concentrated, diluted with EtOAc, washed with brine (1×), dried over MgSO4, filtered, and concentrated. Purification by flash column chromatography on silica gel (eluted with 5% to 10% MeOH (2 M NH3) in DCM) gave 3,3-bis(4-fluorophenyl)-N-(2-(pyrimidin-2-yl)ethyl)propan-1-amine.

Synthesis of Amines of Formula XVII

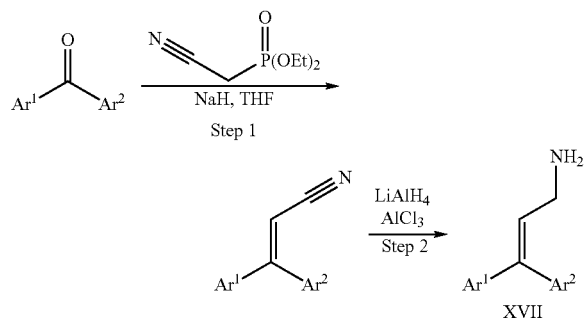

Method T

The synthesis of 3,3-diphenyl-2-propenylamine in which Ar$^1$, Ar$^2$=phenyl is described by way of example of general method H.

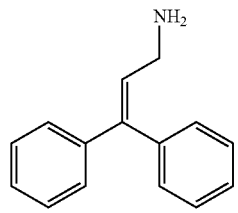

Step 1. To a suspension of sodium hydride (60% wt in mineral oil) (0.780 g, 32.5 mmol) in THF (100 mL) at room temperature was added diethyl cyanomethylphosphonate (4.50 g, 25.4 mmol) (4 mL). The mixture was stirred for 30 min and benzophenone (4.22 g, 23.2 mmol) was added. The reaction mixture was stirred at room temperature for 1d, and partially concentrated, diluted with Et2O, washed with water (1×), brine (1×), dried over MgSO4, filtered, and concentrated. Purification by flash column chromatography on silica gel (eluted with 5% to 20% EtOAc in hexanes) gave 3,3-diphenylacrylonitrile.

Step 2. To a solution of 3,3-diphenylacrylonitrile (4.45 g, 21.7 mmol) in THF (75 mL) at 0° C. was added aluminum(III) chloride (3.27 g, 24.5 mmol) and lithium tetrahydroaluminate (1 M in THF) (0.910 g, 24.0 mmol) (24 mL). The reaction mixture was warmed to room temperatrue and stirred for 1 h, heated to 40° C. for 2 h, heated to 60° C. for 2 h, quenched with water (5 mL), adjusted to pH 12 with ammonium hydroxide, diluted with brine, and EtOAc, extracted with EtOAc (5×), combined organic extracts washed with brine (1×), dried over MgSO4, filtered, and concentrated. Purification by flash column chromatography on silica gel (eluted with 3% to 10% MeOH (2 M NH3) in DCM) gave 3,3-diphenyl-2-propenylamine.

Regarding the molecular structures set forth in methods described above, one of skill in the art will readily appreciate that precursors and intermediates having aryl groups other than phenyl, e.g. naphthyl, can be used to practice the synthetic methods and that a variety of alkyl groups as illustrated by the description for R$^3$ in the invention can be used.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Therapeutic Uses of the Compounds of the Invention

Compounds and compositions of the present application which act on calcium receptors may thus be used, in one aspect, for the treatment or prevention of diseases or disorders linked with abnormal physiological behaviour of inorganic ion receptors and, in particular, of calcium receptors such as membrane calcium receptors capable of binding extracellular calcium. Thus, the compounds and compositions of the present invention are of particular use in regulating the serum levels of PTH and extracellular $Ca^{2+}$. The compounds and compositions of the present invention can be used, in particular, to participate in a reduction of the serum levels in the parathyroid hormone known as PTH: these products could thus be useful, in one aspect, for the treatment of diseases such as hyperparathyroidism. Similarly, abnormalities in calcium homeostasis, such as hypercalcaemia, can be treated with these compounds. Further, the compounds of the invention can treat hyperplasia and parathyroid adenoma. In another aspect, the compounds of the invention can have properties which enable them to reduce bone resorption which depends directly on the fluctuation of circulating PTH levels: these products could be useful, in particular, for the treatment of diseases such as osteoporosis, osteopaenia Paget's disease and the reconstruction of fractures. They can also be used in the treatment and prophylaxis of polyarthritis and osteoarthritis.

In one aspect, the invention provides a method of inhibiting, decreasing or preventing vascular calcification in an individual. The method comprises administering to the individual a therapeutically effective amount of the calcimimetic compound of the invention. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits.

In one aspect, the compounds of the invention may be used to prevent or treat atherosclerotic calcification and medial calcification and other conditions characterized by vascular calcification. In one aspect, vascular calcification may be associated with chronic renal insufficiency or end-stage renal disease. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

In one aspect, administration of an effective amount of the compounds of the invention can reduce serum PTH without causing aortic calcification. In another aspect, administration of the compounds of the invention can reduce serum creatinine level or can prevent increase of serum creatinine level. In another aspect, administration of the compounds of the invention can attenuates parathyroid (PT) hyperplasia.

The compounds of the invention may be administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol. In one aspect, the compounds of the invention can be administered before or after administration of vitamin D sterols. In another aspect, the compounds of the invention can be co-administered with vitamin D sterols. The methods of the invention can be practiced to attenuate the mineralizing effect of calcitriol on vascular tissue. In one aspect, the methods of the invention can be used to reverse the effect of calcitriol of increasing the serum levels of calcium, phosphorus and CaxP product thereby preventing or inhibiting vascular calcification. In another aspect, the compounds of the invention of the invention can be used to stabilize or decrease serum creatinine levels. In one aspect, in addition to creatinine level increase due to a disease, a further increase in creatinine level can be due to treatment with vitamin D sterols such as calcitriol. In addition, the compounds of the invention may be administered in conjunction with surgical and non-surgical treatments. In one aspect, the methods of the invention can be practiced in injunction with dialysis.

In one aspect, the compounds of the invention can be used for treating abnormal intestinal motilities disorders such as diarrhea. The methods of the invention comprise administering to the individual a therapeutically effective amount of the compounds of Formula I.

As used herein, the term "diarrhea" refers to a condition of three or more unformed stools in a 24-hour period of volume more than 200 g per day. In one aspect, diarrhea can be osmotic, i.e., resulting if the osmotic pressure of intestinal contents is higher than that of the serum. This condition may result from malabsorption of fat (e.g., in celiac disease) or of lactose (e.g., in intestinal lactase deficiency), or it can happen due to the use of certain laxatives (e.g., lactulose, magnesium hydroxide) or artificial sweeteners (e.g., sorbitol, mannitol). In another aspect, diarrhea can be secretory, i.e., occurring when there is a net secretion of water into the lumen. This may occur with bacterial toxins (such as those produced, e.g., by *E. coli* and *Vibrio cholerae*), or with hormones, such as vasoactive intestinal polypeptide, which is produced by rare islet cell tumors (pancreatic cholera). Both osmotic and secretory diarrheas result from abnormalities in the small intestine such that the flow of water through the ileocecal area overcomes the absorptive capacity of the colon.

In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with chemotherapy, radiation treatment, inflammation or toxic traumatic injury. In another aspect, exudative diarrhea can be associated with a gastrointestinal or abdominal surgery.

In another aspect, diarrhea can be due to acceleration of intestinal transit (rapid transit diarrhea). Such condition may occur because the rapid flow-through impairs the ability of the gut to absorb water.

In one aspect, the invention provides the compounds and compositions for treating abnormal gastric fluid secretion/absorption disorders in conjunction with treating underlying causes of, for example, diarrhea or with other treatment methods. In one aspect, calcimimetics can be administered to a subject before, after or concurrently with oral rehydration therapy. For example, oral rehydration therapy may contain the following ingredients: sodium, potassium, chloride, bicarbonate, citrate and glucose. In another aspect, the compounds of the invention can be administered to a subject before, after or concurrently with an antimotility agent, such as loperamide (Imodium), diphenoxylate, or bismuth subsalicylate (Pepto-Bismol). In another aspect, calcimimetics can be administered with antibiotics (e.g., trimethoprim-sulfamethoxazole (Bactrim DS), ciprofloxacin (Cipro), norfloxacin (Noroxin), ofloxacin (Floxin), doxycycline (Vibramycin), erythromycin). In one aspect, the compounds of the invention can be administered together with calcium or polyamines such as spermine, spermidine, putrescine, and ornithine metabolites or amino acids such of L-tryptophan, L-phenylalanine. In another aspect, the compounds of the invention can be administered together with sodium and glucose. In addition, the compounds of the invention may be administered in conjunction with surgical and non-surgical treatments.

The invention further provides methods for modulating intestinal fluid secretion and absorption. In one aspect, the purpose can be to increase fluid absorption and/or decrease fluid secretion in a subject and thus the methods of the invention can comprise administering an effective amount of a pharmaceutical composition comprising a compound of the invention.

The invention provides methods of modulation the absorption or secretion of a drug, poison or nutrient in the intestinal tract of a subject, comprising administering an effective amount of a pharmaceutical composition comprising a compound of the invention together with a pharmaceutically acceptable carrier to the subject. In one aspect, the invention provides methods of treatment of a malassimilation or a malabsorption of a subject, comprising administering an effective amount of a pharmaceutical composition comprising a compound of Formula I together with a pharmaceutically acceptable carrier to the subject.

As used herein, the term "malassimilation" encompasses impaired processes of food digestions and absorption occurring in one of two ways (1) through intraluminal disorders (maldigestion of food) and (2) through intramural disorders (malabsorption of food).

Methods of the invention comprising administering a pharmaceutical composition of the invention can also be practiced to treat malnutrition in a subject. For example, a subject can be malnourished if the subject is grossly underweight (weight for height is below 80% of the standard), grossly overweight (weight for height above 120% of the standard), if the subject unintentionally lost 10% or more of body weight, has a gastrointestinal tract surgery, experienced nutrient losses (e.g., from diarrhea, dialysis, vomiting), has increased metabolic needs (e.g., due to pregnancy, lactation, increased physical activity, fever, injury), is an alcoholic or chronic drug user (antibiotics, antidepressants, diuretics), has medical conditions which interfere with nutrient intake, absorption, metabolism, or utilization, has poor dentition (particularly in the elderly subjects), or has mouth sores due to herpes, HIV or chemotherapy. In another aspect, the subject can be malnourished due to dietary risk factors (e.g., loss of appetite, inadequate food or nutrient intake, lack of variety of foods, fad, weight-loss diets, inadequate fiber, excessive fat, sodium, sugar, excess alcohol, eats too few fruits, vegetables) or due to social risk factors (e.g., chronic ill health, poverty, inadequate money to buy food, low socioeconomic status, immobility or inability to purchase, store, or cook food, social isolation, eats alone most of the time, substance abuser, conditions which limit subject's ability to eat). Further, the methods of the invention can be practiced when a subject has limited access to nutrients such as during survival following environmental disasters, survival at sea, marooning and deep-sea living or space travel.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral data. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

EXAMPLE 1

Synthesis of 3-(benzo[d]thiazol-2-yl)-1-(3,3-diphenylpropyl)-1-isopropylurea, 4

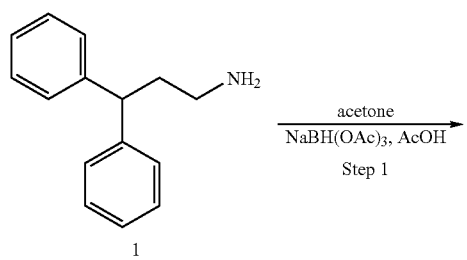

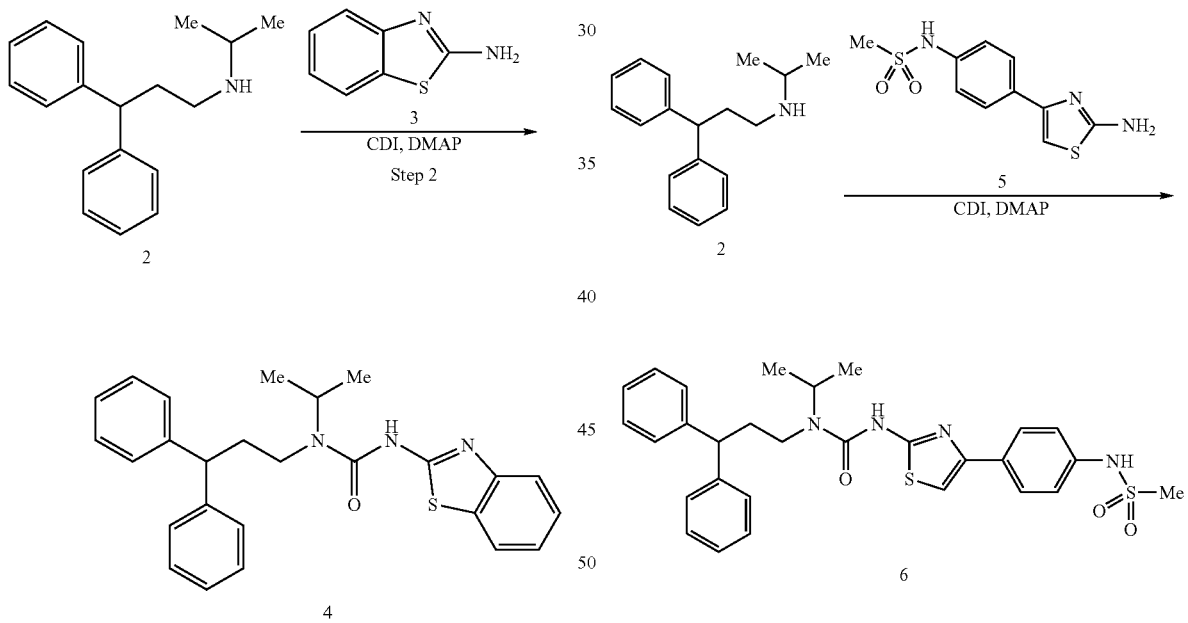

Step 1. To a solution of 3,3-diphenylpropan-1-amine 1 (4.22 g, 20.0 mmol) in DCE (100 mL) at room temperature was added acetone (1.19 g, 20.5 mmol, 1.50 mL), acetic acid (1.21 g, 20.1 mmol, 1.15 mL), and NaBH(OAc)$_3$ (5.98 g, 28.2 mmol). The reaction mixture was stirred at room temperature for 5 min, a significant amount of precipitate formed, THF (40 mL) was added, and stirring was continued at room temperature for 3 h. The reaction mixture was quenched with 5 M NaOH, partially concentrated, and diluted with EtOAc. The aqueous phase was extracted with EtOAc (2×) and the combined organic extracts were washed with brine (1×), dried over MgSO$_4$, filtered, and concentrated. Purification by flash column chromatography on silica gel (eluted with 2% to 8% MeOH (2 M NH$_3$) in DCM) gave N-isopropyl-3,3-diphenylpropan-1-amine 2 (4.60 g, 90.9% yield) as a colorless oil.

Mass spectrum: calculated for $C_{18}H_{23}N$ 253.2; found 254.2 (M++1).

Step 2. To a solution of CDI (0.146 g, 0.900 mmol) and DMAP (small catalytic amount) in DCM (1.3 mL) at room temperature was added benzo[d]thiazol-2-amine 3 (0.101 g, 0.672 mmol). The reaction mixture was stirred at room temperature for 1 d and N-isopropyl-3,3-diphenylpropan-1-amine 2 (0.213 g, 0.841 mmol) and DMF (0.5 mL) were added. The reaction mixture was stirred at room temperature for 3 d. Direct purification by flash column chromatography on silica gel (eluted with 50% to 100% DCM in hexanes) gave 3-(benzo[d]thiazol-2-yl)-1-(3,3-diphenylpropyl)-1-isopropylurea 4 (0.190 g) as a white solid.

Mass spectrum: calculated for $C_{26}H_{27}N_3OS$ 429.2; found 430.2 (M++1).

EXAMPLE 2

Synthesis of 1-(3,3-diphenylpropyl)-1-isopropyl-3-(4-(4-(methylsulfonamido)phenyl)thiazol-2-yl)urea, 6

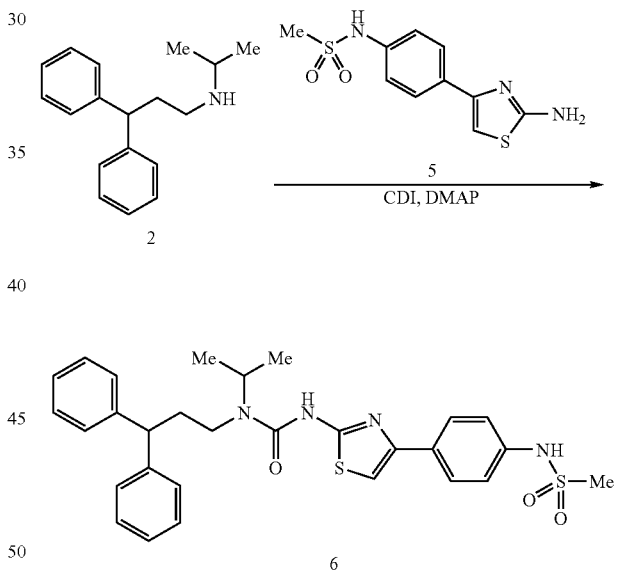

To a solution of CDI (0.163 g, 1.01 mmol) and DMAP (0.129 g, 1.06 mmol) in DMF (1 mL) at room temperature was added N-(4-(2-aminothiazol-4-yl)phenyl)methanesulfonamide 5 (0.178 g, 0.661 mmol). The reaction mixture was stirred at room temperature for 40 h and N-isopropyl-3,3-diphenylpropan-1-amine 2 (0.215 g, 0.849 mmol) was added. The reaction mixture was stirred at room temperature for 8 h and heated to 40° C. for 15 h. Direct purification by flash column chromatography on silica gel (eluted with 10% to 50% EtOAc in DCM) followed by purification by flash column chromatography on silica gel (eluted with 30% to 80% EtOAc in hexanes) gave 1-(3,3-diphenylpropyl)-1-isopropyl-3-(4-(4-(methylsulfonamido)-phenyl)thiazol-2-yl)urea 6 (0.219 g, 60.4% yield) as a white solid.

Mass spectrum: calculated for $C_{29}H_{32}N_4O_3S_2$ 548.2; found 549.2 (M++1).

EXAMPLE 3

Synthesis of 1-(3,3-diphenylpropyl)-3-(4-(4-(methylsulfonamido)phenyl)thiazol-2-yl)-1-propylurea, 8

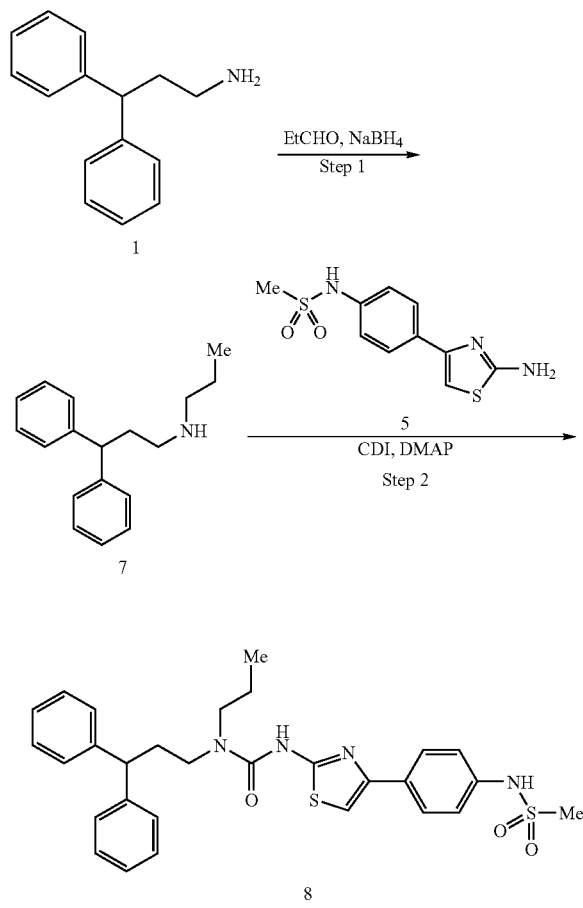

Step 1. To a solution of 3,3-diphenylpropan-1-amine 1 (4.22 g, 20.0 mmol) in MeOH (100 mL) at room temperature was added propionaldehyde (1.16 g, 20.0 mmol) (1.45 mL). The reaction mixture was stirred at room temperature for 3 h and sodium borohydride (1.20 g, 31.7 mmol) was added. The reaction mixture was stirred at room temperature for 2 h, quenched with 5 M NaOH, partially concentrated, and diluted with EtOAc. The aqueous phase was extracted with EtOAc (2×) and combined organic extracts were washed with brine (1×), dried over MgSO$_4$, filtered, and concentrated. Purification by flash column chromatography on silica gel (eluted with 2% to 8% MeOH (2 M NH$_3$) in DCM) gave 3,3-diphenyl-N-propylpropan-1-amine 7 as a pale yellow oil.

Mass spectrum: calculated for $C_{18}H_{23}N$ 253.2; found 254.2 (M++1).

Step 2. The procedure described in Example 2 with the exception of substituting N-isopropyl-3,3-diphenylpropan-1-amine 2 for 3,3-diphenyl-N-propylpropan-1-amine 7 was used to prepare 1-(3,3-diphenylpropyl)-3-(4-(4-(methylsulfonamido)phenyl)thiazol-2-yl)-1-propylurea 8 as a white solid. Mass spectrum: calculated for $C_{29}H_{32}N_4O_3S_2$ 548.2; found 549.2 (M++1).

EXAMPLE 4

Synthesis of 1-cyclopropyl-1-(3,3-diphenylpropyl)-3-(4-(4-(methylsulfonamido)phenyl)thiazol-2-yl)urea, 11

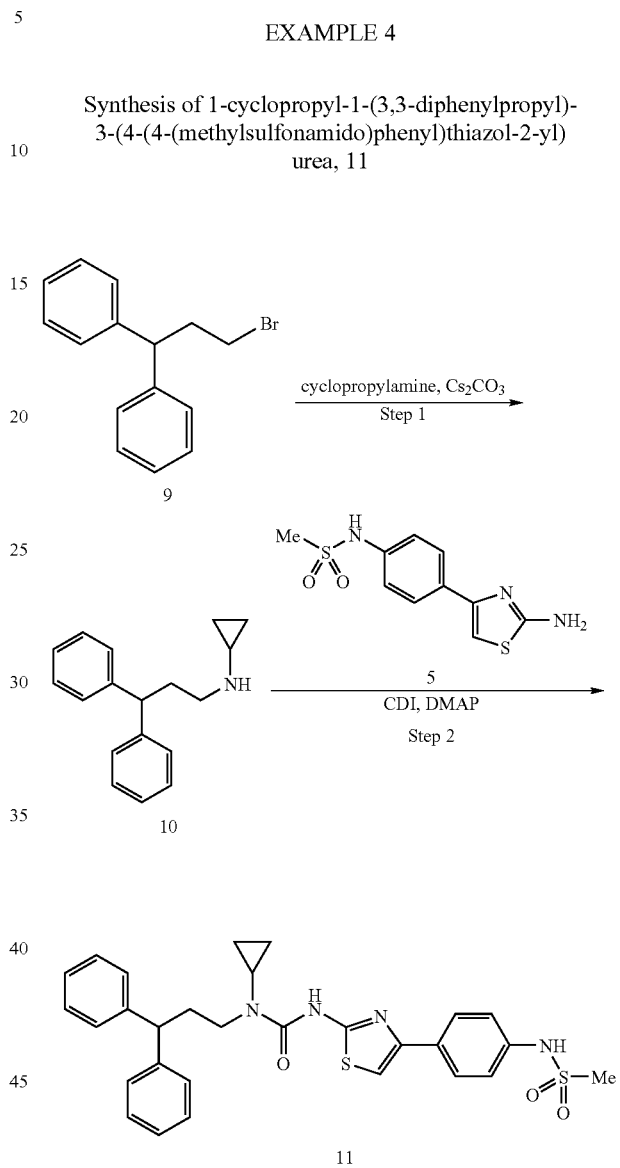

Step 1. To a solution of 3-bromo-1,1-diphenylpropane 9 (2.06 g, 7.49 mmol) in DMF (15 mL) at room temperature was added cyclopropylamine (3.26 g, 57.1 mmol, 4.0 mL) and cesium carbonate (3.19 g, 9.79 mmol). The reaction mixture was stirred at room temperature for 20 h and diluted with EtOAc. The aqueous phase was extracted with EtOAc (2×) and the combined organic extracts were washed with brine (1×), dried over MgSO$_4$, filtered, and concentrated. Purification by flash column chromatography on silica gel (eluted with 1% to 6% MeOH (2 M NH$_3$) in DCM) gave N-(3,3-diphenylpropyl)cyclopropanamine 10 as a colorless oil. Mass spectrum: calculated for $C_{18}H_{21}N$ 251.2; found 252.2 (M++1).

Step 2. The procedure described in Example 2 with the exception of substituting N-isopropyl-3,3-diphenylpropan-1-amine 2 for N-(3,3-diphenylpropyl)cyclopropanamine 10 was used to prepare 1-cyclopropyl-1-(3,3-diphenylpropyl)-3-

(4-(4-(methylsulfonamido)phenyl)thiazol-2-yl)urea 11 as a white solid. Mass spectrum: calculated for $C_{29}H_{30}N_4O_3S_2$ 546.2; found 547.2 (M++1).

EXAMPLE 5

Synthesis of 3-(5-chloro-4-(4-(methylsulfonamido)phenyl)thiazol-2-yl)-1-(3,3-diphenylpropyl)-1-methylurea, 14

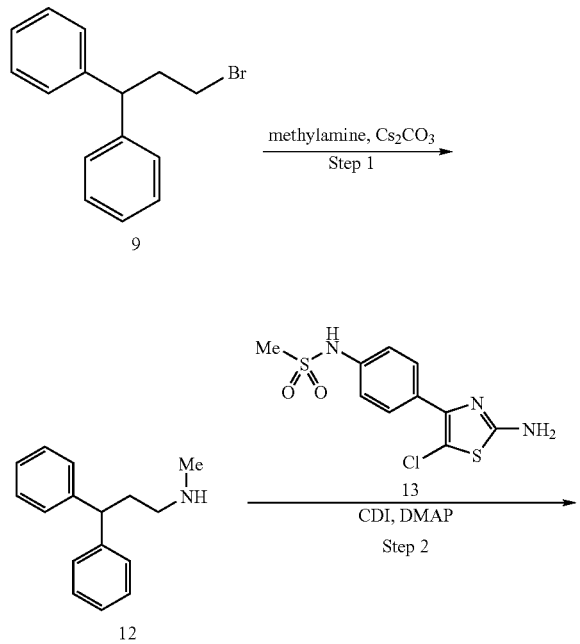

Step 1. The procedure described in Step 1 of Example 4 with the exception of substituting cyclopropylamine for methylamine was used to prepare 12 as a colorless oil.

Mass spectrum: calculated for $C_{16}H_{19}N$ 225.2; found 226.2 (M++1).

Step 2. To a mixture of N-(4-(2-amino-5-chlorothiazol-4-yl)phenyl)methanesulfonamide 13 (0.100 g, 0.33 mmol), DMAP (0.056 g, 0.46 mmol), and CDI (0.085 g, 0.52 mmol) was added DMF (0.5 mL). The reaction mixture was heated to 40° C. for 13 h and N-methyl-3,3-diphenylpropan-1-amine 12 (0.111 g, 0.49 mmol) was added. The reaction mixture was heated to 40° C. for 2 d. Direct purification by flash column chromatography on silica gel (eluted with 10% to 50% EtOAc in DCM), followed by purification by flash column chromatography on silica gel (eluted with 1% to 5% MeOH in DCM) gave 3-(5-chloro-4-(4-(methylsulfonamido)-phenyl)thiazol-2-yl)-1-(3,3-diphenylpropyl)-1-methylurea 14 as a white foam. Mass spectrum: calculated for $C_{27}H_{27}ClN_4O_3S_2$ 554.2; found 555.2 (M++1).

EXAMPLE 6

Synthesis of 1-(3,3-diphenylpropyl)-1-methyl-3-(4-(4-(methylsulfonamido)phenyl)thiazol-2-yl)urea, 15

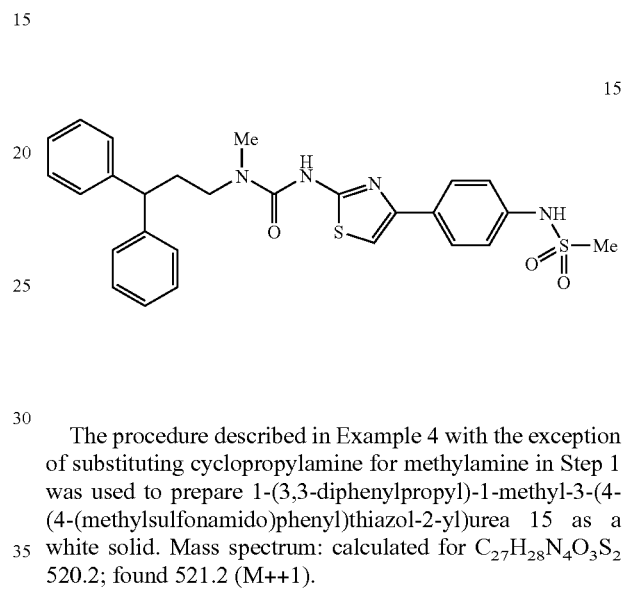

The procedure described in Example 4 with the exception of substituting cyclopropylamine for methylamine in Step 1 was used to prepare 1-(3,3-diphenylpropyl)-1-methyl-3-(4-(4-(methylsulfonamido)phenyl)thiazol-2-yl)urea 15 as a white solid. Mass spectrum: calculated for $C_{27}H_{28}N_4O_3S_2$ 520.2; found 521.2 (M++1).

EXAMPLE 7

Synthesis of 3-(5-chloro-4-(4-(methylsulfonamido)phenyl)thiazol-2-yl)-1-(3,3-diphenylpropyl)-1-phenylurea, 16

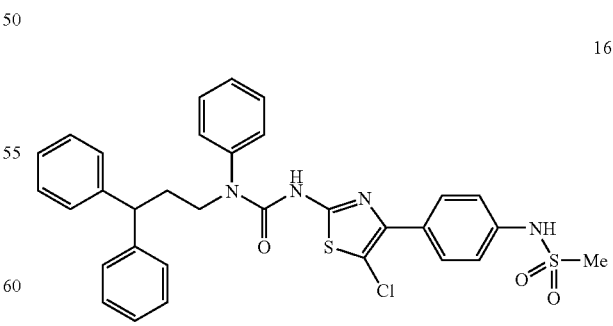

The procedure described in Example 5 with the exception of substituting cyclopropylamine for aniline in Step 1 was used to prepare 3-(5-chloro-4-(4-(methylsulfonamido)phenyl)thiazol-2-yl)-1-(3,3-diphenylpropyl)-1-phenylurea 16 as a white solid. Mass spectrum: calculated for $C_{32}H_{29}ClN_4O_3S_2$ 616.1; found 617.2 (M++1).

EXAMPLE 8

Synthesis of 1-benzyl-3-(5-chloro-4-(4-(methylsulfonamido)phenyl)thiazol-2-yl)-1-(3,3-diphenylpropyl)urea, 18

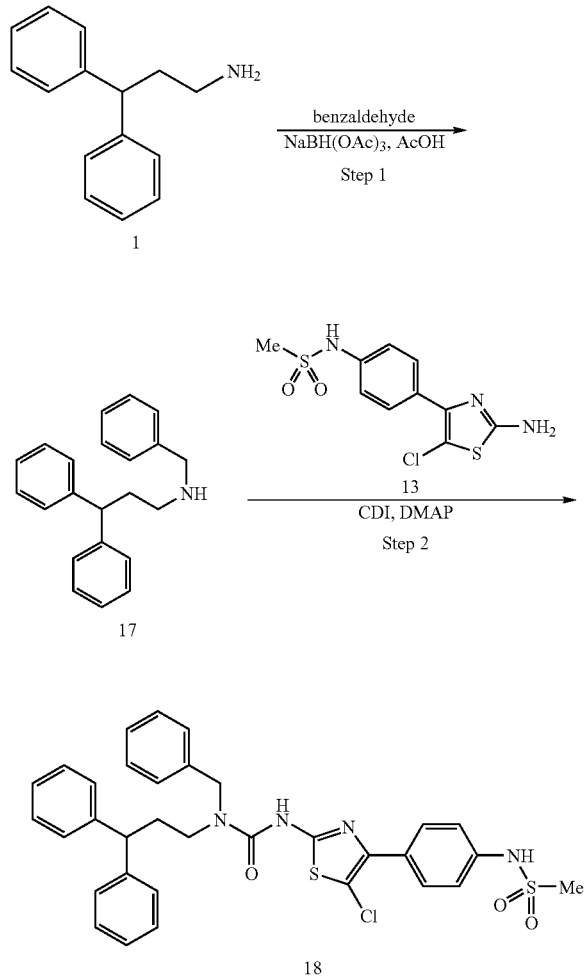

Step 1. The procedure described in Step 1 of Example 1 with the exception of substituting acetone for benzaldehyde was used to prepare N-benzyl-3,3-diphenylpropan-1-amine 17 as a colorless oil. Mass spectrum: calculated for $C_{32}H_{29}ClN_4O_3S_2$ 616.1; found 617.2 (M++1).

Step 2. The procedure described in Step 2 of Example 5 with the exception of substituting N-methyl-3,3-diphenylpropan-1-amine 12 for N-benzyl-3,3-diphenylpropan-1-amine 17 was used to prepare 18 as a white solid. Mass spectrum: calculated for $C_{33}H_{31}ClN_4O_3S_2$ 630.2; found 631.2 (M++1).

EXAMPLE 9

Synthesis of 3-(5-chloro-4-(4-(methylsulfonamido)phenyl)thiazol-2-yl)-1-(3,3-diphenylpropyl)-1-phenethylurea, 19

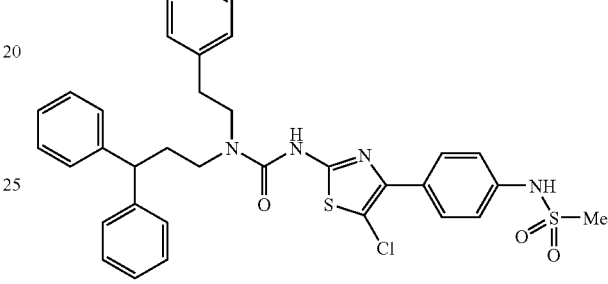

The procedure described in Example 8 with the exception of substituting benzaldehyde for 2-phenylacetaldehyde in Step 1 was used to prepare 3-(5-chloro-4-(4-(methylsulfonamido)-phenyl)thiazol-2-yl)-1-(3,3-diphenylpropyl)-1-phenethylurea 19 as a white solid. Mass spectrum: calculated for $C_{34}H_{33}ClN_4O_3S_2$ 644.2; found 645.2 (M++1).

EXAMPLE 10

Synthesis of 3-(5-chloro-4-(4-(methylsulfonamido)phenyl)thiazol-2-yl)-1-(3,3-diphenylpropyl)-1-(3-phenylpropyl)urea, 20

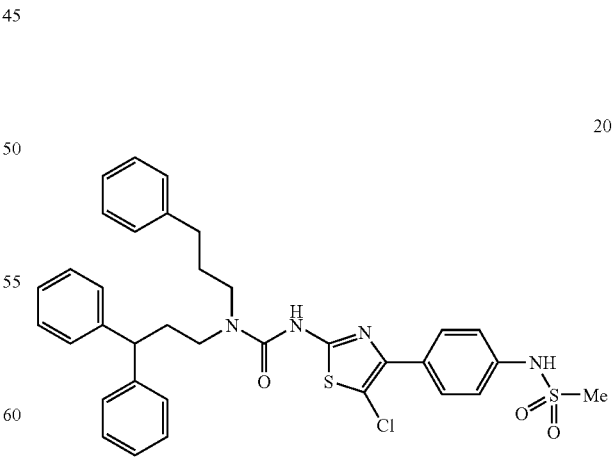

The procedure described in Example 8 with the exception of substituting benzaldehyde for 3-phenylpropanal in Step 1 was used to prepare 3-(5-chloro-4-(4-(methylsulfonamido)-phenyl)thiazol-2-yl)-1-(3,3-diphenylpropyl)-1-(3-phenylpropyl)urea 20 as a white solid. Mass spectrum: calculated for $C_{35}H_{35}ClN_4O_3S_2$ 658.2; found 659.2 (M++1).

EXAMPLE 11

Synthesis of 3-(5-chloro-4-(4-(methylsulfonamido) phenyl)thiazol-2-yl)-1-(3,3-diphenylpropyl)-1-(2-(pyridin-3-yl)ethyl)urea, 21

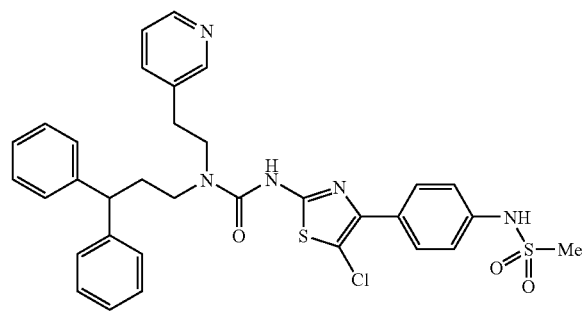

21

The procedure described in Example 8 with the exception of substituting benzaldehyde for 2-(pyridin-3-yl)ethanamine in Step 1 was used to prepare 3-(5-chloro-4-(4-(methylsulfonamido)phenyl)thiazol-2-yl)-1-(3,3-diphenylpropyl)-1-(2-(pyridin-3-yl)ethyl)urea 21 as a white solid. Mass spectrum: calculated for $C_{33}H_{32}ClN_5O_3S_2$ 645.2; found 646.2 (M++1).

EXAMPLE 12

Synthesis of 3-(5-chloro-4-(4-(methylsulfonamido) phenyl)thiazol-2-yl)-1-(3,3-diphenylpropyl)-1-(2-(pyridin-2-yl)ethyl)urea, 22

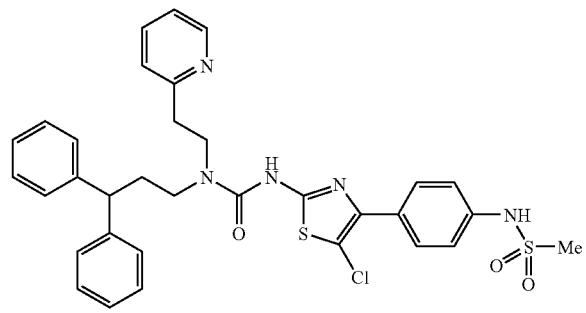

22

The procedure described in Example 8 with the exception of substituting benzaldehyde for 2-(pyridin-2-yl)ethanamine in Step 1 was used to prepare 3-(5-chloro-4-(4-(methylsulfonamido)phenyl)thiazol-2-yl)-1-(3,3-diphenylpropyl)-1-(2-(pyridin-2-yl)ethyl)urea 22 as a white solid. Mass spectrum: calculated for $C_{33}H_{32}ClN_5O_3S_2$ 645.2; found 646.2 (M++1).

EXAMPLE 13

Synthesis of 3-(5-chloro-4-(4-(methylsulfonamido) phenyl)thiazol-2-yl)-1-(3,3-diphenylpropyl)-1-(2-(pyridin-4-yl)ethyl)urea, 23

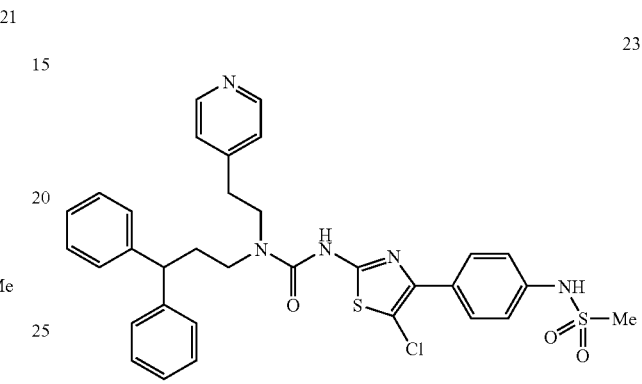

23

The procedure described in Example 8 with the exception of substituting benzaldehyde for 2-(pyridin-4-yl)ethanamine in Step 1 was used to prepare 3-(5-chloro-4-(4-(methylsulfonamido)phenyl)thiazol-2-yl)-1-(3,3-diphenylpropyl)-1-(2-(pyridin-4-yl)ethyl)urea 23 as a white solid. Mass spectrum: calculated 645.2; found 646.2 (M++1).

EXAMPLE 14

Synthesis of 1-(4-methoxyphenethyl)-3-(5-chloro-4-(4-(methylsulfonamido)phenyl)thiazol-2-yl)-1-(3,3-diphenylpropyl)urea, 24

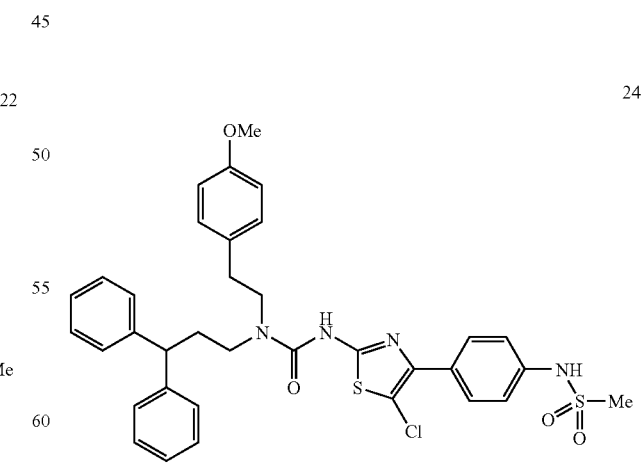

24

The procedure described in Example 8 with the exception of substituting benzaldehyde for 2-(4-methoxyphenyl)ethanamine in Step 1 was used to prepare 1-(4-methoxyphenethyl)-3-(5-chloro-4-(4-(methylsulfonamido)phenyl)thiazol-2-yl)-1-(3,3-diphenylpropyl)urea 24 as a white solid. Mass spectrum: calculated for $C_{35}H_{35}ClN_4O_4S_2$ 674.2; found 675.2 (M++1).

EXAMPLE 15

Synthesis of 1-(4-fluorophenethyl)-3-(5-chloro-4-(4-(methylsulfonamido)phenyl)thiazol-2-yl)-1-(3,3-diphenylpropyl)urea, 25

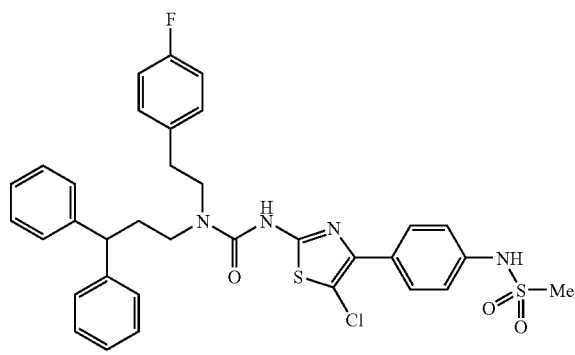

The procedure described in Example 8 with the exception of substituting benzaldehyde for 2-(4-fluorophenyl)ethanamine in Step 1 was used to prepare 1-(4-fluorophenethyl)-3-(5-chloro-4-(4-(methylsulfonamido)phenyl)thiazol-2-yl)-1-(3,3-diphenylpropyl)urea 25 as a white solid. Mass spectrum: calculated for $C_{34}H_{32}ClFN_4O_3S_2$ 662.2; found 663.2 (M++1).

EXAMPLE 16

Synthesis of 3-(benzo[d]thiazol-2-yl)-1-(3,3-diphenylpropyl)-1-methylurea, 26

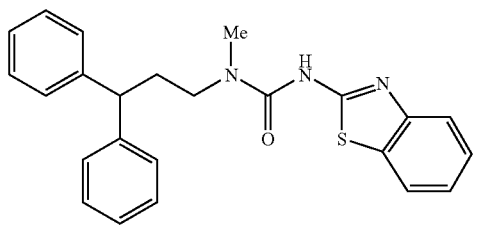

The procedure described in Example 5 with the exception of substituting benzo[d]thiazol-2-amine for N-(4-(2-amino-5-chlorothiazol-4-yl)phenyl)methanesulfonamide 13 in Step 2 was used to prepare 3-(benzo[d]thiazol-2-yl)-1-(3,3-diphenylpropyl)-1-methylurea 26 as a white solid. LCMS (ES) calcd for $C_{24}H_{23}N_3OS$ 401.2 found 402.1 (MH+).

EXAMPLE 17

Synthesis of 1-(3,3-diphenylpropyl)-1-methyl-3-(4-phenylthiazol-2-yl)urea, 27

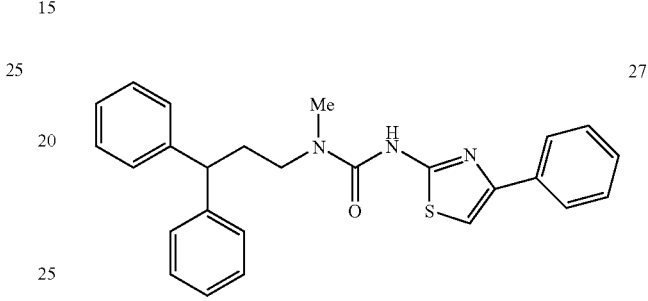

The procedure described in Example 5 with the exception of substituting 4-phenylthiazol-2-amine for N-(4-(2-amino-5-chlorothiazol-4-yl)phenyl)methanesulfonamide 13 in Step 2 was used to prepare 1-(3,3-diphenylpropyl)-1-methyl-3-(4-phenylthiazol-2-yl)urea 27 as a white solid. LCMS (ES) calcd for $C_{26}H_{25}N_3OS$ 427.2 found 428.2 (MH+).

EXAMPLE 18

Synthesis of 3-(benzo[d]thiazol-2-yl)-1-(3,3-diphenylpropyl)-1-propylurea, 28

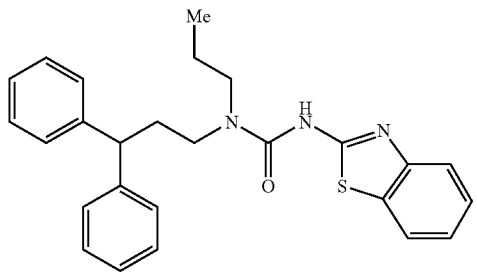

The procedure described in Example 3 with the exception of substituting benzo[d]thiazol-2-amine for N-(4-(2-aminothiazol-4-yl)phenyl)methanesulfonamide 5 in Step 2 was used to prepare 3-(benzo[d]thiazol-2-yl)-1-(3,3-diphenylpropyl)-1-propylurea 28 as a white solid. LCMS (ES) calcd for $C_{26}H_{27}N_3OS$ 429.2 found 430.1 (MH+).

EXAMPLE 19

Synthesis of 3-(3-(benzo[d]thiazol-2-yl)-1-(3,3-diphenylpropyl)ureido)cyclopentanecarboxylic acid, 36

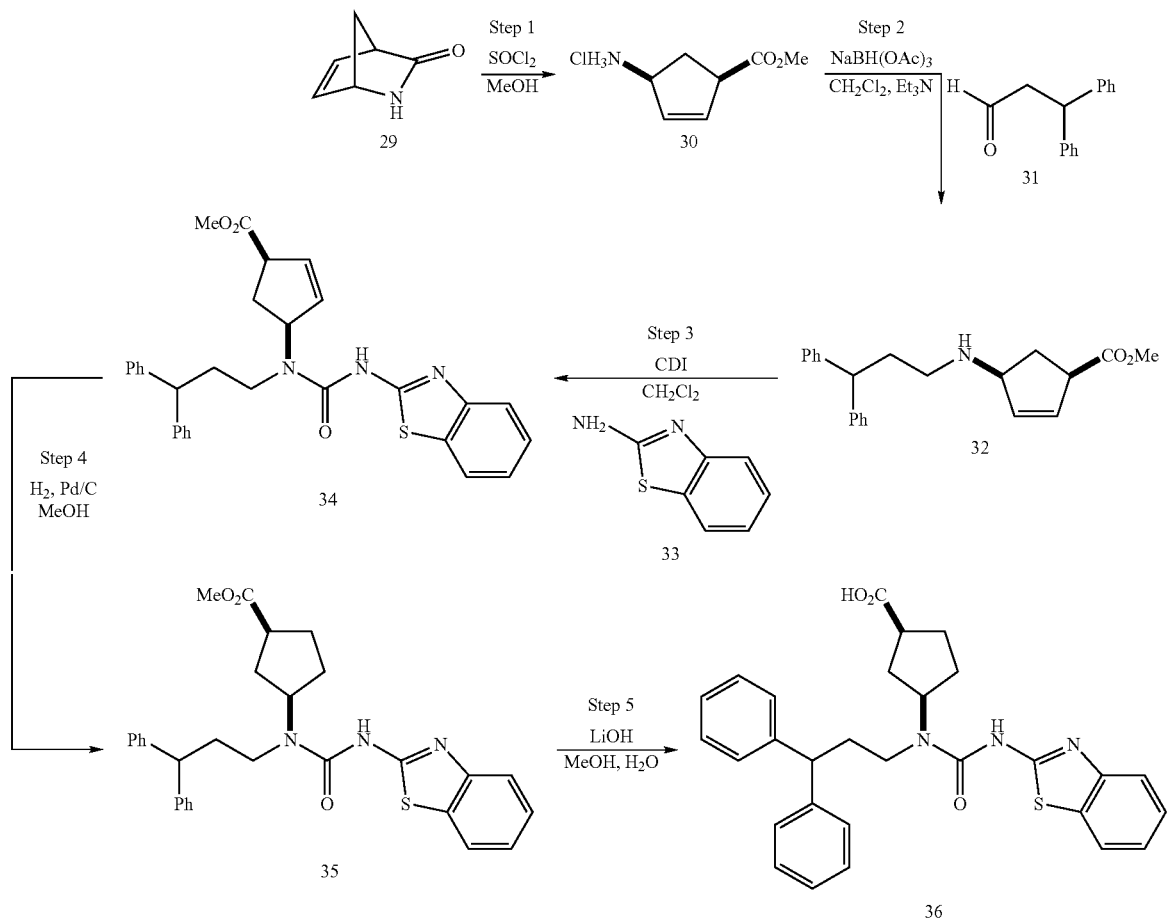

Step 1: A solution of MeOH (20 mL) cooled to −40° C. was carefully treated with SOCl$_2$ (730 µL, 10 mmol). Once the addition was complete the cooling bath was removed and the reaction warmed to room temperature for 1 h. Following this period racemic 2-aza-bicyclo[2.2.1]hept-5-en-3-one 29 (1.08 g, 9.89 mmol) was added and the reaction mixture left to stir for 18 h. Volatiles were removed by concentration under reduced pressure to afford a brown tar. The tar solidified upon heating to 50° C. under high vacuum for 12 h. The resulting solid was used without further purification.

Step 2: A solution of the crude amine salt 30 (~9.8 mmol) and 3,3-diphenylpropanal 31 (1.06 g, 5 mmol) in dichloromethane (35 mL) was treated sequentially with triethylamine (700 µL, 5 mmol) and sodium triacetoxy borohydride (2.65 g, 12.0 mmol). The reaction mixture was stirred for 12 h and was quenched by the addition of 30 mL saturated aqueous NaHCO$_3$. The resulting biphasic mixture stirred for 1 h. The organic layer was separated and the aqueous layer extracted with 2×30 mL CH$_2$Cl$_2$. The combined organic extracts were dried with magnesium sulfate, filtered, and concentrated. Purification by chromatography on silica using gradient 0->10% MeOH/CH$_2$Cl$_2$+0->1% NH$_4$OH as afforded 32 as light brown oil (1.2 g, 71% yield). LCMS (ES) calc'd for C$_{22}$H$_{25}$NO$_2$ 335.2 found 336.2 (MH$^+$).

Step 3: To a solution of benzo[d]thiazol-2-amine 33 (128.7 mg, 0.857 mmol) in CH$_2$Cl$_2$ (10 ml) was added di(1H-imidazol-1-yl)methanone (231.9 mg, 1.43 mmol). The reaction mixture was stirred overnight at 35° C. Methyl 4-(3,3-diphenylpropylamino)cyclopent-2-enecarboxylate 32 (335.4 mg, 1 mmol) was added and the reaction mixture was heated to 35° C. overnight. The reaction mixture was poured into 20 mL of aqueous saturated NaHCO$_3$ and extracted with dichloromethane (3×20 mL). The combined organic extracts were dried with magnesium sulfate, filtered, and concentrated. The residue was purified by chromatography on silica using 10->45% EtOAc/Hexanes as eluant to give 34 as a white solid (245 mg, 48% yield). LCMS (ES) calcd for C$_{30}$H$_{29}$N$_3$O$_3$S 511.2 found 512.2 (MH$^+$).

Step 4: To a solution of methyl 4-(3-(benzo[d]thiazol-2-yl)-1-(3,3-diphenylpropyl)ureido)cyclopent-2-enecarboxylate 34 in MeOH (15 ml) was carefully added 10% palladium on carbon. A balloon containing H$_2$ was then used to bubble H$_2$ into the reaction mixture for 1 min. After this time, the reaction mixture was capped with the balloon of H$_2$ and left to stir for 36 h. The reaction mixture was uncapped and carefully degassed by bubbling N$_2$ through the reaction mixture for 2 min. The black suspension was filtered through a pad of celite to remove the catalyst and then concentrated. The resulting

EXAMPLE 20

Synthesis of (1S,3S)-3-(3-(benzo[d]thiazol-2-yl)-1-(3,3-diphenylpropyl)ureido)cyclopentanecarboxylic acid, 43

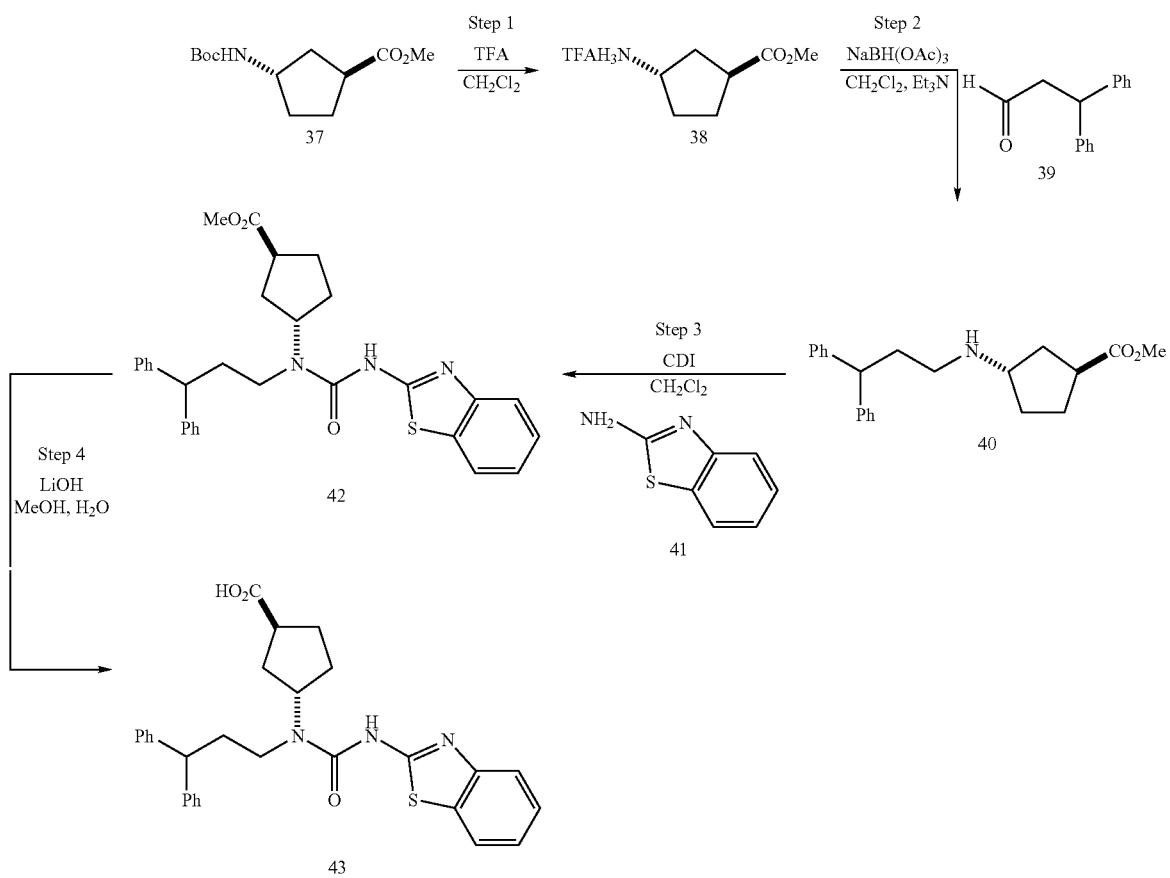

white foam was used without further purification (308 mg). LCMS (ES) calc'd for C$_{30}$H$_{31}$N$_3$O$_3$S 513.2 found 514.2 (MH$^+$).

Step 5: To a solution of methyl 3-(3-(benzo[d]thiazol-2-yl)-1-(3,3-diphenylpropyl)ureido)cyclopentanecarboxylate 35 (308 mg, 600 μmol) in 10:1 MeOH/H$_2$O (5.5 ml) was added lithium hydroxide hydrate (50.3 mg, 1199 μmol). The reaction mixture was stirred for overnight at 55° C. Volatiles were removed by concentration under reduced pressure. The leftover residue was solubilized with 60 mL of a 1:1 mixture of Water and Ethyl Acetate. An additional 2 mL of 2M KOH was added. The organic phase was separated and the aqueous phase was extracted further with ethyl acetate (2×20 mL). The organic extracts were discarded and the aqueous layer was acidified with 10 mL of 10% aqueous HCl and extracted with ethyl acetate (3×20 mL). The combined organic extracts were dried with magnesium sulfate, filtered, and concentrated. The residue was purified by chromatography on silica using 10->45% EtOAc/Hexanes as eluant to afford 36 as a white solid. LCMS (ES) calcd for C$_{29}$H$_{29}$N$_3$O$_3$S 499.2 found 500.2 (MH$^+$).

Step 1: To a solution of (1S,3S)-methyl 3-(tert-butoxycarbonyl)cyclopentanecarboxylate 37 in CH$_2$Cl$_2$ (2 mL) was added trifluoroacetic acid (2 mL). The reaction mixture was allowed to stir for 3 h. Volatiles were removed by concentration under reduced pressure. The resulting residue was reconcentrated twice from toluene (2×10 mL) to ensure removal of all volatiles. The product was used without further purification.

Step 2: A solution of the unpurified amine salt 38 (~2.0 mmol) and 3,3-diphenylpropanal 39 (420 mg, 2 mmol) in dichloromethane (10 mL) was treated sequentially with triethylamine (420 μL, 3 mmol) and sodium triacetoxy borohydride (1.06 g, 5 mmol). The reaction mixture stirred for 12 h and was quenched by the addition of 20 mL saturated aqueous NaHCO$_3$. The resulting biphasic mixture stirred for 1 h. The organic layer was separated and the aqueous layer extracted with 2×30 mL CH$_2$Cl$_2$. The combined organic extracts were dried with magnesium sulfate, filtered, and concentrated. Purification by chromatography on silica using 0->10% MeOH/CH$_2$Cl$_2$+0->1% NH$_4$OH as afforded 40 as white solid. LCMS (ES) calc'd for C$_{22}$H$_{27}$NO$_2$ 337.2 found 338.2 (MH$^+$).

Step 3: To a solution of benzo[d]thiazol-2-amine 41 (90.1 mg, 0.6 mmol) in CH$_2$Cl$_2$ (10 ml) was added di(1H-imidazol- 1-yl)methanone (16.21 mg, 1 mmol). The reaction mixture was stirred overnight at 35° C. (1S,3S)-methyl 3-(3,3-diphenylpropylamino)cyclopentanecarboxylate 40 (236.3 mg, 0.7 mmol) was added and the reaction mixture was heated to 35° C. overnight. The reaction mixture was poured into 20 mL of aqueous saturated NaHCO₃ and extracted with dichloromethane (3×20 mL). The combined organic extracts were dried with magnesium sulfate, filtered, and concentrated. The residue was purified by chromatography on silica using 10->45% EtOAc/Hexanes as eluant to give 42 as a white solid (223 mg). LCMS (ES) calc'd for $C_{30}H_{31}N_3O_3S$ 513.2 found 514.2 (MH⁺).

Step 4: To a solution of (1S,3S)-methyl 3-(3-(benzo[d]thiazol-2-yl)-1-(3,3-diphenylpropyl)ureido)cyclopentanecarboxylate 42 (303 mg, 589 μmol) in 8:1 MeOH/H₂O (18 ml) was added lithium hydroxide hydrate (49.5 mg, 1180 μmol). The reaction mixture was stirred for overnight at 55° C. Volatiles were removed by concentration under reduced pressure. The leftover residue was treated with 10 mL water and 10 mL of aqueous 10% HCl. A precipitate formed upon addition of the acid. After standing for 10 min the precipitate was filtered and washed with copious of amounts of water. After drying under vacuum, the precipitate was purified by injection as a solution in DMF on a reverse phase HPLC column using 5->95% CH₃CN/0.1% aqueous TFA as eluant. Product 43 was isolated as white solid (250 mg). LCMS (ES) calcd for $C_{29}H_{29}N_3O_3S$ 499.2 found 500.2 (MH⁺).

diphenylpropyl)ureido)cyclopentanecarboxylic acid 44 as a white solid. LCMS (ES) calc'd for $C_{29}H_{29}N_3O_3S$ 499.2 found 500.2 (MH⁺).

EXAMPLE 22

Synthesis of trans-3-(3-(benzo[d]thiazol-2-yl)-1-(3,3-diphenylpropyl)ureido)cyclobutanecarboxylic acid, 22

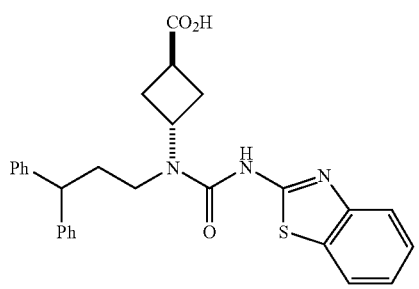

The procedure described in Example 20 with the exception of substituting trans-methyl 3-(tert-butoxycarbonyl)cyclobutanecarboxylate for (1S,3S)-methyl 3-(tert-butoxycarbonyl)cyclopentanecarboxylate 37 in Step 1 was used to prepare trans-3-(3-(benzo[d]thiazol-2-yl)-1-(3,3-diphenylpropyl)ureido)cyclobutanecarboxylic acid 45 as a white solid. LCMS (ES) calc'd for $C_{28}H_{27}N_3O_3S$ 485.2 found 486.2 (MH⁺).

EXAMPLE 21

Synthesis of (1R,3R)-3-(3-(benzo[d]thiazol-2-yl)-1-(3,3-diphenylpropyl)ureido)cyclopentanecarboxylic acid, 44

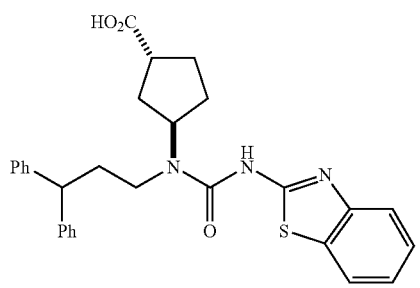

The procedure described in Example 20 with the exception of substituting (1R,3R)-methyl 3-(tert-butoxycarbonyl)cyclopentanecarboxylate for (1S,3S)-methyl 3-(tert-butoxycarbonyl)cyclopentanecarboxylate 37 in Step 1 was used to prepare (1R,3R)-3-(3-(benzo[d]thiazol-2-yl)-1-(3,3-

EXAMPLE 23

Synthesis of cis-3-(3-(benzo[d]thiazol-2-yl)-1-(3,3-diphenylpropyl)ureido)cyclobutanecarboxylic acid, 46

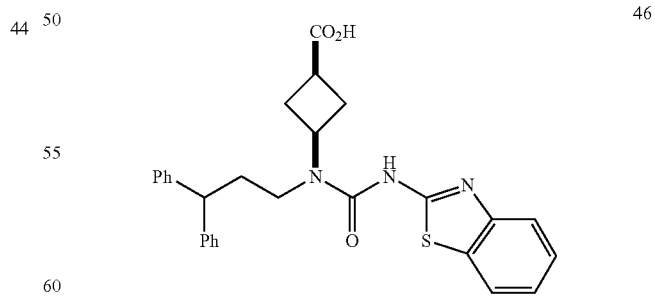

The procedure described in Example 20 with the exception of substituting cis-methyl 3-(tert-butoxycarbonyl)cyclobutanecarboxylate for (1S,3S)-methyl 3-(tert-butoxycarbonyl)cyclopentanecarboxylate 37 in Step 1 was used to prepare cis-3-(3-(benzo[d]thiazol-2-yl)—(3,3-diphenylpropyl)ureido)cyclobutanecarboxylic acid 46 as a white solid. LCMS (ES) calc'd for $C_{28}H_{27}N_3O_3S$ 485.2 found 486.1 (MH+).

EXAMPLE 24

Synthesis of trans-2-((3-(benzo[d]thiazol-2-yl)-1-(3,3-diphenylpropyl)ureido)methyl)cyclopropanecarboxylic acid, 47

The procedure described in Example 20 with the exceptions of omitting Step 1, of not using triethyl amine in Step 2, of substituting 3,3-diphenylpropan-1-amine for unpurified amine salt 38 in Step 2, and of substituting trans-ethyl 2-formylcyclopropanecarboxylate for 3,3-diphenylpropanal 39 in Step 2 was used to prepare trans-2-((3-(benzo[d]thiazol-2-yl)-1-(3,3-diphenylpropyl)ureido)methyl)cyclopropanecarboxylic acid 47 as a white solid.

LCMS (ES) calcd for $C_{28}H_{27}N_3O_3S$ 485.2 found 486.2 (MH+).

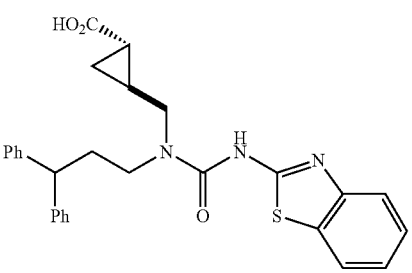

EXAMPLE 25

Synthesis of 3-(5-chloro-4-(4-(methylsulfonamido)phenyl)thiazol-2-yl)-1-(3,3-diphenylpropyl)-1-(2-(piperidin-4-yl)ethyl)urea, 51

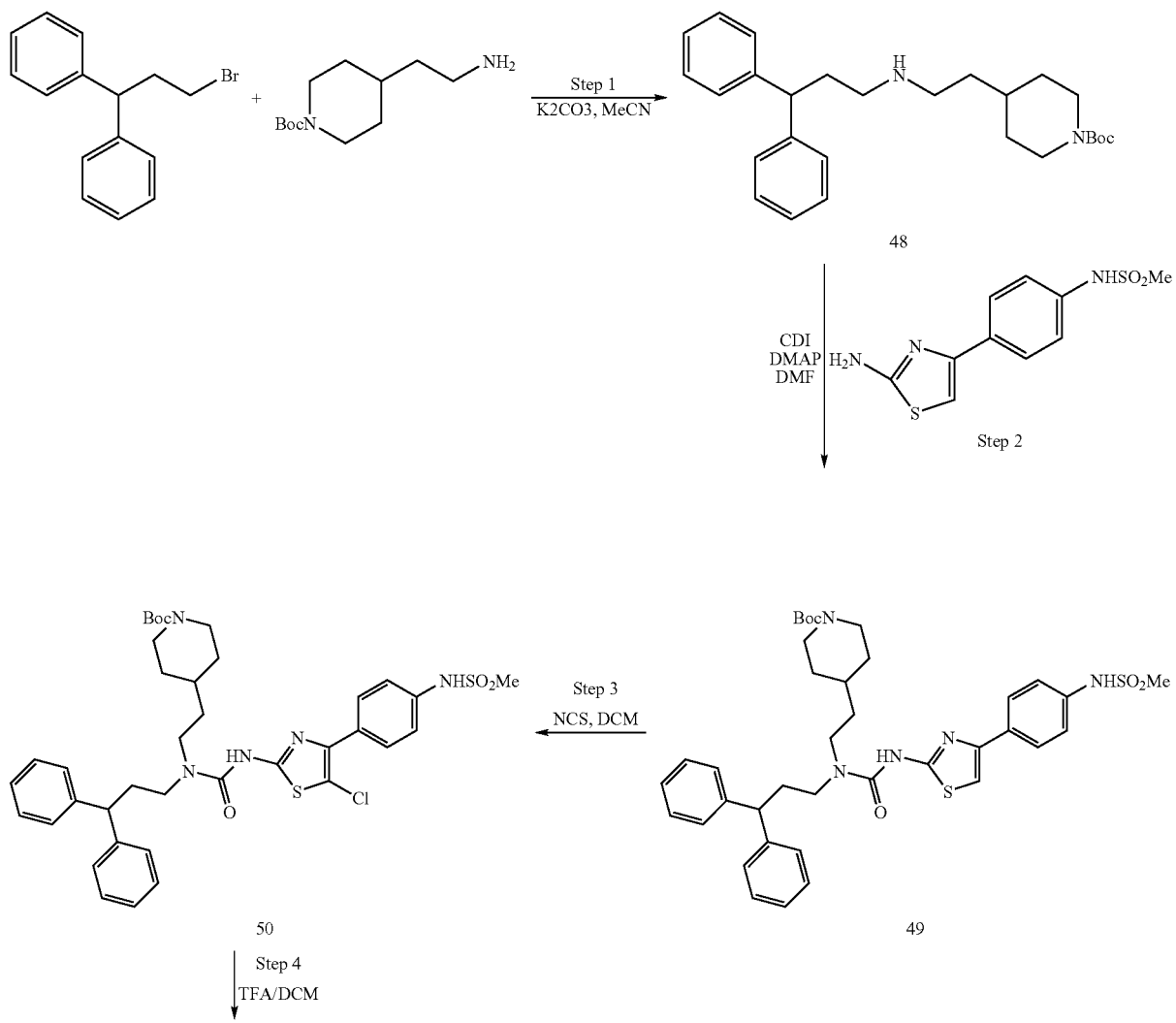

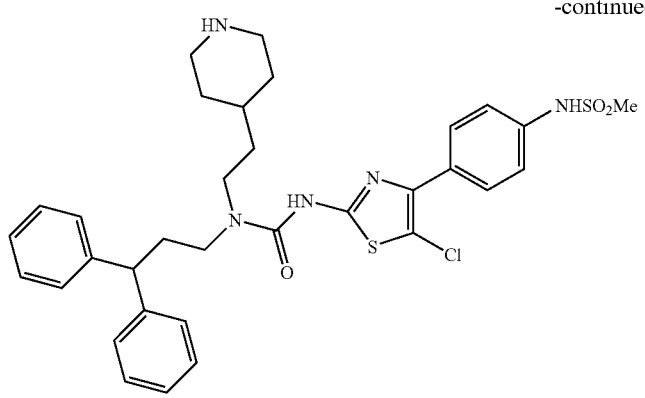

51

Step 1. 3-bromo-1,1-diphenylpropane (2.6 g, 9 mmol) and tert-butyl 4-(2-aminoethyl)piperidine-1-carboxylate (4.7 g, 21 mmol) were mixed together in acetonitrile (100 ml) and potassium carbonate (1.3 g, 9 mmol) was added. The resulting mixture was heated to 65° C. with stirring under $N_2$ overnight. After that time the mixture was cooled and concentrated under reduced pressure. The residue was partitioned between DCM and water. The DCM layer was washed with water, dried over $MgSO_4$ and concentrated under reduced pressure to give the crude product as a clear oil. The crude product was purified by combiflash (0-10% MeOH/DCM) to give tert-butyl 4-(2-(3,3-diphenylpropylamino)ethyl)piperidine-1-carboxylate 48.

Step 2. DMAP (0.17 g, 1 0.4 mmol), CDI (0.23 g, 1.4 mmol) and N-(4-(2-aminothiazol-4-yl)phenyl)-methanesulfonamide (0.25 g, 0.93 mmol) were mixed together in DCM/DMF and then stirred overnight at room temperature. After 24 hrs a precipitate had formed. tert-butyl 4-(2-(3,3-diphenylpropylamino)ethyl)piperidine-1-carboxylate (0.39 g, 0.93 mmol) was then added and the resulting mixture stirred for a further 15 hrs. The crude mixture was concentrated under reduced pressure and the residue purified by combi-flash to give tert-butyl 4-(2-(1-(3,3-diphenylpropyl)-3-(4-(4-(methylsulfonamido)phenyl)thiazol-2-yl)ureido)ethyl)piperidine-1-carboxylate 49 as an oily solid.

Step 3. To tert-butyl 4-(2-(1-(3,3-diphenylpropyl)-3-(4-(4-(methylsulfonamido)phenyl)thiazol-2-yl)ureido)ethyl)piperidine-1-carboxylate (0.35 g, 0.49 mmol) in DMF (10 ml) was added NCS (0.065 g, 0.49 mmol). The resulting mixture was stirred overnight at room temperature. After this time the mixture was concentrated under reduced pressure and the residue partitioned between ethyl acetate and sat. aq. $NaHCO_3$. The organic layer was washed with water and brine, dried over $MgSO_4$ and concentrated under reduced pressure to give the crude product as a thick yellow oil. This crude product was purified by combi-flash (10-50% EtOAc/hexane). To give tert-butyl 4-(2-(3-(5-chloro-4-(4-(methylsulfonamido)phenyl)thiazol-2-yl)-1-(3,3-diphenylpropyl)ureido)ethyl)piperidine-1-carboxylate 50 as a yellow oil.

Step 4. To tert-butyl 4-(2-(3-(5-chloro-4-(4-(methylsulfonamido)phenyl)thiazol-2-yl)-1-(3,3-diphenylpropyl)ureido)ethyl)piperidine-1-carboxylate (0.29 g, 0.4 mmol) dissolved in DCM (2 ml) was added TFA (0.5 ml, 7 mmol). The resulting mixture was stirred at room temperature for 2 hours. After this time the mixture was concentrated under reduced pressure and the residue triturated with diethyl ether. The pale yellow solid was filtered, washed with ether and dried under vacuum. This solid TFA salt was partitioned between DCM and saturated aqueous $NaHCO_3$. The aqueous was re-extracted with DCM (×2). The combined organic extracts were dried over $MgSO_4$ and concentrated up. The residue was taken up in dry DCM and HCl (2M in diethyl ether) was added. The cloudy solution was conc under reduced pressure and dried under high vac to give 3-(5-chloro-4-(4-(methylsulfonamido)phenyl)thiazol-2-yl)-1-(3,3-diphenylpropyl)-1-(2-(piperidin-4-yl)ethyl)urea HCl salt 51 as a pale yellow solid.

LCMS (ES) calcd for $C_{33}H_{38}ClN_5O_3S_2$ 652.27 found 653.3 ($MH^+$).

The following examples were prepared as described for Example 1 using the appropriate piperidine based amine and substituted phenyl thiazole. Some examples were deprotected as described in step 4 without prior chlorination.

EXAMPLE 26

Synthesis of 1-(3,3-diphenylpropyl)-3-(4-(4-(methylsulfonyl)phenyl)thiazol-2-yl)-1-(2-(piperidin-4-yl)ethyl)urea, 52

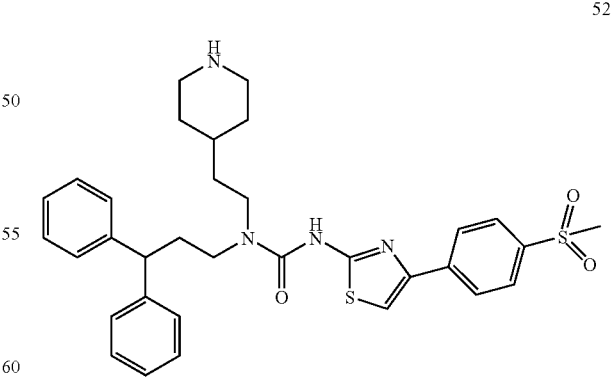

52

The procedure described in Example 25 with the exceptions of substituting 4-(4-(methylsulfonyl)phenyl)thiazol-2-amine for N-(4-(2-aminothiazol-4-yl)phenyl)-methanesulfonamide in Step 2, and omitting Step 3 was used to prepare 1-(3,3-diphenylpropyl)-3-(4-(4-(methylsulfonyl)

phenyl)thiazol-2-yl)-1-(2-(piperidin-4-yl)ethyl)urea 52 as a solid. LCMS (ES) calc'd for $C_{33}H_{38}N_4O_3S_2$ 602.81 found 604.1 (MH+).

EXAMPLE 27

Synthesis of methyl 4-(2-(3-(3,3-diphenylpropyl)-3-(2-(piperidin-4-yl)ethyl)ureido)thiazol-4-yl)benzoate, 53

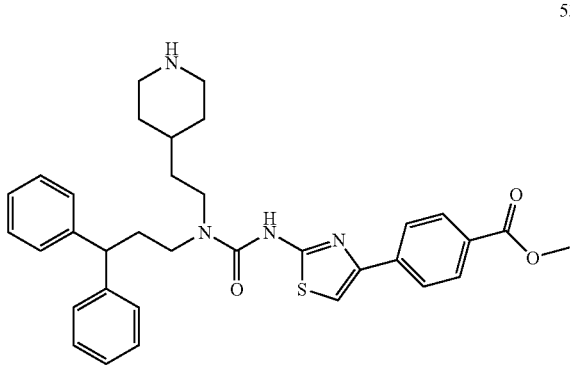

53

The procedure described in Example 25 with the exceptions of substituting methyl 4-(2-aminothiazol-4-yl)benzoate for N-(4-(2-aminothiazol-4-yl)phenyl)-methanesulfonamide in Step 2, and omitting Step 3 was used to prepare methyl 4-(2-(3-(3,3-diphenylpropyl)-3-(2-(piperidin-4-yl)ethyl)ureido)thiazol-4-yl)benzoate 53 as a solid. LCMS (ES) calc'd for $C_{34}H_{38}N_4O_3S$ 582.76 found 583.9 (MH+).

EXAMPLE 28

Synthesis of 3-(5-chloro-4-(4-(methylsulfonyl)phenyl)thiazol-2-yl)-1-(3,3-diphenylpropyl)-1-(2-(piperidin-4-yl)ethyl)urea, 54

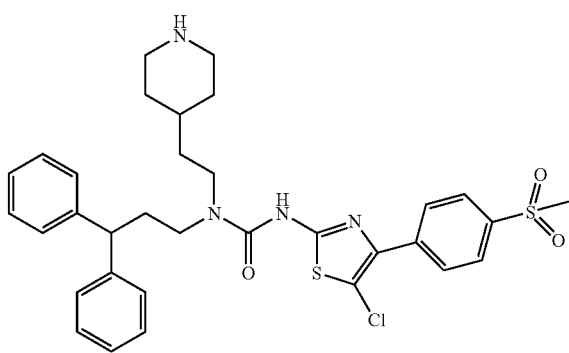

54

The procedure described in Example 25 was used with the exception of substituting 4-(4-(methylsulfonyl)phenyl)thiazol-2-amine for N-(4-(2-aminothiazol-4-yl)phenyl)-methanesulfonamide in Step 2 was used to prepare 3-(5-chloro-4-(4-(methylsulfonyl)phenyl)thiazol-2-yl)-1-(3,3- diphenylpropyl)-1-(2-(piperidin-4-yl)ethyl)urea 54 as a solid. LCMS (ES) calc'd for $C_{33}H_{37}ClN_4O_3S_2$ 637.26 found 638.5 (MH+).

EXAMPLE 29

Synthesis of 1-(3,3-diphenylpropyl)-3-(4-(4-(methylsulfonamido)phenyl)thiazol-2-yl)-1-(2-(piperidin-3-yl)ethyl)urea, 55

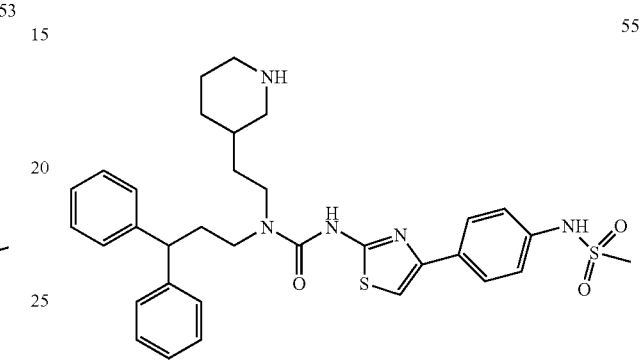

55

The procedure described in Example 25 was used with the exceptions of substituting tert-butyl 3-(2-aminoethyl)piperidine-1-carboxylate for tert-butyl 4-(2-aminoethyl)piperidine-1-carboxylate in Step 1 and omitting Step 3 was used to prepare 1-(3,3-diphenylpropyl)-3-(4-(4-(methylsulfonamido)phenyl)thiazol-2-yl)-1-(2-(piperidin-3-yl)ethyl)urea 55 as a solid. LCMS (ES) calc'd for $C_{33}H_{39}N_5O_3S_2$ 617.82 found 619.0 (MH+).

EXAMPLE 30

Synthesis of 1-(3,3-diphenylpropyl)-3-(4-(4-(methylsulfonamido)phenyl)thiazol-2-yl)-1-(2-(piperidin-4-yl)ethyl)urea, 56

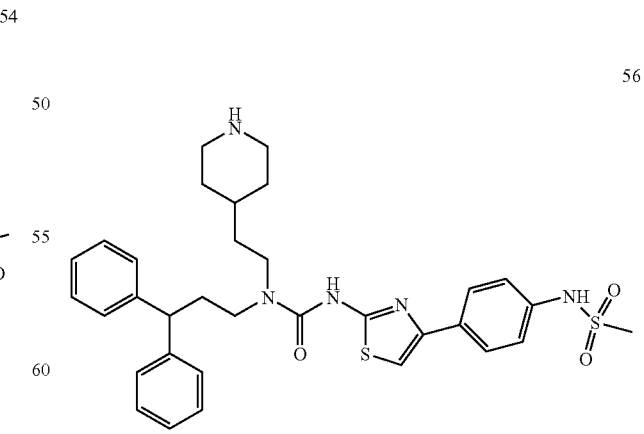

56

The procedure described in Example 25 was used with the exception of omitting Step 3 to prepare 1-(3,3-diphenylpropyl)-3-(4-(4-(methylsulfonamido)phenyl)thiazol-2-yl)-1-(2-

(piperidin-4-yl)ethyl)urea 56 as a solid. LCMS (ES) calc'd for $C_{33}H_{39}N_5O_3S_2$ 617.82 found 618.6 (MH+).

EXAMPLE 31

Synthesis of 3-(5-chloro-4-(4-(methylsulfonamido)phenyl)thiazol-2-yl)-1-(3,3-diphenylpropyl)-1-(2-(piperidin-3-yl)ethyl)urea, 57

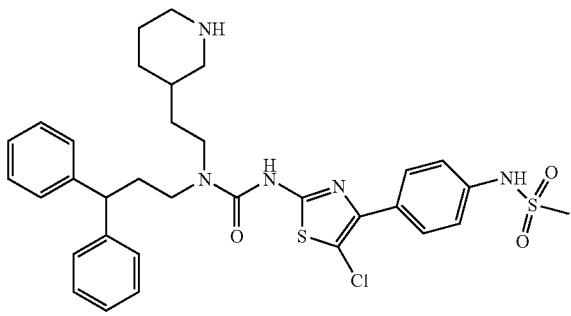

57

The procedure described in Example 25 was used with the exception of substituting tert-butyl 3-(2-aminoethyl)piperidine-1-carboxylate for tert-butyl 4-(2-aminoethyl)piperidine-1-carboxylate in Step 1 to prepare 3-(5-chloro-4-(4-(methylsulfonamido)phenyl)thiazol-2-yl)-1-(3,3-diphenylpropyl)-1-(2-(piperidin-3-yl)ethyl)urea 57 as a solid. LCMS (ES) calc'd for $C_{33}H_{38}ClN_5O_3S_2$ 652.27 found 653.6 (MH+).

EXAMPLE 32

Synthesis of 3-[3-(2-Cyclohexyl-ethyl)-3-(3,3-diphenyl-propyl)-ureido]-benzoic acid methyl ester, 60

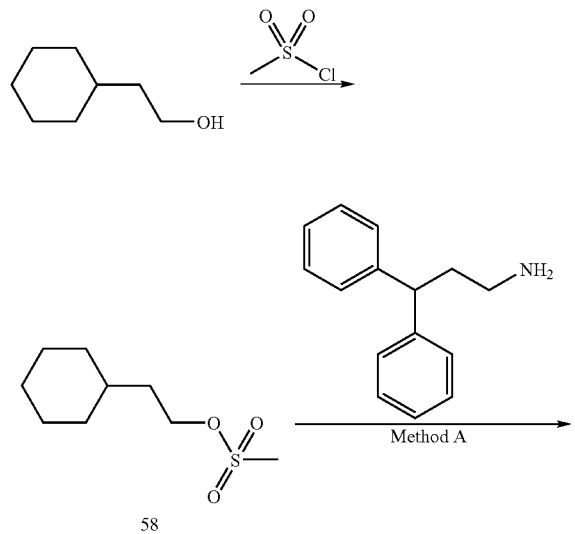

58

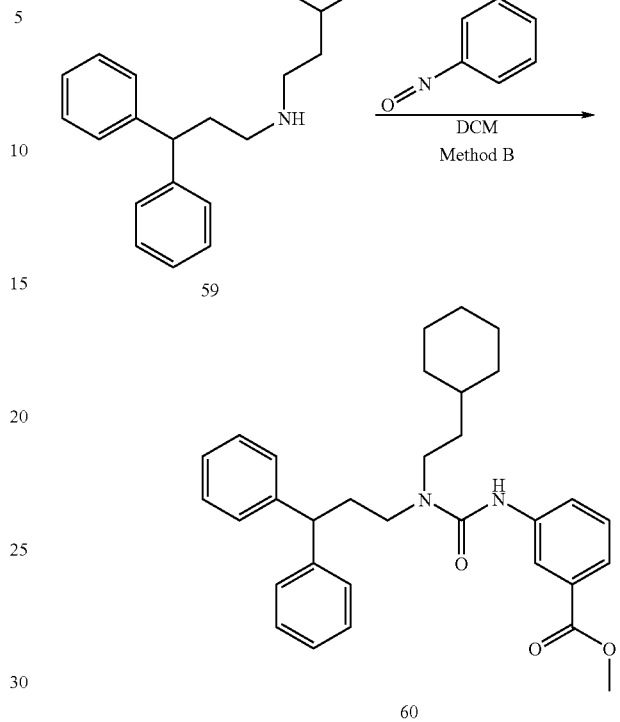

60

Synthesis of methanesulfonic acid 2-cyclohexyl-ethyl ester, 58.

150 mg (1.17 mmol, 1 eq) of 2-cyclohexylethanol were diluted in 4 mL of DCM, 214 µL (1.52 mmol, 1.3 eq) of triethylamine were added. The mixture was cooled to 0° C. and 100 µL (1.29 mmol, 1.1 eq) of mesyl chloride were added. The mixture was stirred for 15 min at 0° C. then water was added. The aqueous phase was extracted with dichloromethane. The organic phase was washed with water, brine, dried over MgSO$_4$, filtered and concentrated in vacuo. The crude product (241 mg) was used directly for synthesis of 2. TLC: Rf: 0.48 (eluant: Heptane/EtOAc: 1/1).

Synthesis of (2-Cyclohexyl-ethyl)-(3,3-diphenyl-propyl)-amine, 59 (Method A).

241 mg (1.17 mmol, 1 eq) of I were dissolved in 5 mL of DMF. 323 mg (2.34 mmol, 2 eq) of K2CO3 and 495 mg (2.34 mmol, 2 eq) of 3,3-diphenylpropylamine were added to the solution. The mixture was stirred overnight at room temperature. Water was added, then the aqueous phase was extracted with EtOAc. The organic phase was washed with water, brine, dried over MgSO4, filtered and concentrated in vacuo. The crude product was purified by flash chromatography over silica gel (eluant: gradient DCM/MeOH/NH4OH: 100/0/0.1 to 95/5/0.1). 46 mg of the desired compound 2 were obtained. TLC: Rf: 0.33 (eluant: DCM/MeOH/NH4OH: 90/10/0.1). MS (ES+): 322.35+(M+H)+

Synthesis of 3-[3-(2-Cyclohexyl-ethyl)-3-(3,3-diphenyl-propyl)-ureido]-benzoic acid methyl ester 60 (Method B).

46 mg of (2-cyclohexyl-ethyl)-(3,3-diphenyl-propyl)-amine (0.147 mmol, 1 eq) were diluted in 1 mL of DCM. 30 mg (0.172 mmol, 1.2 eq) of 3-isocyanato-benzoic acid methyl ester were then added to the mixture. The reaction mixture was stirred at room temperature for 90 min before adding water, then the aqueous phase was extracted with DCM. The organic phase was washed with water, brine, dried over MgSO₄, filtered and concentrated in vacuo. The crude product was purified by flash chromatography over silica gel (eluant: gradient Hept/EtOAc 5/1). 63 mg of the desired urea were obtained. MS (ES⁺): 499.5⁺ (M+H)⁺. TLC: Rf: 0.57 (eluant: heptane/EtOAc: 1/1).

EXAMPLE 33

Synthesis of 3-[3-Benzyl-3-(3,3-diphenyl-propyl)-ureido]-benzoic acid methyl ester, 62

Synthesis of 3-[3-Benzyl-3-(3,3-diphenyl-propyl)-ureido]-benzoic acid methyl ester 62

Method B of Example 32 with 3-isocyanato-benzoic acid methyl ester for urea formation, was used to synthesize the title compound. MS (ES⁺): 479⁺ (M+H)⁺

EXAMPLE 34

Synthesis of 1-(3,3-Diphenyl-propyl)-1-isobutyl-3-(3-methoxy-phenyl)-urea, 64

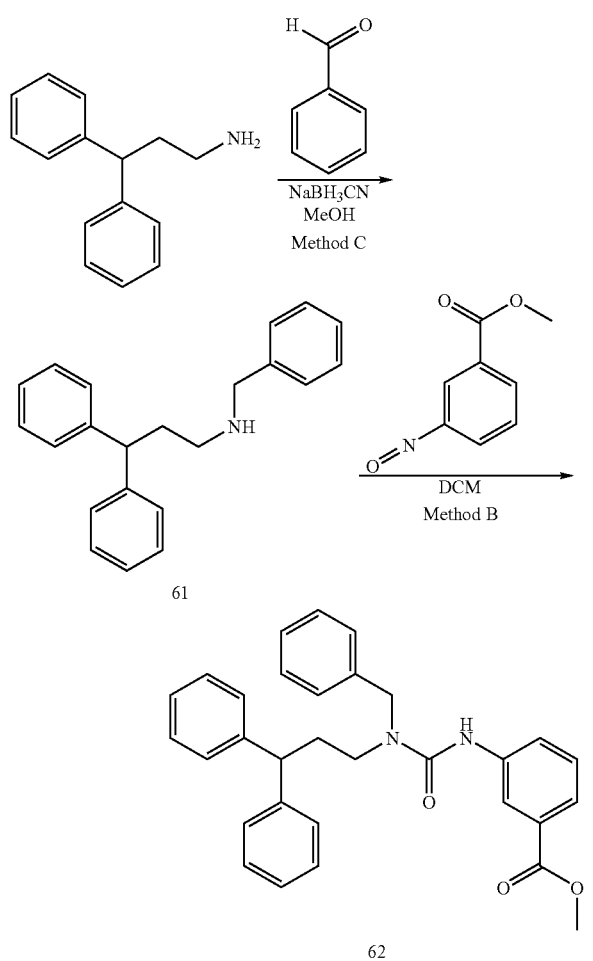

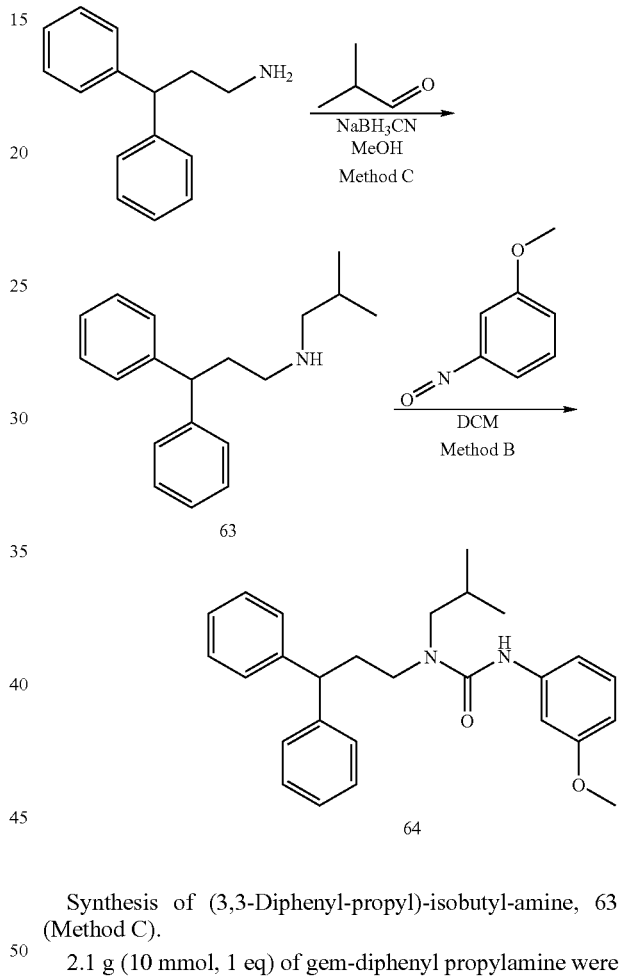

Synthesis of Benzyl-(3,3-diphenyl-propyl)-amine, 61 (Method C)

1.5 g (7.1 mmol, 1 eq) of gem-diphenyl propylamine were diluted in 15 mL of MeOH, 753 mg (7.1 mmol, 1 eq) of benzaldehyde were added to the solution. The mixture was stirred for 45 min at room temperature. 446 mg (7.1 mmol, 1 eq) of sodium cyanoborohydride (NaBH₃CN) were then added. The mixture was stirred for overnight at room temperature. Water was added and MeOH was evaporated. The aqueous phase was extracted with EtOAc. The organic phase was washed with water, brine, dried over MgSO₄, filtered and concentrated in vacuo. The crude product was purified by flash chromatography over silica gel (eluant: gradient DCM/MeOH 95/5). 970 mg of the desired secondary amine 3 were obtained.

Synthesis of (3,3-Diphenyl-propyl)-isobutyl-amine, 63 (Method C).

2.1 g (10 mmol, 1 eq) of gem-diphenyl propylamine were diluted in 20 mL of MeOH, 727 mg (10 mmol, 1 eq) of isobutylaldehyde were added to the solution. The mixture was stirred for 45 min at room temperature. 628 mg (10 mmol, 1 eq) of sodium cyanoborohydride (NaBH₃CN) were then added. The mixture was stirred for overnight at room temperature. Water was added and MeOH was evaporated. The aqueous phase was extracted with EtOAc. The organic phase was washed with water, brine, dried over MgSO₄, filtered and concentrated in vacuo. The crude product was purified by flash chromatography over silica gel (eluant: gradient DCM/MeOH 95/5). Desired secondary amine 63 was obtained.

Synthesis of 1-(3,3-Diphenyl-propyl)-1-isobutyl-3-(3-methoxy-phenyl)-urea 64.

Method B of Example 32 with 1-isocyanato-3-methoxy-benzene for urea formation, was used to synthesise the title compound. MS (ES⁺): 417.2⁺ (M+H)⁺, 833.5⁺ (2M+H)⁺

EXAMPLE 35
Synthesis of N-(4-(5-chloro-2-(((3,3-diphenylpropyl)(4-(2-hydroxyethyl)phenyl)carbamoyl)amino)-1,3-thiazol-4-yl)phenyl)methanesulfonamide, 68
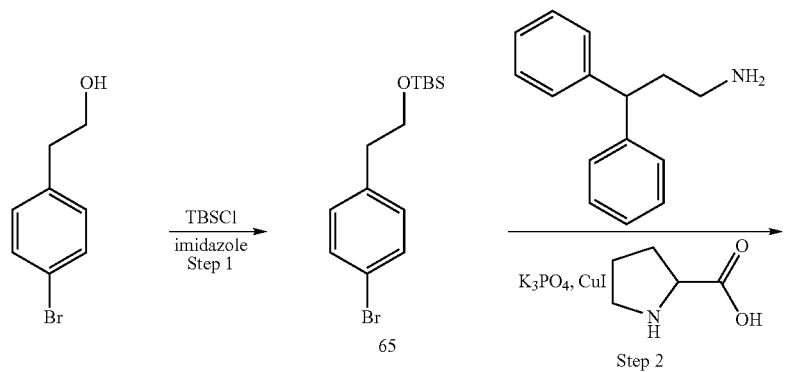
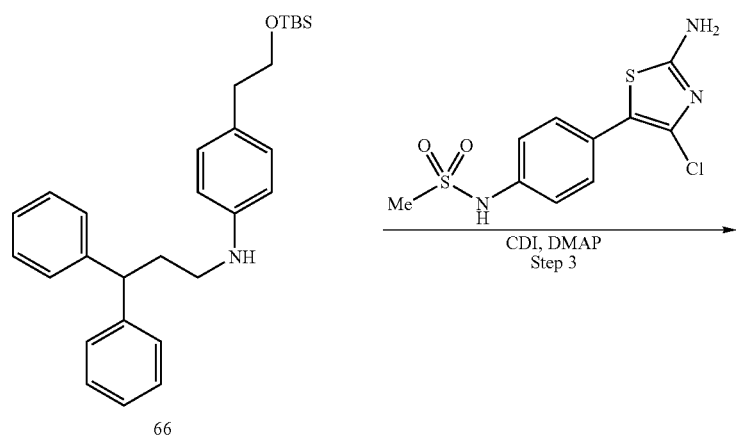
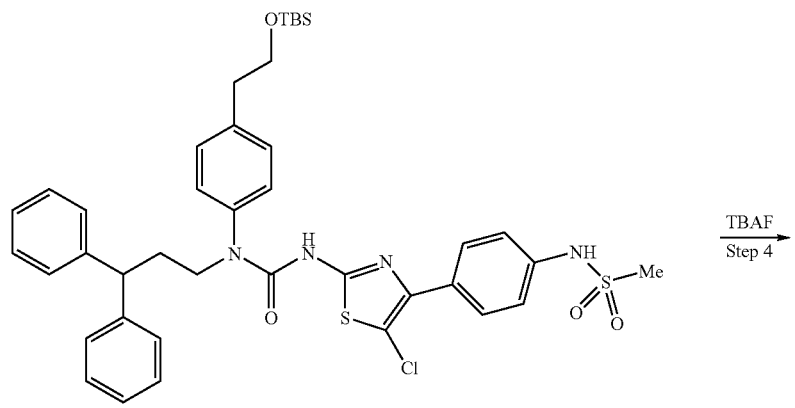

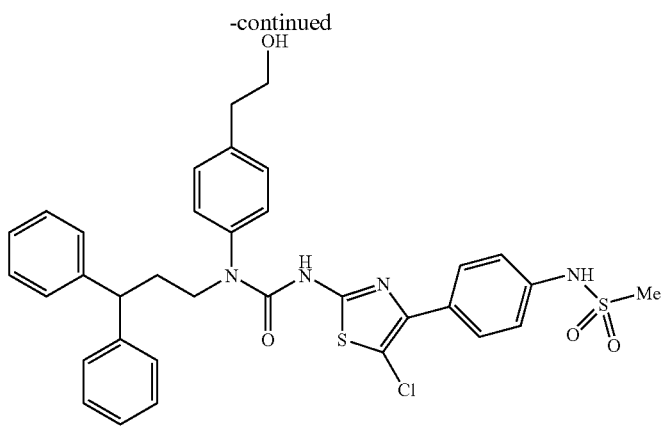

68

Step 1. To a solution of 1H-imidazole (1.06 g, 15.6 mmol) and 2-(4-bromophenyl)ethanol (2.19 g, 10.9 mmol) in THF (20 mL) at room temperature was added tert-butylchlorodimethylsilane (1.81 g, 12.0 mmol). The reaction mixture was stirred at room temperature for 2 h and diluted with hexanes. The organic phase was washed with water (2×), brine (1×), dried over MgSO$_4$, filtered, and concentrated to give (4-bromophenethoxy)(tert-butyl)dimethylsilane 65 which was used in the next step without further purification.

Step 2. To a mixture of copper(I) iodide (0.195 g, 1.02 mmol), (S)-pyrrolidine-2-carboxylic acid (0.223 g, 1.94 mmol), (4-bromophenethoxy)(tert-butyl)dimethylsilane, prepared in the previous step, and 3,3-diphenylpropan-1-amine (3.16 g, 15.0 mmol) was added potassium phosphate (4.27 g, 20.1 mmol), and DMSO (16 mL). The reaction mixture was heated to 90° C. for 1 d and diluted with EtOAc. The organic phase was washed with water (1×), brine (1×), dried over MgSO$_4$, filtered, and concentrated. Purification by flash column chromatography on silica gel (eluted with 5% to 15% EtOAc in hexanes) gave 4-(2-(tert-butyldimethylsilyloxy) ethyl)-N-(3,3-diphenylpropyl)benzenamine 66.

Step 3. To a mixture of N-(4-(2-amino-5-chlorothiazol-4-yl)phenyl)methanesulfonamide (0.201 g, 0.662 mmol), DMAP (0.123 g, 1.01 mmol), and CDI (0.159 g, 0.981 mmol) was added DMF (1 mL). The reaction mixture was heated to 40° C. for 2 d. Direct purification by flash column chromatography on silica gel (eluted with 10% to 40% EtOAc in hexanes) gave 1-(4-(2-(tert-butyldimethylsilyloxy)ethyl)phenyl)-3-(5-chloro-4-(4-(methylsulfonamido)phenyl)thiazol-2-yl)-1-(3,3-diphenylpropyl)urea 67.

Step 4. To a solution of 1-(4-(2-(tert-butyldimethylsilyloxy)ethyl)phenyl)-3-(5-chloro-4-(4-(methylsulfonamido) phenyl)thiazol-2-yl)-1-(3,3-diphenylpropyl)urea (0.289 g, 0.373 mmol) in THF (2 mL) at room temperature was added TBAF (1 M in THF, 1.5 mL, 1.5 mmol). The reaction mixture was stirred at room temperature for 3 h and concentrated. Purification by flash column chromatography on silica gel (eluted with 3% to 10% MeOH in DCM) gave N-(4-(5-chloro-2-(((3,3-diphenylpropyl)(4-(2-hydroxyethyl)phenyl) carbamoyl)amino)-1,3-thiazol-4-yl)phenyl)methanesulfonamide 68. Mass spectrum, calculated for C$_{34}$H$_{33}$ClN$_4$O$_4$S$_2$ 660.2; found 661.2 (M$^+$+1).

EXAMPLE 36

Synthesis of N-(4-(5-chloro-2-(((3,3-diphenylpropyl) (1-methylethyl)carbamoyl)amino)-1,3-thiazol-4-yl) phenyl)methanesulfonamide, 69

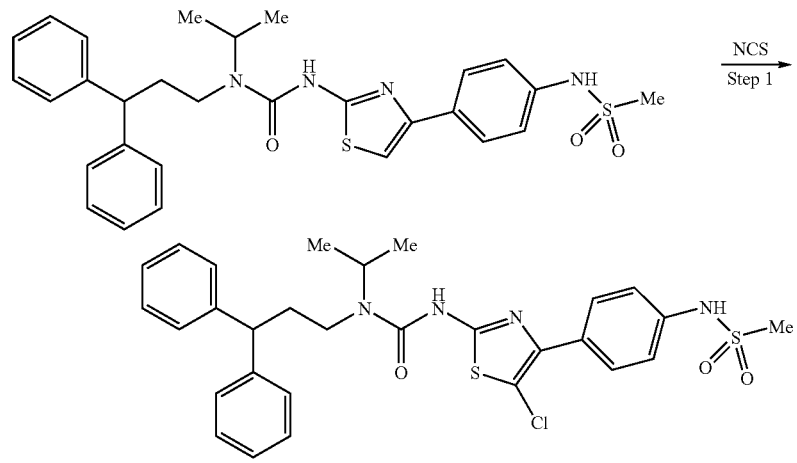

69

Step 1. To a solution of 1-(3,3-diphenylpropyl)-1-isopropyl-3-(4-(4-(methylsulfonamido)phenyl)thiazol-2-yl)urea (0.101 g, 0.18 mmol) in DMF (1 mL) at room temperature was added 1-chloropyrrolidine-2,5-dione (0.035 g, 0.26 mmol). The reaction mixture was stirred at room temperature for 2 d. Direct purification by flash column chromatography on silica gel (eluted with 20% to 60% EtOAc in hexanes) gave N-(4-(5-chloro-2-(((3,3-diphenylpropyl)(1-methylethyl)carbamoyl)amino)-1,3-thiazol-4-yl)phenyl)methanesulfonamide 69. Mass spectrum, calculated for $C_{29}H_{31}ClN_4O_3S_2$ 582.2; found 583.1 ($M^+$+1).

EXAMPLE 37

Synthesis of 1-(3,3-bis(4-fluorophenyl)propyl)-3-(5-chloro-4-(4-(1H-1,2,3-triazol-1-yl)phenyl)-1,3-thiazol-2-yl)-1-(2-(2-pyridinyl)ethyl)urea, 71

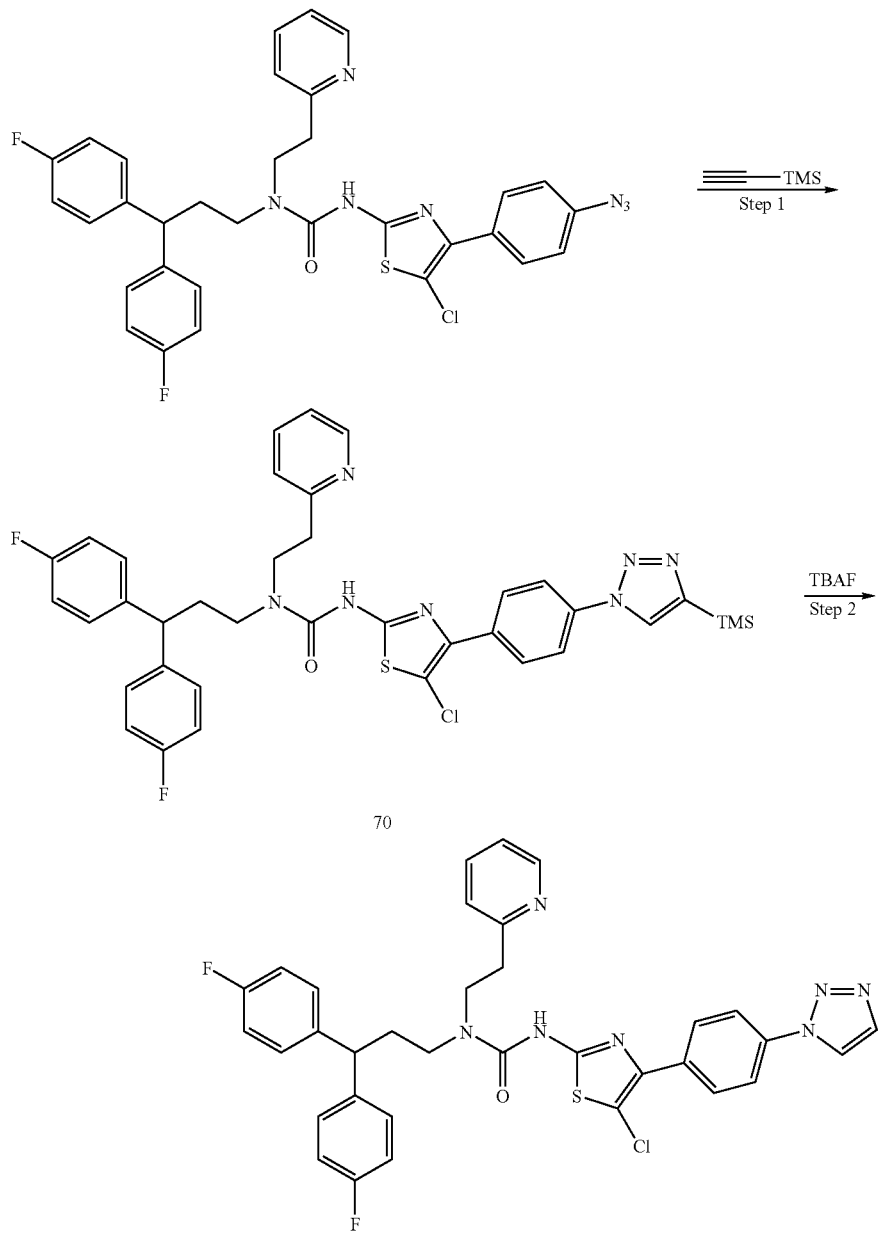

Step 1. To a solution of 1-(3,3-bis(4-fluorophenyl)propyl)-3-(4-(4-azidophenyl)-5-chlorothiazol-2-yl)-1-(2-(pyridin-2-yl)ethyl)urea 70 (0.264 g, 0.419 mmol) in DMF (1 mL) in a sealed tube was added ethynyltrimethylsilane (0.30 mL, 0.213 g, 2.17 mmol). The reaction mixture was heated to 100° C. for 18 h and concentrated. The product, 1-(3,3-bis(4-fluorophenyl)propyl)-3-(5-chloro-4-(4-(4-(trimethylsilyl)-1H-1,2,3-triazol-1-yl)phenyl)thiazol-2-yl)-1-(2-(pyridin-2-yl)ethyl)urea 71, was used in the next step without further purification.

Step 2. To 1-(3,3-bis(4-fluorophenyl)propyl)-3-(5-chloro-4-(4-(4-(trimethylsilyl)-1H-1,2,3-triazol-1-yl)phenyl)thiazol-2-yl)-1-(2-(pyridin-2-yl)ethyl)urea 71, prepared in the previous step, at room temperature was added tetrabutylammonium fluoride (1 M in THF, 3.0 mL, 3.0 mmol). The reaction mixture was stirred at room temperature for 30 min, heated to 40° C. for 3 h, and diluted with EtOAc. The organic phase was washed with water (1×), brine (1×), dried over MgSO$_4$, filtered, and concentrated. Purification by flash column chromatography on silica gel (eluted with 30% to 70% EtOAc in hexanes) gave 1-(3,3-bis(4-fluorophenyl)propyl)-3-(5-chloro-4-(4-(1H-1,2,3-triazol-1-yl)phenyl)-1,3-thiazol-2-yl)-1-(2-(2-pyridinyl)ethyl)urea. Mass spectrum, calculated for C$_{34}$H$_{28}$ClF$_2$N$_7$OS 655.2; found 656.1 (M$^+$+1).

EXAMPLE 38

Synthesis of 3-(5-chloro-4-(4-(1H-1,2,3-triazol-1-yl)phenyl)-1,3-thiazol-2-yl)-1-(3,3-diphenylpropyl)-1-(2-(2-pyridinyl)ethyl)urea 72

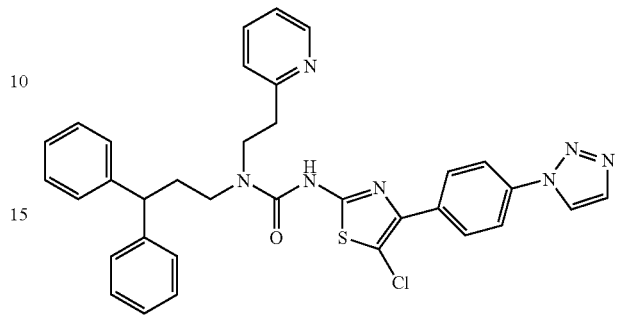

The procedure described in Example 37 with the exception of substituting 1-(3,3-bis(4-fluorophenyl)propyl)-3-(4-(4-azidophenyl)-5-chlorothiazol-2-yl)-1-(2-(pyridin-2-yl)ethyl)urea for 3-(4-(4-azidophenyl)-5-chlorothiazol-2-yl)-1-(3,3-diphenylpropyl)-1-(2-(pyridin-2-yl)ethyl)urea in Step 1 was used to prepare 3-(5-chloro-4-(4-(1H-1,2,3-triazol-1-yl)phenyl)-1,3-thiazol-2-yl)-1-(3,3-diphenylpropyl)-1-(2-(2-pyridinyl)ethyl)urea 72. Mass spectrum, calculated for C$_{34}$H$_{30}$ClN$_7$OS 619.2; found 620.2 (M++1).

EXAMPLE 39

Synthesis of 3-(((5-chloro-4-(4-((methylsulfonyl)amino)phenyl)-1,3-thiazol-2-yl)carbamoyl)(3,3-diphenylpropyl)amino)benzoic acid, 74

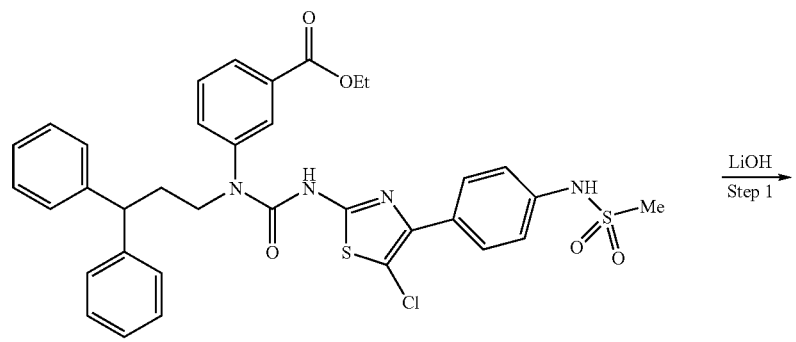

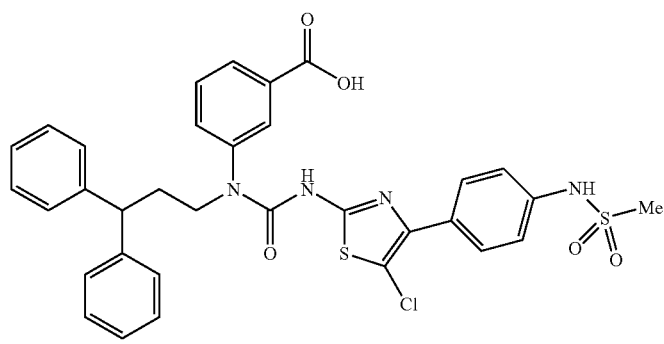

To a solution of ethyl 3-(3-(5-chloro-4-(4-(methylsulfonamido)phenyl)thiazol-2-yl)-1-(3,3-diphenylpropyl)ureido)benzoate 73 (0.366 g, 0.531 mmol) in MeOH (20 mL) was added lithium hydroxide hydrate (0.440 g, 10.5 mmol). The reaction mixture was heated to 60° C. After 3 h, the reaction mixture was partially concentrated, neutralized with 1 M HCl, and diluted with EtOAc. The organic phase was washed with brine (1×), dried over $MgSO_4$, filtered, and concentrated to give 3-(((5-chloro-4-(4-((methylsulfonyl)amino)phenyl)-1,3-thiazol-2-yl)carbamoyl)(3,3-diphenylpropyl)amino) benzoic acid 74. Mass spectrum, calculated for $C_{33}H_{29}ClN_4O_5S_2$ 660.1; found 661.1 (M++1).

Compound 73 was prepared following steps 2 and 3 in example 35. In step 2, (4-bromophenethoxy)(tert-butyl)dimethylsilane was substituted for 3-iodobenzoic acid ethyl ester

EXAMPLES 40

The compounds shown in Table 1 were prepared by the procedure described in Example 39. Specific syntheses of the urea ester precursors are detailed below.

Compound 75: Prepared following steps 2 and 3 in example 35. In step 2, (4-bromophenethoxy)(tert-butyl)dimethylsilane was substituted for ethyl 2-(4-aminophenyl)acetate.

Compound 76: The procedure described in Example 5 with the exception of substituting methylamine for methyl 4-(2-aminoethyl)benzoate in Step 1 was used.

Compound 77: Prepared following steps 2 and 3 in example 35. In step 2, (4-bromophenethoxy)(tert-butyl)dimethylsilane was substituted for 4-iodobenzoic acid ethyl ester.

TABLE 1

| Comp Number | Structure | Name | Exact Mass | MS m/z (M+ + 1) |
|---|---|---|---|---|
| 75 | 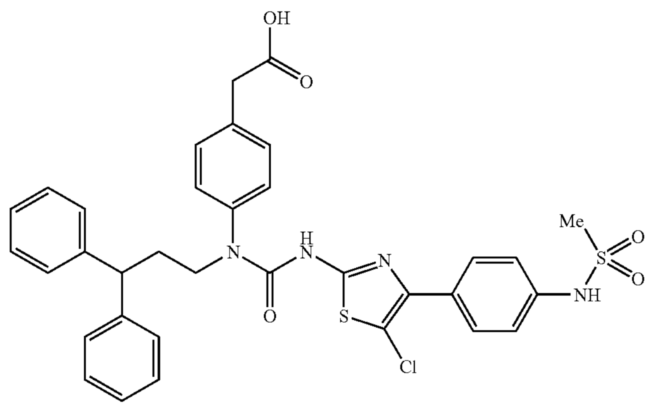 | (4-(((5-chloro-4-(4-((methylsulfonyl)amino)phenyl)-1,3-thiazol-2-yl)carbamoyl)(3,3-diphenylpropyl)amino)phenyl)acetic acid | 674.1 | 675.1 |
| 76 | 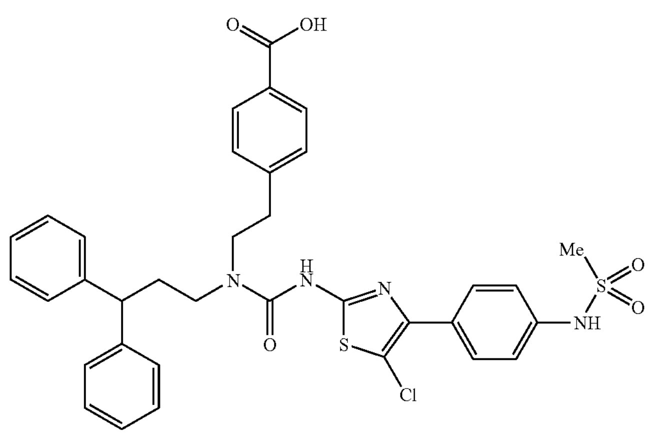 | 4-(2-(((5-chloro-4-(4-((methylsulfonyl)amino)phenyl)-1,3-thiazol-2-yl)carbamoyl)(3,3-diphenylpropyl)amino)ethyl)benzoic acid | 688.2 | 689.2 |
| 77 | 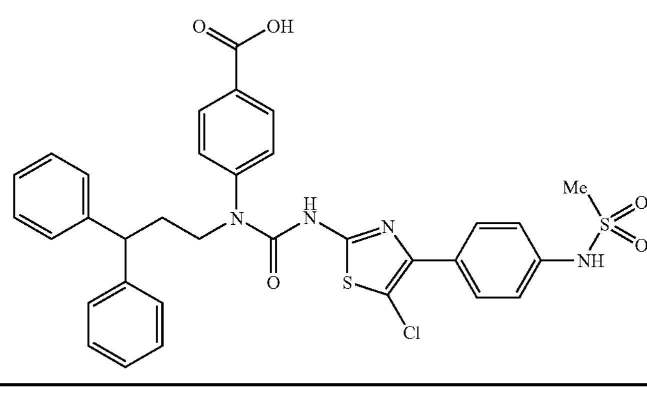 | 4-(((5-chloro-4-(4-((methylsulfonyl)amino)phenyl)-1,3-thiazol-2-yl)carbamoyl)(3,3-diphenylpropyl)amino)benzoic acid | 660.1 | 661.1 |

EXAMPLE 41

Synthesis of 3-(((5-chloro-4-(4-((methylsulfonyl)amino)phenyl)-1,3-thiazol-2-yl)carbamoyl)(3,3-diphenylpropyl)amino)-N-methylbenzamide, 79

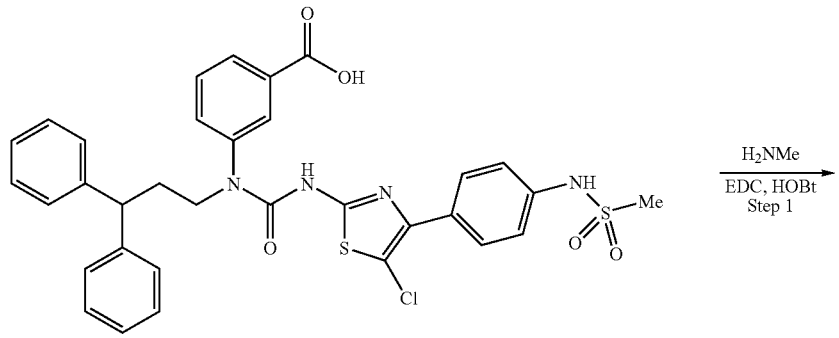

78

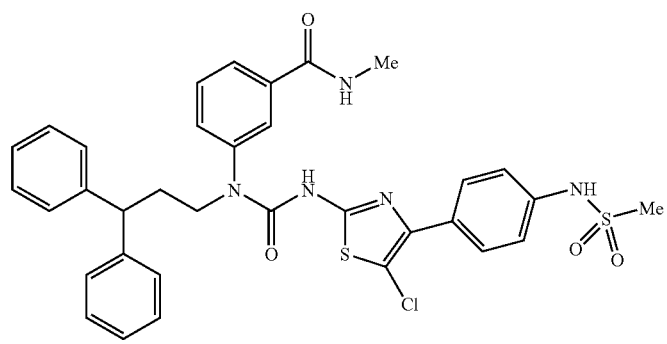

79

To a mixture of HOBt hydrate (0.042 g, 0.27 mmol), EDC (0.037 g, 0.19 mmol), and 3-(3-(5-chloro-4-(4-(methylsulfonamido)phenyl)thiazol-2-yl)-1-(3,3-diphenylpropyl)ureido)benzoic acid 78 (0.089 g, 0.13 mmol) was added DMF (1.5 mL). The reaction mixture was stirred at room temperature for 10 min and methylamine (2 mL, 2 M in MeOH, 4 mmol) was added. The reaction mixture was stirred at room temperature for 1 d and diluted with EtOAc. The organic phase was washed with water (1×), brine (1×), dried over MgSO$_4$, filtered, and concentrated. Purification by flash column chromatography on silica gel (eluted with 20% to 80% EtOAc in hexanes) gave 3-(((5-chloro-4-(4-((methylsulfonyl)amino)phenyl)-1,3-thiazol-2-yl)carbamoyl)(3,3-diphenylpropyl)amino)-N-methylbenzamide 79. Mass spectrum, calculated for $C_{34}H_{32}ClN_5O_4S_2$ 673.2; found 674.2 (M$^+$+1).

EXAMPLE 42

The examples shown in Table 2 were prepared by the procedure described for Example 41 except substituting for the corresponding carboxylic acid and amine starting materials. Specific syntheses of the amides are detailed below.

Compound 80: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for (4-(((5-chloro-4-(4-((methylsulfonyl)amino)phenyl)-1,3-thiazol-2-yl)carbamoyl)(3,3-diphenylpropyl)amino)phenyl)acetic acid 75 (described previously in example 40).

Compound 81: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for (4-(((5-chloro-4-(4-((methylsulfonyl)amino)phenyl)-1,3-thiazol-2-yl)carbamoyl)(3,3-diphenylpropyl)amino)phenyl)acetic acid 75 (described previously in example 40) and substituting methylamine for ammonia.

Compound 82: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for 4-(2-(((5-chloro-4-(4-((methylsulfonyl)amino)phenyl)-1,3-thiazol-2-yl)carbamoyl)(3,3-diphenylpropyl)amino)ethyl)benzoic acid 76 (described previously in example 40).

Compound 83: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for 4-(((5-chloro-4-(4-((methylsulfonyl)amino)phenyl)-1,3-thiazol-2-yl)carbamoyl)(3,3-diphenylpropyl)amino)benzoic acid 77 (described previously in example 40).

TABLE 2

| Comp Number | Structure | Name | Exact Mass | MS m/z (M+ + 1) |
|---|---|---|---|---|
| 80 | 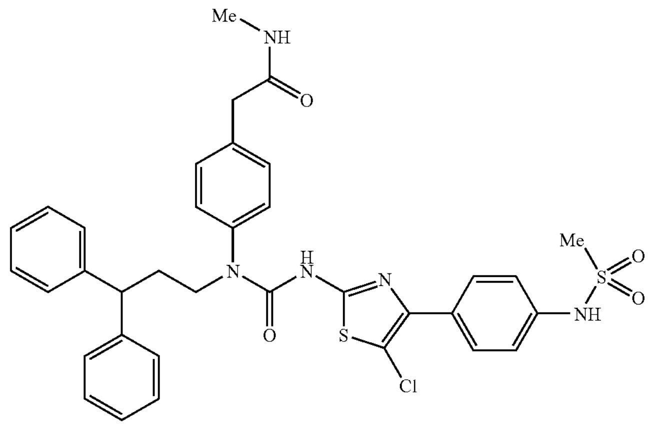 | 2-(4-(((5-chloro-4-(4-((methylsulfonyl)amino)phenyl)-1,3-thiazol-2-yl)carbamoyl)(3,3-diphenylpropyl)amino)phenyl)-N-methylacetamide | 687.2 | 688.2 |
| 81 | 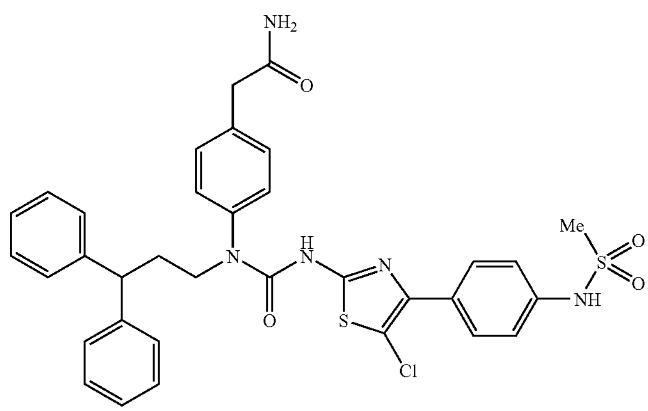 | 2-(4-(((5-chloro-4-(4-((methylsulfonyl)amino)phenyl)-1,3-thiazol-2-yl)carbamoyl)(3,3-diphenylpropyl)amino)phenyl)acetamide | 673.2 | 674.1 |
| 82 | 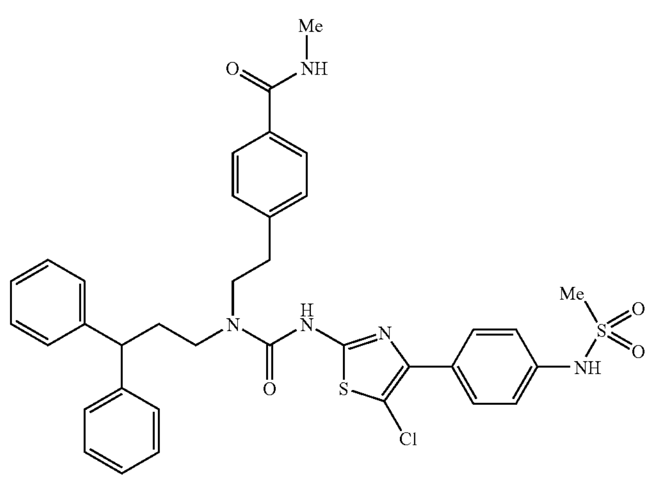 | 4-(2-(((5-chloro-4-(4-((methylsulfonyl)amino)phenyl)-1,3-thiazol-2-yl)carbamoyl)(3,3-diphenylpropyl)amino)ethyl)-N-methylbenzamide | 701.2 | 702.2 |

TABLE 2-continued

| Comp Number | Structure | Name | Exact Mass | MS m/z (M+ + 1) |
|---|---|---|---|---|
| 83 | 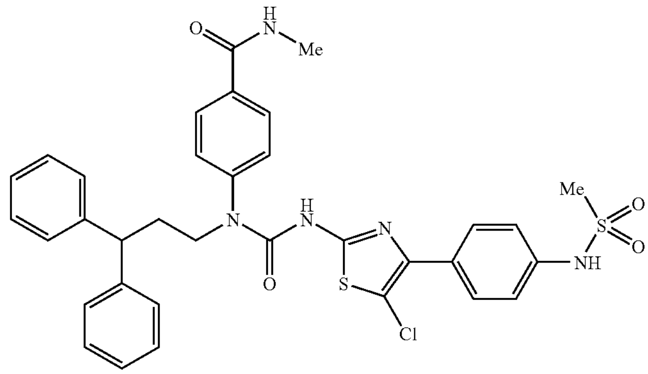 | 4-(((5-chloro-4-(4-((methylsulfonyl)amino)phenyl)-1,3-thiazol-2-yl)carbamoyl)(3,3-diphenylpropyl)amino)-N-methylbenzamide | 673.2 | 674.2 |

EXAMPLE 43

Synthesis of 4-(5-chloro-2-(((3,3-diphenylpropyl)(2-(2-pyridinyl)ethyl)carbamoyl)amino)-1,3-thiazol-4-yl)benzenesulfonamide, 85

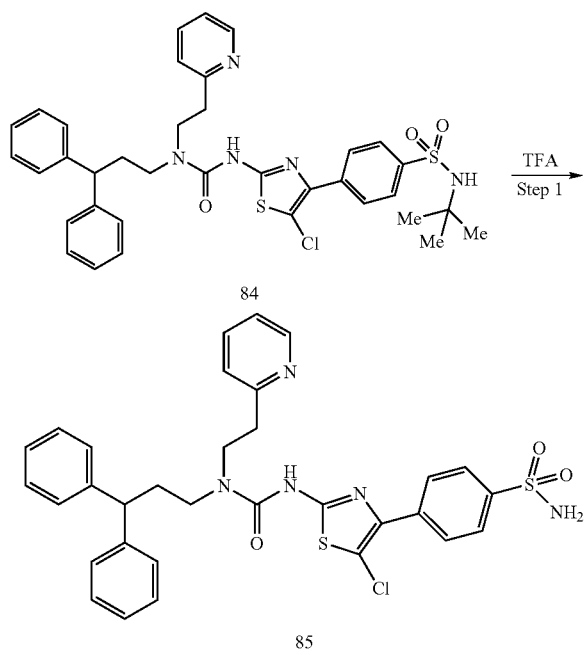

To a solution of N-tert-butyl-4-(5-chloro-2-(((3,3-diphenylpropyl)(2-(2-pyridinyl)ethyl)carbamoyl)amino)-1,3-thiazol-4-yl)benzenesulfonamide 84 (0.187 g, 0.272 mmol) in DCM (1 mL) was added anisol (0.20 mL) and TFA (2 mL). The reaction mixture was stirred at room temperature for 1 d and concentrated. The concentrate was diluted with EtOAc and the organic phase was washed with saturated NaHCO₃ (1×), brine (1×), dried over MgSO₄, filtered, and concentrated. Purification by crystallization from a mixture of DCM and hexanes gave 4-(5-chloro-2-(((3,3-diphenylpropyl)(2-(2-pyridinyl)ethyl)carbamoyl)amino)-1,3-thiazol-4-yl)benzenesulfonamide 85. Mass spectrum, calculated for $C_{32}H_{30}ClN_5O_3S_2$ 631.2; found 632.1 (M++1).

EXAMPLE 44

The examples shown in Table 3 were prepared by the procedure described for Example 43 except substituting for the corresponding sulfonamide starting material. Specific syntheses of the t-butyl sulfonamide precursors are detailed below.

Compound 86: The procedure described in step 2 of example 5 with the exception of substituting N-(4-(2-amino-5-chlorothiazol-4-yl)phenyl)methanesulfonamide for 4-(2-amino-4-chlorothiazol-5-yl)-N-tert-butylbenzenesulfonamide (method Q) and N-methyl-3,3-diphenylpropan-1-amine for 3,3-bis(4-fluorophenyl)-N-(2-(pyridin-2-yl)ethyl)propan-1-amine (method H).

Compound 87: The procedure described in Example 5 with the exception of substituting methylamine for 2-(2-pyridinyl)ethylamine in step 1 and of substituting N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for t-butyl 4-bornobenzenesulfonamide) in step 2.

Compound 88: The procedure described in step 2 of example 5 with the exception of substituting N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for N-tert-butyl 4-bomobenzenesulfonamide) and N-methyl-3,3-diphenylpropan-1-amine for 3,3-bis(4-fluorophenyl)-N-(2-(pyridin-2-yl)ethyl)propan-1-amine (method H).

Compound 89: The procedure described in Example 5 with the exception of substituting methylamine for 2-(2-pyrazinyl)ethylamine in step 1 and of substituting N-(4-(2-amino-5-chlorothiazol-4-yl)phenyl)methanesulfonamide for 4-(2-amino-4-chlorothiazol-5-yl)-N-tert-butylbenzenesulfonamide (method Q) in step 2.

Compound 90: The procedure described in Example 5 with the exception of substituting methylamine for 2-(2-pyrazinyl)ethylamine in step 1 and of substituting N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for t-butyl 4-bornobenzenesulfonamide) in step 2.

Compound 91: The procedure described in step 2 of Example 5 with the exception of substituting N-methyl-3,3-diphenylpropan-1-amine for 3,3-diphenyl-N-(2-(pyrimidin-2-yl)ethyl)propan-1-amine (method K) and N-(4-(2-amino-5-chlorothiazol-4-yl)phenyl)methanesulfonamide for 4-(2-amino-4-chlorothiazol-5-yl)-N-tert-butylbenzenesulfonamide (method Q).

Compound 92: The procedure described in step 2 of Example 5 with the exception of substituting N-methyl-3,3-diphenylpropan-1-amine for N-(2-(4-chloro-2-pyridinyl)ethyl)-3,3-diphenyl-1-propanamine (method K, substituting 2-bromopyrimidine for 2-bromo-4-chloropyridine in step 1) and N-(4-(2-amino-5-chlorothiazol-4-yl)phenyl)methanesulfonamide for 4-(2-amino-4-chlorothiazol-5-yl)-N-tert-butylbenzenesulfonamide (method Q).

Compound 93: The procedure described in step 2 of Example 5 with the exception of substituting N-methyl-3,3-diphenylpropan-1-amine for 3,3-diphenyl-N-(2-(pyrimidin-2-yl)ethyl)propan-1-amine (method K, substituting 2-bromopyrimidine for 2-bromo-4-chloropyridine in step 1) and N-(4-(2-amino-5-chlorothiazol-4-yl)phenyl)methanesulfonamide for 4-(2-amino-4-chlorothiazol-5-yl)-N-tert-butylbenzenesulfonamide (method Q).

Compound 94: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for (4-((((5-chloro-4-(4-((methylsulfonyl)amino)phenyl)-1,3-thiazol-2-yl)carbamoyl)(3,3-diphenylpropyl)amino)phenyl)acetic acid 75 (described previously in example 40).

Compound 95: The procedure described in step 2 of Example 5 with the exception of substituting N-methyl-3,3-diphenylpropan-1-amine for 3,3-diphenyl-N-(2-(pyrimidin-2-yl)ethyl)propan-1-amine (method K) and N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for t-butyl 4-bornobenzenesulfonamide).

Compound 96: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for 4-(2-((((5-chloro-4-(4-((methylsulfonyl)amino)phenyl)-1,3-thiazol-2-yl)carbamoyl)(3,3-diphenylpropyl)amino)ethyl)benzoic acid 76 (described previously in example 40).

Compound 97: The procedure described in Example 41 with the exception of substituting 3-(3-(5-chloro-4-(4-(methylsulfonamido)phenyl)thiazol-2-yl)-1-(3,3-diphenylpropyl)ureido)benzoic acid for 4-((((5-chloro-4-(4-((methylsulfonyl)amino)phenyl)-1,3-thiazol-2-yl)carbamoyl)(3,3-diphenylpropyl)amino)benzoic acid 77 (described previously in example 40).

TABLE 3

| Comp Number | Structure | Name | Exact Mass | MS m/z ($M^+ + 1$) |
|---|---|---|---|---|
| 86 | 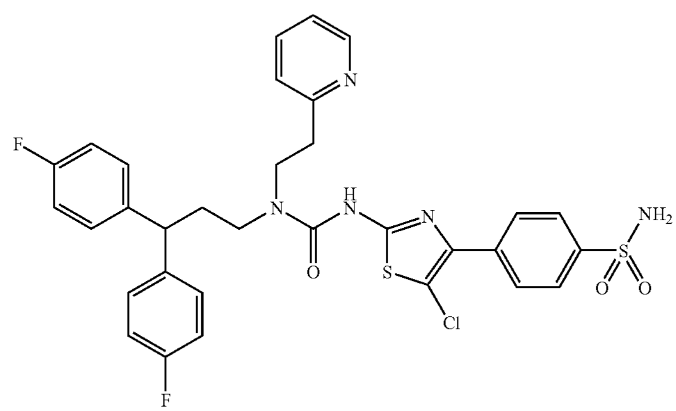 | 4-(2-(((3,3-bis(4-fluorophenyl)propyl)(2-(2-pyridinyl)ethyl)carbamoyl)amino)-5-chloro-1,3-thiazol-4-yl)benzenesulfonamide | 667.1 | 668.0 |
| 87 | 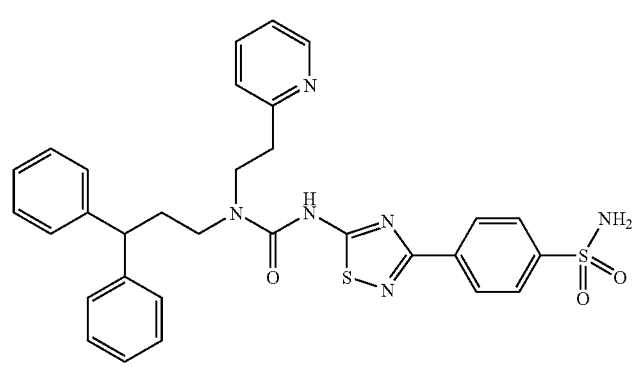 | 4-(5-(((3,3-diphenylpropyl)(2-(2-pyridinyl)ethyl)carbamoyl)amino)-1,2,4-thiadiazol-3-yl)benzenesulfonamide | 589.2 | 599.2 |

TABLE 3-continued

| Comp Number | Structure | Name | Exact Mass | MS m/z (M+ + 1) |
|---|---|---|---|---|
| 88 | 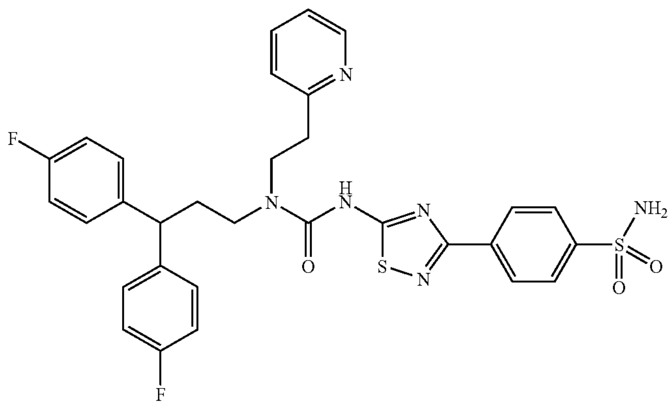 | 4-(5-(((3,3-bis(4-fluorophenyl)propyl)(2-(2-pyridinyl)ethyl)carbamoyl)amino)-1,2,4-thiadiazol-3-yl)benzenesulfonamide | 634.2 | 635.1 |
| 89 | 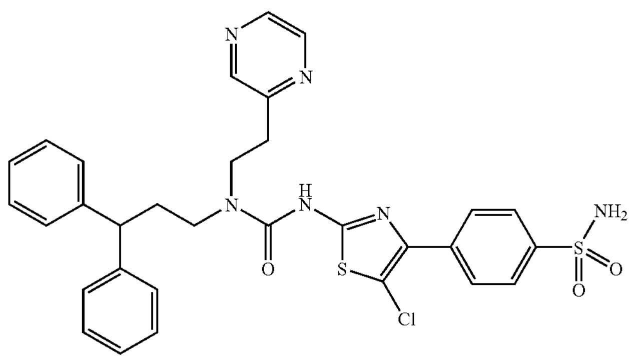 | 4-(5-chloro-2-(((3,3-diphenylpropyl)(2-(2-pyrazinyl)ethyl)carbamoyl)amino)-1,3-thiazol-4-yl)benzenesulfonamide | 632.1 | 633.1 |
| 90 | 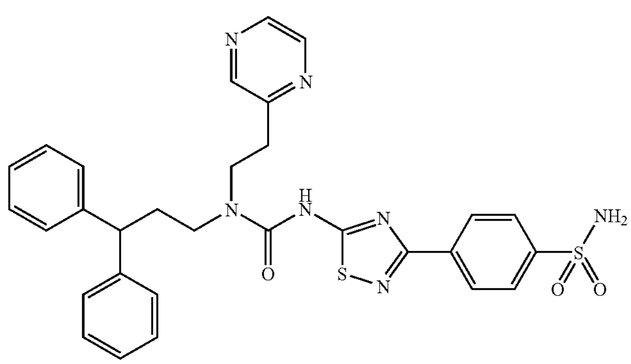 | 4-(5-(((3,3-diphenylpropyl)(2-(2-pyrazinyl)ethyl)carbamoyl)amino)-1,2,4-thiadiazol-3-yl)benzenesulfonamide | 599.2 | 600.2 |
| 91 | 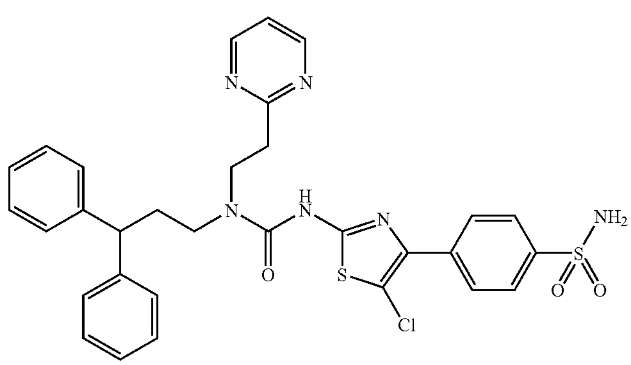 | 4-(5-chloro-2-(((3,3-diphenylpropyl)(2-(2-pyrimidinyl)ethyl)carbamoyl)amino)-1,3-thiazol-4-yl)benzenesulfonamide | 632.1 | 633.1 |

TABLE 3-continued

| Comp Number | Structure | Name | Exact Mass | MS m/z (M+ + 1) |
|---|---|---|---|---|
| 92 | 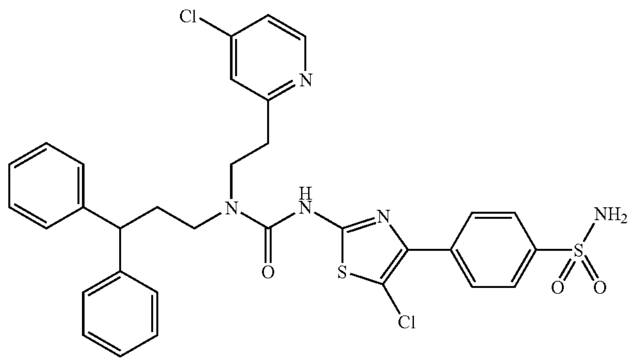 | 4-(5-chloro-2-(((2-(4-chloro-2-pyridinyl)ethyl)(3,3-diphenyl-propyl)carbamoyl)amino)-1,3-thiazol-4-yl)benzenesulfonamide | 665.1 | 666.1 |
| 93 | 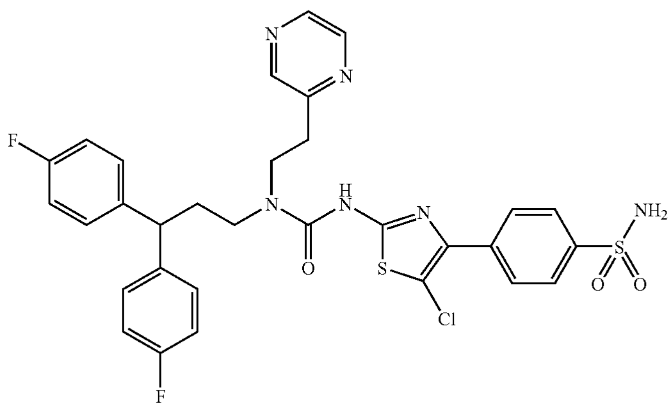 | 4-(2-(((3,3-bis(4-fluorophenyl)propyl)(2-(2-pyrazinyl)ethyl)carbamoyl)amino)-5-chloro-1,3-thiazol-4-yl)benzenesulfonamide | 668.1 | 669.0 |
| 94 | 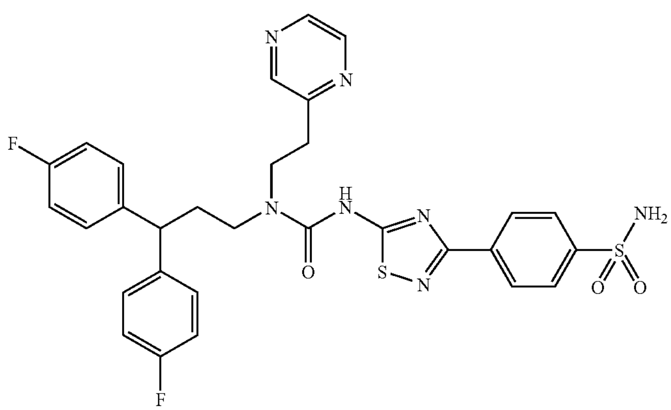 | 4-(5-(((3,3-bis(4-fluorophenyl)propyl)(2-(2-pyrazinyl)ethyl)carbamoyl)amino)-1,2,4-thiadiazol-3-yl)benzenesulfonamide | 635.2 | 636.1 |
| 95 | 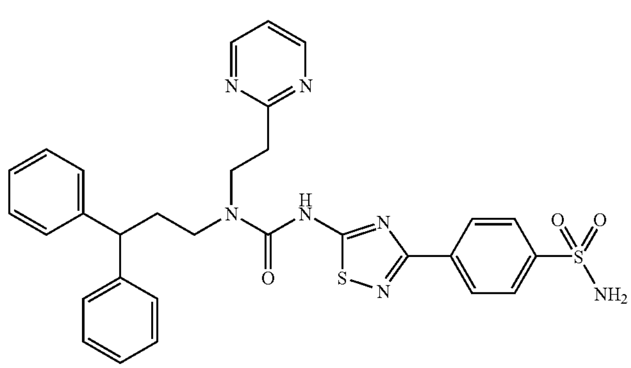 | 4-(5-(((3,3-diphenylpropyl)(2-(2-pyrimidinyl)ethyl)carbamoyl)amino)-1,2,4-thiadiazol-3-yl)benzenesulfonamide | 599.2 | 600.1 |

TABLE 3-continued

| Comp Number | Structure | Name | Exact Mass | MS m/z (M+ + 1) |
|---|---|---|---|---|
| 96 | 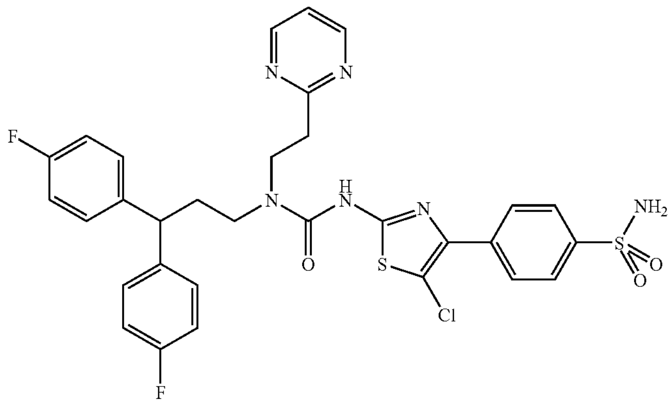 | 4-(2-(((3,3-bis(4-fluorophenyl)propyl)(2-(2-pyrimidinyl)ethyl)carbamoyl)amino)-5-chloro-1,3-thiazol-4-yl)benzenesulfonamide | 668.1 | 669.1 |
| 97 | 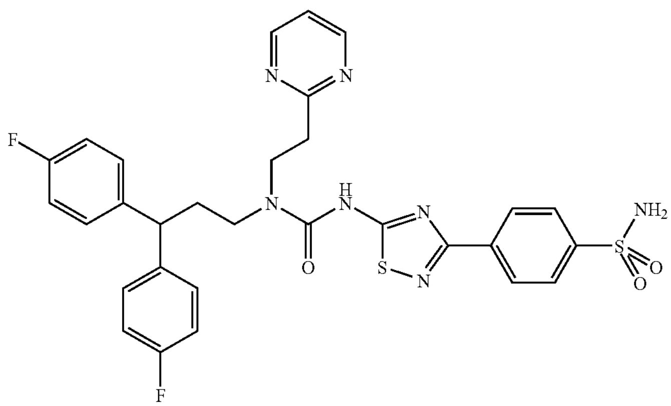 | 4-(5-(((3,3-bis(4-fluorophenyl)propyl)(2-(2-pyrimidinyl)ethyl)carbamoyl)amino)-1,2,4-thiadiazol-3-yl)benzenesulfonamide | 635.2 | 636.1 |

EXAMPLE 45

The examples shown in Table 4 were prepared by the procedure described in Method D except substituting for the corresponding reactants II and V.

Compound 98: Prepared following steps 2 and 3 in example 35. In step 2, (4-bromophenethoxy)(tert-butyl)dimethylsilane was substituted for 3-iodopyridine.

Compound 99: Prepared following steps 2 and 3 in example 35. In step 2, (4-bromophenethoxy)(tert-butyl)dimethylsilane was substituted for 2-bromopyridine.

Compound 100: The procedure described in Example 5 with the exception of substituting methylamine for 2-(3-fluorophenyl)ethanamine in step 1.

Compound 101: The procedure described in Example 5 with the exception of substituting methylamine for 2-(2-fluorophenyl)ethanamine in step 1.

Compound 102: The procedure described in Example 5 with the exception of substituting methylamine for 2-(2-methoxyphenyl)ethanamine in step 1.

Compound 103: The procedure described in Example 5 with the exception of substituting methylamine for 2-fluoroaniline in step 1.

Compound 104: The procedure described in Example 5 with the exception of substituting methylamine for 3-fluoroaniline in step 1.

Compound 105: The procedure described in Example 5 with the exception of substituting methylamine for 4-fluoroaniline in step 1.

Compound 106: See the procedure for compound 75 contained in example 40.

Compound 107: See the procedure for compound 76 contained in example 40.

Compound 108: See the procedure for compound 77 contained in example 40.

Compound 109: The procedure described in Example 25 with the exception of substituting tert-butyl 4-(2-aminoethyl)piperidine-1-carboxylate for cyclopropylamine in step 1 and substituting. Step 4 was not followed.

Compound 110: The procedure described in Example 5 with the exception of substituting methylamine for 2-(2-pyridinyl)ethylamine in step 1 and of substituting N-(4-(2-amino-5-chlorothiazol-4-yl)phenyl)methanesulfonamide for 5-chloro-4-(4-(methylsulfonyl)phenyl)-1,3-thiazol-2-amine (method Q starting from step 2, with substitution of 4-acetyl-N-tert-butylbenzenesulfonamide for 1-(4-(methylsulfonyl)phenyl)ethanone).

Compound 111: The procedure described in Example 5 with the exception of substituting methylamine for 2-(2-pyrazinyl)ethylamine in step 1.

Compound 112: The procedure described in Example 5 with the exception of substituting methylamine for 2-(2-pyrazinyl)ethylamine in step 1 and of substituting N-(4-(2-amino-5-chlorothiazol-4-yl)phenyl)methanesulfonamide for 5-chloro-4-(4-(methylsulfonyl)phenyl)-1,3-thiazol-2-amine (method Q starting from step 2, with substitution of 4-acetyl-N-tert-butylbenzenesulfonamide for 1-(4-(methylsulfonyl)phenyl)ethanone) in step 2.

Compound 113: The procedure described in Example 5 with the exception of substituting methylamine for 2-(2-pyridinyl)ethylamine in step 1 and of substituting N-(4-(2-amino-5-chlorothiazol-4-yl)phenyl)methanesulfonamide for [1,3]thiazolo[5,4-b]pyridin-2-amine (method R with substitution of 4-chloropyridin-3-amine for 2-chloropyridin-3-amine) in step 2.

Compound 114: The procedure described in Example 5 with the exception of substituting methylamine for 2-(2-pyridinyl)ethylamine in step 1 and of substituting N-(4-(2-amino-5-chlorothiazol-4-yl)phenyl)methanesulfonamide for [1,3]thiazolo[4,5-c]pyridin-2-amine (method R) in step 2.

Compound 115: The procedure described in step 2 of example 5 with the exception of substituting N-methyl-3,3-diphenylpropan-1-amine for 3,3-bis(4-fluorophenyl)-N-(2-(pyridin-2-yl)ethyl)propan-1-amine (method H).

Compound 116: The procedure described in Example 5 with the exception of substituting methylamine for 2-(2-pyridinyl)ethylamine in step 1 and of substituting N-(4-(2-amino-5-chlorothiazol-4-yl)phenyl)methanesulfonamide for 4-(2-amino-4-chlorothiazol-5-yl)-N-tert-butylbenzenesulfonamide (method Q).

Compound 117: See the procedure for compound 86 contained in example 44.

Compound 118: The procedure described in step 2 of example 5 with the exception of substituting N-methyl-3,3-diphenylpropan-1-amine for 3,3-bis(4-fluorophenyl)-N-(2-(pyridin-2-yl)ethyl)propan-1-amine (method H) and substituting N-(4-(2-amino-5-chlorothiazol-4-yl)phenyl)methanesulfonamide for N-(4-(5-amino-1,2,4-thiadiazol-3-yl)phenyl)methanesulfonamide (method L, with substitution of 4-(methylsulfonyl)phenylboronic acid) for 4-((methylsulfonyl)amino)phenylboronic acid).

Compound 119: The procedure described in Example 5 with the exception of substituting methylamine for 2-(2-pyridinyl)ethylamine in step 1 and of substituting N-(4-(2-amino-5-chlorothiazol-4-yl)phenyl)methanesulfonamide for 3-(4-(methylsulfonyl)phenyl)-1,2,4-thiadiazol-5-amine (method L).

Compound 120: The procedure described in step 2 of example 5 with the exception of substituting N-methyl-3,3-diphenylpropan-1-amine for 3,3-bis(4-fluorophenyl)-N-(2-(pyridin-2-yl)ethyl)propan-1-amine (method H) and substituting N-(4-(2-amino-5-chlorothiazol-4-yl)phenyl) methanesulfonamide for 3-(4-(methylsulfonyl)phenyl)-1,2,4-thiadiazol-5-amine (method L).

Compound 121: The procedure described in step 2 of example 5 with the exception of substituting methylamine for 2-(2-pyridinyl)ethylamine in step 1 and of substituting N-(4-(2-amino-5-chlorothiazol-4-yl)phenyl)methanesulfonamide for N-(4-(5-amino-1,2,4-thiadiazol-3-yl)phenyl)methanesulfonamide (method L, with substitution of 4-(methylsulfonyl)phenylboronic acid) for 4-((methylsulfonyl)amino)phenylboronic acid) in step 2.

Compound 122: The procedure described in step 2 of example 5 with the exception of substituting methylamine for 2-(2-pyridinyl)ethylamine in step 1 and of substituting N-(4-(2-amino-5-chlorothiazol-4-yl)phenyl)methanesulfonamide for 3-(4-(1H-1,2,3-triazol-1-yl)phenyl)-1,2,4-thiadiazol-5-amine (method L, with substitution of 4-(methylsulfonyl)phenylboronic acid) for 1-(4-(4,4,5,5-tetramethyl-1,3,2-dioxaborolan-2-yl)phenyl)-1H-1,2,3-triazole (described in method O) in step 2.

Compound 123: The procedure described in step 2 of example 5 with the exception of substituting N-methyl-3,3-diphenylpropan-1-amine for 3,3-bis(4-fluorophenyl)-N-(2-(pyridin-2-yl)ethyl)propan-1-amine (method H) and of substituting N-(4-(2-amino-5-chlorothiazol-4-yl)phenyl) methanesulfonamide for 3-(4-(1H-1,2,3-triazol-1-yl) phenyl)-1,2,4-thiadiazol-5-amine (method L, with substitution of 4-(methylsulfonyl)phenylboronic acid) for 1-(4-(4,4,5,5-tetramethyl-1,3,2-dioxaborolan-2-yl)phenyl)-1H-1,2,3-triazole (described in method O) in step 2.

Compound 124: The procedure described in Example 5 with the exception of substituting methylamine for 3-fluoroaniline in step 1.

Compound 125: The procedure described in Example 5 with the exception of substituting methylamine for 4-fluoroaniline in step 1.

Compound 126: See the procedure for compound 75 contained in example 40.

Compound 127: See the procedure for compound 76 contained in example 40.

Compound 128: See the procedure for compound 77 contained in example 40.

Compound 129: The procedure described in Example 25 with the exception of substituting tert-butyl 4-(2-aminoethyl) piperidine-1-carboxylate for cyclopropylamine in step 1 and substituting. Step 4 was not followed.

TABLE 4

| Comp Number | Structure | Name | Exact Mass | MS m/z (M⁺ + 1) |
|---|---|---|---|---|
| 98 | 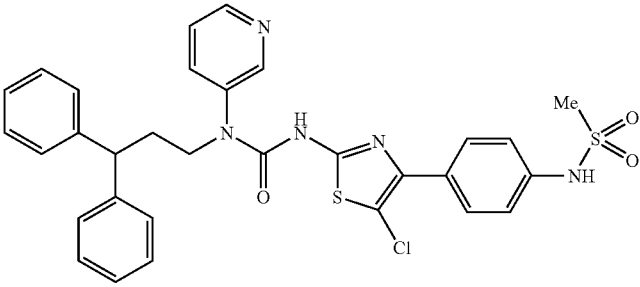 | N-(4-(5-chloro-2-(((3,3-diphenylpropyl)(3-pyridinyl)carbamoyl)amino)-1,3-thiazol-4-yl)phenyl)methanesulfonamide | 617.1 | 618.1 |

TABLE 4-continued

| Comp Number | Structure | Name | Exact Mass | MS m/z (M+ + 1) |
|---|---|---|---|---|
| 99 | 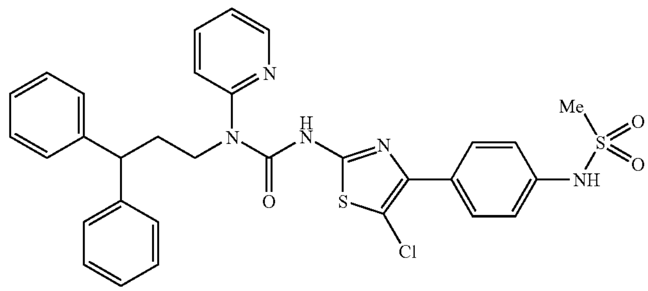 | N-(4-(5-chloro-2-(((3,3-diphenylpropyl)(2-pyridinyl)carbamoyl)amino)-1,3-thiazol-4-yl)phenyl)methanesulfonamide | 617.1 | 618.1 |
| 100 | 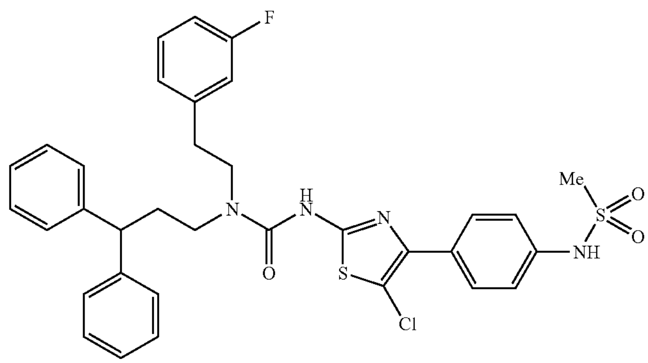 | N-(4-(5-chloro-2-(((3,3-diphenylpropyl)(2-(3-fluorophenyl)ethyl)carbamoyl)amino)-1,3-thiazol-4-yl)phenyl)methanesulfonamide | 662.2 | 663.2 |
| 101 | 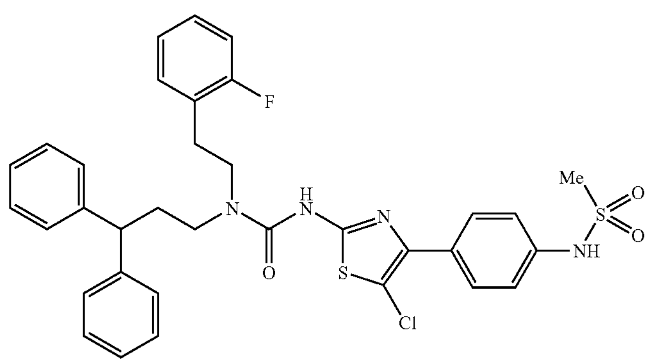 | N-(4-(5-chloro-2-(((3,3-diphenylpropyl)(2-(2-fluorophenyl)ethyl)carbamoyl)amino)-1,3-thiazol-4-yl)phenyl)methanesulfonamide | 662.2 | 663.1 |
| 102 | 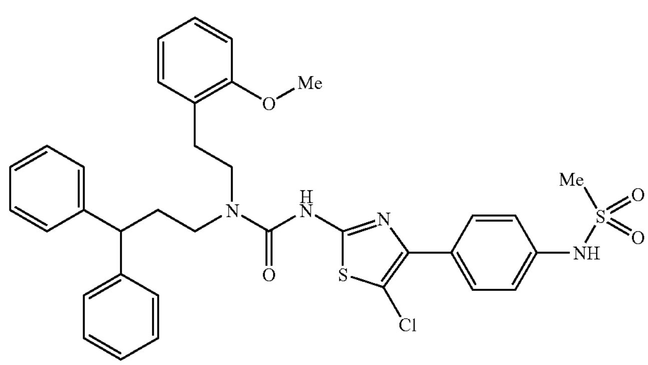 | N-(4-(5-chloro-2-(((3,3-diphenylpropyl)(2-(2-methoxyphenyl)ethyl)carbamoyl)amino)-1,3-thiazol-4-yl)phenyl)methanesulfonamide | 674.2 | 675.2 |

TABLE 4-continued

| Comp Number | Structure | Name | Exact Mass | MS m/z (M+ + 1) |
|---|---|---|---|---|
| 103 | 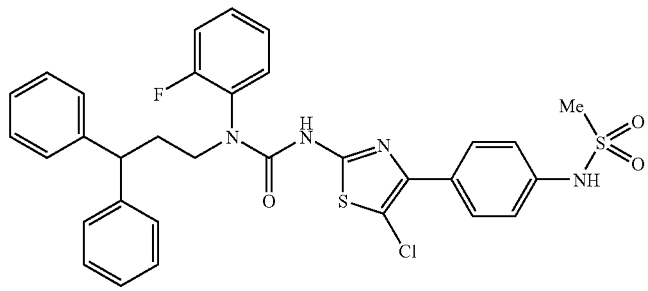 | N-(4-(5-chloro-2-(((3,3-diphenylpropyl)(2-fluorophenyl)carbamoyl)amino)-1,3-thiazol-4-yl)phenyl)methanesulfonamide | 634.1 | 635.1 |
| 104 | 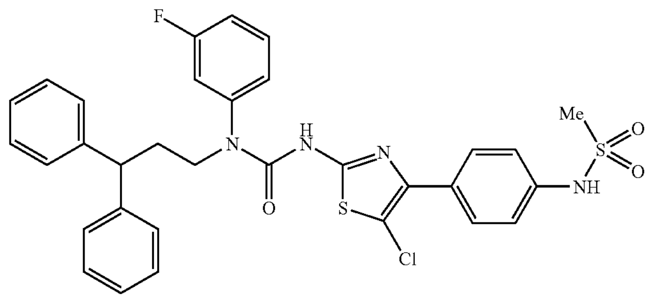 | N-(4-(5-chloro-2-(((3,3-diphenylpropyl)(3-fluorophenyl)carbamoyl)amino)-1,3-thiazol-4-yl)phenyl)methanesulfonamide | 634.1 | 635.1 |
| 105 | 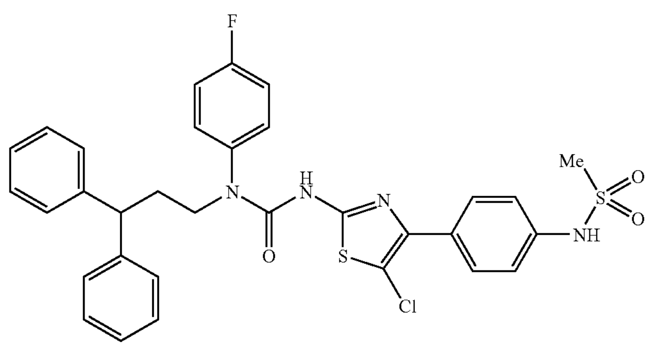 | N-(4-(5-chloro-2-(((3,3-diphenylpropyl)(4-fluorophenyl)carbamoyl)amino)-1,3-thiazol-4-yl)phenyl)methanesulfonamide | 634.1 | 635.1 |
| 106 | 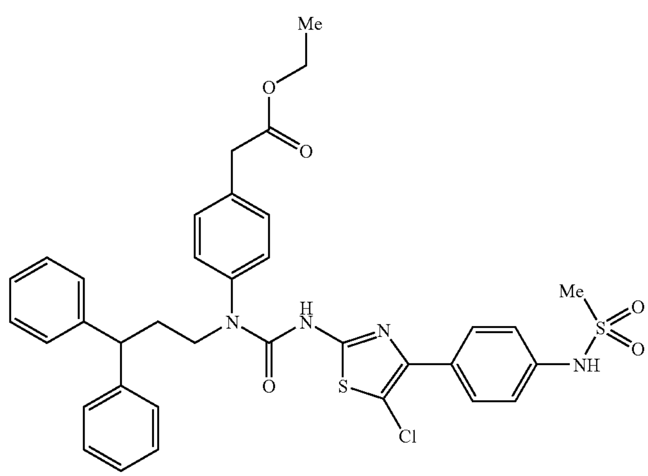 | ethyl (4-(((5-chloro-4-(4-((methylsulfonyl)amino)phenyl)-1,3-thiazol-2-yl)carbamoyl)(3,3-diphenylpropyl)amino)phenyl)acetate | 702.2 | 703.2 |

TABLE 4-continued

| Comp Number | Structure | Name | Exact Mass | MS m/z (M+ + 1) |
|---|---|---|---|---|
| 107 | 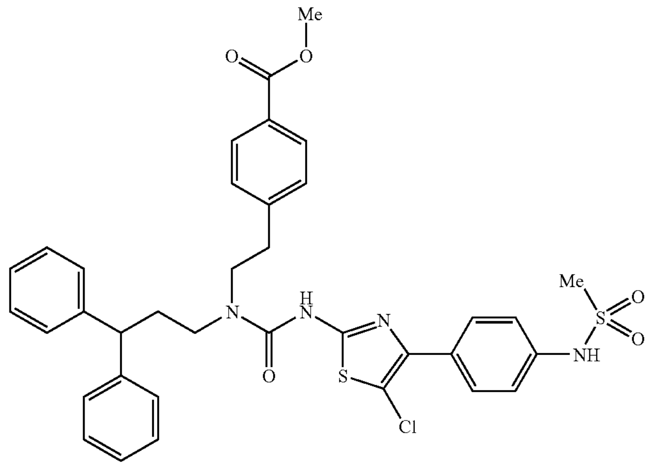 | methyl 4-(2-(((5-chloro-4-(4-((methylsulfonyl)amino)phenyl)-1,3-thiazol-2-yl)carbamoyl)(3,3-diphenylpropyl)amino)ethyl)benzoate | 702.2 | 703.2 |
| 108 | 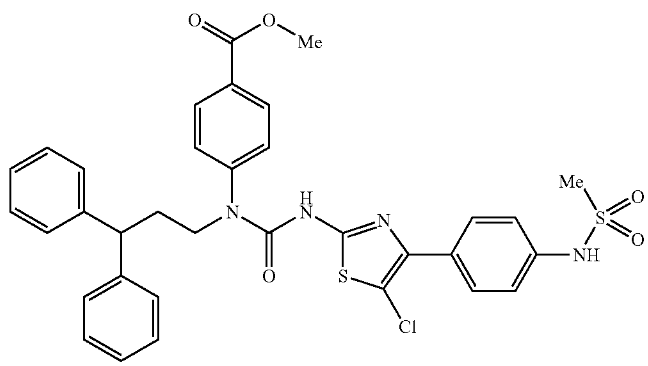 | methyl 4-(((5-chloro-4-(4-((methylsulfonyl)amino)phenyl)-1,3-thiazol-2-yl)carbamoyl)(3,3-diphenylpropyl)amino)benzoate | 674.1 | 675.2 |
| 109 | 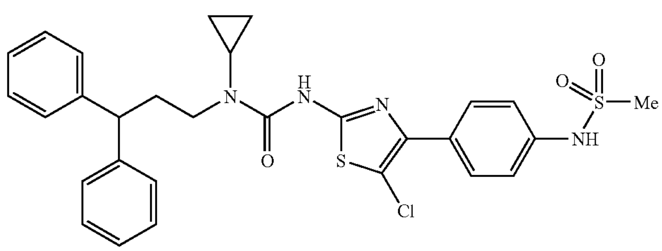 | N-(4-(5-chloro-2-((cyclopropyl(3,3-diphenylpropyl)carbamoyl)amino)-1,3-thiazol-4-yl)phenyl)methanesulfonamide | 580.1 | 581.1 |
| 110 | 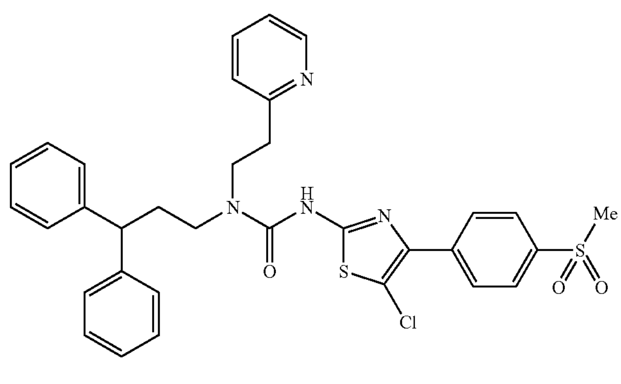 | 3-(5-chloro-4-(4-(methylsulfonyl)phenyl)-1,3-thiazol-2-yl)-1-(3,3-diphenylpropyl)-1-(2-(2-pyridinyl)ethyl)urea | 630.2 | 631.1 |

TABLE 4-continued

| Comp Number | Structure | Name | Exact Mass | MS m/z (M⁺ + 1) |
|---|---|---|---|---|
| 111 | 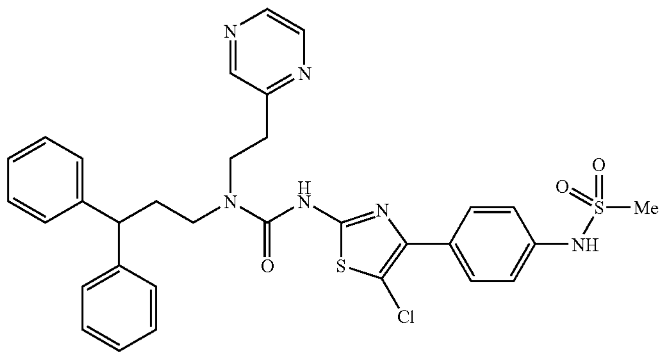 | N-(4-(5-chloro-2-(((3,3-diphenylpropyl)(2-(2-pyrazinyl)ethyl)carbamoyl)amino)-1,3-thiazol-4-yl)phenyl)methanesulfonamide | 646.2 | 647.1 |
| 112 | 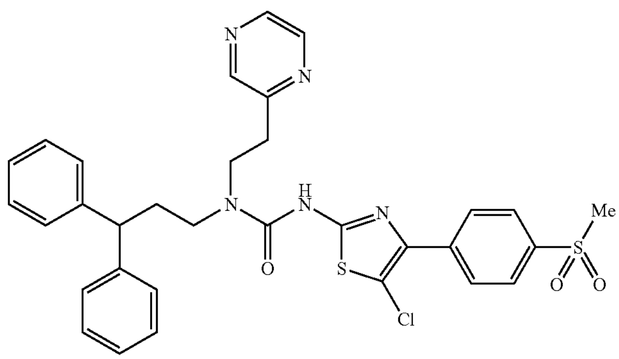 | 3-(5-chloro-4-(4-(methylsulfonyl)phenyl)-1,3-thiazol-2-yl)-1-(3,3-diphenylpropyl)-1-(2-(2-pyrazinyl)ethyl)urea | 631.2 | 632.1 |
| 113 | 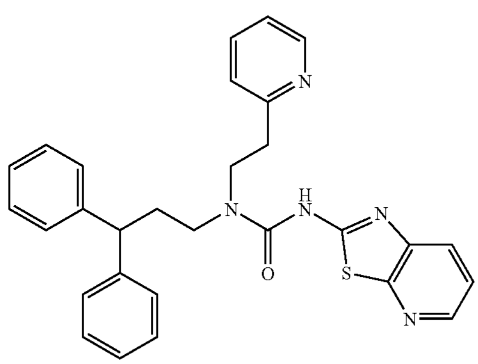 | 1-(3,3-diphenylpropyl)-1-(2-(2-pyridinyl)ethyl)-3-[1,3]thiazolo[5,4-b]pyridin-2-ylurea | 493.2 | 494.1 |
| 114 | 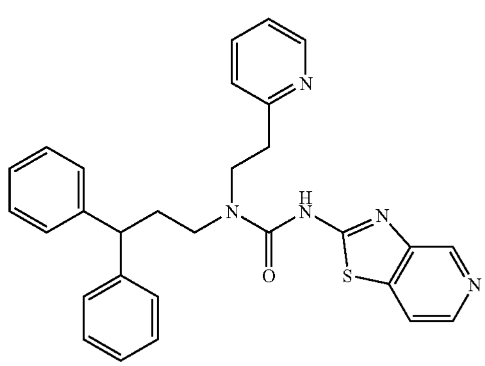 | 1-(3,3-diphenylpropyl)-1-(2-(2-pyridinyl)ethyl)-3-[1,3]thiazolo[4,5-c]pyridin-2-ylurea | 493.2 | 494.1 |

TABLE 4-continued

| Comp Number | Structure | Name | Exact Mass | MS m/z (M+ + 1) |
|---|---|---|---|---|
| 115 | 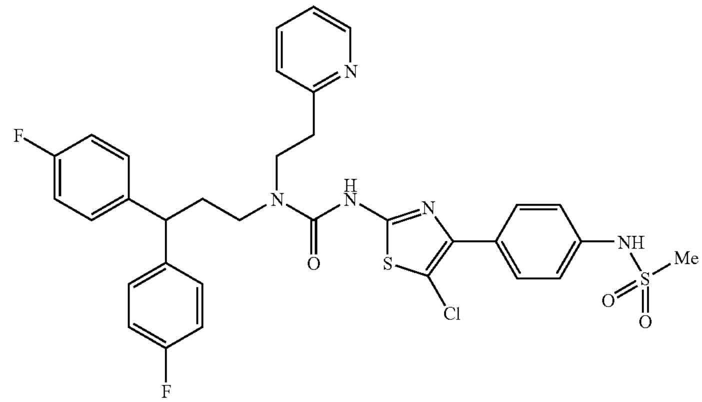 | N-(4-(2-(((3,3-bis(4-fluorophenyl)propyl)(2-(2-pyridinyl)ethyl)carbamoyl)amino)-5-chloro-1,3-thiazol-4-yl)phenyl)methane-sulfonamide | 681.1 | 682.1 |
| 116 | 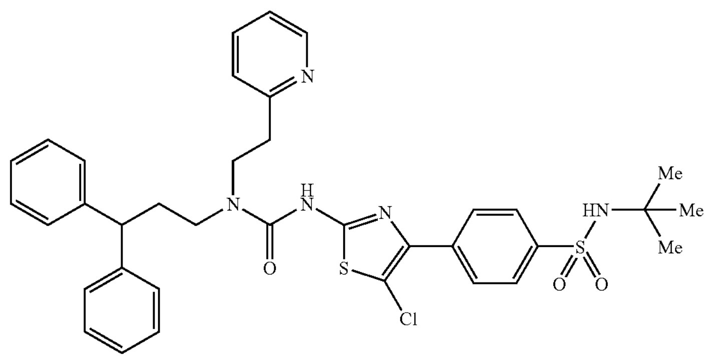 | N-tert-butyl-4-(5-chloro-2-(((3,3-diphenylpropyl)(2-(2-pyridinyl)ethyl)carbamoyl)amino)-1,3-thiazol-4-yl)benzene-sulfonamide | 687.2 | 688.1 |
| 117 | 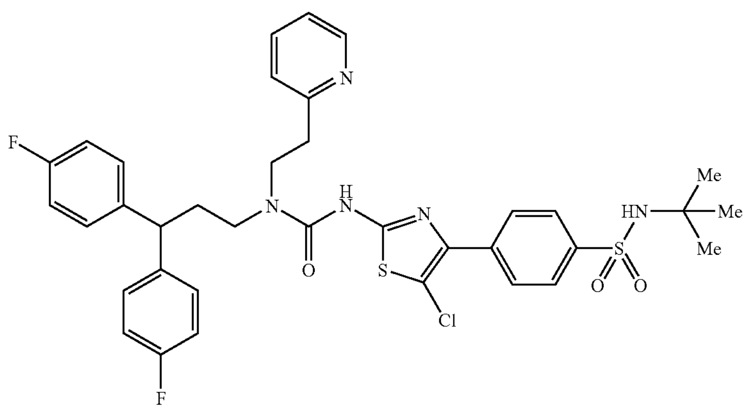 | 4-(2-(((3,3-bis(4-fluorophenyl)propyl)(2-(2-pyridinyl)ethyl)carbamoyl)amino)-5-chloro-1,3-thiazol-4-yl)-N-tert-butylbenzene-sulfonamide | 723.2 | 724.1 |
| 118 | 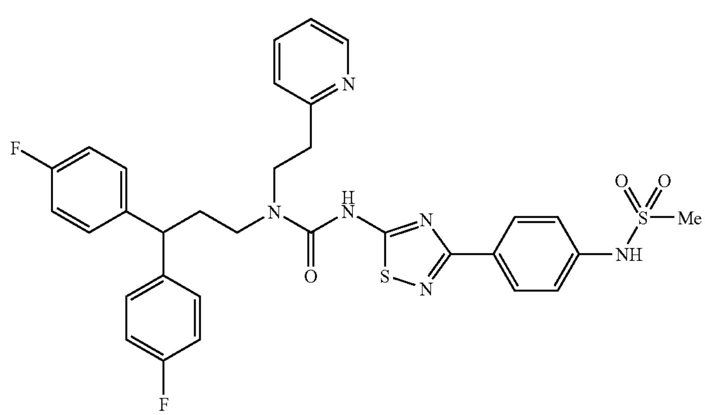 | N-(4-(5-(((3,3-bis(4-fluorophenyl)propyl)(2-(2-pyridinyl)ethyl)carbamoyl)amino)-1,2,4-thiadiazol-3-yl)phenyl)methane-sulfonamide | 648.2 | 649.1 |

TABLE 4-continued

| Comp Number | Structure | Name | Exact Mass | MS m/z (M⁺ + 1) |
|---|---|---|---|---|
| 119 | 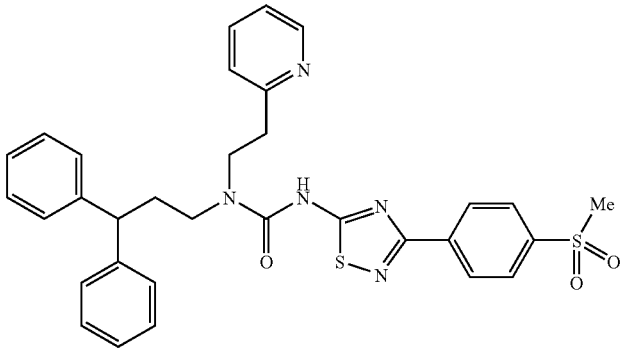 | 1-(3,3-diphenylpropyl)-3-(3-(4-(methylsulfonyl)phenyl)-1,2,4-thiadiazol-5-yl)-1-(2-(2-pyridinyl)ethyl)urea | 597.2 | 598.2 |
| 120 | 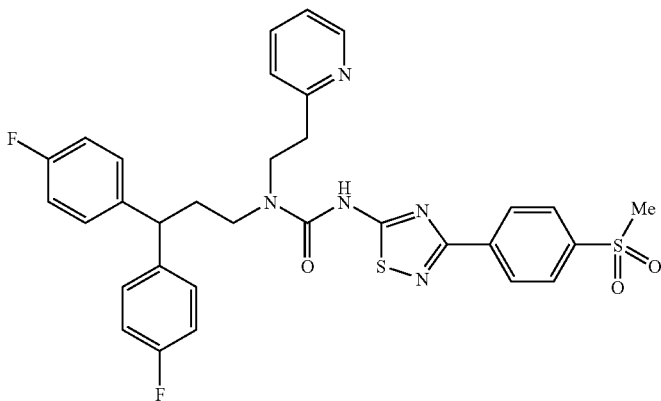 | 1-(3,3-bis(4-fluorophenyl)propyl)-3-(3-(4-(methylsulfonyl)phenyl)-1,2,4-thiadiazol-5-yl)-1-(2-(2-pyridinyl)ethyl)urea | 633.2 | 634.1 |
| 121 | 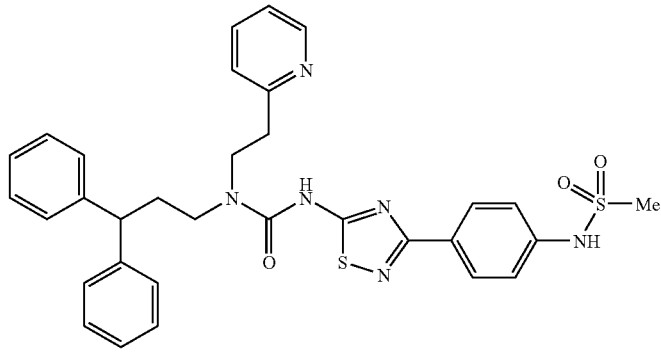 | N-(4-(5-(((3,3-diphenylpropyl)(2-(2-pyridinyl)ethyl)carbamoyl)amino)-1,2,4-thiadiazol-3-yl)phenyl)methanesulfonamide | 612.2 | 613.2 |
| 122 | 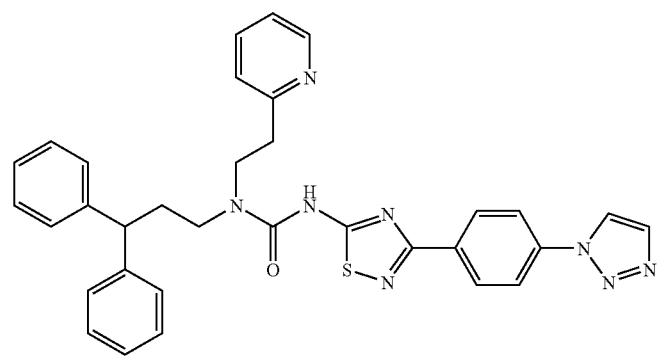 | 1-(3,3-diphenylpropyl)-1-(2-(2-pyridinyl)ethyl)-3-(3-(4-(1H-1,2,3-triazol-1-yl)phenyl)-1,2,4-thiadiazol-5-yl)urea | 586.2 | 587.2 |

TABLE 4-continued

| Comp Number | Structure | Name | Exact Mass | MS m/z (M+ + 1) |
|---|---|---|---|---|
| 123 | 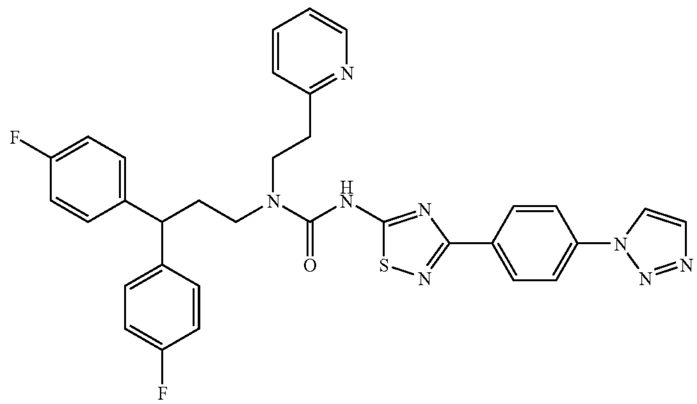 | 1-(3,3-bis(4-fluorophenyl)propyl)-1-(2-(2-pyridinyl)ethyl)-3-(3-(4-(1H-1,2,3-triazol-1-yl)phenyl)-1,2,4-thiadiazol-5-yl)urea | 622.2 | 623.2 |
| 124 | 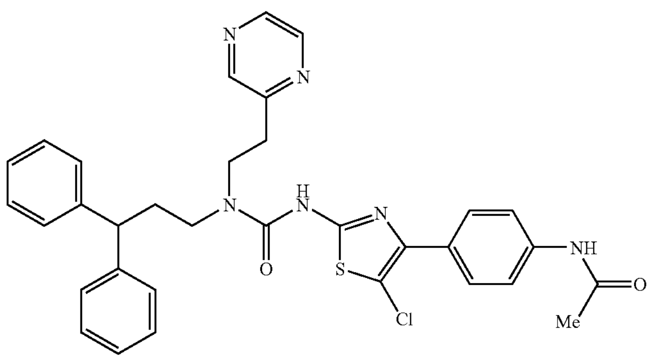 | N-(4-(5-chloro-2-(((3,3-diphenylpropyl)(2-(2-pyrazinyl)ethyl)carbamoyl)amino)-1,3-thiazol-4-yl)phenyl)acetamide | 610.2 | 611.1 |
| 125 | 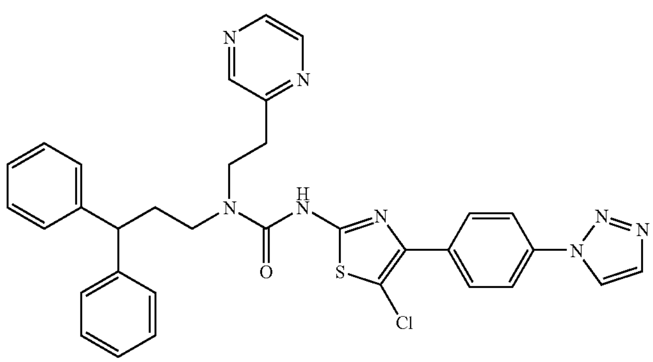 | 3-(5-chloro-4-(4-(1H-1,2,3-triazol-1-yl)phenyl)-1,3-thiazol-2-yl)-1-(3,3-diphenylpropyl)-1-(2-(2-pyrazinyl)ethyl)urea | 620.2 | 621.2 |
| 126 | 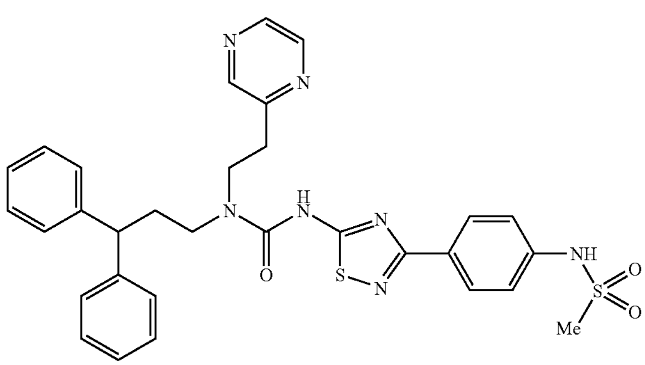 | N-(4-(5-(((3,3-diphenylpropyl)(2-(2-pyrazinyl)ethyl)carbamoyl)amino)-1,2,4-thiadiazol-3-yl)phenyl)methanesulfonamide | 613.2 | 614.2 |

TABLE 4-continued

| Comp Number | Structure | Name | Exact Mass | MS m/z (M⁺ + 1) |
|---|---|---|---|---|
| 127 | 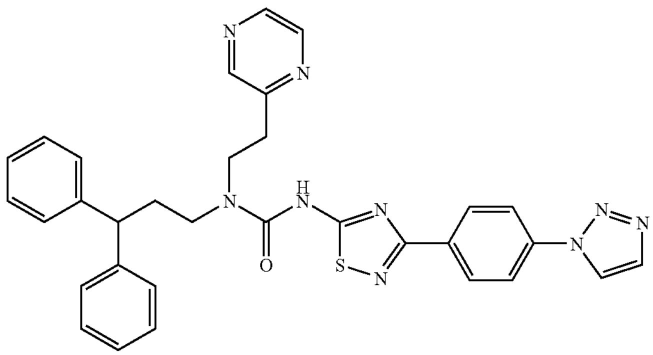 | 1-(3,3-diphenylpropyl)-1-(2-(2-pyrazinyl)ethyl)-3-(3-(4-(1H-1,2,3-triazol-1-yl)phenyl)-1,2,4-thiadiazol-5-yl)urea | 587.2 | 588.2 |
| 128 | 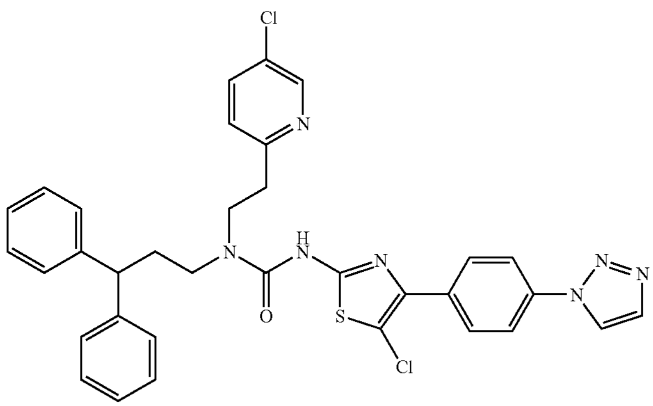 | 1-(2-(5-chloro-2-pyridinyl)ethyl)-3-(5-chloro-4-(4-(1H-1,2,3-triazol-1-yl)phenyl)-1,3-thiazol-2-yl)-1-(3,3-diphenylpropyl)urea | 653.2 | 654.1 |
| 129 | 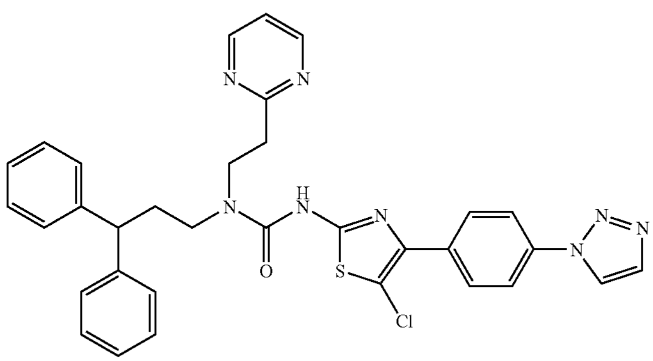 | 3-(5-chloro-4-(4-(1H-1,2,3-triazol-1-yl)phenyl)-1,3-thiazol-2-yl)-1-(3,3-diphenyl-propyl)-1-(2-(2-pyrimidinyl)ethyl)urea | 620.2 | 621.2 |
| 130 | 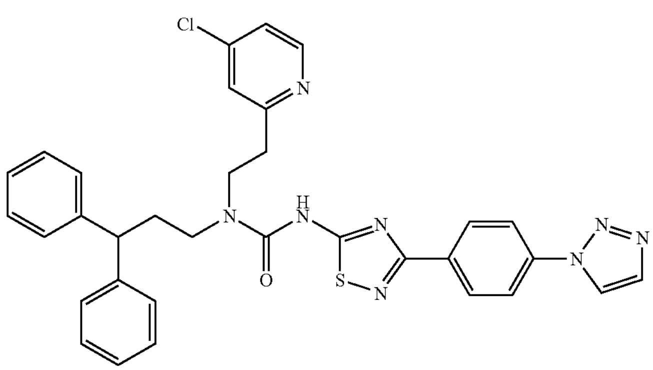 | 1-(2-(4-chloro-2-pyridinyl)ethyl)-1-(3,3-diphenylpropyl)-3-(3-(4-(1H-1,2,3-triazol-1-yl)phenyl)-1,2,4-thiadiazol-5-yl)urea | 620.2 | 621.2 |

TABLE 4-continued

| Comp Number | Structure | Name | Exact Mass | MS m/z (M+ + 1) |
|---|---|---|---|---|
| 131 | 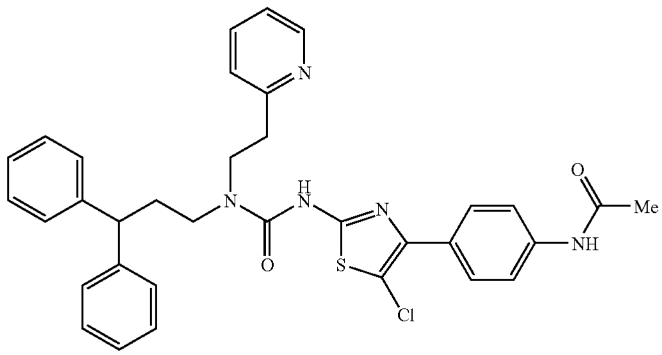 | N-(4-(5-chloro-2-(((3,3-diphenylpropyl)(2-(2-pyridinyl)ethyl)carbamoyl)amino)-1,3-thiazol-4-yl)phenyl)acetamide | 609.2 | 610.2 |
| 132 | 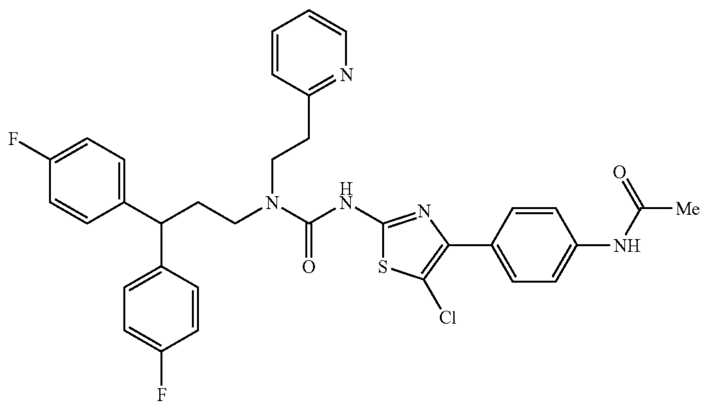 | N-(4-(2-(((3,3-bis(4-fluorophenyl)propyl)(2-(2-pyridinyl)ethyl)carbamoyl)amino)-5-chloro-1,3-thiazol-4-yl)phenyl)acetamide | 645.2 | 646.2 |
| 133 | 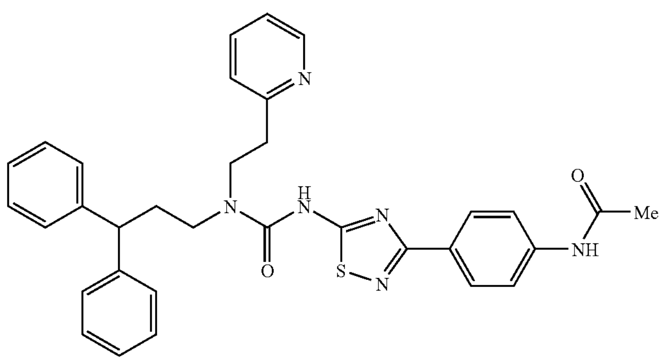 | N-(4-(5-(((3,3-diphenyl-propyl)(2-(2-pyridinyl)ethyl)carbamoyl)amino)-1,2,4-thiadiazol-3-yl)phenyl)acetamide | 576.2 | 577.2 |
| 134 | 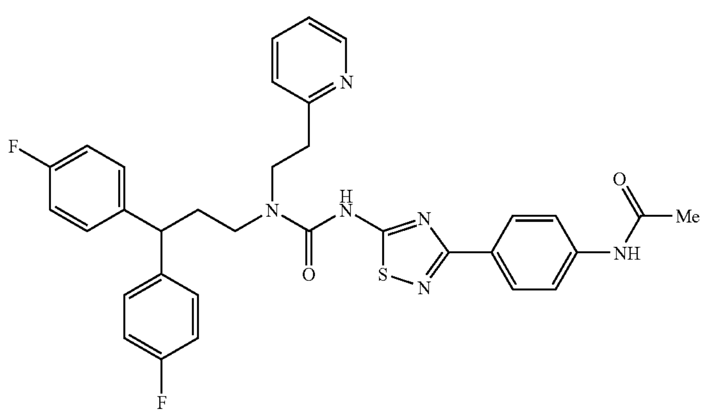 | N-(4-(5-(((3,3-bis(4-fluorophenyl)propyl)(2-(2-pyridinyl)ethyl)carbamoyl)amino)-1,2,4-thiadiazol-3-yl)phenyl)acetamide | 612.2 | 613.2 |

TABLE 4-continued

| Comp Number | Structure | Name | Exact Mass | MS m/z (M+ + 1) |
|---|---|---|---|---|
| 135 | 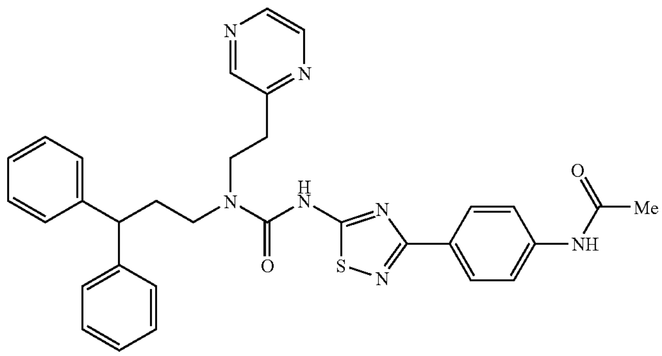 | N-(4-(5-(((3,3-diphenyl-propyl)(2-(2-pyrazinyl)ethyl)carbamoyl)amino)-1,2,4-thiadiazol-3-yl)phenyl)acetamide | 577.2 | 578.2 |
| 136 | 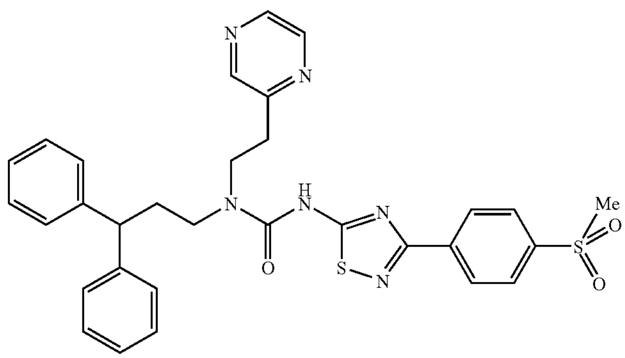 | 1-(3,3-diphenylpropyl)-3-(3-(4-(methylsulfonyl)phenyl)-1,2,4-thiadiazol-5-yl)-1-(2-(2-pyrazinyl)ethyl)urea | 598.2 | 599.2 |
| 137 | 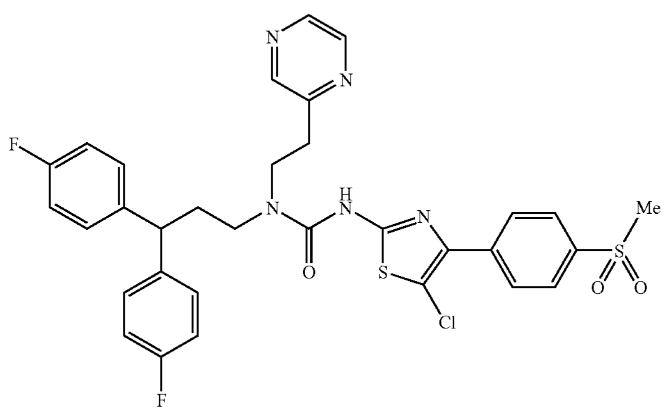 | 1-(3,3-bis(4-fluoro-phenyl)propyl)-3-(5-chloro-4-(4-(methyl-sulfonyl)phenyl)-1,3-thiazol-2-yl)-1-(2-(2-pyrazinyl)ethyl)urea | 667.1 | 668.1 |
| 138 | 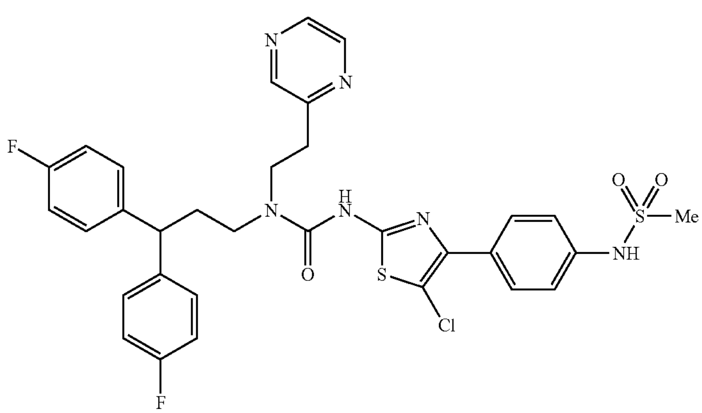 | N-(4-(2-(((3,3-bis(4-fluorophenyl)propyl)(2-(2-pyrazinyl)ethyl)carbamoyl)amino)-5-chloro-1,3-thiazol-4-yl)phenyl)methane-sulfonamide | 682.1 | 683.1 |

TABLE 4-continued

| Comp Number | Structure | Name | Exact Mass | MS m/z (M+ + 1) |
|---|---|---|---|---|
| 139 | 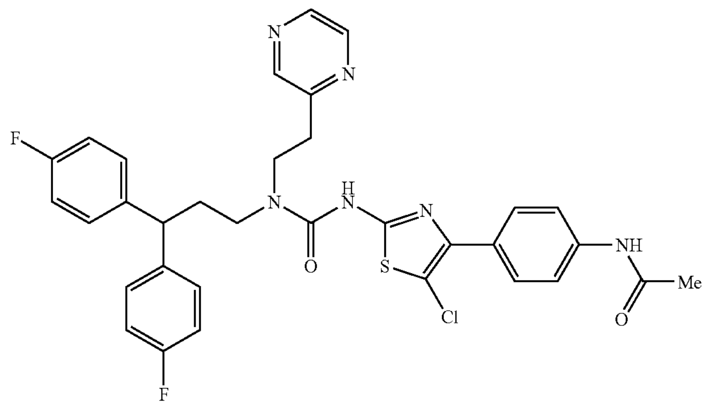 | N-(4-(2-(((3,3-bis(4-fluorophenyl)propyl)(2-(2-pyrazinyl)ethyl)carbamoyl)amino)-5-chloro-1,3-thiazol-4-yl)phenyl)acetamide | 646.2 | 647.1 |
| 140 | 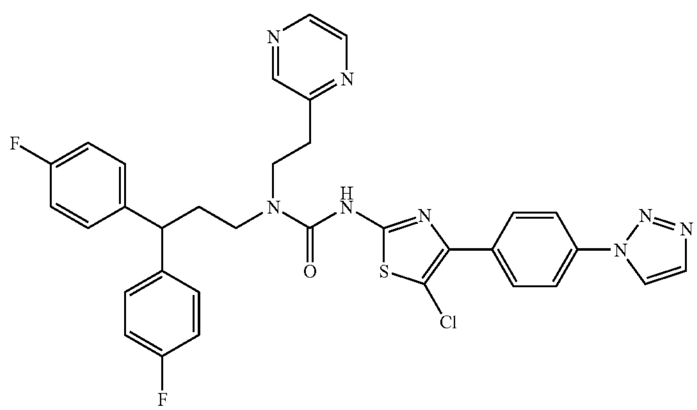 | 1-(3,3-bis(4-fluorophenyl)propyl)-3-(5-chloro-4-(4-(1H-1,2,3-triazol-1-yl)phenyl)-1,3-thiazol-2-yl)-1-(2-(2-pyrazinyl)ethyl)urea | 656.2 | 657.1 |
| 141 | 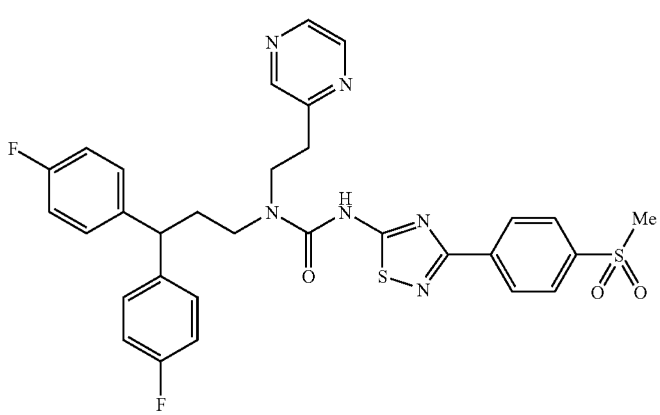 | 1-(3,3-bis(4-fluorophenyl)propyl)-3-(3-(4-(methylsulfonyl)phenyl)-1,2,4-thiadiazol-5-yl)-1-(2-(2-pyrazinyl)ethyl)urea | 634.2 | 635.1 |

| Comp Number | Structure | Name | Exact Mass | MS m/z (M+ + 1) |
|---|---|---|---|---|
| 142 | 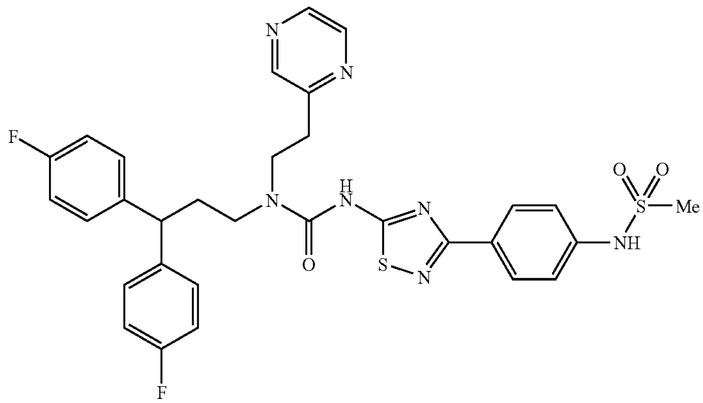 | N-(4-(5-(((3,3-bis(4-fluorophenyl)propyl)(2-(2-pyrazinyl)ethyl)carbamoyl)amino)-1,2,4-thiadiazol-3-yl)phenyl)methanesulfonamide | 649.2 | 650.1 |
| 143 | 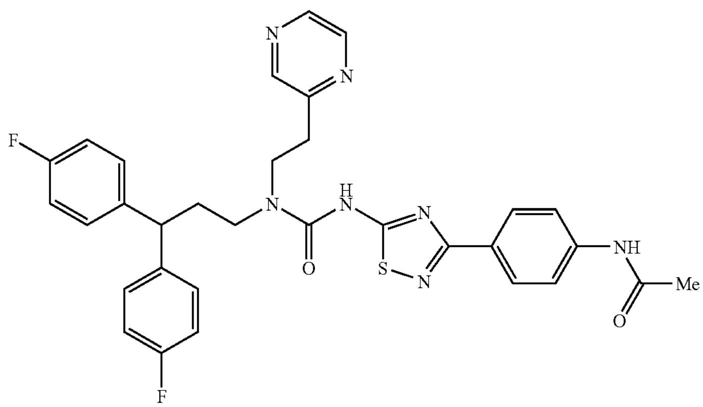 | N-(4-(5-(((3,3-bis(4-fluorophenyl)propyl)(2-(2-pyrazinyl)ethyl)carbamoyl)amino)-1,2,4-thiadiazol-3-yl)phenyl)acetamide | 613.2 | 614.2 |
| 144 | 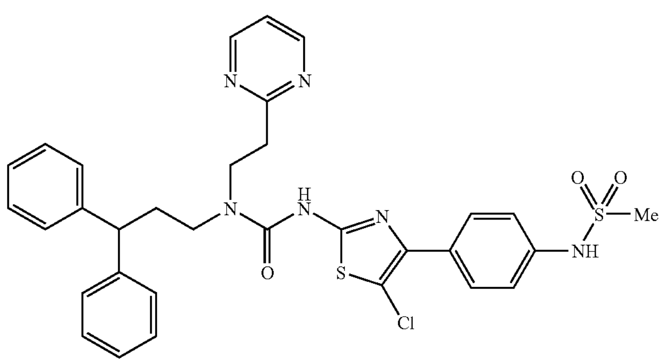 | N-(4-(5-chloro-2-(((3,3-diphenylpropyl)(2-(2-pyrimidinyl)ethyl)carbamoyl)amino)-1,3-thiazol-4-yl)phenyl)methanesulfonamide | 646.2 | 647.1 |
| 145 | 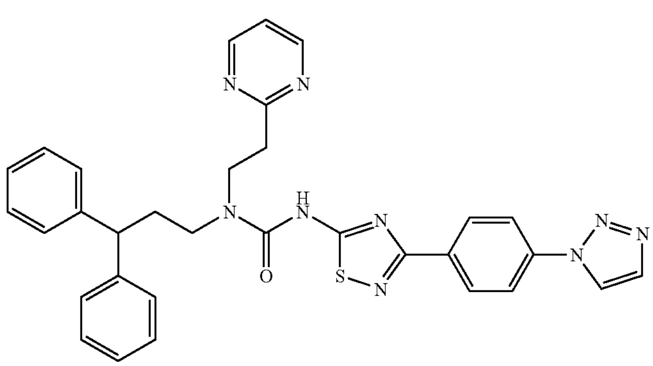 | 1-(3,3-diphenylpropyl)-1-(2-(2-pyrimidinyl)ethyl)-3-(3-(4-(1H-1,2,3-triazol-1-yl)phenyl)-1,2,4-thiadiazol-5-yl)urea | 587.2 | 588.2 |

TABLE 4-continued

| Comp Number | Structure | Name | Exact Mass | MS m/z (M+ + 1) |
|---|---|---|---|---|
| 146 | 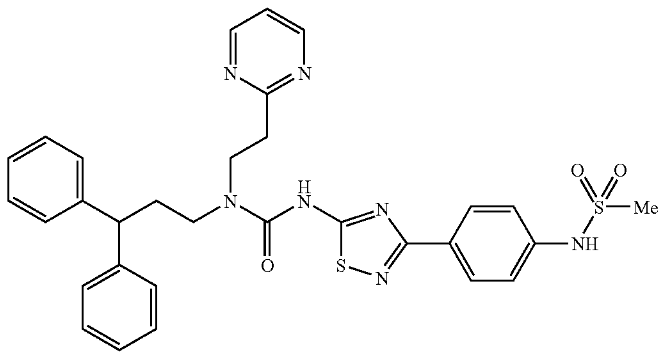 | N-(4-(5-(((3,3-diphenyl-propyl)(2-(2-pyrimidinyl)ethyl)carbamoyl)amino)-1,2,4-thiadiazol-3-yl)phenyl)methane-sulfonamide | 613.2 | 614.2 |
| 147 | 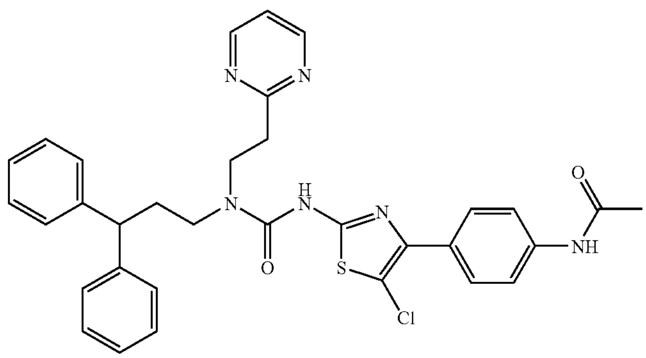 | N-(4-(5-chloro-2-(((3,3-diphenylpropyl)(2-(2-pyrimidinyl)ethyl)carbamoyl)amino)-1,3-thiazol-4-yl)phenyl)acetamide | 610.2 | 611.2 |
| 148 | 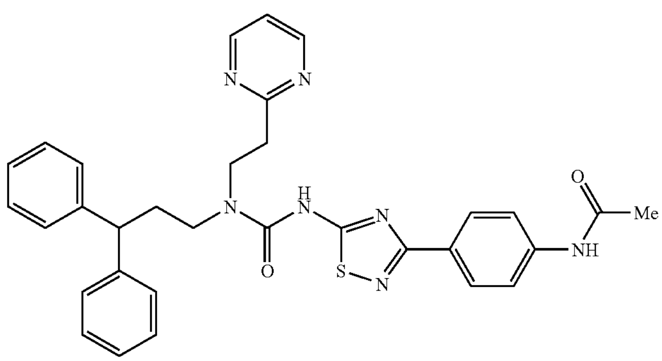 | N-(4-(5-(((3,3-diphenyl-propyl)(2-(2-pyrimidinyl)ethyl)carbamoyl)amino)-1,2,4-thiadiazol-3-yl)phenyl)acetamide | 577.2 | 578.2 |
| 149 | 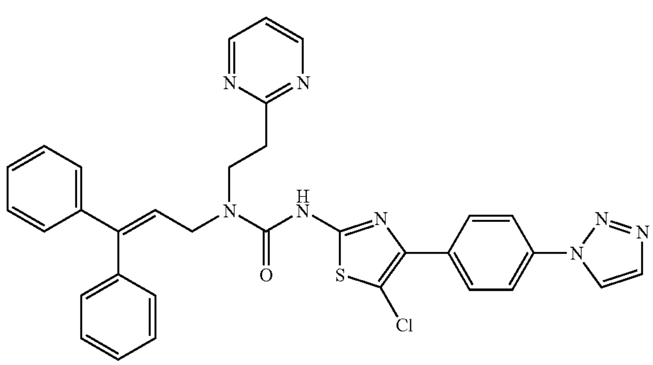 | 3-(5-chloro-4-(4-(1H-1,2,3-triazol-1-yl)phenyl)-1,3-thiazol-2-yl)-1-(3,3-diphenyl-2-propen-1-yl)-1-(2-(2-pyrimidinyl)ethyl)urea | 618.2 | 619.1 |

TABLE 4-continued
| Comp Number | Structure | Name | Exact Mass | MS m/z (M+ + 1) |
|---|---|---|---|---|
| 150 | 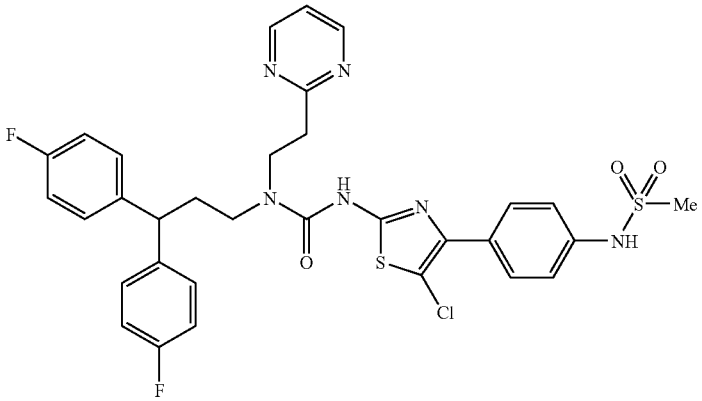 | N-(4-(2-(((3,3-bis(4-fluorophenyl)propyl)(2-(2-pyrimidinyl)ethyl) carbamoyl)amino)-5-chloro-1,3-thiazol-4-yl)phenyl)methane-sulfonamide | 682.1 | 683.1 |
| 151 | 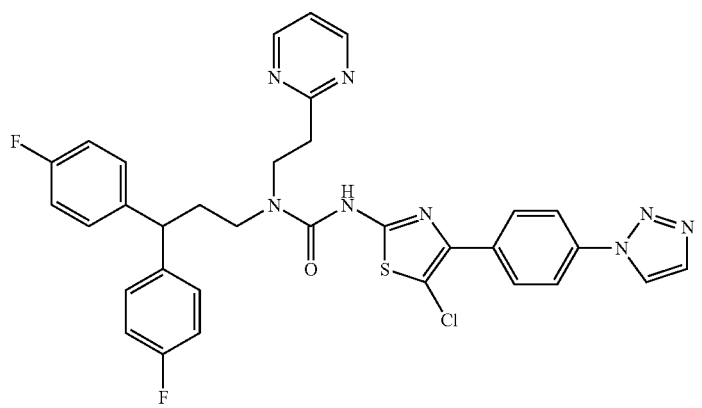 | 1-(3,3-bis(4-fluoro-phenyl)propyl)-3-(5-chloro-4-(4-(1H-1,2,3-triazol-1-yl)phenyl)-1,3-thiazol-2-yl)-1-(2-(2-pyrimidinyl)ethyl)urea | 656.2 | 657.1 |
| 152 | 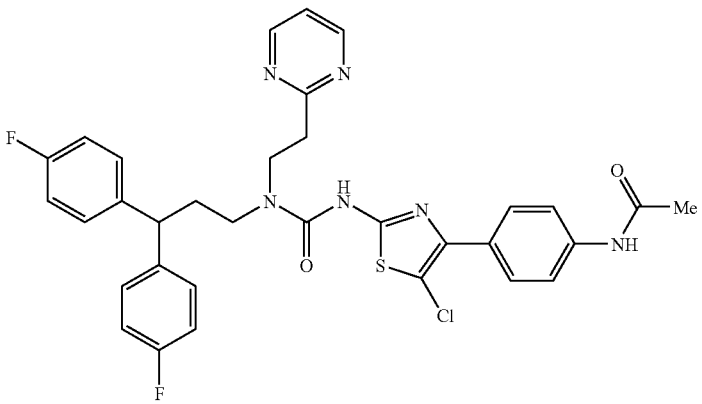 | N-(4-(2-(((3,3-bis(4-fluorophenyl)propyl)(2-(2-pyrimidinyl)ethyl) carbamoyl)amino)-5-chloro-1,3-thiazol-4-yl)phenyl)acetamide | 646.2 | 647.2 |

TABLE 4-continued

| Comp Number | Structure | Name | Exact Mass | MS m/z (M+ + 1) |
|---|---|---|---|---|
| 153 | 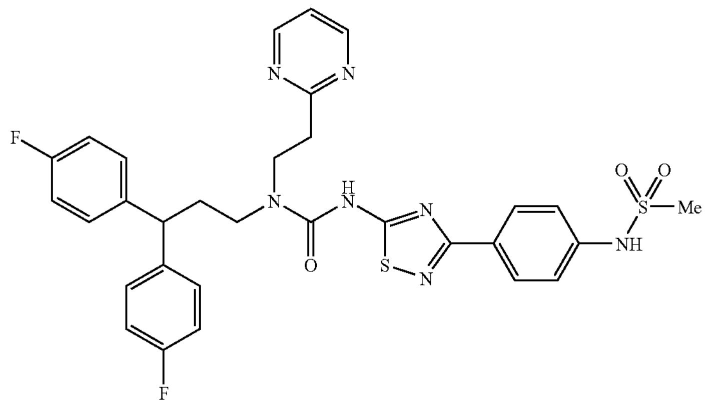 | N-(4-(5-(((3,3-bis(4-fluorophenyl)propyl)(2-(2-pyrimidinyl)ethyl)carbamoyl)amino)-1,2,4-thiadiazol-3-yl)phenyl)methanesulfonamide | 649.2 | 650.2 |
| 154 | 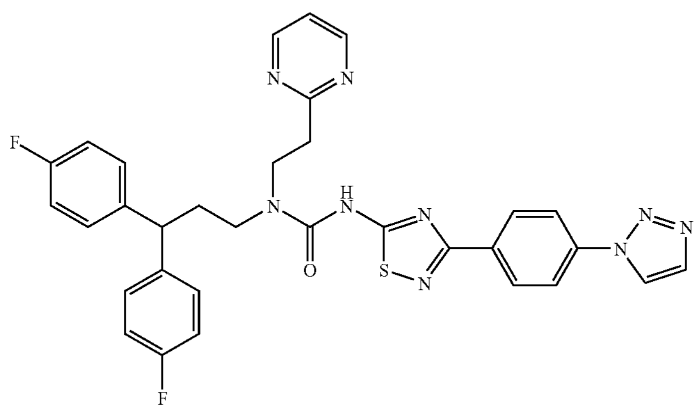 | 1-(3,3-bis(4-fluorophenyl)propyl)-1-(2-(2-pyrimidinyl)ethyl)-3-(3-(4-(1H-1,2,3-triazol-1-yl)phenyl)-1,2,4-thiadiazol-5-yl)urea | 623.2 | 624.2 |
| 155 | 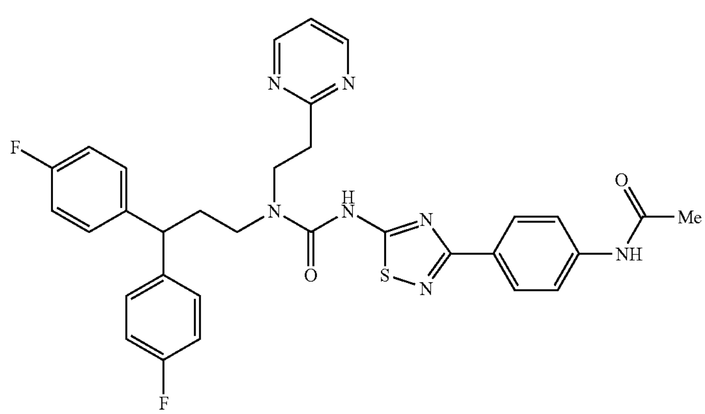 | N-(4-(5-(((3,3-bis(4-fluorophenyl)propyl)(2-(2-pyrimidinyl)ethyl)carbamoyl)amino)-1,2,4-thiadiazol-3-yl)phenyl)acetamide | 613.2 | 614.2 |

EXAMPLE 46

Synthesis of N-(4-(3-(((3,3-diphenylpropyl)(2-(2-pyridinyl)ethyl)carbamoyl)amino)-1,2,4-thiadiazol-5-yl)phenyl)acetamide, 158

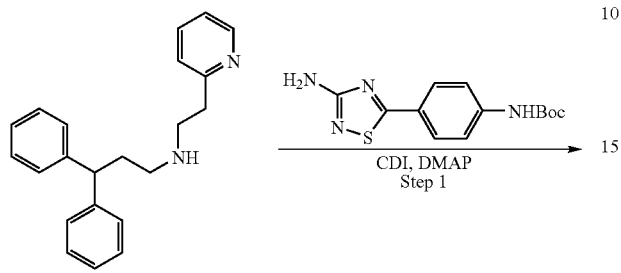

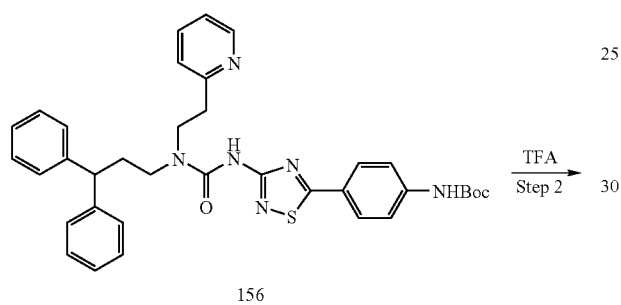

156

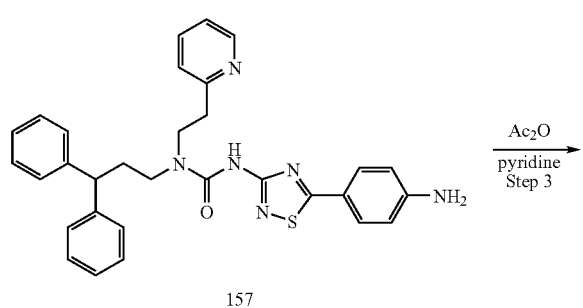

157

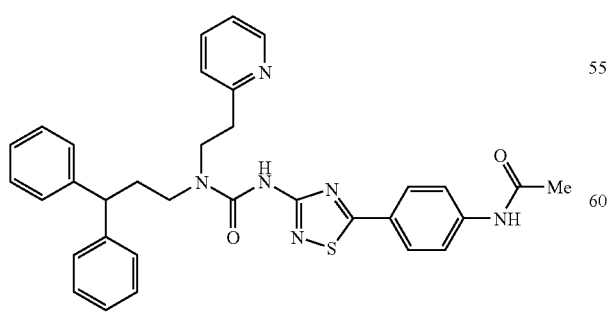

158

Step 1. To a mixture of tert-butyl 4-(3-amino-1,2,4-thiadiazol-5-yl)phenylcarbamate (0.078 g, 0.27 mmol), DMAP (0.049 g, 0.40 mmol), and CDI (0.066 g, 0.41 mmol) was added DMF (1 mL). The reaction mixture was heated to 50° C. for 15 h and 3,3-diphenyl-N-(2-(pyridin-2-yl)ethyl)propan-1-amine (0.090 g, 0.28 mmol) was added. The reaction mixture was heated to 50° C. for 20 h. Direct purification by flash column chromatography on silica gel (eluted with 50% to 100% EtOAc in hexanes) gave tert-butyl 4-(3-(3-(3,3-diphenylpropyl)-3-(2-(pyridin-2-yl)ethyl)ureido)-1,2,4-thiadiazol-5-yl)phenylcarbamate 156.

Step 2. To a solution of tert-butyl 4-(3-(3-(3,3-diphenylpropyl)-3-(2-(pyridin-2-yl)ethyl)ureido)-1,2,4-thiadiazol-5-yl)phenylcarbamate (0.100 g, 0.158 mmol) in DCM (1.5 mL) at room temperature was added anisol (0.20 mL) and TFA (1.5 mL). The reaction mixture was stirred at room temperature for 1.5 h and concentrated. The reaction mixture was diluted with EtOAc, washed with saturated NaHCO$_3$ (1×), brine (1×), dried over MgSO$_4$, filtered, and concentrated. The product, 3-(5-(4-aminophenyl)-1,2,4-thiadiazol-3-yl)-1-(3,3-diphenylpropyl)-1-(2-(pyridin-2-yl)ethyl)urea, was used in the next step without further purification 157.

Step 3. To a solution of 3-(5-(4-aminophenyl)-1,2,4-thiadiazol-3-yl)-1-(3,3-diphenylpropyl)-1-(2-(pyridin-2-yl)ethyl)urea (0.042 g, 0.079 mmol), prepared in the previous step, in DCM (1.5 mL) at 0° C. was added pyridine (50 μL, 49 mg, 0.62 mmol) and acetic anhydride (9.0 μL, 9.0 mg, 0.088 mmol). The reaction mixture was warmed to room temperature. After 1 h, additional acetic anhydride (10 μL) and a small amount of DMAP were added. Stirring was continued at room temperature. After 3 h, the reaction mixture was diluted with EtOAc, washed with saturated NaHCO$_3$ (1×), brine (1×), dried over MgSO$_4$, filtered, and concentrated. The crude reaction mixture was dissolved in DCM (~2 mL) and diluted with ~5 mL of hexanes. The precipitate was collected by filtration and dried under high vacuum to give N-(4-(3-(((3,3-diphenylpropyl)(2-(2-pyridinyl)ethyl)carbamoyl)amino)-1,2,4-thiadiazol-5-yl)phenyl)acetamide 158. Mass spectrum, calculated for $C_{33}H_{32}N_6O_2S$ 576.2; found 577.2 (M$^+$+1).

EXAMPLES 47

The compounds shown in Table 5 were prepared by the procedure described for Example 45 except substituting for the corresponding starting materials.

TABLE 5

| Comp Number | Structure | Name | Exact Mass | MS m/z (M+ + 1) |
|---|---|---|---|---|
| 159 | 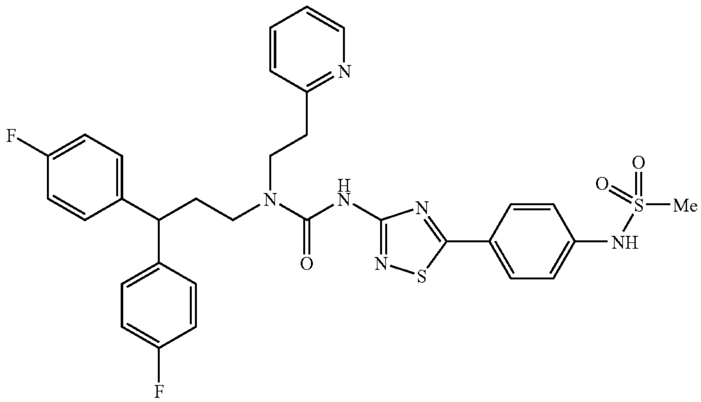 | N-(4-(3-(((3,3-bis(4-fluorophenyl)propyl)(2-(2-pyridinyl)ethyl)carbamoyl)amino)-1,2,4-thiadiazol-5-yl)phenyl)methanesulfonamide | 648.2 | 649.2 |
| 160 | 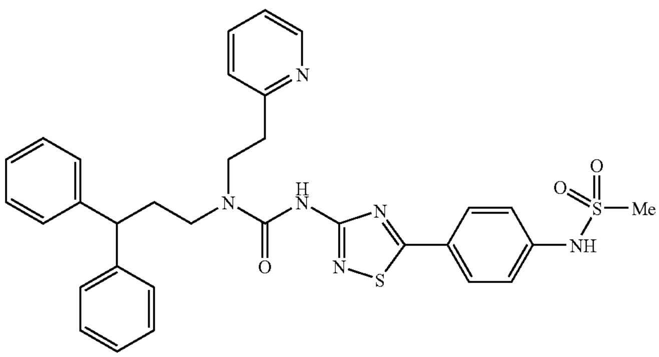 | N-(4-(3-(((3,3-diphenyl-propyl)(2-(2-pyridinyl)ethyl)carbamoyl)amino)-1,2,4-thiadiazol-5-yl)phenyl)methanesulfonamide | 612.2 | 613.2 |

EXAMPLE 48

Synthesis of 4-(3-(benzo[d]thiazol-2-yl)-1-(3,3-diphenylpropyl)ureido)cyclohexanecarboxylic acid, 163

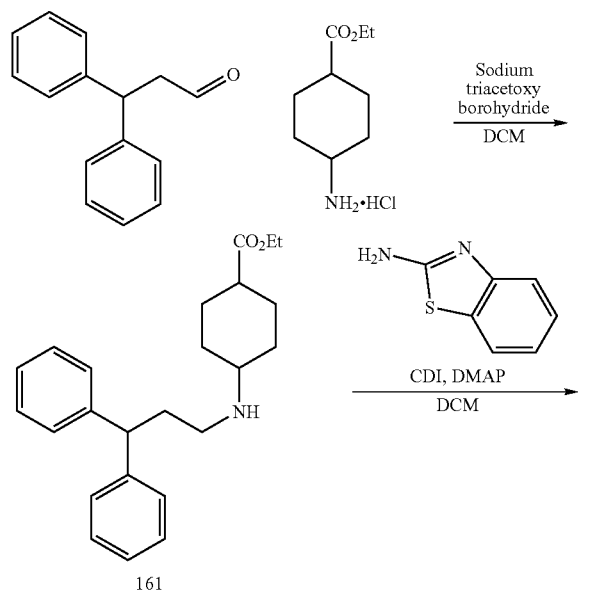

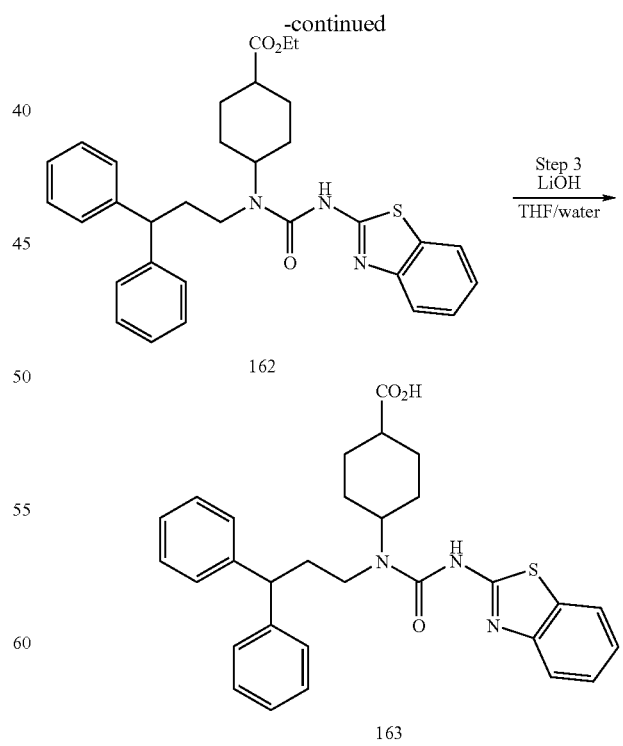

Step 1. 3,3-diphenylpropanal (0.2 g, 0.95 mmol) was dissolved in 5 mL of drydichloromethane. To this solution was added ethyl 4-aminocyclohexanecarboxylate hydrochloride (2, 0.266 g, 1.3 mmol), triethylamine (0.19 mL, 1.3 mmol), and sodium triacetoxyborohydride (0.200 g, 1.2 mmol). The reaction mixture was stirred at room temperature overnight. The mixture was partitioned between water and dichloromethane. The organic layers were washed with brine, dried over sodium sulfate, filtered and concentrated to give the crude product 161 as a clear oil.

Step 2. 2-aminobenzothiazole (0.142 g, 0.95 mmol) was dissolved in 3 mL of dichloromethane. To this solution was added CDI (0.2 g, 1.2 mmol) and stirred at room temperature overnight. A precipitate was visible. Then added 161 (crude product from step 1) and stirred reaction at room temperature for 3 h. Reaction mixture turned clear. The reaction mixture was concentrated and purified by column chromatography on silica using 1:1 EtOAc:Hexane as eluent. Fractions containing product were combined and concentrated to yield the product 162 as a white solid.

Step 3. To a solution of 162 (0.08 g, 0.2 mmol) in 0.8 mL of methanol was added 0.4 mL of 1N sodium hydroxide solution. The reaction mixture was refluxed overnight. The reaction mixture was then made acidic by addition of 2N HCl solution and extracted with ethyl acetate. The organics were washed with brine, dried over sodium sulfate, filtered and concentrated to yield the product as a white solid 4-(3-(benzo[d]thiazol-2-yl)-1-(3, 3-diphenylpropyl)ureido)cyclohexanecarboxylic acid 163 (0.07 g, 90%). Mass spectrum: calculated for $C_{30}H_{31}N_3O_3S$ 513.2; found 512.2 (M−H).

EXAMPLE 49

Synthesis of (1R,4R)-4-(3-(benzo[d]thiazol-2-yl)-1-(3,3-diphenylpropyl)ureido)cyclohexanecarboxylic acid, 164

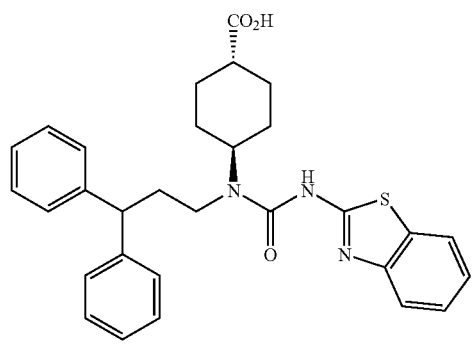

The procedure described in Example 48 was used with the exceptions of substituting (1r,4r)-ethyl 4-aminocyclohexanecarboxylate for ethyl 4-aminocyclohexanecarboxylate hydrochloride in Step 1, and the omission of triethylamine in Step 1 to prepare (1R,4R)-4-(3-(benzo[d]thiazol-2-yl)-1-(3, 3-diphenylpropyl)ureido)cyclohexanecarboxylic acid 164 as a white solid. Mass spectrum: calculated for $C_{30}H_{31}N_3O_3S$ 513.2; found 512.1 (M−H).

EXAMPLE 50

Synthesis of (1R,4R)-methyl 4-(3-(5-chloro-4-(4-(methylsulfonamido)phenyl)thiazol-2-yl)-1-(3,3-diphenylpropyl)ureido)cyclohexanecarboxylate, 165

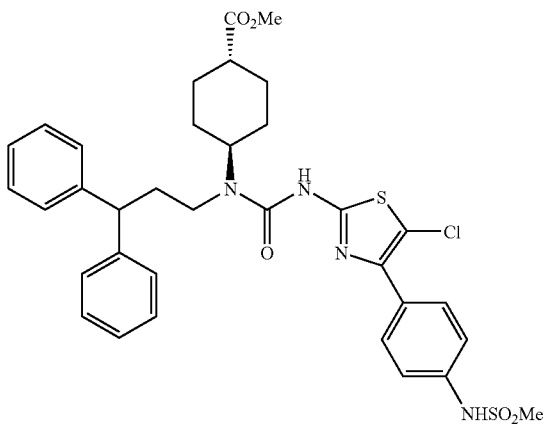

The procedure described in Example 48 was used with the exceptions of substituting (1r,4r)-methyl 4-aminocyclohexanecarboxylate for ethyl 4-aminocyclohexanecarboxylate hydrochloride in Step 1, the omission of triethylamine in Step 1, the procedure for step 2 in example 5 instead of step 2 in example 48, and the omission of Step 3 to prepare (1R,4R)-methyl 4-(3-(5-chloro-4-(4-(methylsulfonamido)phenyl)thiazol-2-yl)-1-(3,3-diphenylpropyl)ureido)cyclohexanecarboxylate 165 as a solid. Mass spectrum: calculated for $C_{34}H_{37}ClN_4O_5S_2$ 680.19; found 681.1 (M+H), 703.0 (M+Na).

EXAMPLE 51

Synthesis of (1R,4R)-4-(3-(5-chloro-4-(4-(methylsulfonamido)phenyl)thiazol-2-yl)-1-(3,3-diphenylpropyl)ureido)cyclohexanecarboxylic acid, 166

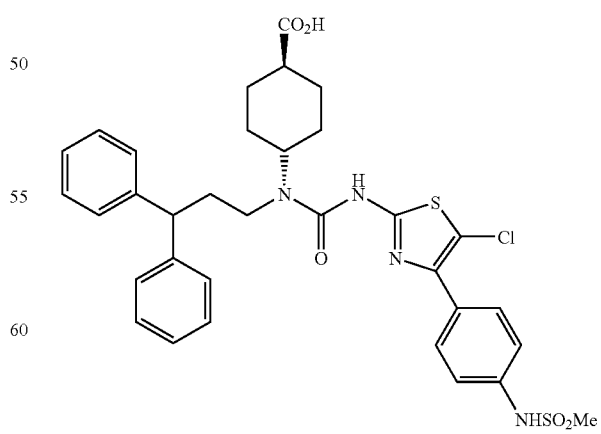

The procedure described in Example 48 was used with the exceptions of substituting (1r,4r)-methyl 4-aminocyclohexanecarboxylate for ethyl 4-aminocyclohexanecarboxylate hydrochloride in Step 1, the omission of triethylamine in Step 1, and the procedure for step 2 in example 5 instead of step 2 in example 48 to prepare (1R,4R)-4-(3-(5-chloro-4-(4-(methylsulfonamido)phenyl)thiazol-2-yl)-1-(3,3-diphenylpropyl)ureido)cyclohexanecarboxylic acid 166 as a solid. Mass spectrum: calculated for $C_{33}H_{35}ClN_4O_5S_2$ 666.17; found 667.2 (M+H).

EXAMPLE 52

Synthesis of (1S,4S)-methyl 4-(1-(3,3-diphenylpropyl)-3-(5-methyl-4-phenylthiazol-2-yl)ureido)cyclohexanecarboxylate, 167

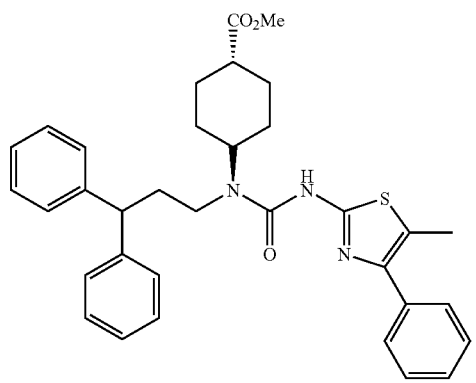

167

The procedure described in Example 48 was used with the exceptions of substituting (1s,4s)-methyl 4-aminocyclohexanecarboxylate hydrochloride for ethyl 4-aminocyclohexanecarboxylate hydrochloride in Step 1, and the substitution of 5-methyl-4-phenylthiazol-2-amine for 2-aminobenzothiazole in Step 2 to prepare (1S,4S)-methyl 4-(1-(3,3-diphenylpropyl)-3-(5-methyl-4-phenylthiazol-2-yl)ureido)cyclohexanecarboxylate 167 as a solid. Mass spectrum: calculated for $C_{34}H_{37}N_3O_3S$ 567.2; found 568.2 (M+H).

EXAMPLE 53

Synthesis of (1S,4S)-methyl 4-(3-(5-chloro-4-(4-(methylsulfonamido)phenyl)thiazol-2-yl)-1-(3,3-diphenylpropyl)ureido)cyclohexanecarboxylate, 168

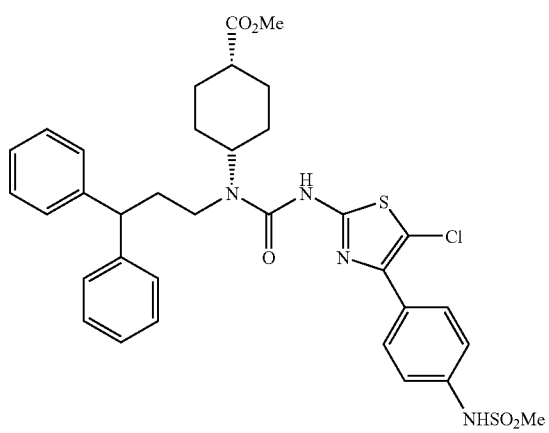

168

The procedure described in Example 48 was used with the exceptions of substituting (1s,4s)-methyl 4-aminocyclohexanecarboxylate hydrochloride for ethyl 4-aminocyclohexanecarboxylate hydrochloride in Step 1, and the procedure for step 2 in example 5 for step 2 in example 48 to prepare (1S,4S)-methyl 4-(3-(5-chloro-4-(4-(methylsulfonamido)phenyl)thiazol-2-yl)-1-(3,3-diphenylpropyl)ureido) cyclohexanecarboxylate 168 as a solid. Mass spectrum: calculated for $C_{34}H_{37}ClN_4O_5S_2$ 680.19; found 681.3 (M+H).

EXAMPLE 54

Synthesis of (1S,4S)-4-(3-(5-chloro-4-(4-(methylsulfonamido)phenyl)thiazol-2-yl)-1-(3,3-diphenylpropyl)ureido)cyclohexanecarboxylic acid, 169

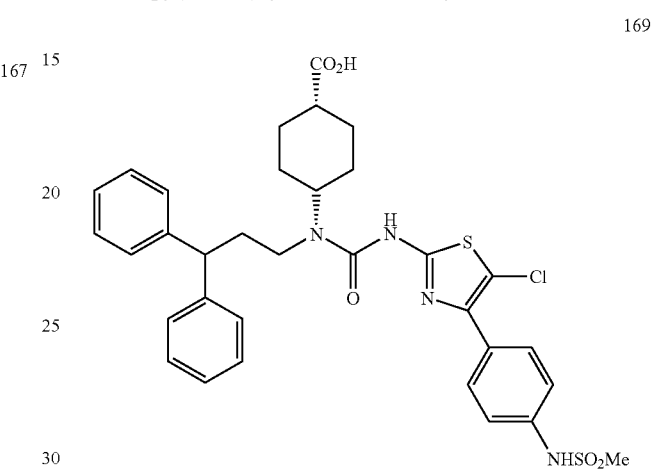

169

The procedure described in Example 48 was used with the exceptions of substituting (1s,4s)-methyl 4-aminocyclohexanecarboxylate hydrochloride for ethyl 4-aminocyclohexanecarboxylate hydrochloride in Step 1, and the procedure for step 2 in example 5 for step 2 in example 48 to prepare (1S,4S)-4-(3-(5-chloro-4-(4-(methylsulfonamido)phenyl)thiazol-2-yl)-1-(3,3-diphenylpropyl)ureido)cyclohexanecarboxylic acid 169 as a solid. Mass spectrum: calculated for $C_{33}H_{35}ClN_4O_5S_2$ 666.17; found 667.2 (M+H).

EXAMPLE 55

Synthesis of (1S,4S)-4-(3-(5-chloro-4-(4-(methylsulfonyl)phenyl)thiazol-2-yl)-1-(3,3-diphenylpropyl)ureido)cyclohexanecarboxylic acid, 170

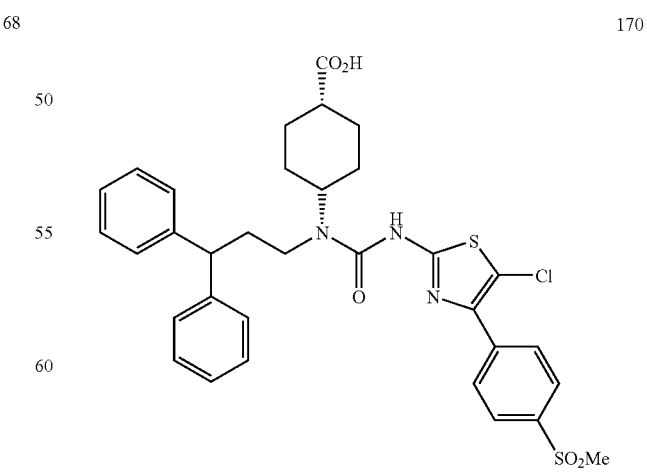

170

The procedure described in Example 48 was used with the exceptions of substituting (1s,4s)-methyl 4-aminocyclohexanecarboxylate hydrochloride for ethyl 4-aminocyclohexanecarboxylate hydrochloride in Step 1, the procedure for step 2 in example 5 for step 2 in example 48, and 5-chloro-4-(4-(methylsulfonyl)phenyl)thiazol-2-amine for N-(4-(2-amino-5-chlorothiazol-4-yl)phenyl)methanesulfonamide to prepare (1S,4S)-4-(3-(5-chloro-4-(4-(methylsulfonyl)phenyl)thiazol-2-yl)-1-(3,3-diphenylpropyl)ureido)cyclohexanecarboxylic acid 170 as a solid. Mass spectrum: calculated for $C_{33}H_{34}ClN_3O_5S_2$ 651.16; found 652.2 (M+H).

EXAMPLE 56

Synthesis of (1R,4R)-4-(3-(5-chloro-4-(4-(methylsulfonyl)phenyl)thiazol-2-yl)-1-(3,3-diphenylpropyl)ureido)cyclohexanecarboxylic acid, 171

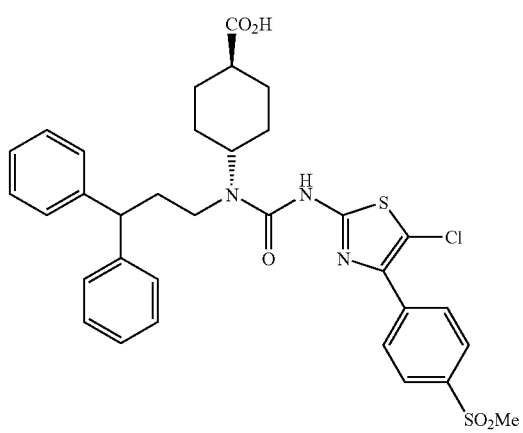

171

The procedure described in Example 48 was used with the exceptions of substituting (1r,4r)-methyl 4-aminocyclohexanecarboxylate hydrochloride for ethyl 4-aminocyclohexanecarboxylate hydrochloride in Step 1, the procedure for step 2 in example 5 for step 2 in example 48, and 5-chloro-4-(4-(methylsulfonyl)phenyl)thiazol-2-amine for N-(4-(2-amino-5-chlorothiazol-4-yl)phenyl)methanesulfonamide to prepare (1R,4R)-4-(3-(5-chloro-4-(4-(methylsulfonyl)phenyl)thiazol-2-yl)-1-(3,3-diphenylpropyl)ureido)cyclohexanecarboxylic acid 171 as a solid. Mass spectrum: calculated for $C_{33}H_{34}ClN_3O_5S_2$ 651.16; found 652.2 (M+H).

EXAMPLE 57

Synthesis of 3-(5-chloro-4-(4-(methylsulfonamido)phenyl)thiazol-2-yl)-1-(2-cyanoethyl)-1-(3,3-diphenylpropyl)urea, 172

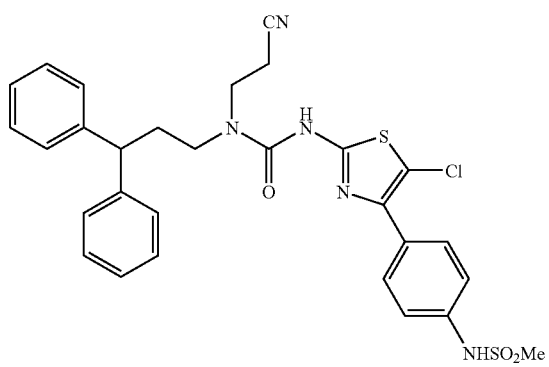

172

The procedure described in Example 4 was used with the exceptions of substituting 3-aminopropionitrile for cyclopropylamine in Step 1, and N-(4-(2-amino-5-chlorothiazol-4-yl)phenyl)methanesulfonamide for N-(4-(2-aminothiazol-4-yl)phenyl)methanesulfonamide to prepare 3-(5-chloro-4-(4-(methylsulfonamido)phenyl)thiazol-2-yl)-1-(2-cyanoethyl)-1-(3,3-diphenylpropyl)urea 172 as a solid. Mass spectrum: calculated for $C_{29}H_{28}ClN_5O_3S_2$ 593.1; found 594.2 (M+H).

EXAMPLE 58

Synthesis of methyl 2-(4-(5-chloro-2-(3-(3,3-diphenylpropyl)-3-isopropylureido)thiazol-4-yl)phenyl)acetate, 173

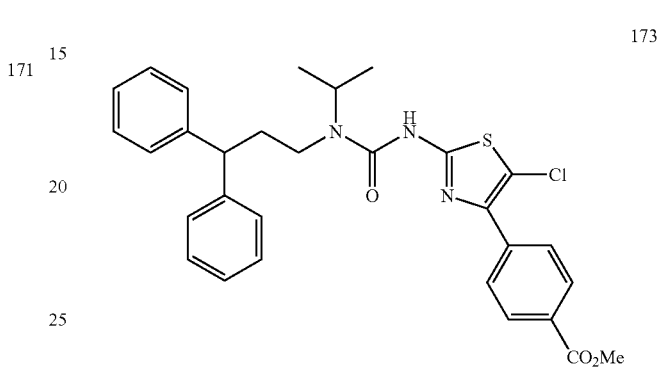

173

The procedure described in Example 2 was used with the exception of substituting methyl 4-(2-amino-5-chlorothiazol-4-yl)benzoate for N-(4-(2-aminothiazol-4-yl)phenyl)methanesulfonamide to prepare 173 as a solid. Mass spectrum: calculated for $C_{30}H_{30}ClN_3O_3S$ 547.2; found 547.9 (M+).

EXAMPLE 59

Synthesis of methyl 4-(5-chloro-2-(3-(3,3-diphenylpropyl)-3-(tetrahydro-2H-pyran-4-yl)ureido)thiazol-4-yl)benzoate, 174

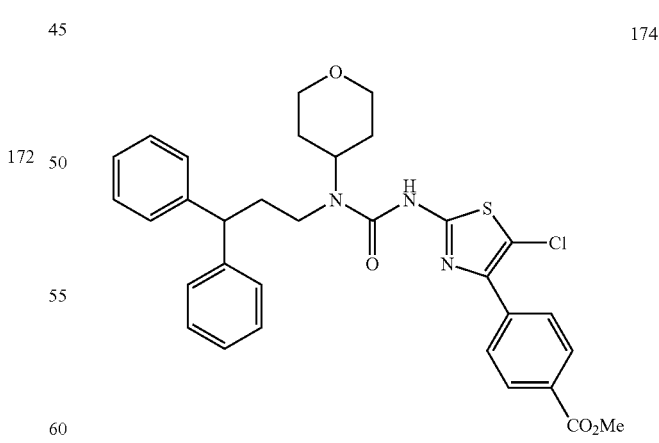

174

The procedure described in Example 2 was used with the exceptions of substituting methyl 4-(2-amino-5-chlorothiazol-4-yl)benzoate for N-(4-(2-aminothiazol-4-yl)phenyl)methanesulfonamide and N-(3,3-diphenylpropyl)-tetrahydro-2H-pyran-4-amine for N-isopropyl-3,3-diphenylpropan- 1-amine to prepare 174 as a solid. Mass spectrum: calculated for $C_{32}H_{32}ClN_3O_4S$ 589.2; found 590.1 (M+H).

EXAMPLE 60

Synthesis of 3-(5-chloro-4-(4-(hydroxymethyl)phenyl)thiazol-2-yl)-1-(3,3-diphenylpropyl)-1-isopropylurea 176

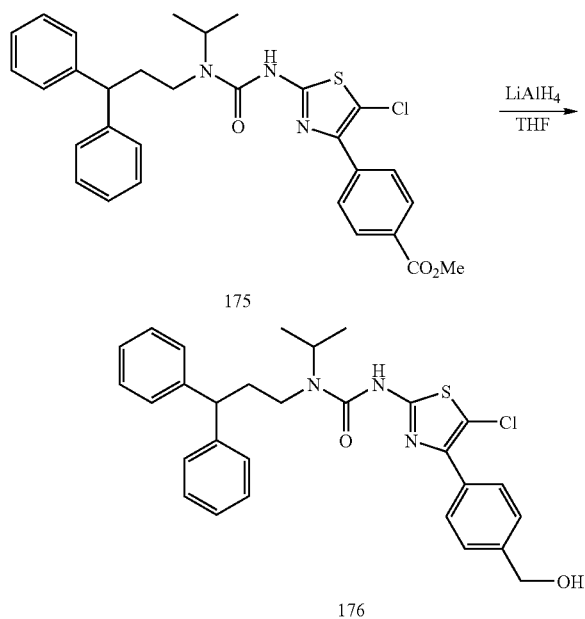

Methyl 4-(5-chloro-2-(3-(3,3-diphenylpropyl)-3-isopropylureido)thiazol-4-yl)benzoate 175 (0.424 g, 0.774 mmol) was dissolved in THF (5 mL) and cooled to 0° C. To this solution, lithium aluminium hydride (2M solution in THF, 0.77 mL) was added dropwise. The reaction mixture was stirred at 0° C. for 1 h, quenched with Rochelle's salt solution and then extracted with ethyl acetate. Organics were concentrated and purified by column chromatography on silica using 1:1 EtOAc:Hexane. Product 176 was obtained as a solid (0.38 g, 95%). Mass spectrum: calculated for $C_{29}H_{30}ClN_3O_2S$ 519.2; found 520.2 (M+H).

EXAMPLE 61

Synthesis of 3-(5-chloro-4-(4-(morpholinomethyl)phenyl)thiazol-2-yl)-1-(3,3-diphenylpropyl)-1-isopropylurea, 178

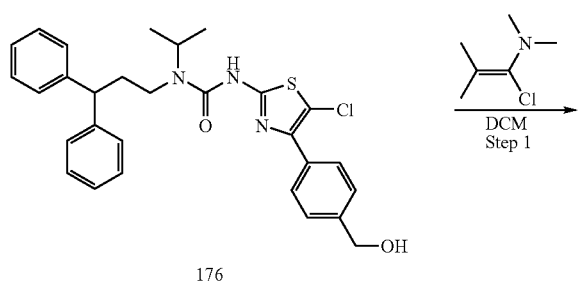

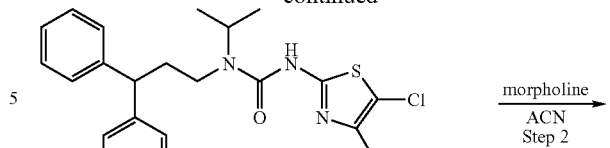

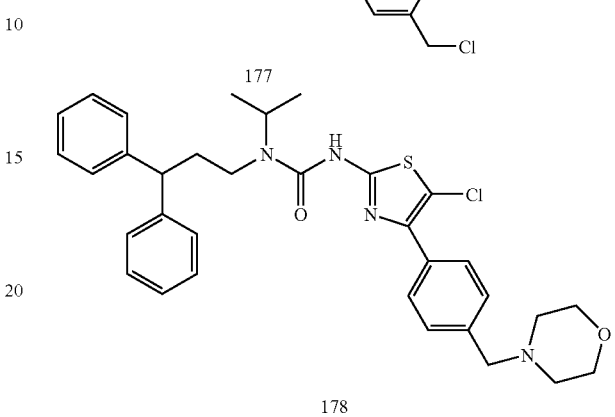

Step 1. 3-(5-chloro-4-(4-(hydroxymethyl)phenyl)thiazol-2-yl)-1-(3,3-diphenylpropyl)-1-isopropylurea 176 (0.35 g, 0.67 mmol) was dissolved in DCM (6 mL). Then added 1-chloro-N,N,2-trimethylprop-1-en-1-amine (0.09 g, 0.67 mmol) and stirred reaction at room temperature overnight. Reaction mixture was concentrated and purified by column chromatography on silica using 1:1 EtOAc:Hexane as eluent. Fractions containing product were combined and concentrated to yield the product 177 as a pale yellow solid (0.36 g, 99%).

Step 2. 3-(5-chloro-4-(4-(chloromethyl)phenyl)thiazol-2-yl)-1-(3,3-diphenylpropyl)-1-isopropylurea 177 (0.2 g, 0.37 mmol) was dissolved in acetonitrile (5 mL). To this solution was added morpholine (0.097 g, 1.11 mmol) and the reaction was heated to reflux for 4 h. The reaction mixture was cooled to room temperature, concentrated and purified directly by column chromatography on silica using 1:1 DCM:Solvent B (Solvent B—90:9:1 DCM:MeOH:ammonium hydroxide). Fractions containing product were combined and concentrated to yield the product 178 as a white solid. Mass spectrum: calculated for $C_{33}H_{37}ClN_4O_2S$ 589.2; found 590.2 (M+H).

EXAMPLE 62

Synthesis of 3-(5-chloro-4-(4-(piperazin-1-ylmethyl)phenyl)thiazol-2-yl)-1-(3,3-diphenylpropyl)-1-isopropylurea, 179

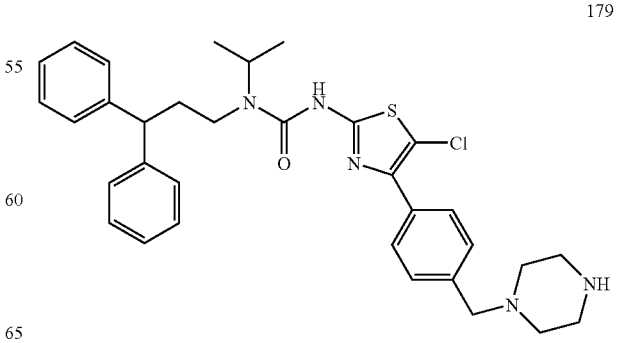

The procedure described in Example 61 was used with the exception of substituting piperazine for morpholine in step 2 to prepare 3-(5-chloro-4-(4-(piperazin-1-ylmethyl)phenyl)thiazol-2-yl)-1-(3,3-diphenylpropyl)-1-isopropylurea 179 as a solid.

Mass spectrum: calculated for $C_{33}H_{38}ClN_5OS$ 587.2; found 588.0 (M+H).

EXAMPLE 63

Synthesis of 3-(5-chloro-4-(4-(morpholinomethyl)phenyl)thiazol-2-yl)-1-(3,3-diphenylpropyl)-1-(tetrahydro-2H-pyran-4-yl)urea, 180

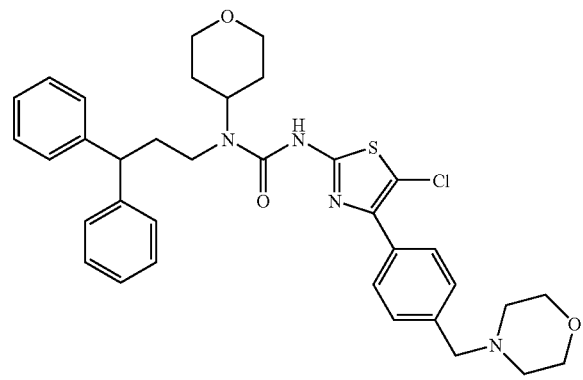

The procedure described in Example 61 was used with the exception of substituting 3-(5-chloro-4-(4-(hydroxymethyl)phenyl)thiazol-2-yl)-1-(3,3-diphenylpropyl)-1-(tetrahydro-2H-pyran-4-yl)urea for 176 in step 1 to prepare 3-(5-chloro-4-(4-(morpholinomethyl)phenyl)thiazol-2-yl)-1-(3,3-diphenylpropyl)-1-(tetrahydro-2H-pyran-4-yl)urea 180 as a solid. 3-(5-chloro-4-(4-(hydroxymethyl)phenyl)thiazol-2-yl)-1-(3,3-diphenylpropyl)-1-(tetrahydro-2H-pyran-4-yl)urea, in turn, was prepared according to the procedure described in Example 59 using 174 instead of 175.

Mass spectrum: calculated for $C_{35}H_{39}ClN_4O_3S$ 630.2; found 630.8 (M+H).

EXAMPLE 64

Synthesis of 4-(2-(((3,3-bis(4-fluorophenyl)propyl)(cyclopropyl)carbamoyl)amino)-5-chloro-1,3-thiazol-4-yl)benzenesulfonamide, 182

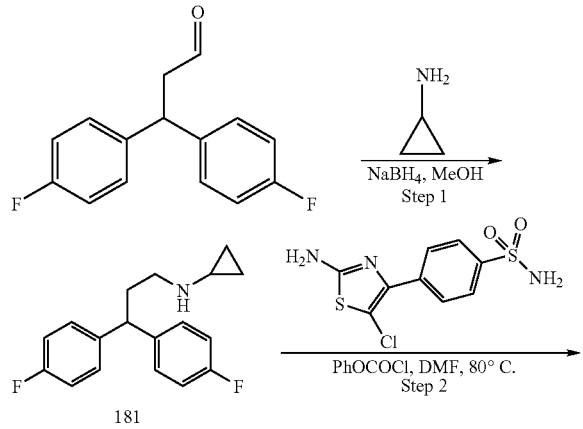

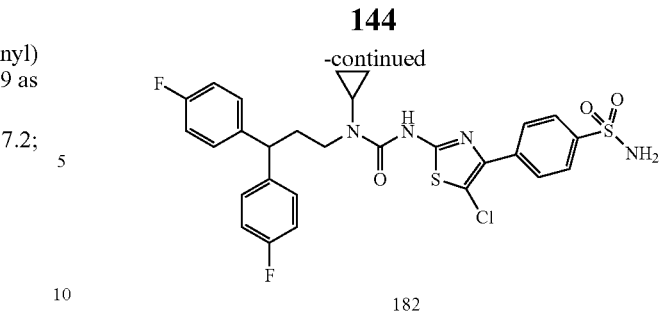

Step 1. To solution of 3,3-bis(4-fluorophenyl)propanal (1.00 g, 4.06 mmol, see Method H for preparation) in MeOH (15 ml) was added cyclopropanamine (0.285 ml, 4.06 mmol). The reaction mixture was stirred for overnight at 25° C. Sodium borohydride (0.307 g, 8.12 mmol) was carefully added to the reaction mixture over 15 min. After stirring an additional 15 min volatiles were removed by concentration under reduced pressure. The leftover residue was solubilized with 60 mL of a 1:2 mixture of 10% NaOH and ethyl acetate. The organic phase was separated and the aqueous phase was extracted further with ethyl acetate (2×40 mL). Purification by chromatography on silica (eluted with 0->10% MeOH/$CH_2Cl_2$+0->1% $NH_4OH$) gave N-(3,3-bis(4-fluorophenyl)propyl)cyclopropanamine 181. The product was dissolved in $CH_2Cl_2$ and made into the HCl salt by precipitation with etheral HCl and then concentration of volatiles.

Step 2. A solution of 4-(2-amino-5-chlorothiazol-4-yl)benzenesulfonamide (318 mg, 1097 μmol) and pyridine (266 μl, 3292 1μmol) in DMF (10 mL) was chilled to 0° C. To this solution was added slowly phenyl chloroformate (131 μl, 1043 μmol) via syringe. The mixture was slowly warmed to RT, and stirred for 2 hr. At this point, 1-methylpyrrolidine (342 μl, 3292 μmol) and N-(3,3-bis(4-fluorophenyl)propyl)cyclopropanamine hydrochloride (338 mg, 1043 μmol) were added consecutively to the reaction mixture. The mixture was heated to 80° C. and was stirred overnight. Volatiles were removed by concentration under reduced pressure. The leftover residue was solubilized with 100 mL of a 1:1 mixture of water and ethyl acetate. The organic phase was separated and the aqueous phase was extracted further with ethyl acetate (2×75 mL). The combined organic extracts were dried with magnesium sulfate, filtered, and concentrated. Purification by chromatography on silica (eluted with EtOAc/Hexanes) gave 4-(2-(((3,3-bis(4-fluorophenyl)propyl)(cyclopropyl)carbamoyl)amino)-5-chloro-1,3-thiazol-4-yl)benzenesulfonamide 182. Mass spectrum, calculated for $C_{28}H_{25}ClF_2N_4O_3S_2$ 602. 1; found 603.1 (M⁺+1).

EXAMPLES 65

The compounds shown in Table 6 were prepared by the procedure described in step 2 of Example 64 substituting for the corresponding dialkyl amine reactants.

Compound 183: The dialkylamine was prepared as described in step 1 of Example 5 with the exception of substituting methylamine for cyclopropylamine.

Compound 184: The dialkylamine was prepared according to Method H. Starting from step 4,3,3-bis(4-fluorophenyl)propan-1-ol was substituted for 3,3-diphenyl-1-propanol. In step 5,2-(pyridin-2-yl)ethanamine was substituted for tetrahydro-2H-pyran-4-ylamine.

Compound 185: The dialkylamine was prepared as described in step 1 of Example 1.

TABLE 6

| Comp Number | Structure | Name | Exact Mass | MS m/z (M⁺ + 1) |
|---|---|---|---|---|
| 183 | 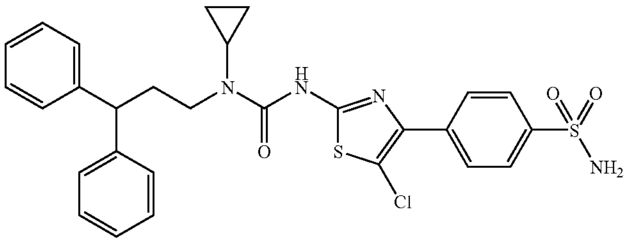 | 4-(5-chloro-2-((cyclopropyl(3,3-diphenylpropyl)carbamoyl)amino)-1,3-thiazol-4-yl)benzenesulfonamide | 566.1 | 567.1 |
| 184 | 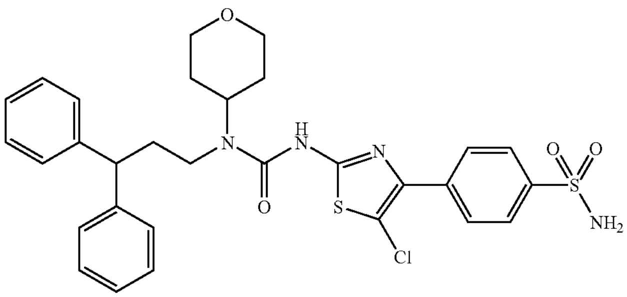 | 4-(5-chloro-2-(((3,3-diphenylpropyl)(tetrahydro-2H-pyran-4-yl)carbamoyl)amino)-1,3-thiazol-4-yl)benzenesulfonamide | 610.1 | 611.1 |
| 185 | 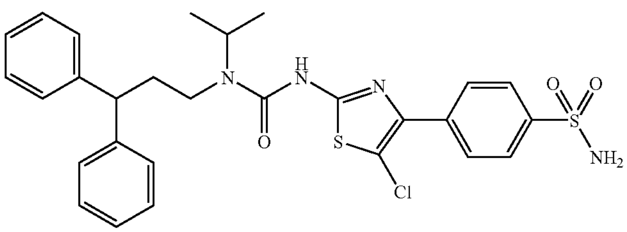 | 4-(5-chloro-2-(((3,3-diphenylpropyl)(1-methylethyl)carbamoyl)amino)-1,3-thiazol-4-yl)benzenesulfonamide | 568.1 | 569.2 |

EXAMPLE 66

The compounds shown in Table 7 were prepared by the procedure described in Example 5. Any modifications are detailed below.

Compound 186: The dialkylamine was prepared according to Method H. Starting from step 4,3,3-bis(4-fluorophenyl)propan-1-ol was substituted for 3,3-diphenyl-1-propanol. In step 5,2-(pyridin-2-yl)ethanamine was substituted for tetrahydro-2H-thiopyran-4-ylamine.

Compound 187: The procedure described in Example 5 with the exception of substituting methylamine for cyclopropylamine in step 1 and of substituting N-(4-(2-amino-5-chlorothiazol-4-yl)phenyl)methanesulfonamide for 3-(pyridin-2-yl)-1,2,4-thiadiazol-5-amine (method N) in step 2.

Compound 188: The procedure described in step 2 of example 5 with the exception of substituting N-methyl-3,3-diphenylpropan-1-amine for N-(3,3-bis(4-fluorophenyl)propyl)cyclopropanamine (method H, substituting 2-(pyridin-2-yl)ethanamine for cyclopropylamine in step 5) and substituting N-(4-(2-amino-5-chlorothiazol-4-yl)phenyl)methanesulfonamide for N-(4-(5-amino-1,2,4-thiadiazol-3-yl)phenyl)methanesulfonamide (method L, with substitution of 4-(methylsulfonyl)phenylboronic acid) for 4-((methylsulfonyl)amino)phenylboronic acid).

Compound 189: The procedure described in step 2 of example 5 with the exception of substituting N-methyl-3,3-diphenylpropan-1-amine for N-(3,3-diphenylpropyl)tetrahydro-2H-pyran-4-amine (method H, starting from step 4,3,3-bis(4-fluorophenyl)propan-1-ol was substituted for 3,3-diphenyl-1-propanol and in step 5,2-(pyridin-2-yl)ethanamine was substituted for tetrahydro-2H-pyran-4-ylamine) and substituting N-(4-(2-amino-5-chlorothiazol-4-yl)phenyl)methanesulfonamide for N-(4-(5-amino-1,2,4-thiadiazol-3-yl)phenyl)methanesulfonamide (method L, with substitution of 4-(methylsulfonyl)phenylboronic acid) for 4-((methylsulfonyl)amino)phenylboronic acid).

Compound 190: The procedure described in step 2 of example 5 with the exception of substituting N-methyl-3,3-diphenylpropan-1-amine for N-(3,3-diphenylpropyl)-N-(1-methylethyl)amine (step 1 in example 1) and substituting N-(4-(2-amino-5-chlorothiazol-4-yl)phenyl)methanesulfonamide for N-(4-(5-amino-1,2,4-thiadiazol-3-yl)phenyl)methanesulfonamide (method L, with substitution of 4-(methylsulfonyl)phenylboronic acid) for 4-((methylsulfonyl)amino)phenylboronic acid).

Compound 191: The procedure described in step 2 of example 5 with the exception of substituting N-methyl-3,3-diphenylpropan-1-amine for N-(3,3-diphenylpropyl)-N-(1-methylethyl)amine (step 1 in example 1) and substituting N-(4-(2-amino-5-chlorothiazol-4-yl)phenyl)methanesulfonamide for 5-(2-amino-5-chloro-1,3-thiazol-4-yl)-1,3-dihydro-2H-indol-2-one (method Q starting from step 3, with substitution of 4-(2-bromoacetyl)-N-tert-butylbenzenesulfonamide for 5-(chloroacetyl)-1,3-dihydro-2H-indol-2-one (commercially available)).

Compound 192: The procedure described in step 2 of example 5 with the exception of substituting N-methyl-3,3-diphenylpropan-1-amine for N-(3,3-diphenylpropyl)tetrahydro-2H-pyran-4-amine (method H, starting from step 4,3,3-bis(4-fluorophenyl)propan-1-ol was substituted for 3,3-diphenyl-1-propanol and in step 5,2-(pyridin-2-yl)ethanamine was substituted for tetrahydro-2H-pyran-4-ylamine) and substituting N-(4-(2-amino-5-chlorothiazol-4-yl)phenyl)methanesulfonamide for 5-(2-amino-5-chloro-1,3-thiazol-4-yl)-1,3-dihydro-2H-indol-2-one (method Q starting from step 3, with substitution of 4-(2-bromoacetyl)-N-tert-butylbenzenesulfonamide for 5-(chloroacetyl)-1,3-dihydro-2H-indol-2-one (commercially available)).

TABLE 7

| Comp Number | Structure | Name | Exact Mass | MS m/z (M⁺ + 1) |
|---|---|---|---|---|
| 186 | 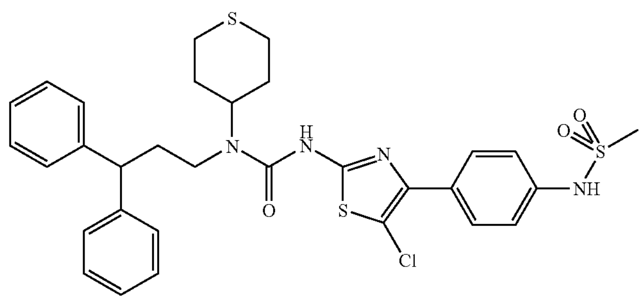 | N-(4-(5-chloro-2-(((3,3-diphenylpropyl)(tetrahydro-2H-thiopyran-4-yl)carbamoyl)amino)-1,3-thiazol-4-yl)phenyl)methanesulfonamide | 640.1 | 641.2 |
| 187 | 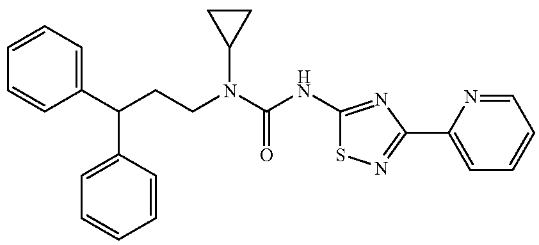 | 1-cyclopropyl-1-(3,3-diphenylpropyl)-3-(3-(2-pyridinyl)-1,2,4-thiadiazol-5-yl)urea | 455.2 | 456.1 |
| 188 | 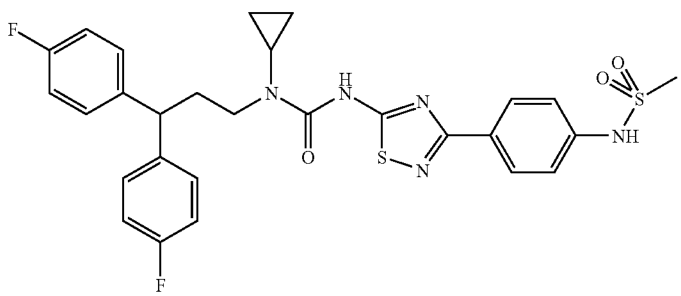 | N-(4-(5-(((3,3-bis(4-fluorophenyl)propyl)(cyclopropyl)carbamoyl)amino)-1,2,4-thiadiazol-3-yl)phenyl)methanesulfonamide | 583.2 | 584.0 |
| 189 | 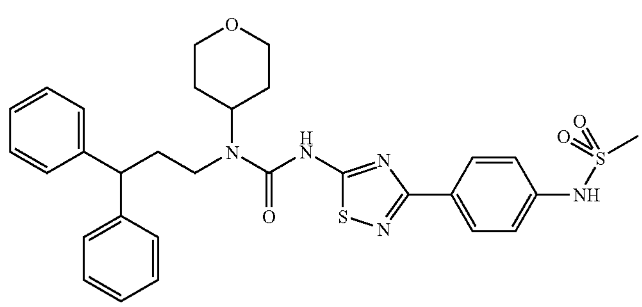 | N-(4-(5-(((3,3-diphenylpropyl)(tetrahydro-2H-pyran-4-yl)carbamoyl)amino)-1,2,4-thiadiazol-3-yl)phenyl)methanesulfonamide | 591.2 | 592.2 |
| 190 | 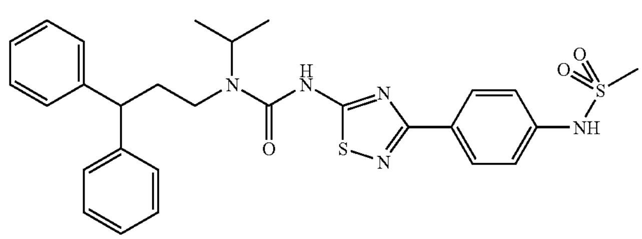 | N-(4-(5-(((3,3-diphenylpropyl)(1-methylethyl)carbamoyl)amino)-1,2,4-thiadiazol-3-yl)phenyl)methanesulfonamide | 549.2 | 550.2 |

TABLE 7-continued

| Comp Number | Structure | Name | Exact Mass | MS m/z (M+ + 1) |
|---|---|---|---|---|
| 191 | 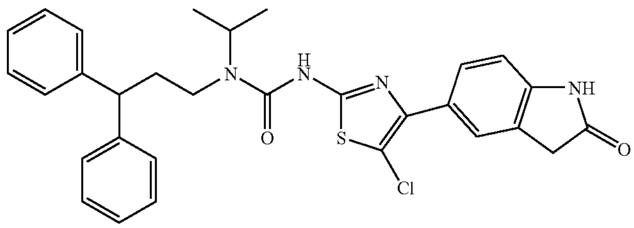 | 3-(5-chloro-4-(2-oxo-2,3-dihydro-1H-indol-5-yl)-1,3-thiazol-2-yl)-1-(3,3-diphenylpropyl)-1-(1-methylethyl)urea | 544.2 | 545.2 |
| 192 | 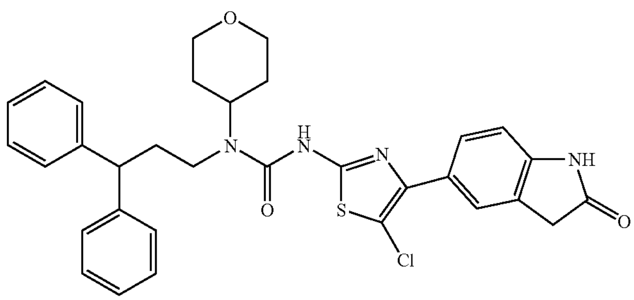 | 3-(5-chloro-4-(2-oxo-2,3-dihydro-1H-indol-5-yl)-1,3-thiazol-2-yl)-1-(3,3-diphenylpropyl)-1-(tetrahydro-2H-pyran-4-yl)urea | 586.2 | 587.2 |

EXAMPLE 67

Synthesis of N-(4-(5-chloro-2-(((1,1-dioxidotetrahydro-2H-thiopyran-4-yl)(3,3-diphenylpropyl)carbamoyl)amino)-1,3-thiazol-4-yl)phenyl)methanesulfonamide, 193

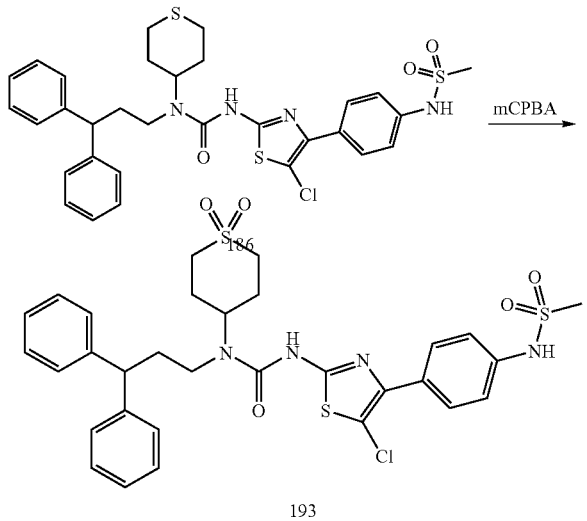

Step 1. To a solution of 3-(5-chloro-4-(4-(methylsulfonamido)phenyl)thiazol-2-yl)-1-(3,3-diphenylpropyl)-1-(tetrahydro-2H-thiopyran-4-yl)urea 186 (60.4 mg, 94.2 μmol) in CH₂Cl₂ (5 ml) was added 70% mCPBA (51.1 μl, 207 μmol). The reaction mixture was stirred for 4 h at 25° C. The reaction mixture was poured into 20 mL of aqueous saturated NaHCO₃ and extracted with ethyl acetate (3×20 mL). The combined organic extracts were dried with magnesium sulfate, filtered, and concentrated. Purification by chromatography on silica (eluted using EtOAc and Hexanes) gave N-(4-(5-chloro-2-(((1,1-dioxidotetrahydro-2H-thiopyran-4-yl)(3,3-diphenylpropyl)carbamoyl)amino)-1,3-thiazol-4-yl) phenyl)methanesulfonamide 193. Mass spectrum, calculated for C₃₁H₃₃ClN₄O₅S₃ 672.1; found 673.2 (M⁺+1).

EXAMPLES 68

The compounds shown in Table 8 were prepared by the procedure described for Example 43 except substituting for the corresponding sulfonamide starting material. Specific syntheses of the t-butyl sulfonamide precursors are detailed below.

Compound 193A: The procedure described in Example 5 with the exception of substituting methylamine for cyclopropylamine in step 1 and of substituting N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for N-tert-butyl 4-bornobenzenesulfonamide) in step 2.

Compound 194: The procedure described in step 2 of example 5 with the exception of substituting N-methyl-3,3-diphenylpropan-1-amine for N-(3,3-bis(4-fluorophenyl)propyl)cyclopropanamine (method H, substituting 2-(pyridin-2-yl)ethanamine for cyclopropylamine in step 5) and substituting N-(4-(2-amino-5-chlorothiazol-4-yl)phenyl) methanesulfonamide for 4-(5-amino-1,2,4-thiadiazol-3-yl)-N-tert-butylbenzenesulfonamide (method L, with substitution of 4-(methylsulfonyl)phenylboronic acid) for N-tert-butyl 4-bomobenzenesulfonamide).

Compound 195: The procedure described in step 2 of example 5 with the exception of substituting N-methyl-3,3-diphenylpropan-1-amine for N-(3,3-diphenylpropyl)tetrahydro-2H-pyran-4-amine (method H, starting from step 4,3,3-bis(4-fluorophenyl)propan-1-ol was substituted for 3,3-diphenyl-1-propanol and in step 5,2-(pyridin-2-yl) ethanamine was substituted for tetrahydro-2H-pyran-4-ylamine) and substituting N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for N-tert-butyl 4-bornobenzenesulfonamide).

Compound 196: The procedure described in step 2 of example 5 with the exception of substituting N-methyl-3,3-diphenylpropan-1-amine for N-(3,3-diphenylpropyl)-N-(1-methylethyl)amine (step 1 in example 1) and substituting N-(4-(2-amino-5-chlorothiazol-4-yl)phenyl)methanesulfonamide for 4-(5-amino-1,2,4-thiadiazol-3-yl)-N-tert-butylbenzenesulfonamide (method L, with substitution of 4-(methylsulfonyl)phenylboronic acid) for N-tert-butyl 4-bromobenzenesulfonamide).

TABLE 8

| Comp Number | Structure | Name | Exact Mass | MS m/z (M+ + 1) |
|---|---|---|---|---|
| 193A | 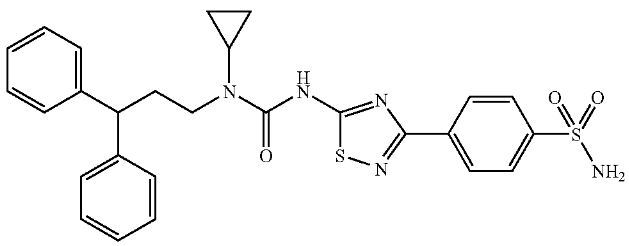 | 4-(5-((cyclopropyl(3,3-diphenylpropyl)carbamoyl)amino)-1,2,4-thiadiazol-3-yl)benzenesulfonamide | 533.2 | 534.2 |
| 194 | 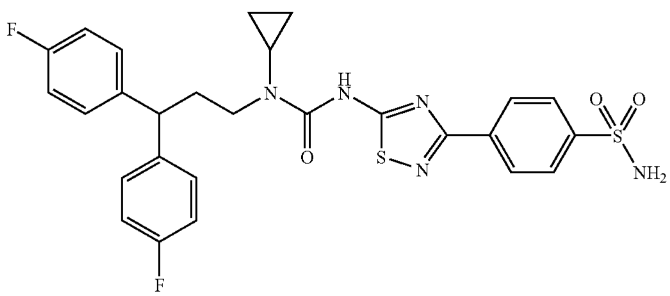 | 4-(5-(((3,3-bis(4-fluorophenyl)propyl)(cyclopropyl)carbamoyl)amino)-1,2,4-thiadiazol-3-yl)benzenesulfonamide | 569.1 | 570.1 |
| 195 | 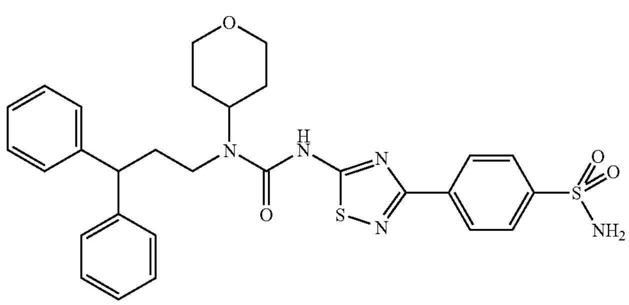 | 4-(5-(((3,3-diphenylpropyl)(tetrahydro-2H-pyran-4-yl)carbamoyl)amino)-1,2,4-thiadiazol-3-yl)benzenesulfonamide | 577.2 | 578.2 |
| 196 | 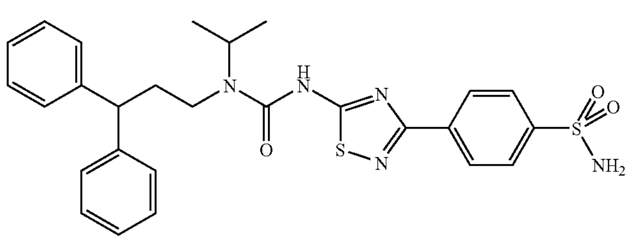 | 4-(5-(((3,3-diphenylpropyl)(1-methylethyl)carbamoyl)amino)-1,2,4-thiadiazol-3-yl)benzenesulfonamide | 535.2 | 536.2 |

EXAMPLE 69

Synthesis of 3-(5-chloro-4-(6-methylpyridin-3-yl)thiazol-2-yl)-1-(3,3-diphenylpropyl)-1-(piperidin-4-yl)urea, 197

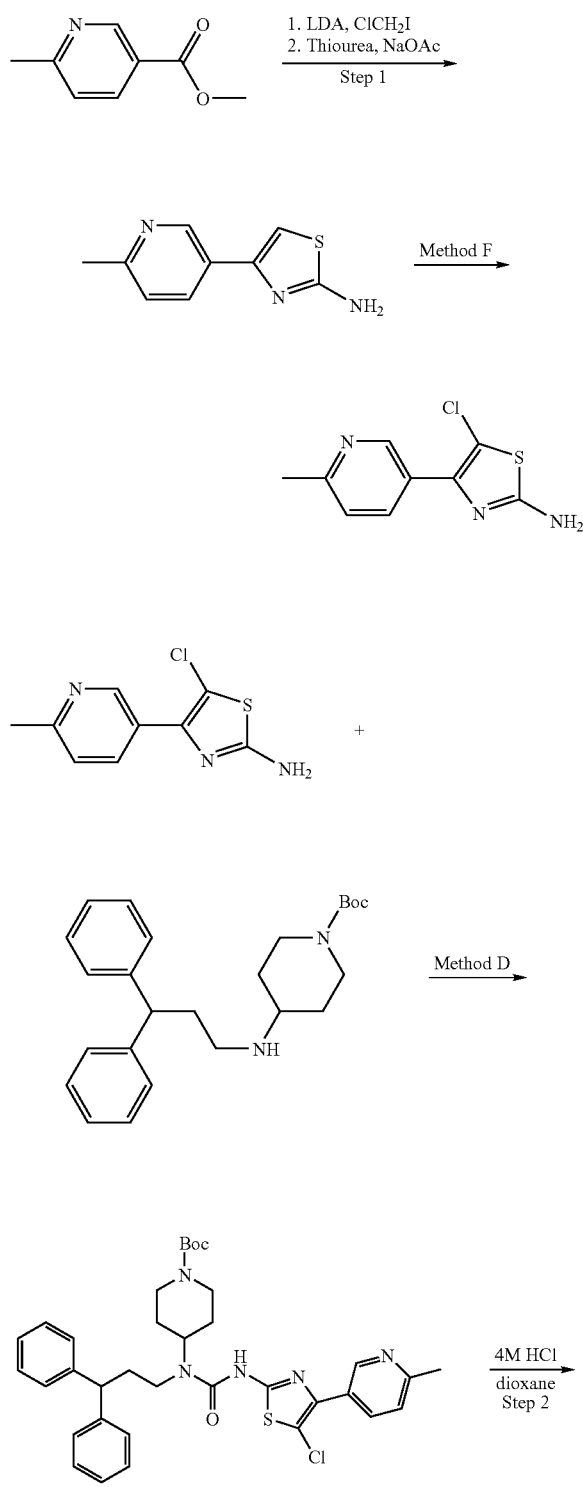

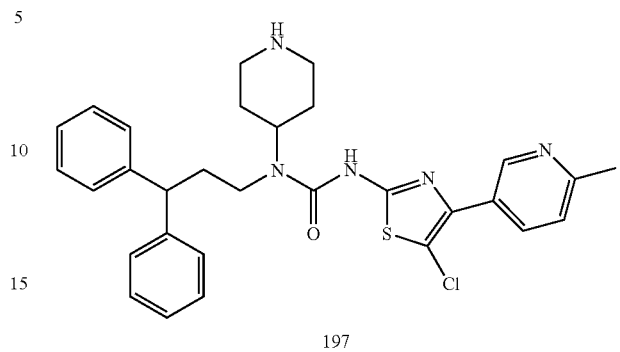

197

Step 1. A 500 mL round-bottomed flask was charged with methyl 6-methylnicotinate (3.0 g, 20 mmol), chloroiodomethane (7.1 ml, 97 mmol), and 50 mL of THF. After cooling to −78° C., a freshly prepared solution of LDA (1M in THF made from diisopropylamine (14 ml, 99 mmol) and BuLi (39 ml, 97 mmol)) was added drop-wise over 1.5 h. After that time, the reaction was quenched with a solution of 5 mL HOAc in 15 mL of THF. The mixture was warmed to rt and diluted with sat. aq. NaHCO$_3$. The mixture was concentrated then portioned between EtOAc and water. The organic layer was separated, dried over MgSO$_4$, filtered, and concentrated to give a brown oil. To this oil was added thiourea (1.5 g, 20 mmol), NaOAc (4.9 g, 60 mmol) and 30 mL of EtOH. The mixture was heated at 80° C. for 15 min then cooled to rt. The mixture was concentrated in vacuo then diluted with water and EtOAc. The layers were separated and the organics were dried (MgSO$_4$), filtered and concentrated to give an oil. Purification by MPLC (80 g, 10-100% EA/Hex) gave 4-(6-methylpyridin-3-yl)thiazol-2-amine as a yellow solid.

Step 2. The crude Boc-protected intermediate was dissolved in 4N HCl in dioxane. This solution was stirred for 2 days at rt. The solvent was removed and residue was diluted with sat. aq. NaHCO$_3$. The resulting solid was collected and purified by MPLC (1-6% MeOH/DCM) to give 3-(5-chloro-4-(6-methyl-3-pyridinyl)-1,3-thiazol-2-yl)-1-(3,3-diphenylpropyl)-1-(4-piperidinyl)urea 197 as a bright white solid. Mass spectrum, calculated for C$_{30}$H$_{32}$ClN$_5$OS 545.2; found 546.2 (M$^+$+1).

The compounds shown in Table 9 were prepared by the procedure described for Example 25 with the following modifications Compound 198: Prepared by the procedure described for Example 25 except substituting tert-butyl 4-aminopiperidine-1-carboxylate for tert-butyl 4-(2-aminoethyl)piperidine-1-carboxylate in step 1.

Compound 199: Prepared by the procedure described for Example 25 except substituting tert-butyl 4-aminopiperidine-1-carboxylate for tert-butyl 4-(2-aminoethyl)piperidine-1-carboxylate in step 1 and 4-(6-methylpyridin-3-yl)thiazol-2-amine for N-(4-(2-aminothiazol-4-yl)phenyl)methanesulfonamide in step 2.

TABLE 9

| Comp Number | Structure | Name | Exact Mass | MS m/z (M⁺ + 1) |
|---|---|---|---|---|
| 198 | 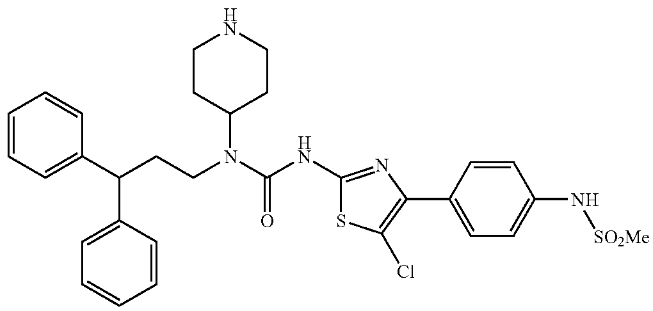 | N-(4-(5-chloro-2-(((3,3-diphenylpropyl)(4-piperidinyl)carbamoyl)amino)-1,3-thiazol-4-yl)phenyl)methanesulfonamide | 623.2 | 624.2 |
| 199 | 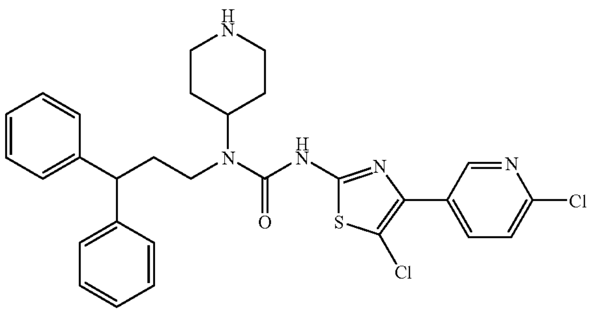 | 3-(5-chloro-4-(6-chloro-3-pyridinyl)-1,3-thiazol-2-yl)-1-(3,3-diphenylpropyl)-1-(4-piperidinyl)urea | 565.1 | 566.1 |

EXAMPLE 71

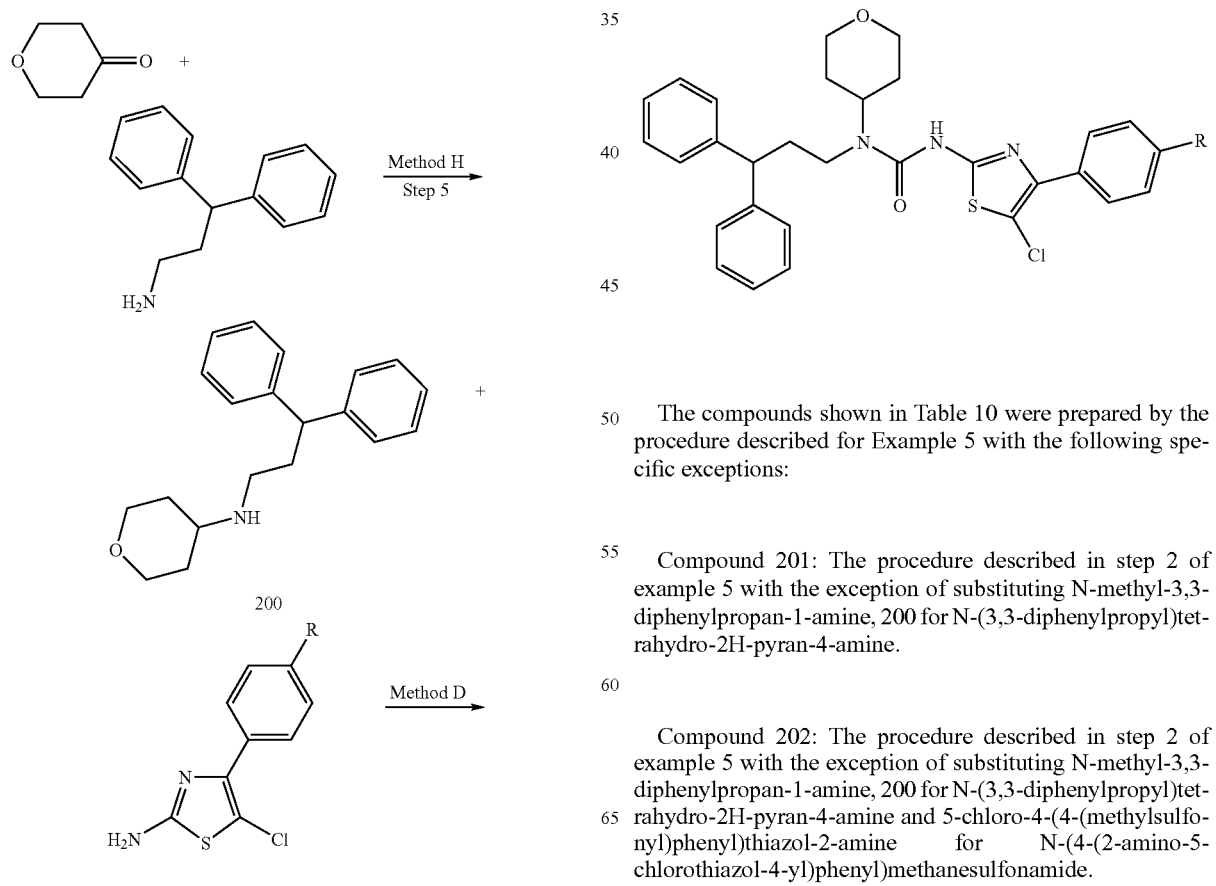

The compounds shown in Table 10 were prepared by the procedure described for Example 5 with the following specific exceptions:

Compound 201: The procedure described in step 2 of example 5 with the exception of substituting N-methyl-3,3-diphenylpropan-1-amine, 200 for N-(3,3-diphenylpropyl)tetrahydro-2H-pyran-4-amine.

Compound 202: The procedure described in step 2 of example 5 with the exception of substituting N-methyl-3,3-diphenylpropan-1-amine, 200 for N-(3,3-diphenylpropyl)tetrahydro-2H-pyran-4-amine and 5-chloro-4-(4-(methylsulfonyl)phenyl)thiazol-2-amine for N-(4-(2-amino-5-chlorothiazol-4-yl)phenyl)methanesulfonamide.

TABLE 10

| Comp Number | Structure | Name | Exact Mass | MS m/z (M⁺ + 1) |
|---|---|---|---|---|
| 201 | 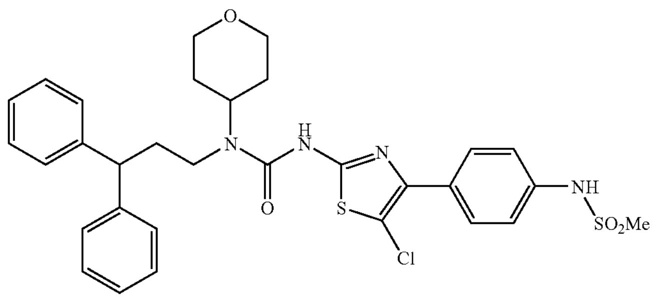 | N-(4-(5-chloro-2-(((3,3-diphenylpropyl)(tetrahydro-2H-pyran-4-yl)carbamoyl)amino)-1,3-thiazol-4-yl)phenyl)methane sulfonamide | 624.2 | 625.0 |
| 202 | 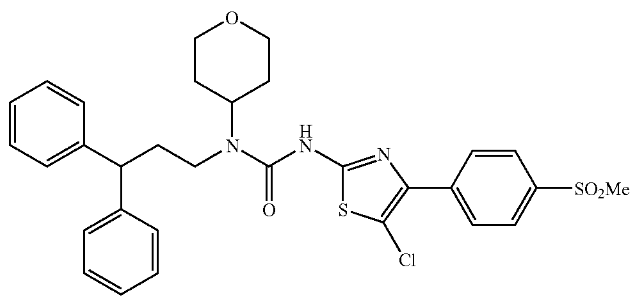 | 3-(5-chloro-4-(4-(methylsulfonyl)phenyl)-1,3-thiazol-2-yl)-1-(3,3-diphenylpropyl)-1-(tetrahydro-2H-pyran-4-yl)urea | 609.2 | 610.1 |

EXAMPLE 72

Synthesis of 3-(5-chloro-4-(4-(methylsulfonamido)phenyl)thiazol-2-yl)-1-(3,3-diphenylpropyl)-1-((1R,4R)-4-hydroxycyclohexyl)urea, 203

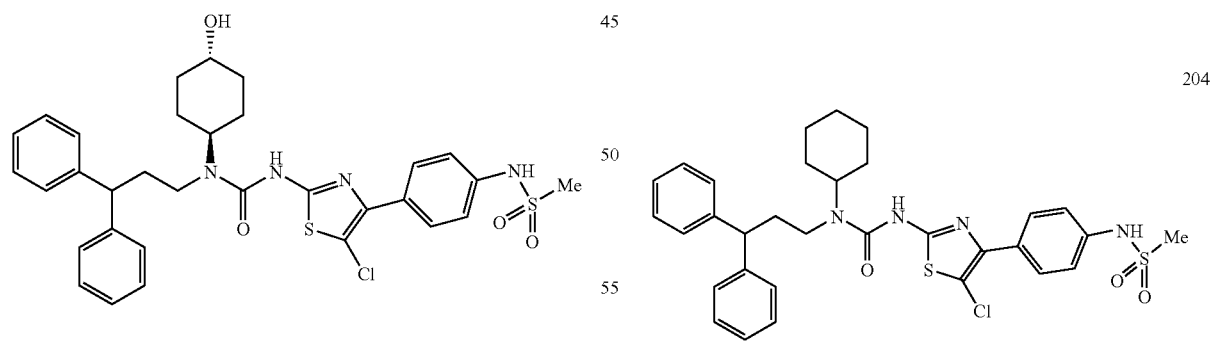

The procedure described in Example 5 with the exception of substituting cyclopropylamine for trans-4-aminocyclohexanol hydrochloride and an additional equivalent of cesium carbonate in Step 1 was used to prepare 3-(5-chloro-4-(4-(methylsulfonamido)phenyl)thiazol-2-yl)-1-(3,3-diphenyl-propyl)-1-((1R,4R)-4-hydroxycyclohexyl)urea 203. Mass spectrum: calculated for $C_{32}H_{35}ClN_4O_4S_2$ 638.2; found 639.2 (M++1).

EXAMPLE 73

Synthesis of 3-(5-chloro-4-(4-(methylsulfonamido)phenyl)thiazol-2-yl)-1-cyclohexyl-1-(3,3-diphenylpropyl)urea, 204

The procedure described in Example 5 with the exception of substituting cyclopropylamine for cyclohexylamine in Step 1 was used to prepare 3-(5-chloro-4-(4-(methylsulfonamido)phenyl)thiazol-2-yl)-1-cyclohexyl-1-(3,3-diphenylpropyl)urea 204. Mass spectrum: calculated for $C_{32}H_{35}ClN_4O_3S_2$ 622.2; found 623.2 (M++1).

EXAMPLE 74

Synthesis of 3-(5-chloro-4-(4-(methylsulfonamido)phenyl)thiazol-2-yl)-1-(3,3-diphenylpropyl)-1-((1R,4R)-4-hydroxycyclohexyl)urea, 205

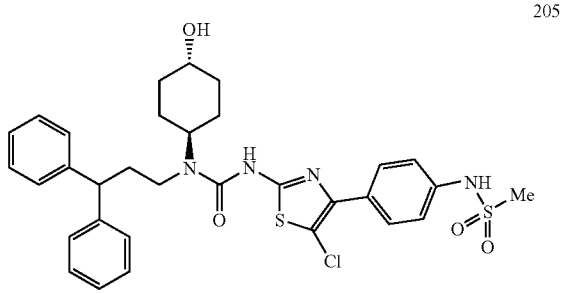

205

The procedure described in Example 5 with the exception of substituting 4-aminocyclohexanol for cyclohexylamine in Step 1 was used to prepare 3-(5-chloro-4-(4-(methylsulfonamido)phenyl)thiazol-2-yl)-1-(3,3-diphenylpropyl)-1-((1R,4R)-4-hydroxycyclohexyl)urea, 205. Mass spectrum: calculated for $C_{32}H_{35}ClN_4O_4S_2$ 638.2; found 639.2 (M++1).

EXAMPLE 75

Synthesis of 3-(5-chloro-4-(4-(methylsulfonyl)phenyl)thiazol-2-yl)-1-(3,3-diphenylpropyl)-1-(2-(tetrahydro-2H-pyran-4-yl)ethyl)urea, 206

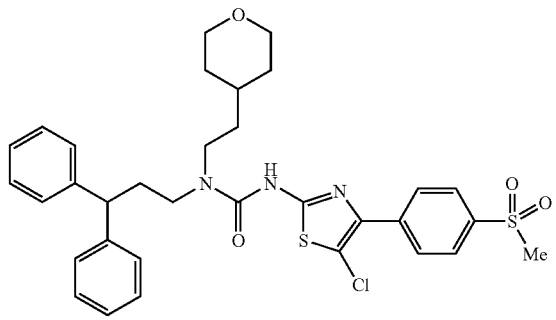

206

Compound 206 was prepared according to Method D using 5-chloro-4-(4-(methylsulfonyl)phenyl)thiazol-2-amine instead of N-(4-(2-amino-5-chlorothiazol-4-yl)phenyl)methanesulfonamide and 3,3-diphenyl-N-(2-(tetrahydro-2H-pyran-4-yl)ethyl)propan-1-amine instead of N-methyl-3,3-diphenylpropan-1-amine. 3,3-diphenyl-N-(2-(tetrahydro-2H-pyran-4-yl)ethyl)propan-1-amine was prepared according to Method C using 3,3-diphenylpropan-1-amine instead of tert-butyl 4-(2-aminoethyl)piperidine-1-carboxylate and 4-(2-bromoethyl)-tetrahydro-2H-pyran instead of 3-bromo-1,1-diphenylpropane.

LC-MS ESI (pos.) m/e: 637.9 (M+1)

EXAMPLE 76

Synthesis of 4-(5-chloro-2-(((3,3-diphenylpropyl)(2-(4-tetrahydropyranyl)ethyl)carbamoyl)amino)-1,3-thiazol-4-yl)benzenesulfonamide 207

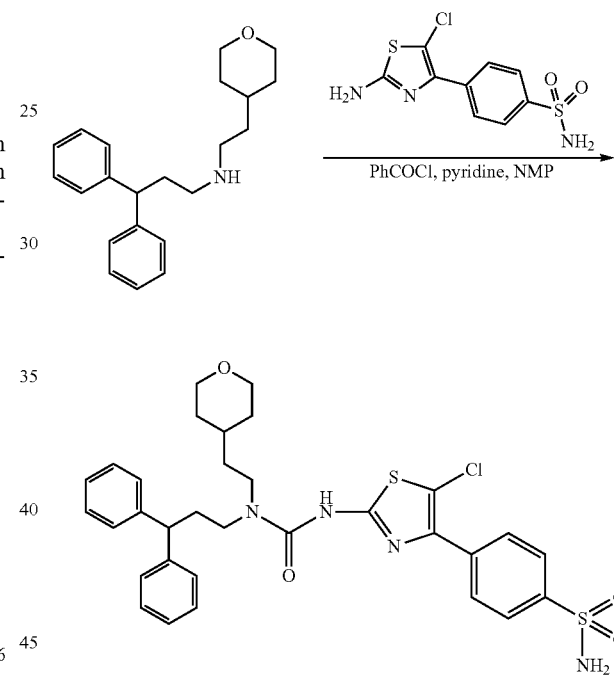

207

A solution of 4-(2-amino-5-chlorothiazol-4-yl)benzenesulfonamide (0.100 g, 0.35 mmol) and pyridine (0.084 ml, 1 mmol) in 1 ml DMF was cooled to 0° C. and phenylcarbonochloridate (0.041, 0.33 mmol) was added dropwise. The mixture was warmed to room temperature and stirred for 2 hours. At this point 1-methylpyrrolidine (0.11, 1 mmol) and 3,3-diphenyl-N-(2-(tetrahydro-2H-pyran-4-yl)ethyl)propan-1-amine (0.11 g, 0.33 mmol) were added to the reaction mixture consecutively. The reaction mixture was heated to 60° C. and stirred overnight after which it was cooled to room temperature and purified directly over silica (eluted with 0-50% Ethylacetate in hexanes) to give 4-(5-chloro-2-(((3,3- diphenylpropyl)(2-(4-tetrahydropyranyl)ethyl)carbamoyl) amino)-1,3-thiazol-4-yl)benzenesulfonamide. LC-MS ESI (pos.) m/e: 638.8 (M+1).

EXAMPLE 77

Synthesis of 4-(2-(((3,3-bis(4-fluorophenyl)propyl) (2-(4-tetrahydropyranyl)ethyl)carbamoyl)amino)-5-chloro-1,3-thiazol-4-yl)benzenesulfonamide, 208

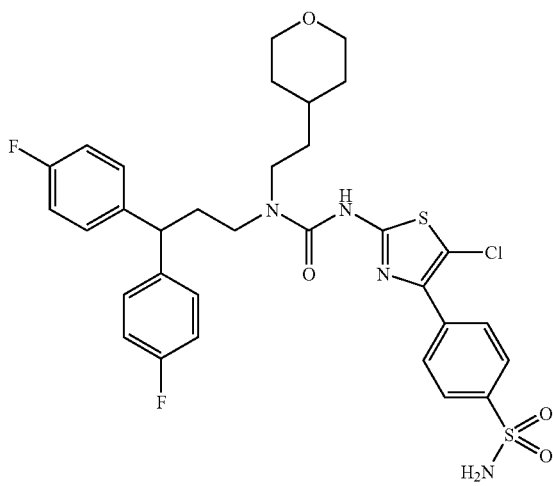

Compound 208 was prepared analogous to the procedure described in Example 76 except using 3,3-bis(4-fluorophenyl)-N-(2-(tetrahydro-2H-pyran-4-yl)ethyl)propan-1-amine instead of 3,3-diphenyl-N-(2-(tetrahydro-2H-pyran-4-yl)ethyl)propan-1-amine
LC-MS ESI (pos.) m/e: 674.8 (M+1)

EXAMPLE 78

Synthesis of 3-(5-chloro-4-(4-(methylsulfonamido) phenyl)thiazol-2-yl)-1-(3,3-diphenylpropyl)-1-(2-(tetrahydro-2H-pyran-4-yl)ethyl)urea, 209

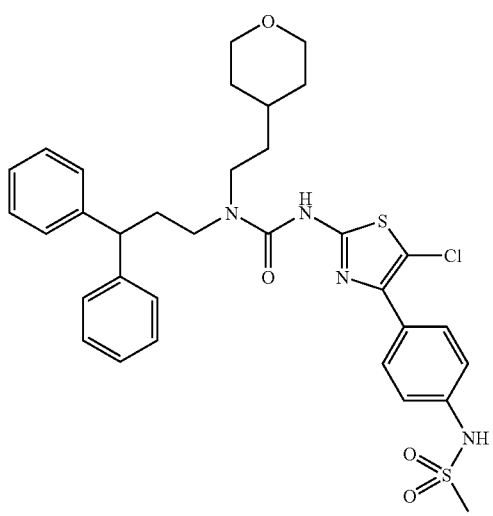

Compound 209 was prepared according to Method D using 3,3-diphenyl-N-(2-(tetrahydro-2H-pyran-4-yl)ethyl)propan-1-amine instead of N-methyl-3,3-diphenylpropan-1-amine. LC-MS ESI (pos.) m/e: 652.9 (M+1).

EXAMPLE 79

Synthesis of 1-(3,3-diphenylpropyl)-3-(3-(4-(methylsulfonamido)phenyl)-1,2,4-thiadiazol-5-yl)-1-(2-(tetrahydro-2H-pyran-4-yl)ethyl)urea, 210

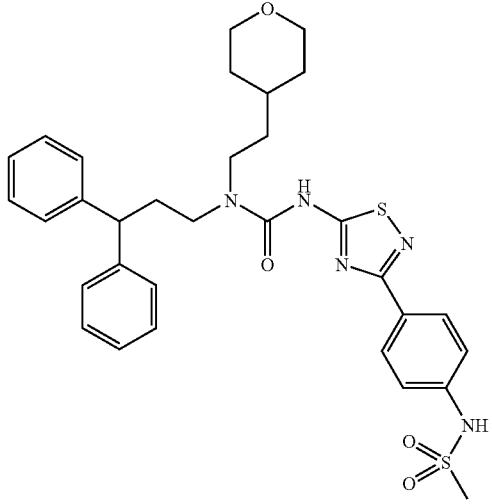

Compound 210 was prepared according to Method D using 3,3-diphenyl-N-(2-(tetrahydro-2H-pyran-4-yl)ethyl)propan-1-amine instead of N-methyl-3,3-diphenylpropan-1-amine and N-(4-(5-amino-1,2,4-thiadiazol-3-yl)phenyl)methanesulfonamide instead of N-(4-(2-amino-5-chlorothiazol-4-yl) phenyl)methanesulfonamide. LC-MS ESI (pos.) m/e: 619.9 (M+1).

EXAMPLE 80

Synthesis of 4-(5-(((3,3-diphenylpropyl)(2-(4-tetrahydropyranyl)ethyl)carbamoyl)amino)-1,2,4-thiadiazol-3-yl)benzenesulfonamide, 211

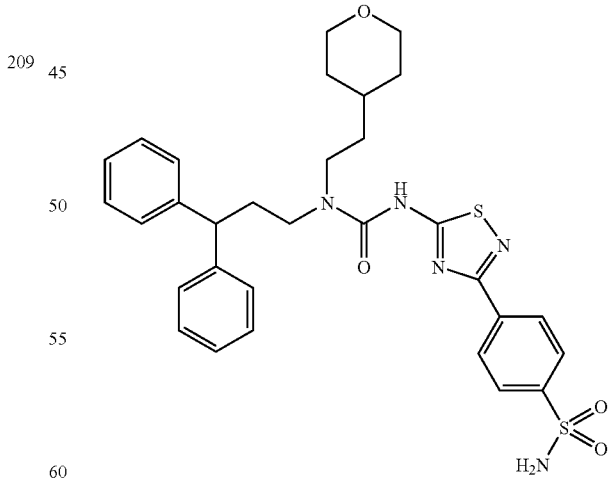

Compound 211 was prepared analogous to the procedure described in step 2 of Example 5 with the exception of substituting N-methyl-3,3-diphenylpropan-1-amine for 3,3-diphenyl-N-(2-(tetrahydro-2H-pyran-4-yl)ethyl)propan-1-amine and N-(4-(2-amino-5-chlorothiazol-4-yl)phenyl) methanesulfonamide for 4-(5-amino-1,2,4-thiadiazol-3-yl)-

N-tert-butylbenzenesulfonamide (method L, with substitution of 4-(methylsulfonyl)phenylboronic acid) for t-butyl 4-bornobenzenesulfonamide).
LC-MS ESI (pos.) m/e: 605.9 (M+1).

EXAMPLE 81

Synthesis of 1-(3,3-bis(4-fluorophenyl)propyl)-3-(3-(4-(methylsulfonamido)phenyl)-1,2,4-thiadiazol-5-yl)-1-(2-(tetrahydro-2H-pyran-4-yl)ethyl)urea, 212

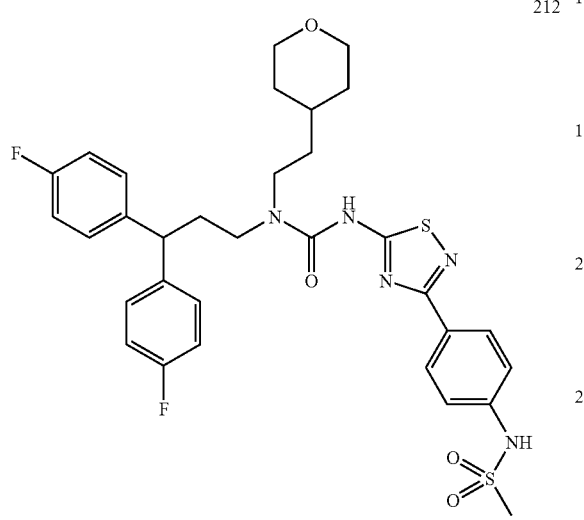

Compound 212 was prepared according to Method D using N-(4-(5-amino-1,2,4-thiadiazol-3-yl)phenyl)methanesulfonamide instead of N-(4-(2-amino-5-chlorothiazol-4-yl)phenyl)methanesulfonamide and 3,3-bis(4-fluorophenyl)-N-(2-(tetrahydro-2H-pyran-4-yl)ethyl)propan-1-amine (Method H) instead of N-methyl-3,3-diphenylpropan-1-amine
LC-MS ESI (pos.) m/e: 655.9 (M+1).

EXAMPLE 82

Synthesis of 4-(5-(((3,3-bis(4-fluorophenyl)propyl)(2-(4-tetrahydropyranyl)ethyl)carbamoyl)amino)-1,2,4-thiadiazol-3-yl)benzenesulfonamide, 213

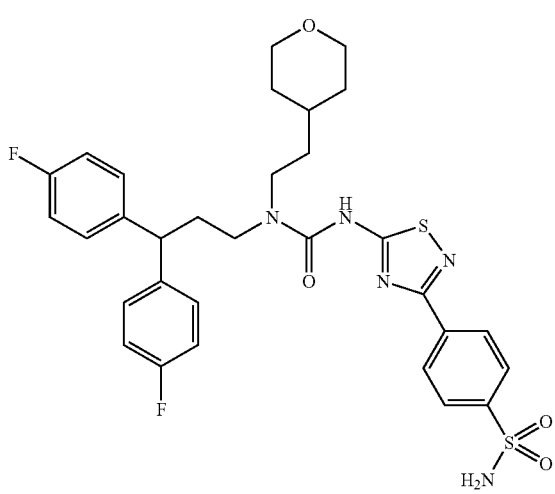

Compound 213 was prepared analogous to the procedure described in Example 43 except substituting for the corresponding sulfonamide starting material. The specific t-butyl sulfonamide precursor was prepared according to Example 94, using 3,3-bis(4-fluorophenyl)-N-(2-(tetrahydro-2H-pyran-4-yl)ethyl)propan-1-amine instead of 3,3-bis(4-fluorophenyl)-N-(2-(pyrazin-2-yl)ethyl)propan-1-amine.
LC-MS ESI (pos.) m/e: 641.8 (M+1).

EXAMPLE 83 methyl 2-(4-(5-chloro-2-(3-(3,3-diphenylpropyl)-3-(2-(tetrahydro-2H-pyran-4-yl)ethyl)ureido)thiazol-4-yl)phenyl)acetate, 214

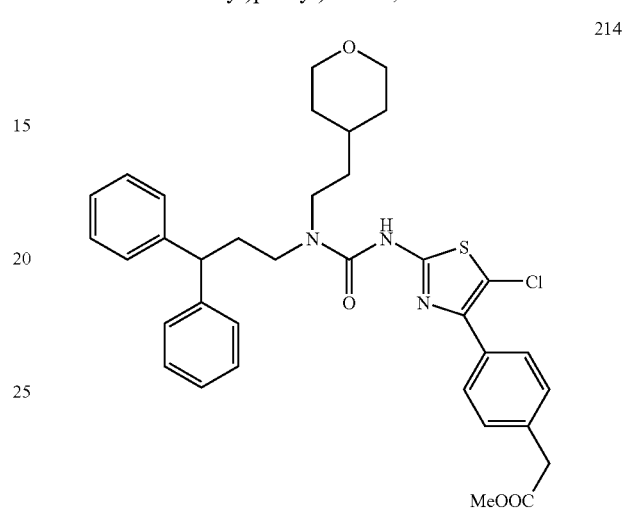

The compound 214 was prepared analogous to the procedure described in Example 58 except using 3,3-diphenyl-N-(2-(tetrahydro-2H-pyran-4-yl)ethyl)propan-1-amine instead of N-isopropyl-3,3-diphenylpropan-1-amine. LC-MS ESI (pos.) m/e: 632.2 (M+1)

EXAMPLE 84

Synthesis of 3-(5-chloro-4-(4-(hydroxymethyl)phenyl)thiazol-2-yl)-1-(3,3-diphenylpropyl)-1-(2-(tetrahydro-2H-pyran-4-yl)ethyl)urea, 215

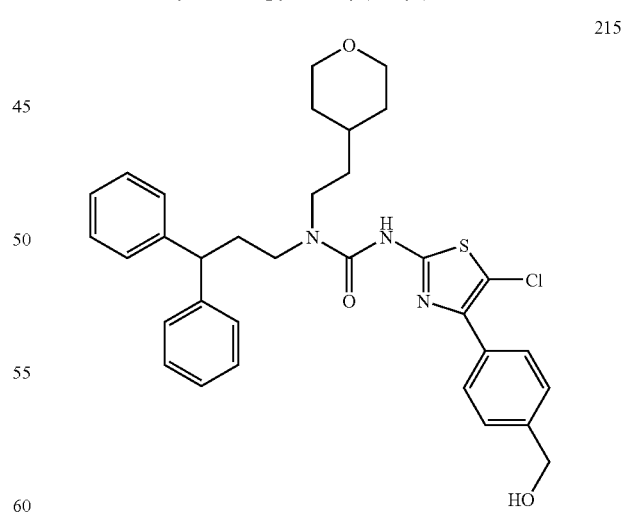

Compound 215 was prepared according to the procedure described in Example 60 except using methyl 4-(5-chloro-2-(3-(3,3-diphenylpropyl)-3-(2-(tetrahydro-2H-pyran-4-yl)ethyl)ureido)thiazol-4-yl)benzoate (Example 84) instead of methyl 4-(5-chloro-2-(3-(3,3-diphenylpropyl)-3-isopropylureido)thiazol-4-yl)benzoate
LC-MS ESI (pos.) m/e: 589.9 (M+1). .

EXAMPLE 85

Synthesis of 3-(5-chloro-4-(4-(morpholinomethyl) phenyl)thiazol-2-yl)-1-(3,3-diphenylpropyl)-1-(2-(tetrahydro-2H-pyran-4-yl)ethyl)urea, 216

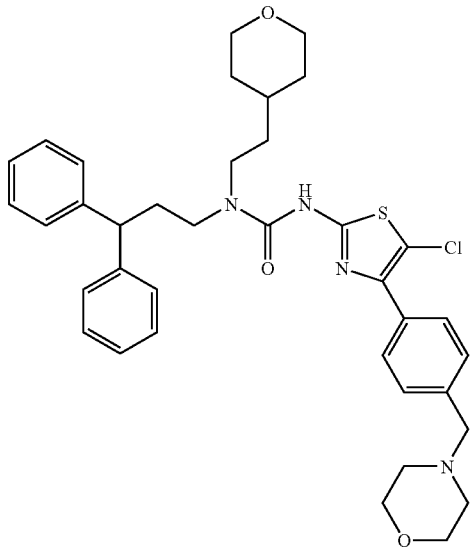

216

Compound 216 was prepared analogous to the procedure described in Example 61 except using 3-(5-chloro-4-(4-(hydroxymethyl)phenyl)thiazol-2-yl)-1-(3,3-diphenylpropyl)-1-(2-(tetrahydro-2H-pyran-4-yl)ethyl)urea (Example 84) instead of 3-(5-chloro-4-(4-(hydroxymethyl)phenyl)thiazol-2-yl)-1-(3,3-diphenylpropyl)-1-isopropylurea.

LC-MS ESI (pos.) m/e: 658.9 (M+1).

EXAMPLE 86

Synthesis of 3-(5-chloro-4-(4-(piperazin-1-ylmethyl) phenyl)thiazol-2-yl)-1-(3,3-diphenylpropyl)-1-(2-(tetrahydro-2H-pyran-4-yl)ethyl)urea, 217

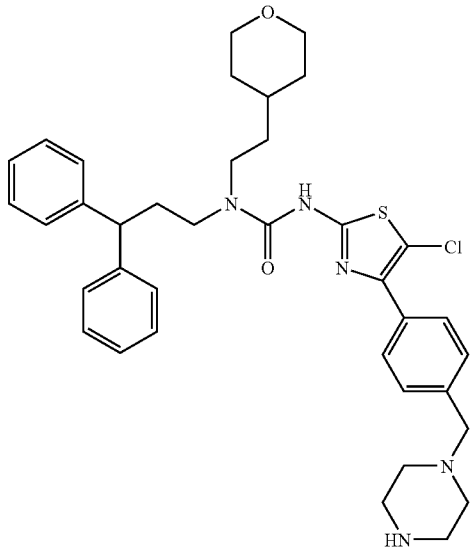

217

Compound 216 was prepared analogous to the procedure described in Example 60 except using 3-(5-chloro-4-(4-(hydroxymethyl)phenyl)thiazol-2-yl)-1-(3,3-diphenylpropyl)-1-(2-(tetrahydro-2H-pyran-4-yl)ethyl)urea (Example 84) instead of 3-(5-chloro-4-(4-(hydroxymethyl)phenyl)thiazol-2-yl)-1-(3,3-diphenylpropyl)-1-isopropylurea and piperazine instead of morpholine. LC-MS ESI (pos.) m/e: 658 (M+1).

EXAMPLE 86

Biological Activity In Vitro

The activities of the compounds of the present invention on calcium receptors were measured in accordance with the method described in Example 4 of Nemeth et al., PCT/US95/13704 (International Publication No. WO 96/12697).

A 4.0-kb NotI-HindIII fragment of the human parathyroid cell $Ca^{2+}$ receptor (hPCaR) cDNA was subcloned into the mammalian expression vector pCEP4 (Invitrogen) containing the hygromycin-resistant gene as a selectable marker. This plasmid was transfected into HEK 293 cells by calcium phosphate precipitation. Transfected cells were grown in Dulbecco's modified Eagle's medium containing 10% fetal bovine serum and hygromycin (200 µg/mL). Hygromycin-resistant colonies were subcloned and assayed for hPCaR mRNA by solution hybridization using a $^{32}P$-labeled RNA probe complementary to the (4.0 kb) hPCaR sequence (Garrett, et al., J. Biol. Chem. 270, 12919-12925 (1995)). Clone 7 was used to assess the effects of compounds on $[Ca^{2+}]_i$. This stably transfected cell line was termed HEK 293 4.0-7. For measurements of $[Ca^{2+}]_i$, the cells were recovered from tissue culture flasks by brief treatment with Versene (Invitrogen; containing 0.2 g/L EDTA.4Na in phosphate-buffered saline) and then seeded in collagen coated 384-well plates (BD Biosciences) at 20K cells per well in the growth media (same as above). Cells are grown in 37° C. TC incubator overnight. Then, the media is discarded and cells are loaded with 1× dye from $Ca^{2+}$ Assay Kit I (BD Biosciences) in parathyroid cell buffer (126 mM NaCl, 4 mM KCl, 1 mM $MgSO_4$, 0.7 mM $K_2HPO_4/KH_2PO_4$, 20 mM HEPES.NaOH (pH 7.45)) containing 0.5% BSA and 1 mM $CaCl_2$. Cells were loaded at room temperature for 90 minutes. Each test compound was added to the cells and the fluorescence was recorded by using excitation and emission wavelengths of 485 and 530 nm, respectively.

The calcimimetic compounds of the invention were tested according to the procedure described above and were found to have the following $EC_{50}<5$ µM.

The activities of some compounds of the present invention on calcium receptors were measured in accordance with the method described hereinbelow.

Human $Ca^{2+}$ receptor cDNA was subcloned into the mammalian expression vector PECE as described in Ellis, L et al. (1986) Cell vol. 45, 721-732. The luciferase reporter was subcloned into the mammalian expression vector pGL3basic (Promega). Resistance to neomycin (pSV2-neo) and resistance to puromycin (pSG5-puro) were used as selection markers. All these plasmids were simultaneously transfected into CHO cells by calcium phosphate precipitation. Transfected cells were grown in F12 medium containing 7.5% foetal bovine serum, 100 U/ml penicillin and 100 µg/ml streptomycin (as 1% Pen-Strep, BioWithaker), neomycin (750 µg/ml) and puromycin (5 µg/ml). Neomycin and puromycin resistant colonies were subcloned and assayed for activation against a range of calcium concentration. Clone 8-5-5 was used to assess the effects of compounds on $[Ca^{2+}]_i$. This stably transfected cell line was termed ET8-5-5.

For measurements of $[Ca^{2+}]_i$, the cells were recovered from tissue culture flasks by brief treatment with Trypsin- EDTA (Invitrogen; containing 0.53 mM EDTA.4Na in HBSS) and then seeded in culture-treated 96-well plates (Greiner) at 50k cells per well in the growth media (same as above, except neomycin 400 μg/ml). Cells were grown in 37° C. TC incubator for 24 h. The culture medium was then removed and replaced with F12 medium, 1% Pen-Strep for an overnight foetal bovine serum starvation in 37° C. TC incubator. Then the starvation medium was removed and replaced with a test buffer (20 mM HEPES pH 7.4, 125 mM NaCl, 5 mM KCl, 1 mM $MgCl_2$, 5.5 mM Glucose, 2 g/l lysosyme and 0.3 mM $CaCl_2$) supplemented with a range of test compound concentrations crossed against a super-added range of $CaCl_2$ concentrations. The cells were incubated with the test compounds for 5 h in 37° C. TC incubator. Then the test buffer was discarded, and cells were added with the substrate for Luciferase from SteadyLite Kit (Perkin-Elmer). The luminescence was recorded.

The compounds of the invention were tested according to this procedure described above and all were found to have an $EC_{50}$ of 5 μM or less.

EXAMPLE 87

In Vivo Measurements

Male Sprague-Dawley rats weighing 250-400 g were given free access to food and water. Unanesthetized rats were gavaged with an 18-gauge balled needle at a volume between 0.5 and 1 ml. Compounds were formulated in 20% captisol in water at pH 7.0 or 2% hydroxypropyl methylcellulose (HPMC)/1% Tween 80/5% Captisol in water pH 2.0. Compounds of the invention were administered at various doses covering the following range 0.03-30 mg/kg in 20% captisol. Vehicle-treated rats received one of the above two vehicles at the maximum volume (0.5-1 ml) used for the compounds of the invention. Each rat was bled at time 0 (pre-calcimimetic or vehicle administration) and at various times (1, 2, 4, 8 and 24 h) after oral gavage of compounds or vehicle.

For measurements of blood-ionized $Ca^{2+}$ levels, blood (50 μl) was collected from the orbital sinus of anesthetized rats (3% isoflurane in $O_2$) with heparinized capillary tubes. Blood samples were analyzed within seconds of collection using a Rapidlab 348 Blood Gas Analyzer (Bayer HealthCare LLC Diagnostic Division; Tarrytown, N.Y.).

For measurements of serum PTH, phosphorus, a nonheparinized capillary tube was inserted into the orbital sinus and blood (0.5 ml) was collected into SST (clot activator) brand blood tubes. Blood samples were allowed to clot for 15-30 min and centrifuged (3000 rpm; Sorvall RT 600B) at 4° C. Serum was removed and stored below 0° C. until assayed. Serum PTH levels were quantified according to the vendor's instructions using rat PTH immunoradiometric assay kits (Immutopics, San Clemente, Calif.) or rat bioactive intact PTH elisa kit (Immutopics, San Clemente, Calif.). Serum phosphorus levels were determined using a blood chemistry analyzer (AU 400; Olympus, Melville, N.Y.).

All compounds tested by this method demonstrated serum PTH and $Ca^{2+}$ lowering properties.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound selected from the group consisting of:
3-(benzo[d]thiazol-2-yl)-1-(3,3-diphenylpropyl)-1-isopropylurea,
1-(3,3-diphenylpropyl)-1-isopropyl-3-(4-(4-(methylsulfonamido)phenyl)thiazol-2-yl)urea,
1-(3,3-diphenylpropyl)-3-(4-(4-(methylsulfonamido)phenyl)thiazol-2-yl)-1-propylurea,
1-cyclopropyl-1-(3,3-diphenylpropyl)-3-(4-(4-(methylsulfonamido)phenyl)thiazol-2-yl)urea,
3-(5-chloro-4-(4-(methylsulfonamido)-phenyl)thiazol-2-yl)-1-(3,3-diphenylpropyl)-1-methylurea,
1-(3,3-diphenylpropyl)-1-methyl-3-(4-(4-(methylsulfonamido)phenyl)thiazol-2-yl)urea,
3-(5-chloro-4-(4-(methylsulfonamido)phenyl)thiazol-2-yl)-1-(3,3-diphenylpropyl)-1-phenylurea,
1-benzyl-3-(5-chloro-4-(4-(methylsulfonamido)phenyl)thiazol-2-yl)-1-(3,3-diphenylpropyl)urea,
3-(5-chloro-4-(4-(methylsulfonamido)phenyl)thiazol-2-yl)-1-(3,3-diphenylpropyl)-1-phenethylurea,
3-(5-chloro-4-(4-(methylsulfonamido)phenyl)thiazol-2-yl)-1-(3,3-diphenylpropyl)-1-(3-phenylpropyl)urea,
3-(5-chloro-4-(4-(methylsulfonamido)phenyl)thiazol-2-yl)-1-(3,3-diphenylpropyl)-1-(2-(pyridin-3-yl)ethyl)urea,
3-(5-chloro-4-(4-(methylsulfonamido)phenyl)thiazol-2-yl)-1-(3,3-diphenylpropyl)-1-(2-(pyridin-2-yl)ethyl)urea,
3-(5-chloro-4-(4-(methylsulfonamido)phenyl)thiazol-2-yl)-1-(3,3-diphenylpropyl)-1-(2-(pyridin-4-yl)ethyl)urea,
1-(4-methoxyphenethyl)-3-(5-chloro-4-(4-(methylsulfonamido)phenyl)thiazol-2-yl)-1-(3,3-diphenylpropyl)urea,
1-(4-fluorophenethyl)-3-(5-chloro-4-(4-(methylsulfonamido)phenyl)thiazol-2-yl)-1-(3,3-diphenylpropyl)urea,
3-(benzo[d]thiazol-2-yl)-1-(3,3-diphenylpropyl)-1-methylurea,
1-(3,3-diphenylpropyl)-1-methyl-3-(4-phenylthiazol-2-yl)urea,
3-(benzo[d]thiazol-2-yl)-1-(3,3-diphenylpropyl)-1-propylurea,
3-(3-(benzo[d]thiazol-2-yl)-1-(3,3-diphenylpropyl)ureido)cyclopentanecarboxylic acid,
2-((3-(benzo[d]thiazol-2-yl)-1-(3,3-diphenylpropyl)ureido)methyl) cyclopropanecarboxylic acid,
3-(5chloro-4-(4-(methylsulfonamido)phenyl)thiazol-2-yl)-1-(3,3-diphenylpropyl)-1-(2-(piperidin-4-yl)ethyl)urea,
1-(3,3-diphenylpropyl)-3-(4-(4-(methylsulfonyl)phenyl)thiazol-2-yl)-1-(2-(piperidin-4-yl)ethyl)urea,
methyl 4-(2-(3-(3,3-diphenylpropyl)-3-(2-(piperidin-4-yl)ethyl)ureido)thiazol-4-yl)benzoate,
3-(5chloro-4-(4-(methylsulfonyl)phenyl)thiazol-2-yl)-1-(3,3-diphenylpropyl)-1-(2-(piperidin-4-yl)ethyl)urea,
1-(3,3-diphenylpropyl)-3-(4-(4-(methylsulfonamido)phenyl)thiazol-2-yl)-1-(2-(piperidin-3-yl)ethyl)urea,
1-(3,3-diphenylpropyl)-3-(4-(4-(methylsulfonamido)phenyl)thiazol-2-yl)-1-(2-(piperidin-4-yl)ethyl)urea,
3(5-chloro-4-(4-(methylsulfonamido)phenyl)thiazol-2-yl)-1-(3,3-diphenylpropyl)-1-(2-(piperidin-3-yl)ethyl)urea,
3- [3-(2-Cyclohexyl-ethyl)-3-(3,3-diphenyl-propyl)-ureido]-benzoic acid methyl ester,
3-[3-Benzyl-3-(3,3-diphenyl-propyl)-ureido]-benzoic acid methyl ester,

N-(4-(5-chloro-2-(((3,3-diphenylpropyl)(4-(2-hydroxyethyl)phenyl)carbamoyl)amino)-1,3-thiazol-4-yl)phenyl)methanesulfonamide,
N-(4-(5-chloro-2-(((3,3-diphenylpropyl)(1-methylethyl)carbamoyl)amino)-1,3-thiazol-4-yl)phenyl)methanesulfonamide,
1-(3,3-bis(4-fluorophenyl)propyl)-3-(5-chloro-4-(4-(1H-1,2,3-triazol-1-yl)phenyl)-1,3-thiazol-2-yl)-1-(2-(2-pyridinyl)ethyl)urea,
3-(5-chloro-4-(4-(1H-1,2,3-triazol-1-yl)phenyl)-1,3-thiazol-2-yl)-1-(3,3-diphenylpropyl)-1-(2-(2-pyridinyl)ethyl)urea,
3-(((5-chloro-4-(4-((methylsulfonyl)amino)phenyl)-1,3-thiazol-2-yl)carbamoyl)(3,3-diphenylpropyl)amino)benzoic acid,
(4-(((5-chloro-4-(4-((methylsulfonyl)amino)phenyl)-1,3-thiazol-2-yl)carbamoyl)(3,3-diphenylpropyl)amino)phenyl)acetic acid,
4-(2-(((5-chloro-4-(4-((methylsulfonyl)amino)phenyl)-1,3-thiazol-2-yl)carbamoyl)(3,3-diphenylpropyl)amino)ethyl)benzoic acid,
4-(((5-chloro-4-(4-((methylsulfonyl)amino)phenyl)-1,3-thiazol-2-yl)carbamoyl)(3,3-diphenylpropyl)amino)benzoic acid,
3-(3-(5-chloro-4-(4-(methylsulfonamido)phenyl)thiazol-2-yl)-1-(3,3-diphenylpropyl)ureido)benzoic acid,
3-(((5-chloro-4-(4-((methylsulfonyl)amino)phenyl)-1,3-thiazol-2-yl)carbamoyl)(3,3-diphenylpropyl)amino)-N-methylbenzamide,
2-(4-(((5-chloro-4-(4-((methylsulfonyl)amino)phenyl)-1,3-thiazol-2-yl)carbamoyl)(3,3-diphenylpropyl)amino)phenyl)-N-methylacetamide,
2-(4-(((5-chloro-4-(4-((methylsulfonyl)amino)phenyl)-1,3-thiazol-2-yl)carbamoyl)(3,3-diphenylpropyl)amino)phenyl)acetamide,
4-(2-(((5-chloro-4-(4-((methylsulfonyl)amino)phenyl)-1,3-thiazol-2-yl)carbamoyl)(3,3-diphenylpropyl)amino)ethyl)-N-methylbenzamide,
4-(((5-chloro-4-(4-((methylsulfonyl)amino)phenyl)-1,3-thiazol-2-yl)carbamoyl)(3,3-diphenylpropyl)amino)-N-methylbenzamide,
4-(5-chloro-2-(((3,3-diphenylpropyl)(2-(2-pyridinyl)ethyl)carbamoyl)amino)-1,3-thiazol-4-yl)benzenesulfonamide,
4-(2-(((3,3-bis(4-fluorophenyl)propyl)(2-(2-pyridinyl)ethyl)carbamoyl)amino)-5-chloro-1,3-thiazol-4-yl)benzenesulfonamide,
4-(5-(((3,3-diphenylpropyl)(2-(2-pyridinyl)ethyl)carbamoyl)amino)-1,2,4-thiadiazol-3-yl)benzenesulfonamide,
4-(5-(((3,3-bis(4-fluorophenyl)propyl)(2-(2-pyridinyl)ethyl)carbamoyl)amino)-1,2,4-thiadiazol-3-yl)benzenesulfonamide,
4-(5-chloro-2-(((3,3-diphenylpropyl)(2-(2-pyrazinyl)ethyl)carbamoyl)amino)-1,3-thiazol-4-yl)benzenesulfonamide,
4-(5-(((3,3-diphenylpropyl)(2-(2-pyrazinyl)ethyl)carbamoyl)amino)-1,2,4-thiadiazol-3-yl)benzenesulfonamide,
4-(5-chloro-2-(((3,3-diphenylpropyl)(2-(2-pyrimidinyl)ethyl)carbamoyl)amino)-1,3-thiazol-4-yl)benzenesulfonamide,
4-(5-chloro-2-(((2-(4-chloro-2-pyridinyl)ethyl)(3,3-diphenylpropyl)carbamoyl)amino)-1,3-thiazol-4-yl)benzenesulfonamide,
4-(2-(((3,3-bis(4-fluorophenyl)propyl)(2-(2-pyrazinyl)ethyl)carbamoyl)amino)-5-chloro-1,3-thiazol-4-yl)benzenesulfonamide,
4-(5-(((3,3-bis(4-fluorophenyl)propyl)(2-(2-pyrazinyl)ethyl)carbamoyl)amino)-1,2,4-thiadiazol-3-yl)benzenesulfonamide,
4-(5-(((3,3-diphenylpropyl)(2-(2-pyrimidinyl)ethyl)carbamoyl)amino)-1,2,4-thiadiazol-3-yl)benzenesulfonamide,
4-(2-(((3,3-bis(4-fluorophenyl)propyl)(2-(2-pyrimidinyl)ethyl)carbamoyl)amino)-5-chloro-1,3-thiazol-4-yl)benzenesulfonamide,
4-(5-(((3,3-bis(4-fluorophenyl)propyl)(2-(2-pyrimidinyl)ethyl)carbamoyl)amino)-1,2,4-thiadiazol-3-yl)benzenesulfonamide,
N-(4-(5-chloro-2-(((3,3-diphenylpropyl)(3-pyridinyl)carbamoyl)amino)-1,3-thiazol-4-yl)phenyl)methanesulfonamide,
N-(4-(5-chloro-2-(((3,3-diphenylpropyl)(2-pyridinyl)carbamoyl)amino)-1,3-thiazol-4-yl)phenyl)methanesulfonamide,
N-(4-(5-chloro-2-(((3,3-diphenylpropyl)(2-(3-fluorophenyl)ethyl)carbamoyl)amino)-1,3-thiazol-4-yl)phenyl)methanesulfonamide,
N-(4-(5-chloro-2-(((3,3-diphenylpropyl)(2-(2-fluorophenyl)ethyl)carbamoyl)amino)-1,3-thiazol-4-yl)phenyl)methanesulfonamide,
N-(4-(5-chloro-2-(((3,3-diphenylpropyl)(2-(2-methoxyphenyl)ethyl)carbamoyl)amino)-1,3-thiazol-4-yl)phenyl)methanesulfonamide,
N-(4-(5-chloro-2-(((3,3-diphenylpropyl)(2-fluorophenyl)carbamoyl)amino)-1,3-thiazol-4-yl)phenyl)methanesulfonamide,
N-(4-(5-chloro-2-(((3,3-diphenylpropyl)(3-fluorophenyl)carbamoyl)amino)-1,3-thiazol-4-yl)phenyl)methanesulfonamide,
N-(4-(5-chloro-2-(((3,3-diphenylpropyl)(4-fluorophenyl)carbamoyl)amino)-1,3-thiazol-4-yl)phenyl)methanesulfonamide,
ethyl (4-(((5-chloro-4-(4-((methylsulfonyl)amino)phenyl)-1,3-thiazol-2-yl)carbamoyl)(3,3-diphenylpropyl)amino)phenyl)acetate,
methyl 4-(2-(((5-chloro-4-(4-((methylsulfonyl)amino)phenyl)-1,3-thiazol-2-yl)carbamoyl)(3,3-diphenylpropyl)amino)ethyl)benzoate,
methyl 4-(((5-chloro-4-(4-((methylsulfonyl)amino)phenyl)-1,3-thiazol-2-yl)carbamoyl)(3,3-diphenylpropyl)amino)benzoate,
N-(4-(5-chloro-2-((cyclopropyl(3,3-diphenylpropyl)carbamoyl)amino)-1,3-thiazol-4-yl)phenyl)methanesulfonamide,
3-(5-chloro-4-(4-(methylsulfonyl)phenyl)-1,3-thiazol-2-yl)-1-(3,3-diphenylpropyl)-1-(2-(2-pyridinyl)ethyl)urea,
N-(4-(5-chloro-2-(((3,3-diphenylpropyl)(2-(2-pyrazinyl)ethyl)carbamoyl)amino)-1,3-thiazol-4-yl)phenyl)methanesulfonamide,
3-(5-chloro-4-(4-(methylsulfonyl)phenyl)-1,3-thiazol-2-yl)-1-(3,3-diphenylpropyl)-1-(2-(2-pyrazinyl)ethyl)urea,
1-(3,3-diphenylpropyl)-1-(2-(2-pyridinyl)ethyl)-3-[1,3]thiazolo[5,4-b]pyridin-2-ylurea,
1-(3,3-diphenylpropyl)-1-(2-(2-pyridinyl)ethyl)-3-[1,3]thiazolo[4,5-c]pyridin-2-ylurea,
N-(4-(2-(((3,3-bis(4-fluorophenyl)propyl)(2-(2-pyridinyl)ethyl)carbamoyl)amino)-5-chloro-1,3-thiazol-4-yl)phenyl)methanesulfonamide,
N-tert-butyl-4-(5-chloro-2-(((3,3-diphenylpropyl)(2-(2-pyridinyl)ethyl)carbamoyl)amino)-1,3-thiazol-4-yl)benzenesulfonamide, 4-(2-(((3,3-bis(4-fluorophenyl)propyl)(2-(2-pyridinyl)ethyl)carbamoyl)amino)-5-chloro-1,3-thiazol-4-yl)-N-tert-butylbenzenesulfonamide,
N-(4-(5-(((3,3-bis(4-fluorophenyl)propyl)(2-(2-pyridinyl)ethyl)carbamoyl)amino)-1,2,4-thiadiazol-3-yl)phenyl)methanesulfonamide,
1-(3,3-diphenylpropyl)-3-(3-(4-(methylsulfonyl)phenyl)-1,2,4-thiadiazol-5-yl)-1-(2-(2-pyridinyl)ethyl)urea,
1-(3,3-bis(4-fluorophenyl)propyl)-3-(3-(4-(methylsulfonyl)phenyl)-1,2,4-thiadiazol-5-yl)-1-(2-(2-pyridinyl)ethyl)urea,
N-(4-(5-(((3,3-diphenylpropyl)(2-(2-pyridinyl)ethyl)carbamoyl)amino)-1,2,4-thiadiazol-3-yl)phenyl)methanesulfonamide,
1-(3,3-diphenylpropyl)-1-(2-(2-pyridinyl)ethyl)-3-(3-(4-(1H-1,2,3-triazol-1-yl)phenyl)-1,2,4-thiadiazol-5-yl)urea,
1-(3,3-bis(4-fluorophenyl)propyl)-1-(2-(2-pyridinyl)ethyl)-3-(3-(4-(1H-1,2,3-triazol-1-yl)phenyl)-1,2,4-thiadiazol-5-yl)urea,
N-(4-(5-chloro-2-(((3,3-diphenylpropyl)(2-(2-pyrazinyl)ethyl)carbamoyl)amino)-1,3-thiazol-4-yl)phenyl)acetamide,
3-(5-chloro-4-(4-(1H-1,2,3-triazol-1-yl)phenyl)-1,3-thiazol-2-yl)-1-(3,3-diphenylpropyl)-1-(2-(2-pyrazinyl)ethyl)urea,
N-(4-(5-(((3,3-diphenylpropyl)(2-(2-pyrazinyl)ethyl)carbamoyl)amino)-1,2,4-thiadiazol-3-yl)phenyl)methanesulfonamide,
1-(3,3-diphenylpropyl)-1-(2-(2-pyrazinyl)ethyl)-3-(3-(4-(1H-1,2,3-triazol-1-yl)phenyl)-1,2,4-thiadiazol-5-yl)urea,
1-(2-(5-chloro-2-pyridinyl)ethyl)-3-(5-chloro-4-(4-(1H-1,2,3-triazol-1-yl)phenyl)-1,3-thiazol-2-yl)-1-(3,3-diphenylpropyl)urea,
3-(5-chloro-4-(4-(1H-1,2,3-triazol-1-yl)phenyl)-1,3-thiazol-2-yl)-1-(3,3-diphenylpropyl)-1-(2-(2-pyrimidinyl)ethyl)urea,
1-(2-(4-chloro-2-pyridinyl)ethyl)-1-(3,3-diphenylpropyl)-3-(3-(4-(1H-1,2,3-triazol-1-yl)phenyl)-1,2,4-thiadiazol-5-yl)urea,
N-(4-(5-chloro-2-(((3,3-diphenylpropyl)(2-(2-pyridinyl)ethyl)carbamoyl)amino)-1,3-thiazol-4-yl)phenyl)acetamide,
N-(4-(2-(((3,3-bis(4-fluorophenyl)propyl)(2-(2-pyridinyl)ethyl)carbamoyl)amino)-5-chloro-1,3-thiazol-4-yl)phenyl)acetamide,
N-(4-(5-(((3,3-diphenylpropyl)(2-(2-pyridinyl)ethyl)carbamoyl)amino)-1,2,4-thiadiazol-3-yl)phenyl)acetamide,
N-(4-(5-(((3,3-bis(4-fluorophenyl)propyl)(2-(2-pyridinyl)ethyl)carbamoyl)amino)-1,2,4-thiadiazol-3-yl)phenyl)acetamide.
N-(4-(5-(((3,3-diphenylpropyl)(2-(2-pyrazinyl)ethyl)carbamoyl)amino)-1,2,4-thiadiazol-3-yl)phenyl)acetamide,
1-(3,3-diphenylpropyl)-3-(3-(4-(methylsulfonyl)phenyl)-1,2,4-thiadiazol-5-yl)-1-(2-(2-pyrazinyl)ethyl)urea,
1-(3,3-bis(4-fluorophenyl)propyl)-3-(5-chloro-4-(4-(methylsulfonyl)phenyl)-1,3-thiazol-2-yl)-1-(2-(2-pyrazinyl)ethyl)urea,
N-(4-(2-(((3,3-bis(4-fluorophenyl)propyl)(2-(2-pyrazinyl)ethyl)carbamoyl)amino)-5-chloro-1,3-thiazol-4-yl)phenyl)methanesulfonamide,
N-(4-(2-(((3,3-bis(4-fluorophenyl)propyl)(2-(2-pyrazinyl)ethyl)carbamoyl)amino)-5-chloro-1,3-thiazol-4-yl)phenyl)acetamide,
1-(3,3-bis(4-fluorophenyl)propyl)-3-(5-chloro-4-(4-(1H-1,2,3-triazol-1-yl)phenyl)-1,3-thiazol-2-yl)-1-(2-(2-pyrazinyl)ethyl)urea,
1-(3,3-bis(4-fluorophenyl)propyl)-3-(3-(4-(methylsulfonyl)phenyl)-1,2,4-thiadiazol-5-yl)-1-(2-(2-pyrazinyl)ethyl)urea,
N-(4-(5-(((3,3-bis(4-fluorophenyl)propyl)(2-(2-pyrazinyl)ethyl)carbamoyl)amino)-1,2,4-thiadiazol-3-yl)phenyl)methanesulfonamide,
N-(4-(5-(((3,3-bis(4-fluorophenyl)propyl)(2-(2-pyrazinyl)ethyl)carbamoyl)amino)-1,2,4-thiadiazol-3-yl)phenyl)acetamide,
N-(4-(5-chloro-2-(((3,3-diphenylpropyl)(2-(2-pyrimidinyl)ethyl)carbamoyl)amino)-1,3-thiazol-4-yl)phenyl)methanesulfonamide,
1-(3,3-diphenylpropyl)-1-(2-(2-pyrimidinyl)ethyl)-3-(3-(4-(1H-1,2,3-triazol-1-yl)phenyl)-1,2,4-thiadiazol-5-yl)urea,
N-(4-(5-(((3,3-diphenylpropyl)(2-(2-pyrimidinyl)ethyl)carbamoyl)amino)-1,2,4-thiadiazol-3-yl)phenyl)methanesulfonamide,
N-(4-(5-chloro-2-(((3,3-diphenylpropyl)(2-(2-pyrimidinyl)ethyl)carbamoyl)amino)-1,3-thiazol-4-yl)phenyl)acetamide,
N-(4-(5-(((3,3-diphenylpropyl)(2-(2-pyrimidinyl)ethyl)carbamoyl)amino)-1,2,4-thiadiazol-3-yl)phenyl)acetamide,
3-(5-chloro-4-(4-(1H-1,2,3-triazol-1-yl)phenyl)-1,3-thiazol-2-yl)-1-(3,3-diphenyl-2-propen-1-yl)-1-(2-(2-pyrimidinyl)ethyl)urea,
N-(4-(2-(((3,3-bis(4-fluorophenyl)propyl)(2-(2-pyrimidinyl)ethyl)carbamoyl)amino)-5-chloro-1,3-thiazol-4-yl)phenyl)methanesulfonamide,
1-(3,3-bis(4-fluorophenyl)propyl)-3-(5-chloro-4-(4-(1H-1,2,3-triazol-1-yl)phenyl)-1,3-thiazol-2-yl)-1-(2-(2-pyrimidinyl)ethyl)urea,
N-(4-(2-(((3,3-bis(4-fluorophenyl)propyl)(2-(2-pyrimidinyl)ethyl)carbamoyl)amino)-5-chloro-1,3-thiazol-4-yl)phenyl)acetamide,
N-(4-(5-(((3,3-bis(4-fluorophenyl)propyl)(2-(2-pyrimidinyl)ethyl)carbamoyl)amino)-1,2,4-thiadiazol-3-yl)phenyl)methanesulfonamide,
1-(3,3-bis(4-fluorophenyl)propyl)-1-(2-(2-pyrimidinyl)ethyl)-3-(3-(4-(1H-1,2,3-triazol-1-yl)phenyl)-1,2,4-thiadiazol-5-yl)urea,
N-(4-(5-(((3,3-bis(4-fluorophenyl)propyl)(2-(2-pyrimidinyl)ethyl)carbamoyl)amino)-1,2,4-thiadiazol-3-yl)phenyl)acetamide,
N-(4-(3-(((3,3-diphenylpropyl)(2-(2-pyridinyl)ethyl)carbamoyl)amino)-1,2,4-thiadiazol-5-yl)phenyl)acetamide,
N-(4-(3-(((3,3-bis(4-fluorophenyl)propyl)(2-(2-pyridinyl)ethyl)carbamoyl)amino)-1,2,4-thiadiazol-5-yl)phenyl)methanesulfonamide,
N-(4-(3-(((3,3-diphenylpropyl)(2-(2-pyridinyl)ethyl)carbamoyl)amino)-1,2,4-thiadiazol-5-yl)phenyl)methanesulfonamide,
4-(3-(benzo[d]thiazol-2-yl)-1-(3,3-diphenylpropyl)ureido)cyclohexanecarboxylic acid,
4-(3-(benzo[d]thiazol-2-yl)-1-(3,3-diphenylpropyl)ureido)cyclohexanecarboxylic acid,
Methyl 4-(3-(5-chloro-4-(4-(methylsulfonamido)phenyl)thiazol-2-yl)-1-(3,3-diphenylpropyl)ureido)cyclohexanecarboxylate,
4-(3-(5-chloro-4-(4-(methylsulfonamido)phenyl)thiazol-2-yl)-1-(3,3-diphenylpropyl)ureido)cyclohexanecarboxylic acid, methyl 4-(1-(3,3-diphenylpropyl)-3-(5-methyl-4-phenylthiazol-2-yl)ureido)cyclohexanecarboxylate, methyl 4-(3-(5-chloro-4-(4-(methylsulfonamido)phenyl)thiazol-2-yl)-1-(3,3-diphenylpropyl)ureido)cyclohexanecarboxylate, 4-(3-(5-chloro-4-(4-(methylsulfonamido)phenyl)thiazol-2-yl)-1-(3,3-diphenylpropyl)ureido)cyclohexanecarboxylic acid, 4-(3-(5-chloro-4-(4-(methylsulfonyl)phenyl)thiazol-2-yl)-1-(3,3-diphenylpropyl)ureido) cyclohexanecarboxylic acid, 4-(3-(5-chloro-4-(4-(methylsulfonyl)phenyl)thiazol-2-yl)-1-(3,3-diphenylpropyl)ureido) cyclohexanecarboxylic acid, 3-(5-chloro-4-(4-(methylsulfonamido)phenyl)thiazol-2-yl)-1-(2-cyanoethyl)-1-(3,3-diphenylpropyl)urea, methyl 2-(4-(5-chloro-2-(3-(3,3-diphenylpropyl)-3-isopropylureido)thiazol-4-yl)phenyl)acetate, methyl 4-(5-chloro-2-(3-(3,3-diphenylpropyl)-3-(tetrahydro-2H-pyran-4-yl)ureido)thiazol-4-yl)benzoate, 3-(5-chloro-4-(4-(hydroxymethyl)phenyl)thiazol-2-yl)-1-(3,3-diphenylpropyl)-1-isopropylurea, 3-(5-chloro-4-(4-(morpholinomethyl)phenyl)thiazol-2-yl)-1-(3,3-diphenylpropyl)-1-isopropylurea, 3-(5-chloro-4-(4-(piperazin-l-ylmethyl)phenyl)thiazol-2-yl)-1-(3,3-diphenylpropyl)-1-isopropylurea, 3-(5-chloro-4-(4-(morpholinomethyl)phenyl)thiazol-2-yl)-1-(3,3-diphenylpropyl)-1-(tetrahydro-2H-pyran-4-yl)urea, 4-(2-(((3,3-bis(4-fluorophenyl)propyl)(cyclopropyl)carbamoyl)amino)-5-chloro-1,3-thiazol-4-yl)benzenesulfonamide, 4-(5-chloro-2-((cyclopropyl(3,3-diphenylpropyl)carbamoyl)amino)-1,3-thiazol-4-yl)benzenesulfonamide, 4-(5-chloro-2-(((3,3-diphenylpropyl)(tetrahydro-2H-pyran-4-yl)carbamoyl)amino)-1,3-thiazol-4-yl)benzenesulfonamide, 4-(5-chloro-2-(((3,3-diphenylpropyl)(1-methylethyl)carbamoyl)amino)-1,3-thiazol-4-yl)benzenesulfonamide, N-(4-(5-chloro-2-(((3,3-diphenylpropyl)(tetrahydro-2H-thiopyran-4-yl)carbamoyl)amino)-1,3-thiazol-4-yl)phenyl)methanesulfonamide, 1-cyclopropyl-1-(3,3-diphenylpropyl)-3-(3-(2-pyridinyl)-1,2,4-thiadiazol-5-yl)urea, N-(4-(5-(((3,3-bis(4-fluorophenyl)propyl)(cyclopropyl)carbamoyl)amino)-1,2,4-thiadiazol-3-yl)phenyl)methanesulfonamide, N-(4-(5-(((3,3-diphenylpropyl)(tetrahydro-2H-pyran-4-yl)carbamoyl)amino)-1,2,4-thiadiazol-3-yl)phenyl)methanesulfonamide, N-(4-(5-(((3,3-diphenylpropyl)(1-methylethyl)carbamoyl)amino)-1,2,4-thiadiazol-3-yl)phenyl)methanesulfonamide, 3-(5-chloro-4-(2-oxo-2,3-dihydro-1H-indol-5-yl)-1,3-thiazol-2-yl)-1-(3,3-diphenylpropyl)-1-(1-methylethyl)urea, 3-(5-chloro-4-(2-oxo-2,3-dihydro-1H-indol-5-yl)-1,3-thiazol-2-yl)-1-(3,3-diphenylpropyl)-1-(tetrahydro-2H-pyran-4-yl)urea, N-(4-(5-chloro-2-(((1,1-dioxidotetrahydro-2H-thiopyran-4-yl)(3,3-diphenylpropyl)carbamoyl)amino)-1,3-thiazol-4-yl)phenyl)methanesulfonamide, 4-(5-((cyclopropyl(3,3-diphenylpropyl)carbamoyl)amino)-1,2,4-thiadiazol-3-yl)benzenesulfonamide, 4-(5-(((3,3-bis(4-fluorophenyl)propyl)(cyclopropyl)carbamoyl)amino)-1,2,4-thiadiazol-3-yl)benzenesulfonamide, 4-(5-(((3,3-diphenylpropyl)(tetrahydro-2H-pyran-4-yl)carbamoyl)amino)-1,2,4-thiadiazol-3-yl)benzenesulfonamide, 4-(5-(((3,3-diphenylpropyl)(1-methylethyl)carbamoyl)amino)-1,2,4-thiadiazol-3-yl)benzenesulfonamide, 3-(5-chloro-4-(6-methylpyridin-3-yl)thiazol-2-yl)-1-(3,3-diphenylpropyl)-1-(piperidin-4-yl)urea, N-(4-(5-chloro-2-(((3,3-diphenylpropyl)(4-piperidinyl)carbamoyl)amino)-1,3-thiazol-4-yl)phenyl)methanesulfonamide, 3-(5-chloro-4-(6-chloro-3-pyridinyl)-1,3-thiazol-2-yl)-1-(3,3-diphenylpropyl)-1-(4-piperidinyl)urea, N-(4-(5-chloro-2-(((3,3-diphenylpropyl)(tetrahydro-2H-pyran-4-yl)carbamoyl)amino)-1,3-thiazol-4-yl)phenyl)methanesulfonamide, 3-(5-chloro-4-(4-(methylsulfonyl)phenyl)-1,3-thiazol-2-yl)-1-(3,3-diphenylpropyl)-1-(tetrahydro-2H-pyran-4-yl)urea, 3-(5-chloro-4-(4-(methylsulfonamido)phenyl)thiazol-2-yl)-1-(3,3-diphenylpropyl)-1-(4-hydroxycyclohexyl)urea, 3-(5-chloro-4-(4-(methylsulfonamido)phenyl)thiazol-2-yl)-1-cyclohexyl-1-(3,3-diphenylpropyl)urea, 3-(5-chloro-4-(4-(methylsulfonyl)phenyl)thiazol-2-yl)-1-(3,3-diphenylpropyl)-1-(2-(tetrahydro-2H-pyran-4-yl)ethyl)urea, 4-(5-chloro-2-(((3,3-diphenylpropyl)(2-(4-tetrahydropyranyl)ethyl)carbamoyl)amino)-1,3-thiazol-4-yl)benzenesulfonamide, 4-(2-(((3,3-bis(4-fluorophenyl)propyl)(2-(4-tetrahydropyranyl)ethyl)carbamoyl)amino)-5-chloro-1,3-thiazol-4-yl)benzenesulfonamide, 3-(5-chloro-4-(4-(methylsulfonamido)phenyl)thiazol-2-yl)-1-(3,3-diphenylpropyl)-1-(2-(tetrahydro-2H-pyran-4-yl)ethyl)urea, 1-(3,3-diphenylpropyl)-3-(3-(4-(methylsulfonamido)phenyl)-1,2,4-thiadiazol-5-yl)-1-(2-(tetrahydro-2H-pyran-4-yl)ethyl)urea, 4-(5-(((3,3-diphenylpropyl)(2-(4-tetrahydropyranyl)ethyl)carbamoyl)amino)-1,2,4-thiadiazol-3-yl)benzenesulfonamide, 1-(3,3-bis(4-fluorophenyl)propyl)-3-(3-(4-(methylsulfonamido)phenyl)-1,2,4-thiadiazol-5-yl)-1-(2-(tetrahydro-2H-pyran-4-yl)ethyl)urea, 4-(5-(((3,3-bis(4-fluorophenyl)propyl)(2-(4-tetrahydropyranyl)ethyl)carbamoyl)amino)-1,2,4-thiadiazol-3-yl)benzenesulfonamide, 2-(4-(5-chloro-2-(3-(3,3-diphenylpropyl)-3-(2-(tetrahydro-2H-pyran-4-yl)ethyl)ureido)thiazol-4-yl)phenyl)acetate, 3-(5-chloro-4-(4-(hydroxymethyl)phenyl)thiazol-2-yl)-1-(3,3-diphenylpropyl)-1-(2-(tetrahydro-2H-pyran-4-yl)ethyl)urea, 3-(5-chloro-4-(4-(morpholinomethyl)phenyl)thiazol-2-yl)-1-(3,3-diphenylpropyl)-1-(2-(tetrahydro-2H-pyran-4-yl)ethyl)urea, and 3-(5-chloro-4-(4-(piperazin-1-ylmethyl)phenyl)thiazol-2-yl)-1-(3,3-diphenylpropyl)-1-(2-(tetrahydro-2H-pyran-4-yl)ethyl)urea, or a stereoisomer or a pharmaceutically acceptable salt thereof.

2. A pharmaceutical composition comprising a compound of claim 1 and a pharmaceutically acceptable carrier.

3. A compound, wherein the compound is N-(4-(5-chloro-2-(((3,3-diphenylpropyl)(tetrahydro-2H-pyran-4-yl)carbamoy)amino)-1,3-thiazol-4-yl)phenyl)methanesulfonamide, or a stereoisomer, or a pharmaceutically acceptable salt thereof.

4. The compound of claim 3, wherein the compound is the neutral compound.

5. The compound of claim 3, wherein the compound is the pharmaceutically acceptable salt.

6. A pharmaceutical composition comprising the compound of claim 3 and a pharmaceutically acceptable carrier.

* * * * *